United States Patent
Shunatona et al.

(10) Patent No.: US 11,739,101 B2
(45) Date of Patent: Aug. 29, 2023

(54) BIFUNCTIONAL DEGRADERS OF HEMATOPOIETIC PROGENITOR KINASE AND THERAPEUTIC USES THEREOF

(71) Applicants: Nurix Therapeutics, Inc., San Francisco, CA (US); Gilead Sciences, Inc., Foster City, CA (US)

(72) Inventors: Hunter P. Shunatona, San Francisco, CA (US); Galen Paul Shearn-Nance, San Francisco, CA (US); Scott A. Mitchell, Foster City, CA (US); John Buell, San Francisco, CA (US)

(73) Assignees: Nurix Therapeutics, Inc., San Francisco, CA (US); Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 17/308,879

(22) Filed: May 5, 2021

(65) Prior Publication Data
US 2021/0355140 A1    Nov. 18, 2021

Related U.S. Application Data

(60) Provisional application No. 63/021,045, filed on May 6, 2020.

(51) Int. Cl.
| | | |
|---|---|---|
| C07D 519/00 | (2006.01) |
| C07D 471/04 | (2006.01) |
| C07D 487/14 | (2006.01) |
| C07D 471/10 | (2006.01) |
| A61P 31/12 | (2006.01) |
| A61P 35/00 | (2006.01) |
| A61P 37/02 | (2006.01) |
| A61P 31/18 | (2006.01) |
| A61P 31/20 | (2006.01) |
| A61K 31/4545 | (2006.01) |
| A61K 47/55 | (2017.01) |

(52) U.S. Cl.
CPC ................ *C07D 519/00* (2013.01)

(58) Field of Classification Search
CPC .. C07D 519/00; C07D 471/04; C07D 487/14; C07D 471/10; A61P 31/12; A61P 35/00; A61P 37/02; A61P 31/18; A61P 31/20; A61K 31/4545; A61K 47/55
See application file for complete search history.

(56) References Cited

U.S. PATENT DOCUMENTS

| | | |
|---|---|---|
| 2015/0038488 A1 | 2/2015 | Currie et al. |
| 2019/0151295 A1 | 5/2019 | Crew et al. |
| 2019/0192668 A1 | 6/2019 | Mainolfi et al. |

FOREIGN PATENT DOCUMENTS

| | | | |
|---|---|---|---|
| WO | 2019/099926 A1 | 5/2019 | |
| WO | 2020/023851 A1 | 1/2020 | |
| WO | 2020/038415 A1 | 2/2020 | |
| WO | 2020/092528 A1 | 5/2020 | |
| WO | 2020/092621 A1 | 5/2020 | |
| WO | WO-2020227325 A1 * | 11/2020 | ......... A61K 39/3955 |
| WO | 2021/168197 A1 | 8/2021 | |
| WO | 2021/226262 A1 | 11/2021 | |

OTHER PUBLICATIONS

International Search Report and Written Opinion, dated Jul. 20, 2021, for International Application No. PCT/US2021/030928. (12 pages).
International Search Report and Written Opinion, dated Apr. 19, 2023, for International Application No. PCT/US2022/049426. (12 pages).

* cited by examiner

*Primary Examiner* — John M Mauro
(74) *Attorney, Agent, or Firm* — Seed IP Law Group LLP

(57) ABSTRACT

The present disclosure provides bifunctional compounds as HPK1 degraders via ubiquitin proteosome pathway, and method for treating diseases modulated by HPK1.

40 Claims, No Drawings

BIFUNCTIONAL DEGRADERS OF HEMATOPOIETIC PROGENITOR KINASE AND THERAPEUTIC USES THEREOF

CROSS-REFERENCE TO RELATED APPLICATIONS

This application claims the benefit of priority to U.S. Provisional Application No. 63/021,045, filed May 6, 2020, which application is hereby incorporated by reference in its entirety.

BACKGROUND

Technical Field

The present invention provides novel bifunctional compounds for proteolytically degrading Hematopoietic progenitor kinase (HPK1) and methods for treating diseases modulated by HPK1.

Description of the Related Art

Immuno-oncology utilizes inhibitor antibodies against the immune checkpoint receptors CTLA4, PD-1 and PD-L1. Targeted disruption of these checkpoint pathways releases the immune cell from key regulatory pathways, allowing for a boost in the immune response against cancer cells. Current therapies utilizing these antibodies are highlighted by both significant and durable response to many different cancers but also by low overall response rates (<25%). Improvement in these response rates could benefit from a combination of checkpoint blockade with other immune activating agents or cell based therapies.

Hematopoietic progenitor kinase 1, a STE20 ser/thr kinase from the germinal center family of kinases, regulates the function of diverse immune populations including T cells, B cells, and dendritic cells (Hu et al., Gens Dev, 1996; Alzabin et al., J Immunol 2009). In T cells, HPK1 serves as a negative regulator of T cell receptor (TCR) signaling (Liou et al., Immunity 2000; Sauer et al., JBC 2001) by phosphorylating SLP76 on serine 376, which induces the association of SLP76 with 14-3-3 proteins, and leads to the disassociation of the signaling complex (Di Bartolo et al., JEM 2007). Further supporting the role of HPK1 as a negative regulator of TCR signaling, murine HPK1 deficient T cells or HPK1 kinase inactive mutant T cells have enhanced ERK 1/2 activation and effector cytokine secretion upon TCR activation compared to their wild-type counterparts (Shui et al., Nat Immunol 2007; Hernandez et al., Cell Reports 2018).

Thus, HPK1 may be targeted for degradation, thereby providing therapeutic opportunities in enhancing anti-tumor immunity and increasing the response to checkpoint receptor blockade.

BRIEF SUMMARY

Provided herein are bifunctional compounds represented by Formula (I):

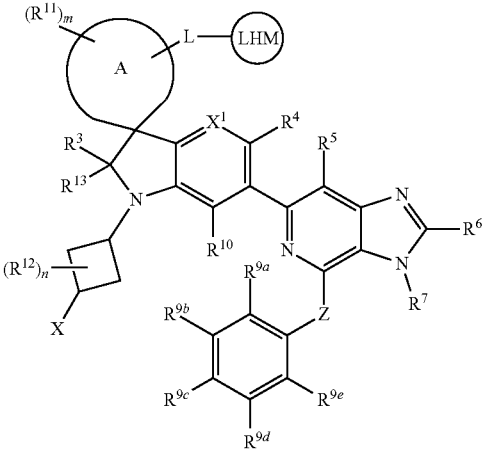

Formula (I)

or a pharmaceutically acceptable salt thereof,
wherein:
  m is 0, 1, 2, 3, or 4;
  n is 0, 1, 2, 3, 4, 5, or 6;
  A is a $C_{3-7}$ monocyclic cycloalkyl ring or a 4-6 membered monocyclic heterocyclyl ring having 1 or 2 heteroatoms independently selected from N, O, and S;
  L is a linker moiety having a length of 2-24 continuously covalently-bonded atoms selected from the group consisting of C, O, N and S;
  LHM is a ligase harness moiety;
  $R^{11}$ is
  i) selected from the group consisting of —OH, halogen, oxo, $C_{1-3}$ alkyl, and $C_{1-3}$ alkoxy; or
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iii) —S(O)$_2$C$_{1-6}$ alkyl,
  iv) —S(O)$_2$C$_{3-7}$ monocyclic cycloalkyl,
  v) $C_{1-6}$ alkyl optionally substituted with 1-3 groups independently selected from —CN, —OH, halogen, $C_{1-3}$ alkoxy, and $C_{3-7}$ monocyclic cycloalkyl, or
  vi) —C(O)$R^{21}$;
  each $R^{12}$ is independently selected from —OH, halogen, $C_{1-3}$ alkyl, and $C_{1-3}$ alkoxy;
  $R^{21}$ is
  i) H,
  ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
  iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
  iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy,
v) —NH$_2$,
vi) —NH($C_{1-6}$ alkyl), wherein the $C_{1-6}$ alkyl is optionally substituted with 1-3 groups independently selected from —CN, —OH, halogen, and $C_{1-3}$ alkoxy,
vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy,
viii) $C_{1-6}$ alkoxy optionally substituted with 1-3 groups independently selected from —OH, halogen, $C_{1-3}$ alkyl, and $C_{3-7}$ monocyclic cycloalkyl, or
ix) $C_{1-6}$ alkyl optionally substituted with 1-3 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —CN, —OH, halogen, $C_{1-3}$ alkyl, and $C_{1-3}$ alkoxy,
  f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
  g) —OC(O)$C_{1-6}$ alkyl optionally substituted with one —OH;
$R^3$ and $R^{13}$ are each H, or
$R^3$ and $R^{13}$ together form =O;
X is —NR$^{15}$R$^{16}$, wherein R$^{15}$ and R$^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —OH, halogen, $C_{1-3}$ alkyl, and $C_{1-3}$ alkoxy, and
  f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) —C(O)N(R$^{22}$)$_2$, wherein each R$^{22}$ is independently H or $C_{1-6}$ alkyl;
X$^1$ is N or CR$^{17}$;
R$^4$, R$^5$, R$^6$, R$^{10}$ and R$^{17}$ are each independently H, halogen, $C_{1-3}$ alkyl, or $C_{1-3}$ alkoxy;
R$^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;
Z is —O—, —C(R$^8$)$_2$—, or —NR$^8$—;
each R$^8$ is independently H or $C_{1-3}$ alkyl;
R$^{9a}$, R$^{9b}$, R$^{9c}$, R$^{9d}$, and R$^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —NH$_2$,
v) —NH($C_{1-6}$ alkyl), wherein the $C_{1-6}$ alkyl is optionally substituted with 1-3 groups independently selected from —OH, halogen, and $C_{1-3}$ alkoxy,
vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —S(O)$_2$$C_{1-6}$ alkyl,
ix) —S(O)$_2$N(R$^{23}$)$_2$, wherein each R$^{23}$ is independently H or $C_{1-6}$ alkyl,
x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  f) —NR$^{20}$C(O)OC$_{1-3}$ alkyl, wherein R$^{20}$ is H or $C_{1-3}$ alkyl,
xi) $C_{3-7}$ monocyclic cycloalkyl optionally substituted with 1-3 groups independently selected from —OH, halogen, $C_{1-3}$ alkyl, and $C_{1-3}$ alkoxy, xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy, xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, xiv) —COOH, xv) —C(O)N($R^{19}$)$_2$, or xvi) —$C_{1-3}$ alkylene-C(O)N($R^{19}$)$_2$, wherein one or more of $R^{9a}$, $R^{9b}$, $R^{9c}$, $R^{9d}$, and $R^{9e}$ is —C(O)N($R^{19}$)$_2$ or —$C_{1-3}$ alkylene-C(O)N($R^{19}$)$_2$; and each $R^{19}$ is independently i) H, ii) —S(O)$_2$C$_{1-6}$ alkyl, iii) $C_{1-6}$ alkyl optionally substituted with 1-6 groups independently selected from —CN, —OH, halogen, $C_{1-3}$ alkoxy, and $C_{3-7}$ monocyclic cycloalkyl, iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

In various embodiments, Z is NH, $X^1$ is CH, $R^6$ is H, and the compound of Formula (I) has a structure of Formula (Ia):

Formula (Ia)

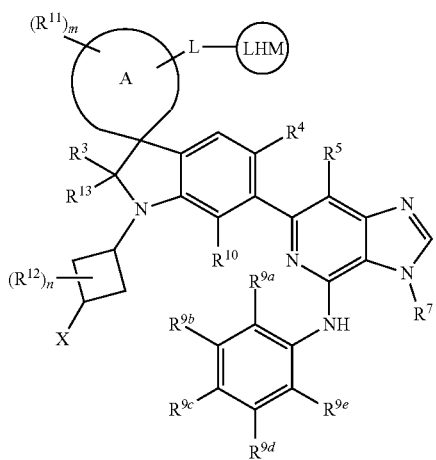

In more specific embodiments, the compound of Formula (I) has a structure of Formula (Ib):

Formula (Ib)

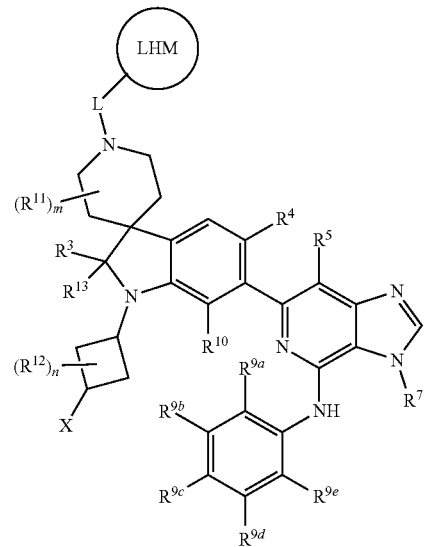

In various more specific embodiments, each $R^{9a}$, $R^{9b}$, $R^{9c}$, $R^{9d}$, and $R^{9e}$ is independently H, halogen, $C_{1-6}$ alkyl, or —C(O)N($R^{19}$)$_2$, wherein $R^{19}$ is $C_{1-6}$ alkyl; $R^4$, $R^5$ and $R^{10}$ are each H; and $R^7$ is $C_{1-6}$ alkyl.

In various more specific embodiments, $R^3$ and $R^{13}$ together form =O. or X is piperdinyl.

In more specific embodiments, the compound of Formula (I) has a structure of Formula (Ic):

Formula (Ic)

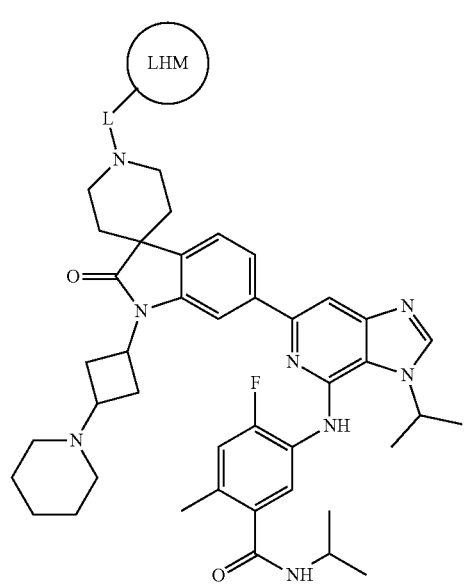

In various more specific embodiments, L is represented by:

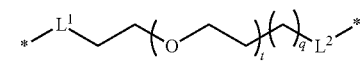

wherein, t is 0, 1, 2, 3, 4, 5, 6, or 7;

q is 0, 1, 2, 3, 4, 5, 6, or 7;

$L^1$ is a direct bond, —C(O)NH—, or —C(O)—; and $L^2$ is —C(O)NH—, —O—, or —NH—.

In more specific embodiments, t is 0, q is 3, 4, 5, 6, or 7.

In other more specific embodiments, q is 0, t is 1, 3, 5 or 7.

In various other more specific embodiments, L is represented by:

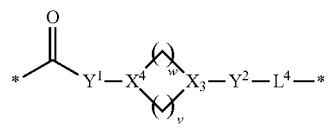

wherein, w is 1, 2, or 3;

v is 1 or 2;

p is 1, 2, 3, 4, or 5;

$Y^1$ is a direct bond, —(CH$_2$)$_p$—, or —O—;

$Y^2$ is a direct bond, —(CH$_2$)$_p$—, —C(O)—, or —C(O)—CH$_2$—;

$X^3$ and $X^4$ are independently N or C(R), wherein R is H or C$_{1-3}$alkyl;

$L^4$ is a direct bond, —NH—, —NHC(O)—, or $L^4$ is

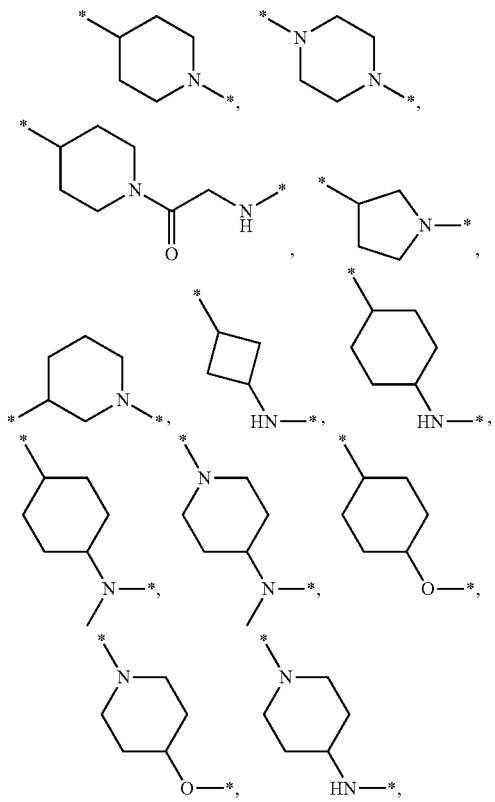

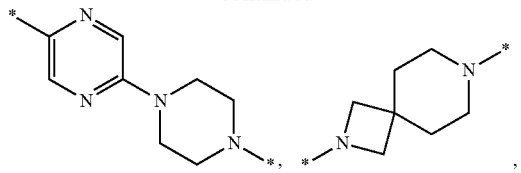

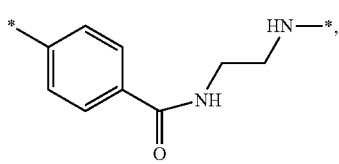

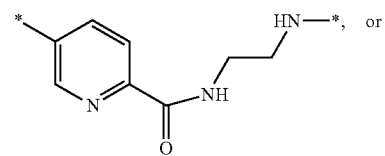

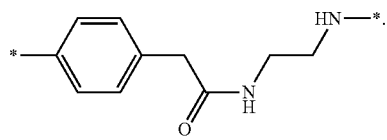

In other embodiments, L comprises a rigid ring system such as an aryl ring (e.g., phenyl), a heteroaryl ring, a bridged ring, a spiro ring, or a mixture thereof.

In various more specific embodiments, the LHM targets CRBN has a structure of Formula (Id)

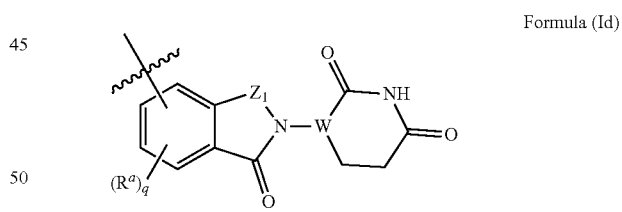

Formula (Id)

wherein,

W is —C(R$^g$)— or —N—;

$Z_1$ is —C(O)—, —C(S)—, —C(NR$^g$)—, —C(R$^g$)$_2$—, —C(R$^g$)$_2$—C(O)—, —C(O)—N(R$^g$)—, —CR$^g$=CR$^g$—, —C(R$^g$)=N—, —C(R$^g$)$_2$—C(S)—, or —C(R$^g$)$_2$—C(R$^g$)$_2$—;

q is 0, 1 or 2;

$R^g$ is hydrogen or C$_{1-6}$ alkyl; and $R^a$ is C$_{1-6}$alkyl, halo, halo C$_{1-6}$alkyl, —N(R$^g$)$_2$, CN, nitro, hydroxyl, or —O—C$_{1-4}$alkyl.

In other specific embodiments, LHM targets VHL and has a structure of Formula (Ie) or (If):

Formula (Ie)

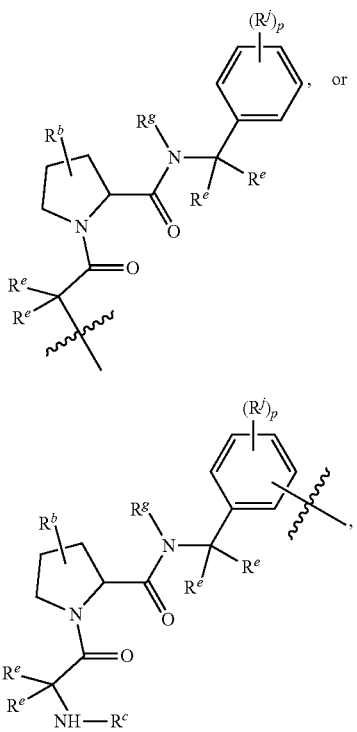

Formula (If)

wherein, p is 0 or 1;

$R^j$ is 5-6 member heteroaryl optionally substituted with 1 to 3 $R^k$, each $R^k$ is independently halo, oxo, —CN, —OH, $C_{1-6}$ alkyl, $C_{3-8}$ cycloalkyl, or —O—$C_{1-6}$ alkyl.

each $R^e$ is independently hydrogen, $C_{1-6}$ alkyl or $C_{3-8}$ cycloalkyl;

$R^b$ is hydrogen or hydroxyl;

$R^c$ is —C(O)$R^f$, wherein $R^f$ is $C_{1-6}$ alkyl or $C_{3-8}$ cycloalkyl, each being optionally substituted with halo or —CN.

In other embodiments, the present disclosure provides a compound having a structure of Formula (II):

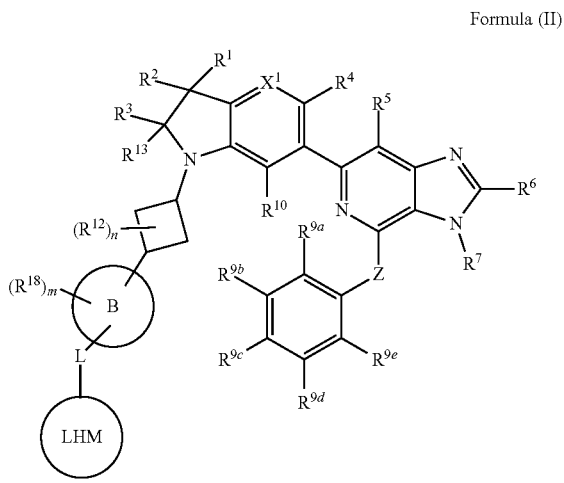

Formula (II)

or a pharmaceutically acceptable salt thereof, wherein:

m is 0, 1, 2, 3, 4 or 5;

n is 0, 1, 2, 3, 4, 5, or 6;

B is a 4-10 membered monocyclic, fused bicyclic, bridged bicyclic, or spirocyclic heterocyclyl ring having 1-3 heteroatoms independently selected from N, O, and S;

L is a linker moiety having a length of 2-24 continuously covalently-bonded atoms selected from the group consisting of C, O, N and S;

LHM is a ligase harness moiety;

one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or $R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or $R^1$ and $R^2$ together form =O;

$R^{11}$ is i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, ii) —S(O)$_2$$C_{1-6}$ alkyl, iii) —S(O)$_2$$C_{3-7}$ monocyclic cycloalkyl, iv) $C_{1-6}$ alkyl optionally substituted with 1-3 groups independently selected from —CN, —OH, halogen, $C_{1-3}$ alkoxy, and $C_{3-7}$ monocyclic cycloalkyl, or v) —C(O)$R^{21}$;

$R^{21}$ is i) H, ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy, v) —NH$_2$, vi) —NH($C_{1-6}$ alkyl), wherein the $C_{1-6}$ alkyl is optionally substituted with 1-3 groups independently selected from —CN, —OH, halogen, and $C_{1-3}$ alkoxy, vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy, viii) $C_{1-6}$ alkoxy optionally substituted with 1-3 groups independently selected from —OH, halogen, $C_{1-3}$ alkyl, and $C_{3-7}$ monocyclic cycloalkyl, or ix) $C_{1-6}$ alkyl optionally substituted with 1-3 groups independently selected from
   a) —CN,
   b) —OH,
   c) halogen,
   d) $C_{1-3}$ alkoxy,
   e) $C_{3-7}$ monocyclic cycloalkyl optionally substituted with 1-3 groups independently selected from —CN, —OH, halogen, $C_{1-3}$ alkyl, and $C_{1-3}$ alkoxy,
   f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
   g) —OC(O)$C_{1-6}$ alkyl optionally substituted with one —OH;

$R^3$ and $R^{13}$ are each H, or
$R^3$ and $R^{13}$ together form =O;
each $R^{12}$ is independently selected from —OH, halogen, $C_{1-3}$ alkyl, and $C_{1-3}$ alkoxy; each $R^{18}$ is independently
   i) —CN,
   ii) a halogen,
   iii) —OH,
   iv) $C_{1-6}$ alkoxy optionally substituted with 1-3 groups independently selected from —OH, halogen, $C_{1-3}$ alkoxy, and $C_{3-7}$ monocyclic cycloalkyl,
   v) $C_{1-6}$ alkyl optionally substituted with 1-3 groups independently selected from —OH, halogen, $C_{1-3}$ alkoxy, and $C_{3-7}$ monocyclic cycloalkyl,
   vi) —COOH, or
   vii) —C(O)N($R^{22}$)$_2$, wherein each $R^{22}$ is independently H or $C_{1-6}$ alkyl;
$X^1$ is N or $CR^{17}$;
$R^4$, $R^5$, $R^6$, $R^{10}$ and $R^{17}$ are each independently H, halogen, $C_{1-3}$ alkyl, or $C_{1-3}$ alkoxy;
$R^7$ is
   i) H,
   ii) $C_{1-6}$ alkyl optionally substituted with 1-3 groups independently selected from —OH, halogen, $C_{1-3}$ alkoxy, and $C_{3-7}$ monocyclic cycloalkyl, or
   iii) $C_{3-7}$ monocyclic cycloalkyl optionally substituted with 1-3 groups independently selected from —OH, halogen, $C_{1-3}$ alkyl, and $C_{1-3}$ alkoxy;
Z is —O—, —C($R^8$)$_2$—, or —$NR^8$—;
each $R^8$ is independently H or $C_{1-3}$ alkyl;
$R^{9a}$, $R^{9b}$, $R^{9c}$, $R^{9d}$, and $R^{9e}$ are independently
   i) H,
   ii) halogen,
   iii) $C_{1-6}$ alkoxy optionally substituted with 1-3 groups independently selected from —OH, halogen, $C_{1-3}$ alkyl, and $C_{3-7}$ monocyclic cycloalkyl,
   iv) —NH$_2$,
   v) —NH($C_{1-6}$ alkyl), wherein the $C_{1-6}$ alkyl is optionally substituted with 1-3 groups independently selected from —OH, halogen, and $C_{1-3}$ alkoxy,
   vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
   vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
   viii) —S(O)$_2 C_{1-6}$ alkyl,
   ix) —S(O)$_2$N($R^{23}$)$_2$, wherein each $R^{23}$ is independently H or $C_{1-6}$ alkyl,
   x) $C_{1-6}$ alkyl optionally substituted with 1-3 groups independently selected from
      a) —OH,
      b) halogen,
      c) $C_{1-3}$ alkoxy,
      d) $C_{3-7}$ monocyclic cycloalkyl,
      e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
      f) —$NR^{20}$C(O)O$C_{1-3}$ alkyl, wherein $R^{20}$ is H or $C_{1-3}$ alkyl,
   xi) $C_{3-7}$ monocyclic cycloalkyl optionally substituted with 1-3 groups independently selected from —OH, halogen, $C_{1-3}$ alkyl, and $C_{1-3}$ alkoxy,
   xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
   xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
   xiv) —COOH,
   xv) —C(O)N($R^{19}$)$_2$, or
   xvi) —$C_{1-3}$ alkylene-C(O)N($R^{19}$)$_2$,
wherein one or more of $R^{9a}$, $R^{9b}$, $R^{9c}$, $R^{9d}$, and $R^{9e}$ is —C(O)N($R^{19}$)$_2$ or —$C_{1-3}$ alkylene-C(O)N($R^{19}$)$_2$; and
each $R^{19}$ is independently
   i) H,
   ii) —S(O)$_2 C_{1-6}$ alkyl,
   iii) $C_{1-6}$ alkyl optionally substituted with 1-6 groups independently selected from —CN, —OH, halogen, $C_{1-3}$ alkoxy, and $C_{3-7}$ monocyclic cycloalkyl,
   iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or
   v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

In more specific embodiments, Z is NH, $X^1$ is CH, $R^6$ is H, and the compound of Formula (II) has a structure of Formula (IIa):

Formula (IIa)

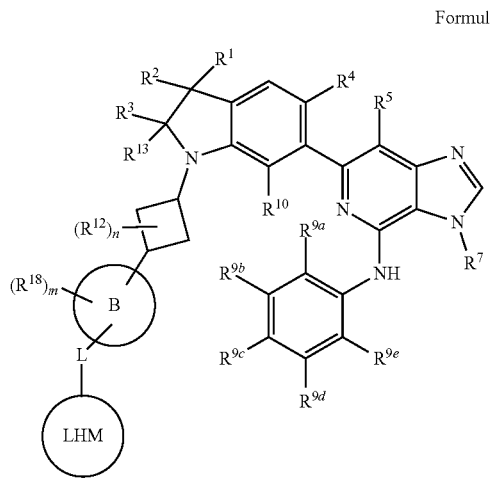

In more specific embodiments, the compound of Formula (II) has a structure of Formula (IIb):

Formula (IIb)

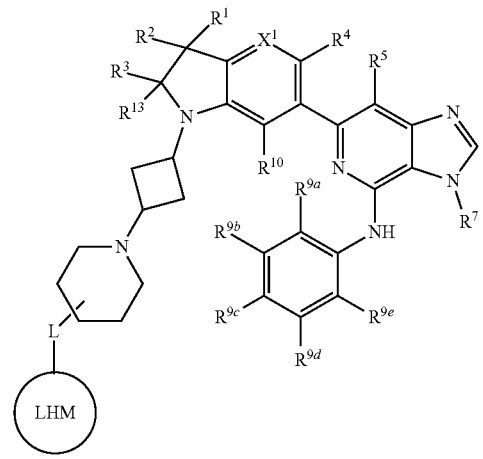

In further embodiments, each $R^{9a}$, $R^{9b}$, $R^{9c}$, $R^{9d}$, and $R^{9e}$ is independently H, halogen, $C_{1-6}$ alkyl, or —C(O)N($R^{19}$)$_2$; wherein $R^{19}$ is $C_{1-6}$ alkyl; $R^4$, $R^5$ and $R^{10}$ are each H; and $R^7$ is $C_{1-6}$ alkyl.

In further more specific embodiments, $R^3$ and $R^{13}$ together form =O; and $R^1$ and $R^2$ together with the carbon to which they are attached form a 4-6 membered monocyclic heterocyclyl having 1 or 2 heteroatoms independently selected from N, O, and S, and wherein the 4-6 membered monocyclic heterocyclyl is optionally substituted with one $R^{11}$.

In a preferred embodiment, the compound of Formula (II) has a structure of Formula (IIc):

Formula (IIc)

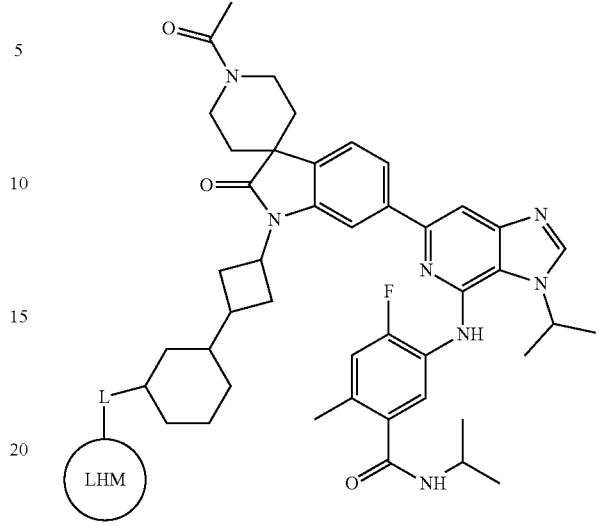

In further embodiments, L has the following structure:

$$*-L^1-\left(\phantom{x}\right)\left(O\phantom{x}\right)_t\left(\phantom{x}\right)_q L^2-*$$

wherein, t is 0, 1, 2, 3, 4, 5, 6, or 7; q is 0, 1, 2, 3, 4, 5, 6, or 7; $L^1$ is —C(O)NH—; and $L^2$ is —O—, or —NH—. In more specific embodiments, t is 0 and q is 3, 5, or 7.

In more specific embodiments, the LHM targets VHL and has a structure of Formula (If):

Formula (If)

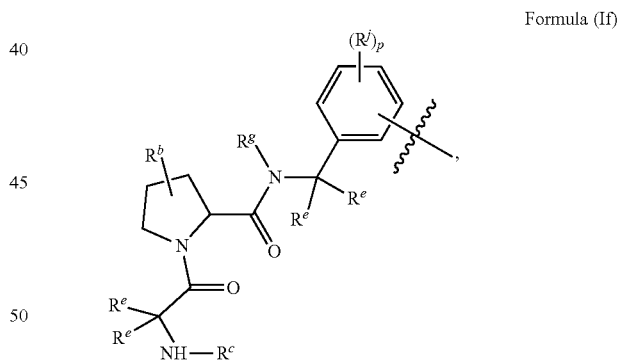

wherein,
p is 0 or 1;
$R^j$ is 5-6 member heteroaryl optionally substituted with 1 to 3 $R^k$,
each $R^k$ is independently halo, oxo, —CN, —OH, $C_{1-6}$ alkyl, $C_{3-8}$ cycloalkyl, or —O—$C_{1-6}$ alkyl.
each $R^e$ is independently hydrogen, $C_{1-6}$ alkyl or $C_{3-8}$ cycloalkyl;
$R^b$ is hydrogen or hydroxyl;
$R^c$ is —C(O)$R^f$, wherein $R^f$ is $C_{1-6}$ alkyl or $C_{3-8}$ cycloalkyl, each being optionally substituted with halo or —CN.

In other embodiments, the LHM targets CRBN and has a structure of Formula (Id):

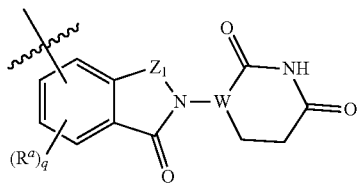

Formula (Id)

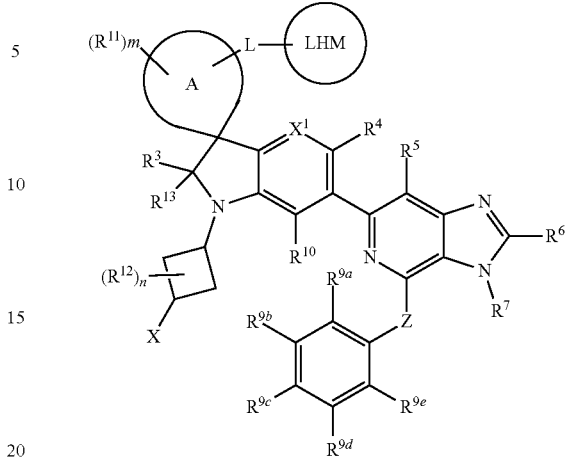

Formula (I)

wherein,

W is —C(R$^g$)— or —N—;

Z$_1$ is —C(O)—, —C(S)—, —C(NR$^g$)—, —C(R$^g$)$_2$—, —C(R$^g$)$_2$—C(O)—, —C(O)—N(R$^g$)—, —CR$^g$=CR$^g$—, —C(R$^g$)=N—, —C(R$^g$)$_2$—C(S)—, or —C(R$^g$)$_2$—C(R$^g$)$_2$—;

q is 0, 1 or 2;

R$^g$ is hydrogen or C$_{1-6}$ alkyl; and

R$^a$ is C$_{1-6}$alkyl, halo, halo C$_{1-6}$alkyl, —N(R$^g$)$_2$, CN, nitro, hydroxyl, or —O—C$_{1-4}$alkyl.

Also provided herein is a pharmaceutical composition comprising a compound of Formula (I) or Formula (II), or any one of the substructures or specific compounds of Examples 1-97, or a pharmaceutically acceptable salt thereof, and a pharmaceutically acceptable excipient or carrier.

Further embodiments provide methods for treating a disease or disorder associated with increased hematopoietic progenitor kinase 1 (HPK1) activity, for increasing T-cell activation, for treating cancer, for inhibiting the growth or proliferation of cancer cells, for treating or preventing a hepatitis B virus (HBV) infection, or for treating or preventing a human immunodeficiency virus (HIV) infection, the method comprising administering to a subject in need thereof a therapeutically effective amount of a compound of Formula (I) or Formula (II), any one of the substructures or compounds of Examples 1-97.

DETAILED DESCRIPTION

Specific degradation of HPK1 could be accomplished by using heterobifunctional small molecules to recruit HPK1 to a ubiquitin ligase and thus promoting ubiquitylation and proteasomal degradation of HPK1. Thus, provided herein are bifunctional compounds, each comprising an HPK1 binder, which is covalently conjugated via a linker to a ligase harness moiety (LHM) for targeting ubiquitin ligase. Preferably, the LHM targets cereblon (CRBN) or von Hippel-Lindau (VHL) proteins, which are substrate recognition subunits of two ubiquitously expressed and biologically important Cullin RING E3 ubiquitin ligase complexes. See, e.g., WO 2019/099926, WO 2020/023851, and U.S. Published Application No. 2019/0192668.

One embodiment provides a bifunctional compound of Formula (I):

or a pharmaceutically acceptable salt, isotopic form, isolated stereoisomer, or a mixture of stereoisomers thereof, wherein, wherein:

m is 0, 1, 2, 3, or 4;

n is 0, 1, 2, 3, 4, 5, or 6;

A is a C$_{3-7}$ monocyclic cycloalkyl ring or a 4-6 membered monocyclic heterocyclyl ring having 1 or 2 heteroatoms independently selected from N, O, and S;

L is a linker moiety having a length of 2-24 continuously covalently-bonded atoms selected from the group consisting of C, O, N and S;

LHM is a ligase harness moiety;

R$^{11}$ is
  i) selected from the group consisting of —OH, halogen, oxo, C$_{1-3}$ alkyl, and C$_{1-3}$ alkoxy; or
  ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy,
  iii) —S(O)$_2$C$_{1-6}$ alkyl,
  iv) —S(O)$_2$C$_{3-7}$ monocyclic cycloalkyl,
  v) C$_{1-6}$ alkyl optionally substituted with 1-3 groups independently selected from —CN, —OH, halogen, C$_{1-3}$ alkoxy, and C$_{3-7}$ monocyclic cycloalkyl, or
  vi) —C(O)R$^{21}$;

each R$^{12}$ is independently selected from —OH, halogen, C$_{1-3}$ alkyl, and C$_{1-3}$ alkoxy;

R$^{21}$ is
  i) H,
  ii) C$_{3-7}$ monocyclic or bridged bicyclic cycloalkyl optionally substituted with 1-3 groups independently selected from —CN, —OH, halogen, C$_{1-3}$ alkyl, and C$_{1-3}$ alkoxy, wherein the C$_{1-3}$ alkyl is optionally substituted with 1-3 groups independently selected from —OH, halogen, and C$_{1-3}$ alkoxy,
  iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy,
  iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy, v) —$NH_2$, vi) —NH($C_{1-6}$ alkyl), wherein the $C_{1-6}$ alkyl is optionally substituted with 1-3 groups independently selected from —CN, —OH, halogen, and $C_{1-3}$ alkoxy, vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy, viii) $C_{1-6}$ alkoxy optionally substituted with 1-3 groups independently selected from —OH, halogen, $C_{1-3}$ alkyl, and $C_{3-7}$ monocyclic cycloalkyl, or ix) $C_{1-6}$ alkyl optionally substituted with 1-3 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —CN, —OH, halogen, $C_{1-3}$ alkyl, and $C_{1-3}$ alkoxy,
  f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
  g) —OC(O)$C_{1-6}$ alkyl optionally substituted with one —OH;

$R^3$ and $R^{13}$ are each H, or $R^3$ and $R^{13}$ together form =O;

X is —$NR^{15}R^{16}$, wherein $R^{15}$ and $R^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —OH, halogen, $C_{1-3}$ alkyl, and $C_{1-3}$ alkoxy, and
  f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 $R^{18}$;

each $R^{18}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) —C(O)N($R^{22}$)$_2$, wherein each $R^{22}$ is independently H or $C_{1-6}$ alkyl;

$X^1$ is N or $CR^{17}$;

$R^4$, $R^5$, $R^6$, $R^{10}$ and $R^{17}$ are each independently H, halogen, $C_{1-3}$ alkyl, or $C_{1-3}$ alkoxy;

$R^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;

Z is —O—, —C($R^8$)$_2$—, or —$NR^8$—;

each $R^8$ is independently H or $C_{1-3}$ alkyl;

$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —$NH_2$,
v) —NH($C_{1-6}$ alkyl), wherein the $C_{1-6}$ alkyl is optionally substituted with 1-3 groups independently selected from —OH, halogen, and $C_{1-3}$ alkoxy,
vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —S(O)$_2$$C_{1-6}$ alkyl,
ix) —S(O)$_2$N($R^{23}$)$_2$, wherein each $R^{23}$ is independently H or $C_{1-6}$ alkyl,
x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  f) —$NR^{20}$C(O)O$C_{1-3}$ alkyl, wherein $R^{20}$ is H or $C_{1-3}$ alkyl,
xi) $C_{3-7}$ monocyclic cycloalkyl optionally substituted with 1-3 groups independently selected from —OH, halogen, $C_{1-3}$ alkyl, and $C_{1-3}$ alkoxy, xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy, xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy, xiv) —COOH, xv) —C(O)N($R^{19}$)$_2$, or xvi) —$C_{1-3}$ alkylene-C(O)N($R^{19}$)$_2$, provided one or more of $R^{9a}$, $R^{9b}$, $R^{9c}$, $R^{9d}$, and $R^{9e}$ is —C(O)N($R^{19}$)$_2$ or —$C_{1-3}$ alkylene-C(O)N($R^{19}$)$_2$; and each $R^{19}$ is independently i) H, ii) —S(O)$_2$$C_{1-6}$ alkyl, iii) $C_{1-6}$ alkyl optionally substituted with 1-6 groups independently selected from —CN, —OH, halogen, $C_{1-3}$ alkoxy, and $C_{3-7}$ monocyclic cycloalkyl, iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

An alternative embodiment provides a compound of Formula (II):

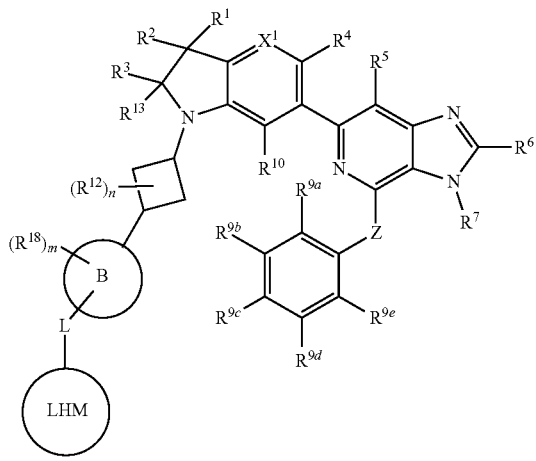

Formula (II)

or a pharmaceutically acceptable salt, isotopic form, isolated stereoisomer, or a mixture of stereoisomers thereof, wherein:

m is 0, 1, 2, 3, 4 or 5;

n is 0, 1, 2, 3, 4, 5, or 6;

B is a 4-10 membered monocyclic, fused bicyclic, bridged bicyclic, or spirocyclic heterocyclyl ring having 1-3 heteroatoms independently selected from N, O, and S;

L is a linker moiety having a length of 2-24 continuously covalently-bonded atoms selected from the group consisting of C, O, N and S;

LHM is a ligase harness moiety;

one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or $R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or $R^1$ and $R^2$ together form =O;

$R^{11}$ is i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, ii) —S(O)$_2$$C_{1-6}$ alkyl, iii) —S(O)$_2$$C_{3-7}$ monocyclic cycloalkyl, iv) $C_{1-6}$ alkyl optionally substituted with 1-3 groups independently selected from —CN, —OH, halogen, $C_{1-3}$ alkoxy, and $C_{3-7}$ monocyclic cycloalkyl, or v) —C(O)$R^{21}$ $R^{21}$ is i) H, ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy, iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy, v) —NH$_2$, vi) —NH($C_{1-6}$ alkyl), wherein the $C_{1-6}$ alkyl is optionally substituted with 1-3 groups independently selected from —CN, —OH, halogen, and $C_{1-3}$ alkoxy, vii) —N($C_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy, viii) $C_{1-6}$ alkoxy optionally substituted with 1-3 groups independently selected from —OH, halogen, $C_{1-3}$ alkyl, and $C_{3-7}$ monocyclic cycloalkyl, or ix) $C_{1-6}$ alkyl optionally substituted with 1-3 groups independently selected from a) —CN, b) —OH, c) halogen, d) $C_{1-3}$ alkoxy,
e) $C_{3-7}$ monocyclic cycloalkyl optionally substituted with 1-3 groups independently selected from —CN, —OH, halogen, $C_{1-3}$ alkyl, and $C_{1-3}$ alkoxy,
f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
g) —OC(O)$C_{1-6}$ alkyl optionally substituted with one —OH;

$R^3$ and $R^{13}$ are each H, or
$R^3$ and $R^{13}$ together form =O;
each $R^{12}$ is independently selected from —OH, halogen, $C_{1-3}$ alkyl, and $C_{1-3}$ alkoxy;
each $R^{18}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) —C(O)N($R^{22}$)$_2$, wherein each $R^{22}$ is independently H or $C_{1-6}$ alkyl;

$X^1$ is N or $CR^{17}$;
$R^4$, $R^5$, $R^6$, $R^{10}$ and $R^{17}$ are each independently H, halogen, $C_{1-3}$ alkyl, or $C_{1-3}$ alkoxy;
$R^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;
Z is —O—, —C(R')$_2$—, or —NR$^8$—;
each $R^8$ is independently H or $C_{1-3}$ alkyl;
$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —NH$_2$,
v) —NH($C_{1-6}$ alkyl), wherein the $C_{1-6}$ alkyl is optionally substituted with 1-3 groups independently selected from —OH, halogen, and $C_{1-3}$ alkoxy,
vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —S(O)$_2C_{1-6}$ alkyl,
ix) —S(O)$_2$N($R^{23}$)$_2$, wherein each $R^{23}$ is independently H or $C_{1-6}$ alkyl,
x) $C_{1-6}$ alkyl optionally substituted with 1-3 groups independently selected from
a) —OH,
b) halogen,
c) $C_{1-3}$ alkoxy,
d) $C_{3-7}$ monocyclic cycloalkyl,
e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
f) —NR$^{20}$C(O)O$C_{1-3}$ alkyl, wherein $R^{20}$ is H or $C_{1-3}$ alkyl,
xi) $C_{3-7}$ monocyclic cycloalkyl optionally substituted with 1-3 groups independently selected from —OH, halogen, $C_{1-3}$ alkyl, and $C_{1-3}$ alkoxy,
xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
xiv) —COOH,
xv) —C(O)N($R^{19}$)$_2$, or
xvi) —$C_{1-3}$ alkylene-C(O)N($R^{19}$)$_2$,
wherein one or more of $R^{9a}$, $R^{9b}$, $R^{9c}$, $R^{9d}$, and $R^{9e}$ is —C(O)N($R^{19}$)$_2$ or —$C_{1-3}$ alkylene-C(O)N($R^{19}$)$_2$; and
each $R^{19}$ is independently
i) H,
ii) —S(O)$_2C_{1-6}$ alkyl,
iii) $C_{1-6}$ alkyl optionally substituted with 1-6 groups independently selected from —CN, —OH, halogen, $C_{1-3}$ alkoxy, and $C_{3-7}$ monocyclic cycloalkyl,
iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or
v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

HPK1 Binders

The HPK1 Binders of the bifunctional compounds of Formula (I) or (II) generally have a 6-azabenzimidazole core that is further derivatized to include a cyclobutyl substituted indoline or 4-azaindoline moiety, as well as a benzamide moiety. The HPK1 Binders provide various sites for coupling to an LHM via a linker (i.e., the Linker-LHM portion). More specifically, in bifunctional compounds of Formula (I), the HPK1 Binder moiety is coupled to the Linker-LHM portion through the A ring, as shown in a structure represented by Formula (A) (the wavy line indicates the coupling site to the Linker-LHM portion):

Formula (A)

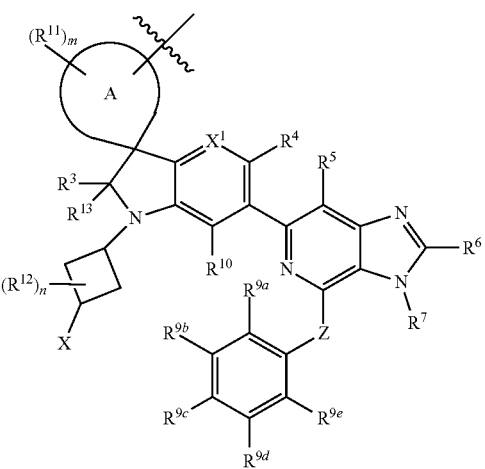

wherein, $R^3$, $R^4$, $R^5$, $R^6$, $R^7$, $R^{9a}$, $R^{9b}$, $R^{9c}$, $R^{9d}$, $R^{9e}$; $R^{10}$; $R^{11}$, $R^{12}$ and $R^{13}$, $X^1$, Z, m and n are defined above.

In more specific embodiments, Z is NH, $X^1$ is CH, $R^6$ is H, and the HPK1 Binder moiety compound has a structure of Formula (Aa):

Formula (Aa)

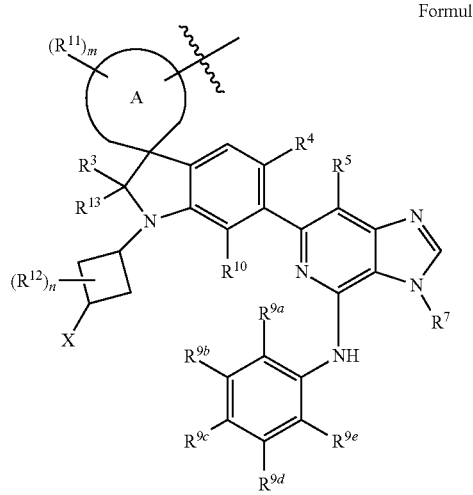

In preferred embodiments, the Ring A is piperidinyl and the HPK1 Binder moiety has the following structure:

Formula (Ab)

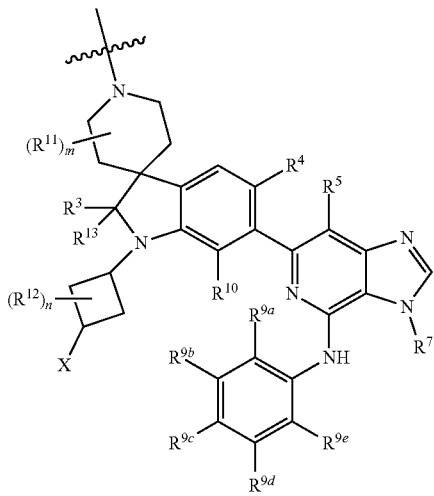

In various embodiments, each $R^{9a}$, $R^{9b}$, $R^{9c}$, $R^{9d}$, and $R^{9e}$ is independently H, halogen, $C_{1-6}$ alkyl, or $—C(O)N(R^{19})_2$, wherein $R^{19}$ is $C_{1-6}$ alkyl; $R^4$, $R^5$ and $R^{10}$ are each H; and $R^7$ is $C_{1-6}$ alkyl.

In other embodiments, $R^3$ and $R^{13}$ together form =O.

In other embodiments, X is piperidinyl.

In yet other embodiments, n is 0 and p is 0.

In preferred embodiments, the HPK1 Binder moiety has a structure of Formula (Ac):

Formula (Ac)

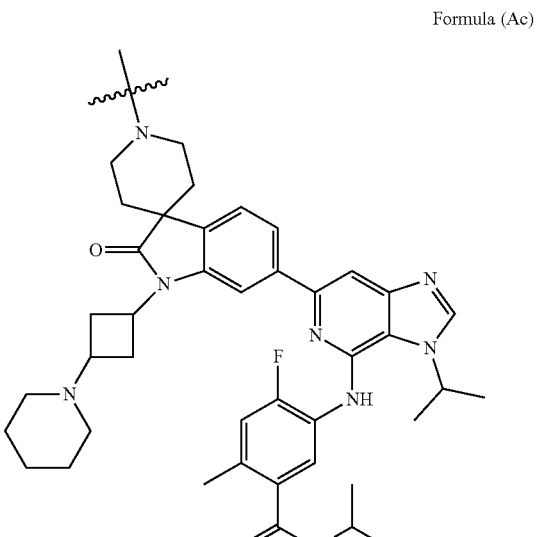

In more specific embodiments, a compound of Formula (Ac) may have one of the following diastereomeric structures:

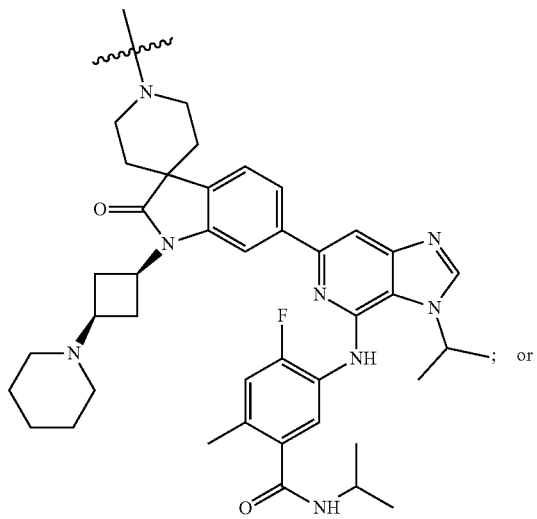

; or

-continued

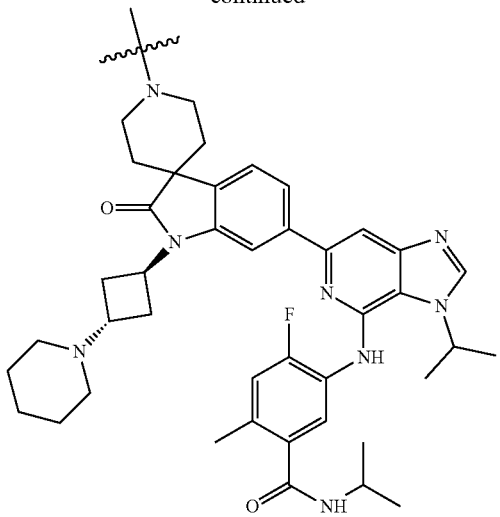

Alternatively, for bifunctional compounds of Formula (II), the HPK1 Binder moiety is coupled to the linker-LHM portion through the B ring, as shown in a structure represented by Formula (B) (the wavy line indicates the coupling site to the linker-LHM portion):

Formula (B)

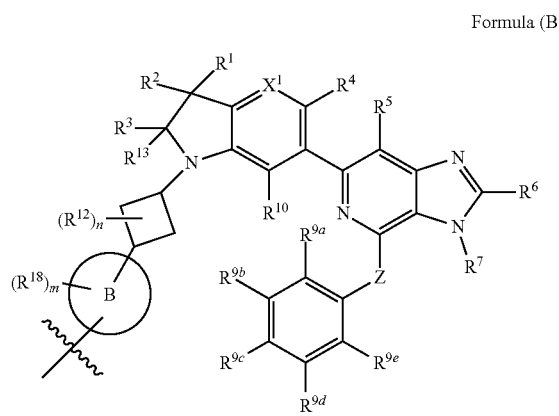

wherein, $R^1$, $R^2$, $R^3$, $R^4$, $R^5$, $R^6$, $R^7$, $R^{9a}$, $R^{9b}$, $R^{9c}$, $R^{9d}$, $R^{9e}$; $R^{10}$; $R^{12}$, $R^{13}$, $R^{18}$, $X^1$, Z, m and n are defined above.

In preferred embodiments, Z is NH, $X^1$ is CH, $R^6$ is H, and the HPK1 Binder moiety has a structure of Formula (Ba):

Formula (Ba)

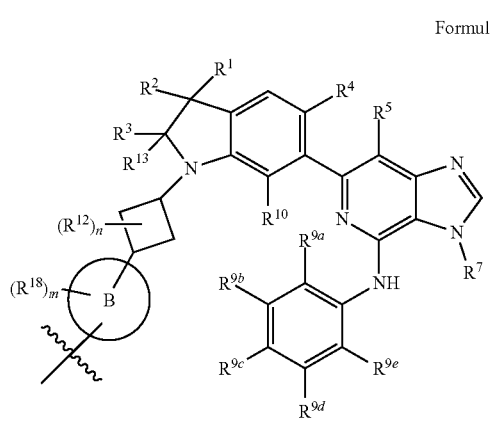

In preferred embodiments, the B ring is piperidinyl and the HPK1 Binder moiety has a structure of Formula (Bb):

Formula (Bb)

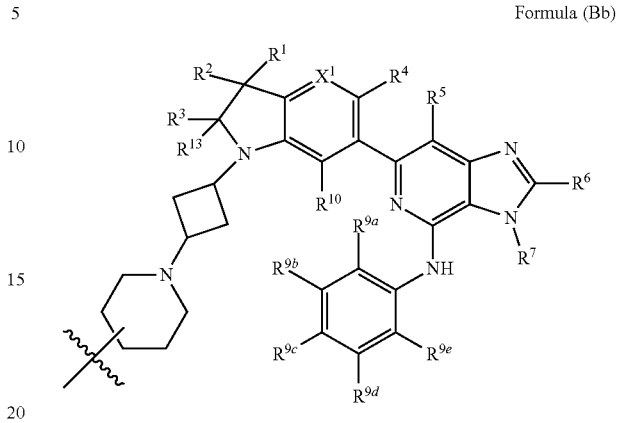

In various further embodiments, each $R^{9a}$, $R^{9b}$, $R^{9c}$, $R^{9d}$, and $R^{9e}$ is independently H, halogen, $C_{1-6}$ alkyl, or —C(O)N(R^{19})_2$, wherein $R^{19}$ is $C_{1-6}$ alkyl; $R^4$, $R^5$ and $R^{10}$ are each H; and $R^7$ is $C_{1-6}$ alkyl.

In various further embodiments, $R^3$ and $R^{13}$ together form =O; and $R^1$ and $R^2$ together with the carbon to which they are attached form a 4-6 membered monocyclic heterocyclyl having 1 or 2 heteroatoms independently selected from N, O, and S, and wherein the 4-6 membered monocyclic heterocyclyl is optionally substituted with one $R^{11}$. $R^{11}$ is as defined herein.

In preferred embodiments, the HPK1 Binder moiety has a structure of Formula (Bc):

Formula (Bc)

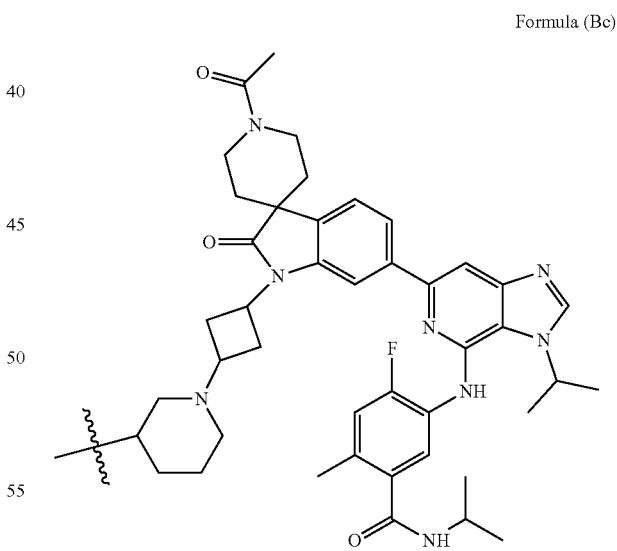

Ligase Harness Moieties (LHM)

The LHMs of compounds of Formula (I) or Formula (II) target VHL or CRBN of E3 ligases, which are harnessed by the bifunctional compounds to induce ubiquitination and subsequent proteasomal degradation of HPK1.

Thalidomide derivatives, such as lenalidomide or pomalidomide, can be used to recruit potential substrates to CRBN, a component of a ubiquitin ligase complex.

One embodiment provides a CRBN-targeting LHM having the following structure (the wavy line shows the bond attached to the remainder of the compound of Formula (I)):

Formula (Id)

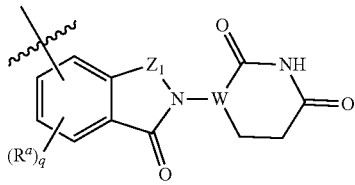

wherein,

W is —C(R$^g$)— or —N—;

Z$_1$ is —C(O)—, —C(S)—, —C(NR$^g$)—, —C(R$^g$)$_2$—, —C(R$^g$)$_2$—C(O)—, —C(O)—N(R$^g$)—, —CR$^g$=CR$^g$—, —C(R$^g$)=N—, —C(R$^g$)$_2$—C(S)—, or —C(R$^g$)$_2$—C(R$^g$)$_2$—;

q is 0, 1 or 2;

R$^g$ is hydrogen or C$_{1-6}$ alkyl; and

R$^a$ is C$_{1-6}$alkyl, halo, halo C$_{1-6}$alkyl, —N(R$^g$)$_2$, CN, nitro, hydroxyl, or —O—C$_{1-4}$alkyl.

In more specific embodiments, the LHM has one of the following structures:

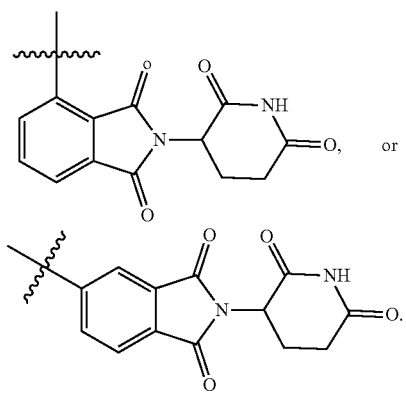

In other embodiments, the LHM targets VHL and has a structure of Formula (Ie) or (If):

Formula (Ie)

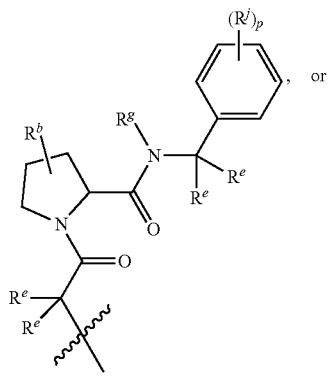

Formula (If)

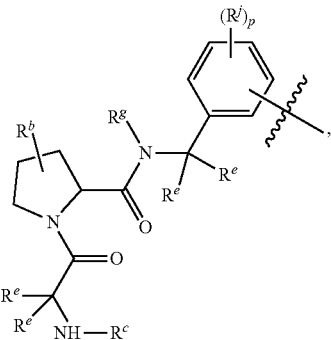

wherein, p is 0 or 1;

R$^j$ is 5-6 member heteroaryl optionally substituted with 1 to 3 R$^k$, each R$^k$ is independently halo, oxo, —CN, —OH, C$_{1-6}$ alkyl, C$_{3-8}$ cycloalkyl, or —O—C$_{1-6}$ alkyl.

each R$^e$ is independently hydrogen, C$_{1-6}$ alkyl or C$_{3-8}$ cycloalkyl;

R$^b$ is hydrogen or hydroxyl;

R$^c$ is —C(O)R$^f$, wherein R$^f$ is C$_{1-6}$ alkyl or C$_{3-8}$ cycloalkyl, each being optionally substituted with halo or —CN.

In more specific embodiments, the LHM has one of the following structures:

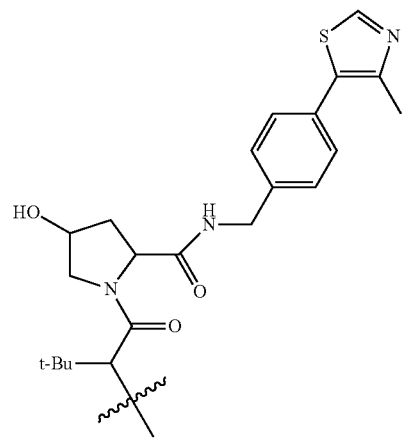

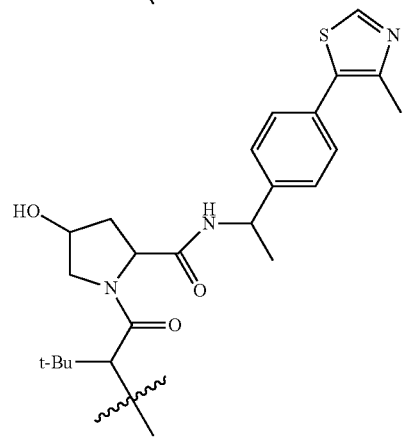

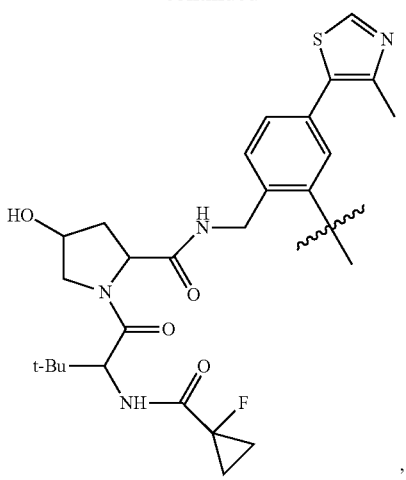

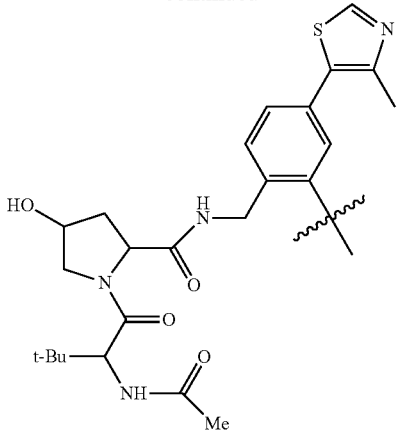

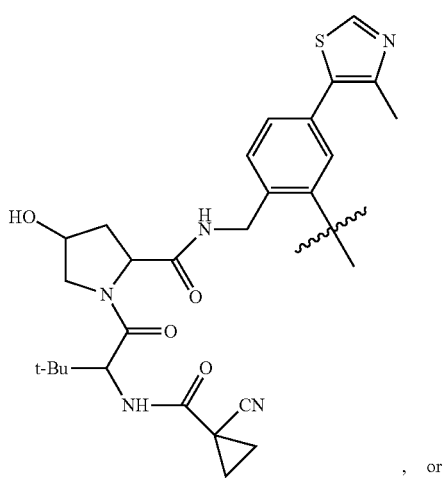

, or

Linker

Each bifunctional compound of Formula (I) or Formula (II) comprises a linker, which is a bivalent moiety that couples the HPK1 Binder moiety to the LHM. The structure (e.g., length or rigidity) of the linker moiety may impact the efficiency or selectivity of the degradation process. Typically, the linker moiety comprises multiple segments, which contribute to the overall length and rigidity of the linker, in addition to providing the respective attachment points to the HPK1 Binder moiety and the LHM.

As used herein, a linker moiety typically has a length of 2-24 continuously covalently-bonded atoms selected from the group consisting of C, O, N and S. In particular, the Linker moiety comprises a continuous sequence of covalent bonds between the respective attachment points to the HPK1 Binder moiety and the LHM, inclusive of the bond indicated by a wavy line of Formulae (A), (B), (Id), (Ie) and (If), and their respective substructures.

In some embodiments, the Linker moiety has the following chain-like structure:

$$*-L^1-\!\!\left(\!\!-\!\!O\!\!-\!\!\right)_{\!t}\!\!\left(\!\!-\!\!\right)_{\!q}\!\!L^2-\!*$$

wherein, t is 0, 1, 2, 3, 4, 5, 6, or 7;
q is 0, 1, 2, 3, 4, 5, 6, or 7;
$L^1$ is a direct bond, —C(O)NH—, or —C(O)—; and
$L^2$ is —C(O)NH—, —O—, or —NH—.

In more specific embodiments, t is 0, q is 3, 4, 5, 6, or 7.
In other more specific embodiments, q is 0, t is 1, 3, 5 or 7.

In further more specific embodiments, the Linker has one of the following structures:

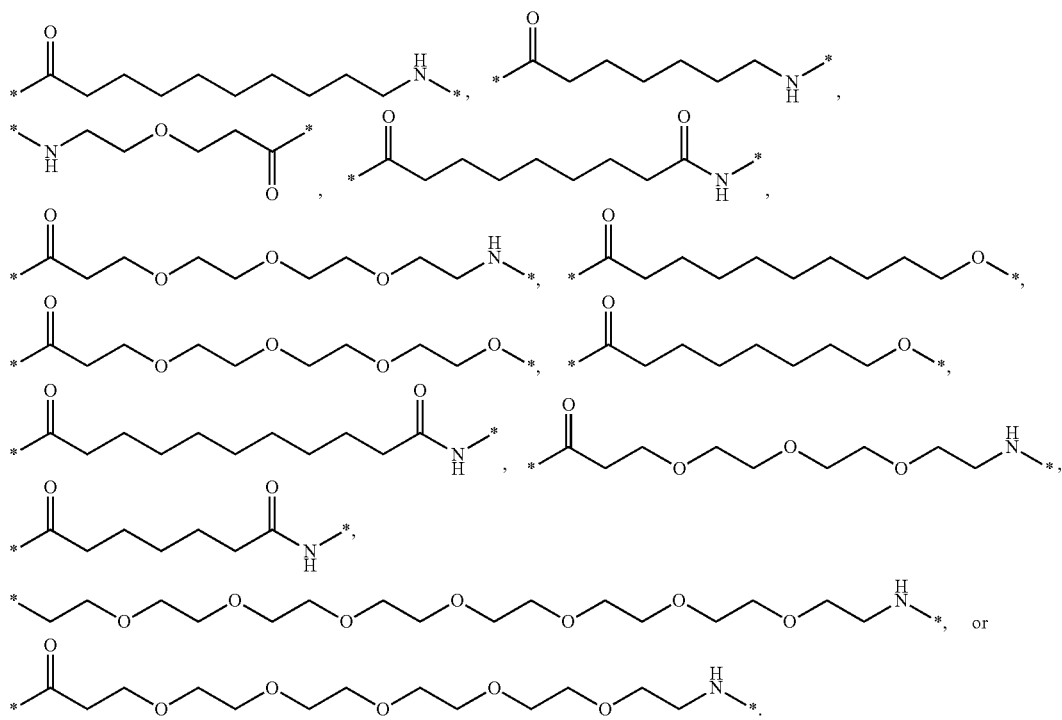

As used herein, * of a bivalent moiety typically indicates the respective attachment points to the remainder of the compounds, e.g., HPK1 Binder moiety and the LHM; or other linker segments. * and a wavy line are understood to be interchangeable.

The length of the linker can be determined by the total number of atoms that form the continuously connecting bonds. Using the above Linker moiety as an example, the total number of the atoms counts from the atom that directly attaches to the HPK1 Binder moiety (e.g., C atom of $L^1$), and the atoms (e.g., C, N or O) forming the continuous covalent bonds, to the atom (e.g., C, O or N of $L^2$) that directly attaches to the Linker moiety. Atoms that do not participate in the continuous covalent bonding (e.g., H or O when connected by a double bond) are excluded from the counting of the total number of atom. For a Linker moiety that contains one or more ring structures, the total number of the atoms counts only along a single linearly connected sequence of atoms, rather than going around a ring. For instance, a bivalent 1,6-cyclohexyl ring moiety counts as 4 atoms instead of 6.

It is to be understood that, unless otherwise specified and provided that the valence is satisfied, the bivalent moieties described herein (e.g., $L^1$ or $L^2$) are not limited to the direction in which they are expressed. For instance, for a given $L^1$, e.g., —C(O)—NH—, the manner in which it is connected to the remainder of the molecule may be either direction: i.e., —C(O)—NH— or —NH—C(O)—, provided that the connection does not violate valence rules.

One or more linker segments may be direct bonds. To illustrate, in a sequence of linker segments represented by -$L_2$-$L_3$-$L_4$-, when $L_3$ is a direct bond, it is effectively absent because $L_2$ and $L_4$ are attached directly to each other.

In another embodiment, the Linker moiety has one or more rings, which tend to increase the linker rigidity. A combination of chain bonds and ring(s) may be used to tune the relative orientations of the bifunctional groups or the distance therebetween.

In more specific embodiments, the Linker moeity has the following structure:

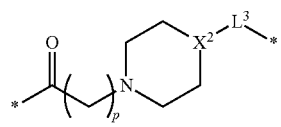

wherein,
 p is 1 or 2;
 q is 0, 1, 2, or 3;
 $X^2$ is CH or N;
 $L^3$ is
 i) —$(CH_2)_q$—;
 ii) —$(CH_2)_q$—C(O)NH—; or
 iii)

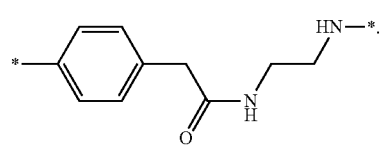

In yet another embodiment, the Linker moiety has the following structure:

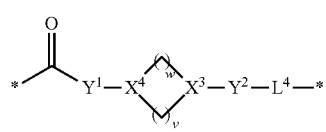

wherein,
 w is 1, 2, or 3;
 v is 1 or 2;
 p is 1, 2, 3, 4, or 5;
 $Y^1$ is a direct bond, —(CH$_2$)$_p$—, or —O—;
 $Y^2$ is a direct bond, —(CH$_2$)$_p$—, —C(O)—, or —C(O)—CH$_2$—,
 $X^3$ and $X^4$ are independently N or C(R), wherein R is H or C$_{1-3}$alkyl;
 $L^4$ is a direct bond, —NH—, —NHC(O)—, or
 $L^4$ is
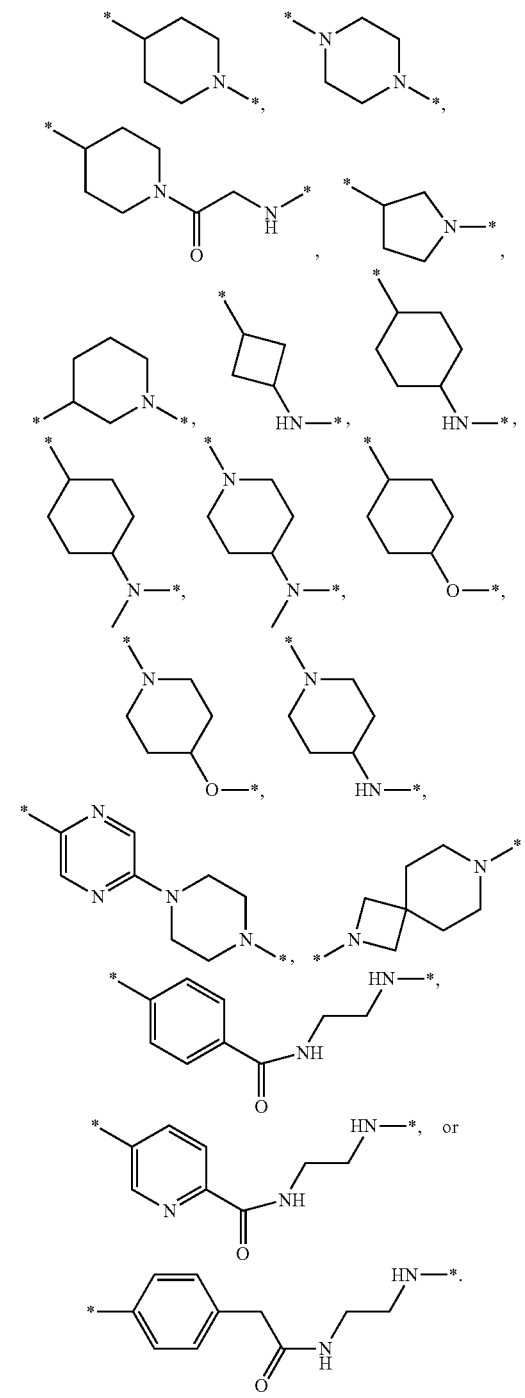
In further specific embodiments, the Linker moiety has the following structure:
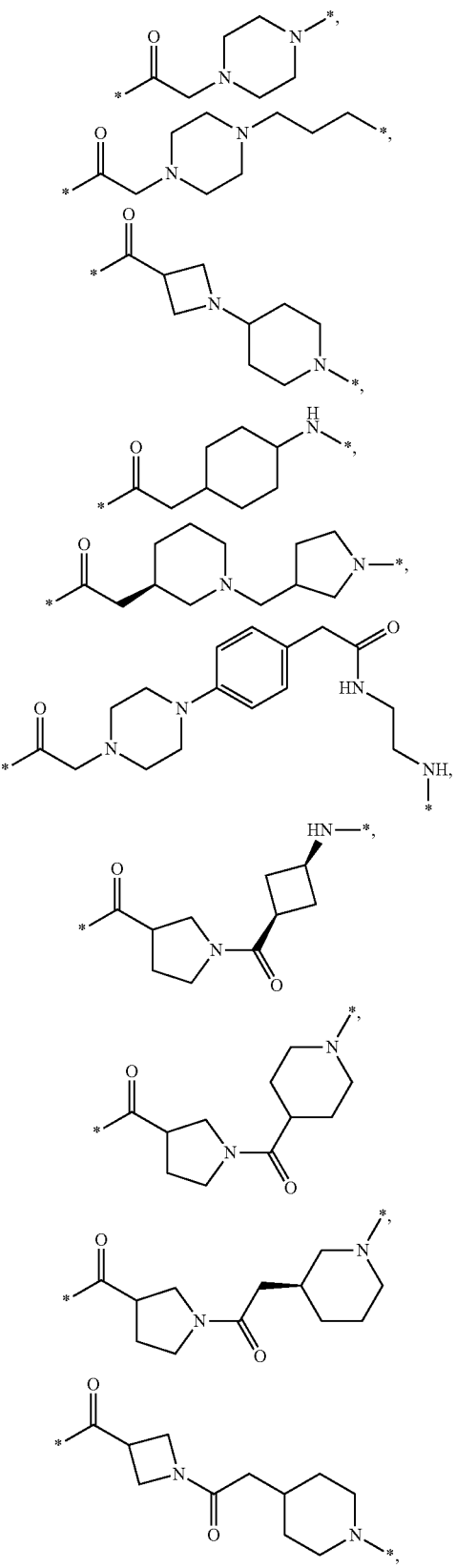

35
-continued
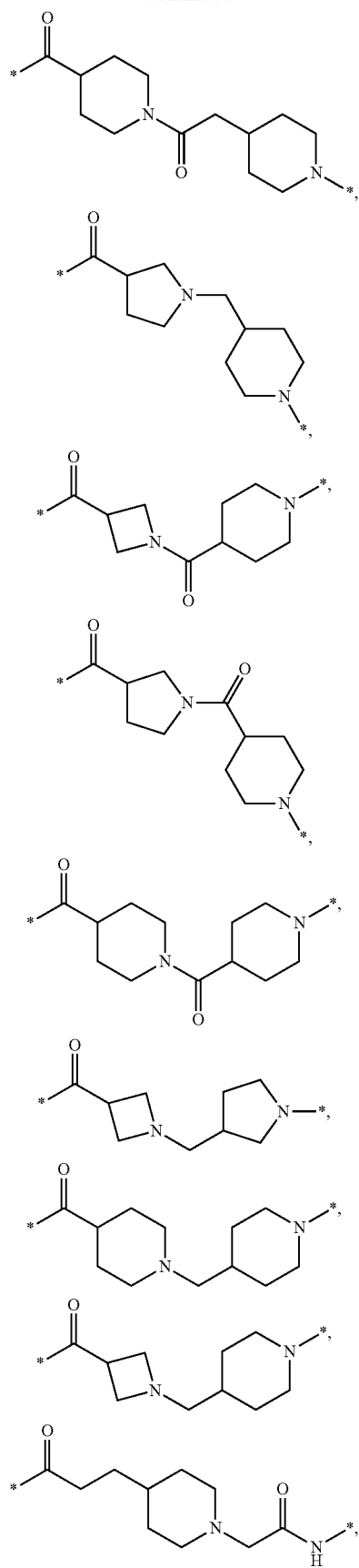
36
-continued
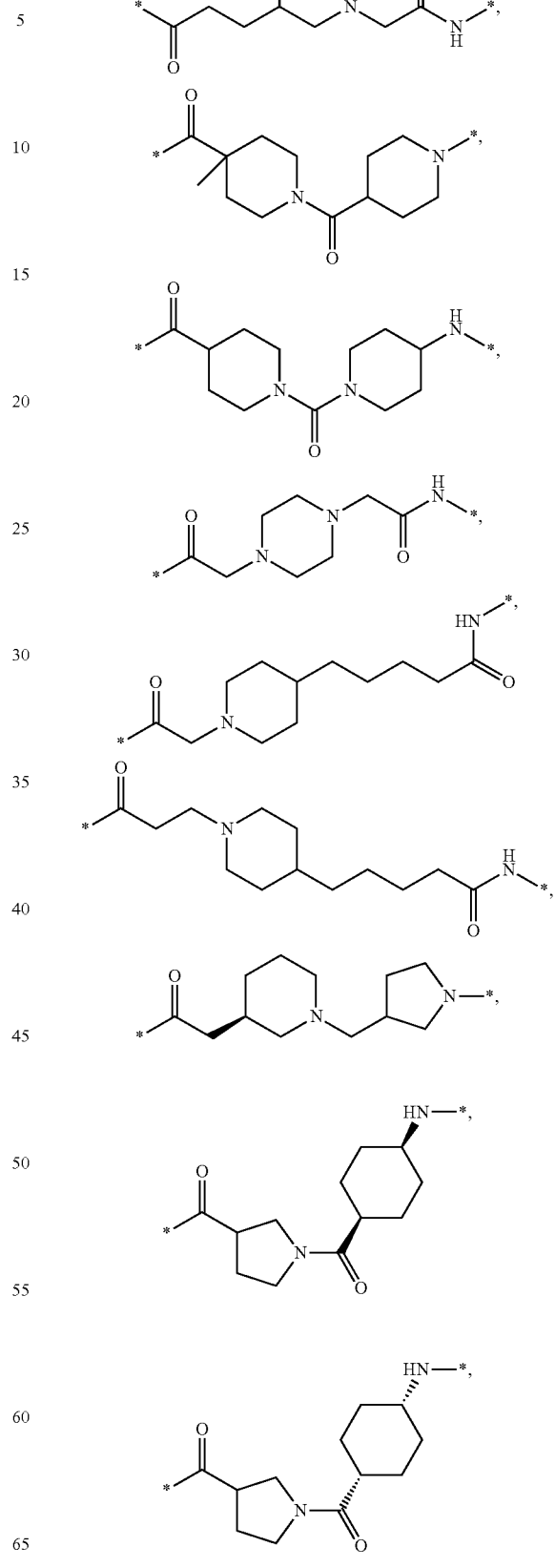

37
-continued
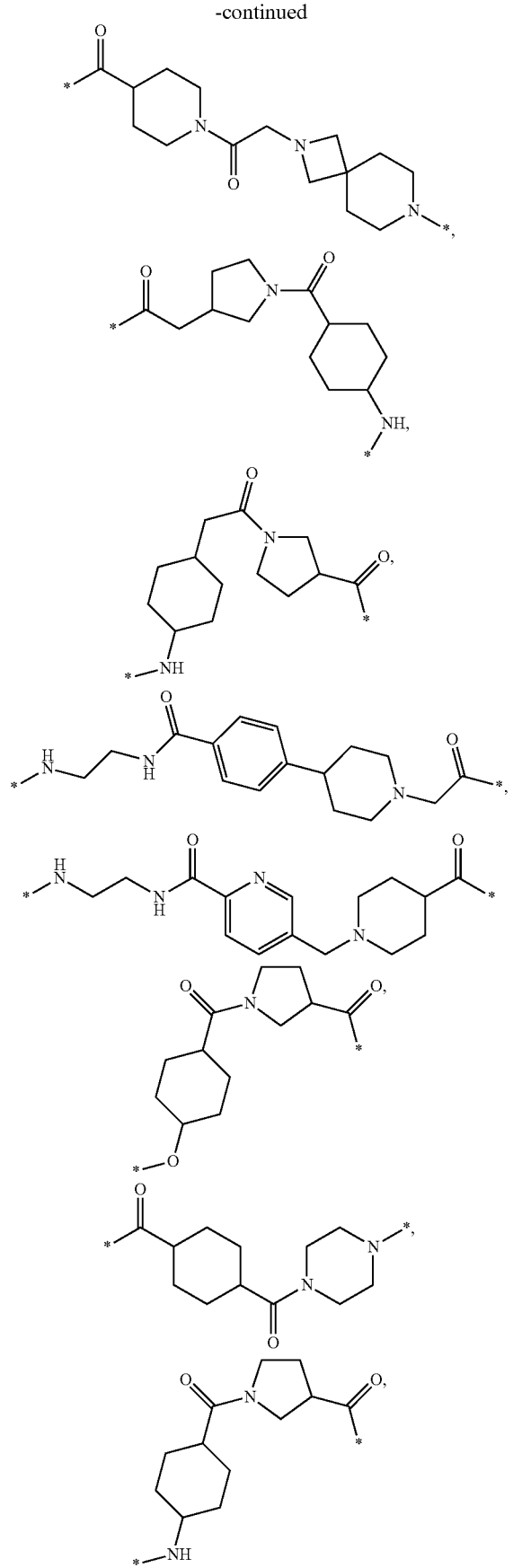
38
-continued
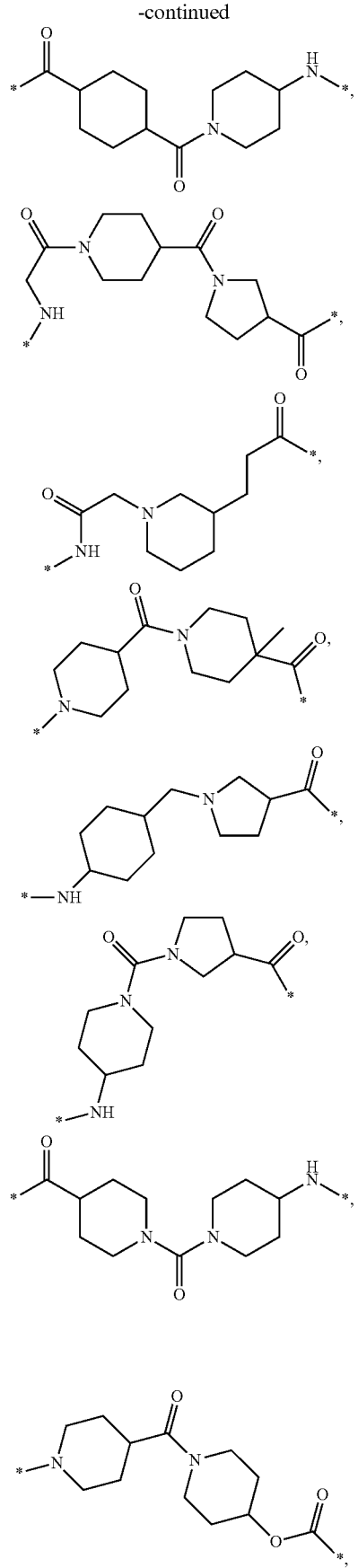

-continued
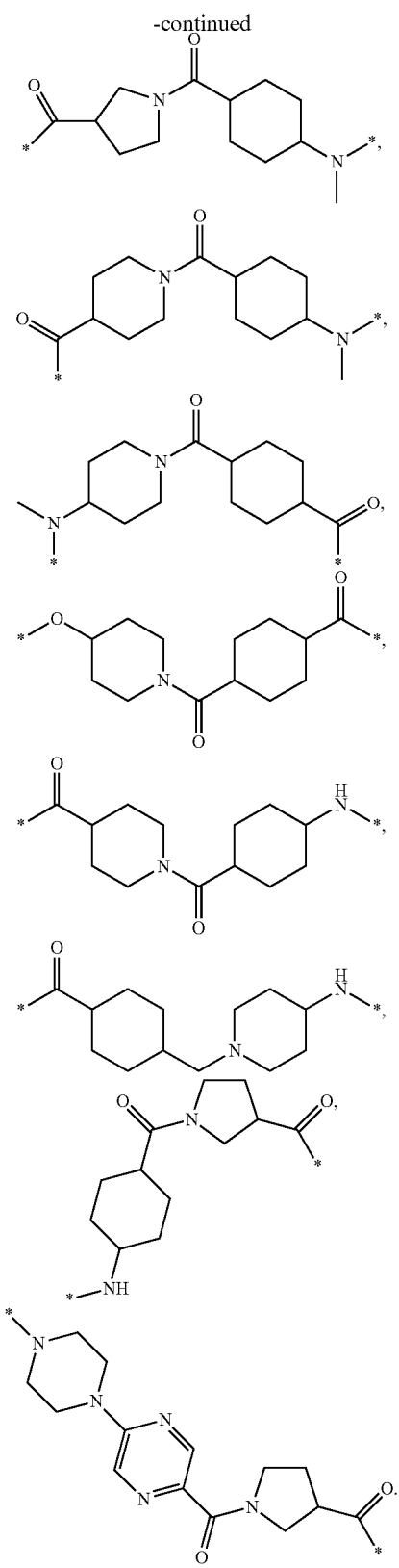
In other embodiments, the Linker moiety comprises a rigid ring system such as an aryl ring (e.g., phenyl), a heteroaryl ring, a bridged ring, a spiro ring, or a mixture thereof.
In more specific embodiments, the Linder moiety has one of the following structures:
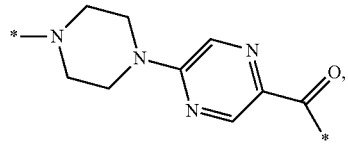
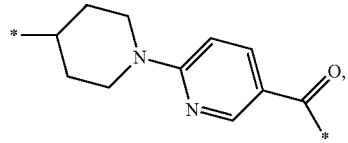
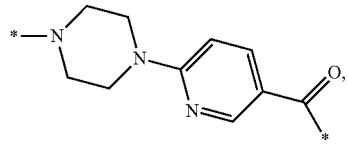
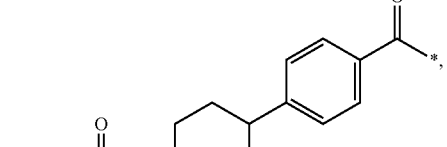
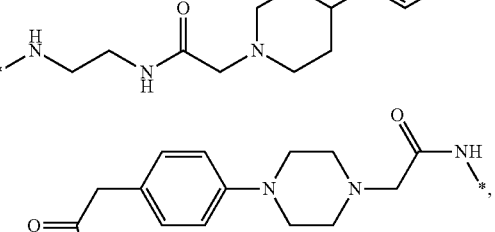
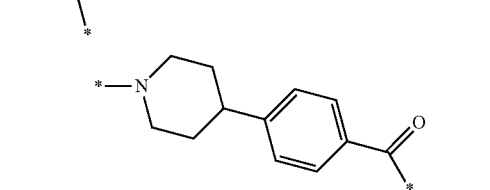
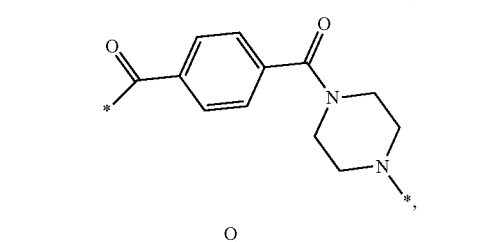
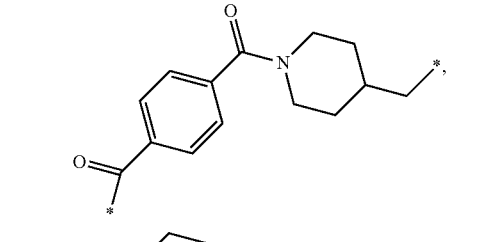
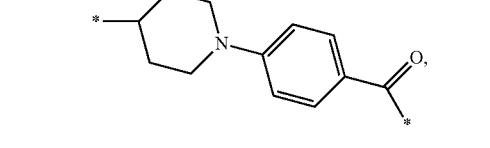

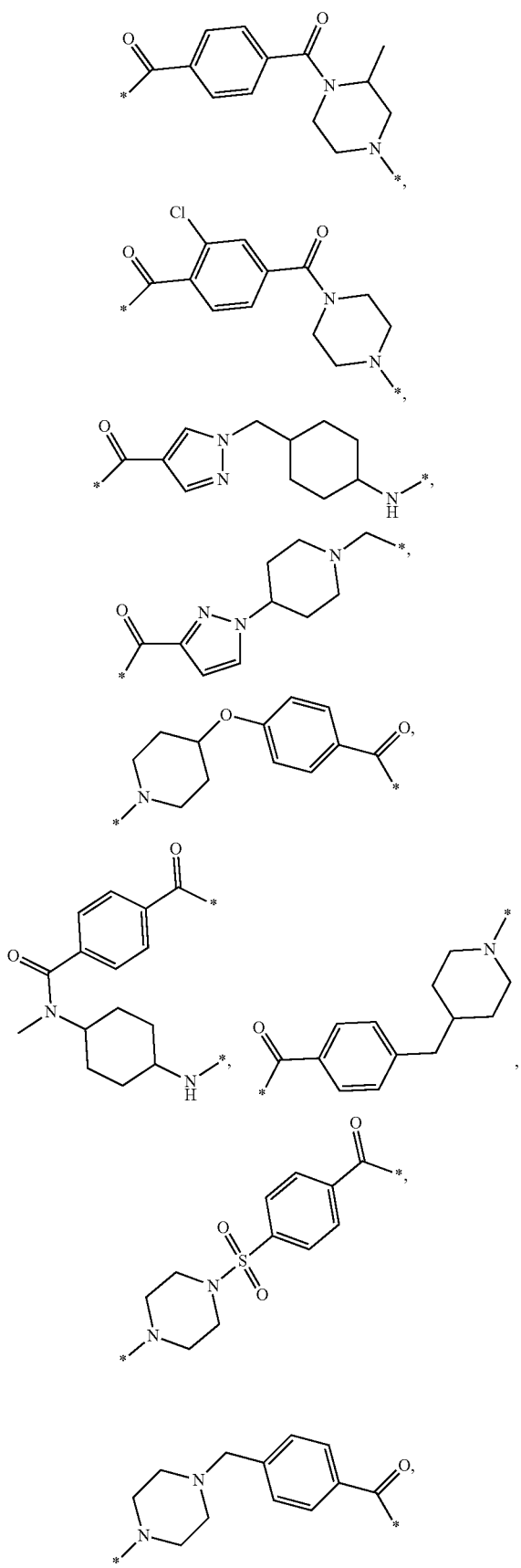

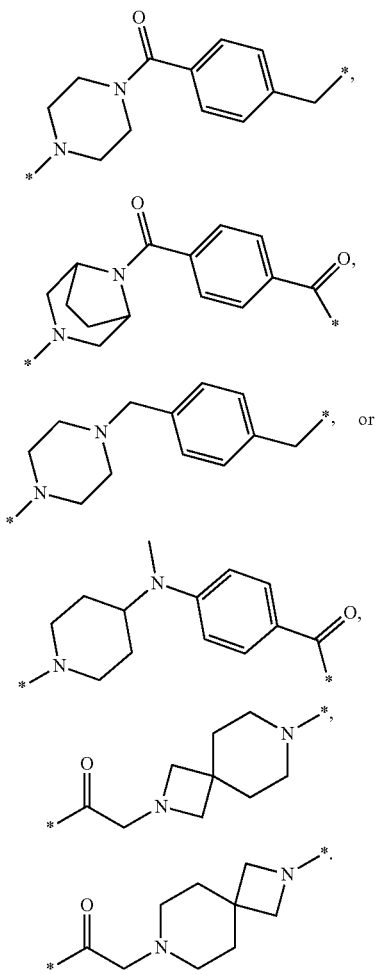

Construction of Compounds of Formulae (I) and (II)

The synthesis or construction of the compounds of Formula (I) or Formula (II) can be carried out in multiple steps, typically involving separately preparing building blocks of the HPK1 binder and the LHM moiety, followed by joining the respective building blocks through covalent bond formation. Generally speaking, either or both building blocks may be prepared with one or more linker precursors ($L_x$). A linker precursor comprises one or more linker segments ($L_s$) and has a terminal reactive group for further coupling. The two building blocks can be finally coupled (via formation of an $L_s$ segment) to afford a compound of Formula (I) or Formula (II).

The following schemes demonstrate the general approaches of preparing building blocks. Specific examples (Examples 1-97) were synthesized and characterized by their respective physiochemical properties according to the general schemes described herein.

A. General Schemes for Preparing HPK1 Binder Building Blocks

The HPK1 Binder building blocks may be prepared using the methods similar to the Reaction Scheme A shown below. For compounds of Formula (I), $R^1$ and $R^2$ together with the carbons to which they are attached form the A ring; for compounds of Formula (II), X is the B ring.

Reaction Scheme A
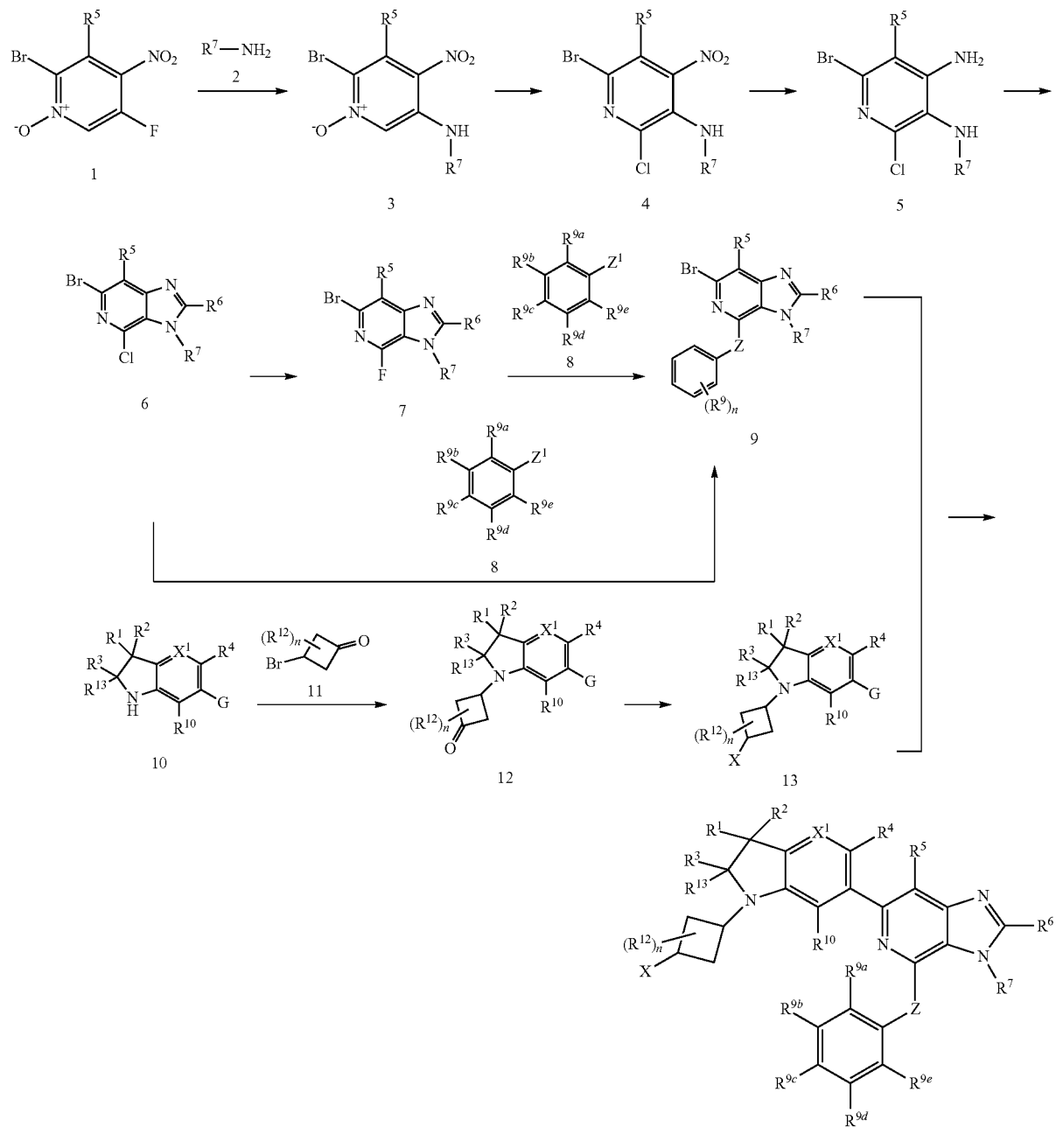
HPK1 Binder
Building Block
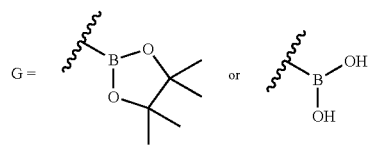
$Z^1$ = NH($R^8$) or OH or CH($R^8$)$_2$ Step 1—Preparation of a Compound of Formula (3)

The compounds of formula (3) can be made by combining compounds (1) and (2). Compounds (1) and (2) are commercially available or can be made by methods known in the art. Compounds (1) and (2) can be mixed in a suitable solvent such as THF. After stirring at a temperature between 0° C. and 100° C. for between 10 minutes and 24 h or until reaction is complete, the reaction is allowed to cool to room temperature. The compound of formula (3) can be obtained by filtration or precipitation.

Step 2—Preparation of a Compound of Formula (4)

The compounds of formula (4) may be prepared by chlorination of the compounds of formula (3) by methods known in the art. A compound of formula (3) may be mixed with $POCl_3$ in a suitable solvent such as toluene. After stirring at a temperature between 0° C. and 100° C. for between 10 minutes and 24 h or until reaction is complete, the reaction is allowed to cool to room temperature. The solvent can then be removed under reduced pressure. To extract the compound of formula (4), an organic solvent such as ethyl acetate may be added, followed by washing with water and brine. The organic phase can be concentrated to obtain the compound of formula (4). The compound of formula (4) may be purified by any suitable methods known in the art such as chromatography on silica gel, trituration, precipitation, or crystallization.

Step 3—Preparation of a Compound of Formula (5)

The compounds of formula (5) may be prepared by reduction of the compounds of formula (4) by methods known in the art. A compound of formula (4) can be mixed with Zinc dust and ammonium chloride in suitable solvent such as THF, MeOH, or water, or a mixture of solvent consisting of THF, MeOH, and water. After stirring at a temperature between 0° C. and 100° C. for between 1 h and 24 h or until reaction is complete, the reaction is allowed to cool to room temperature and filtered through celite bed. To extract the compound of formula (5), an organic solvent such as ethyl acetate may be added, followed by washing with water and brine. The organic phase can be concentrated to obtain the compound of formula (5). The compound of formula (5) may be purified by any suitable methods known in the art such as chromatography on silica gel, trituration, precipitation, or crystallization.

Step 4—Preparation of a Compound of Formula (6)

The compounds of formula (6) may be prepared by cyclization of the compounds of formula (5) by methods known in the art. A compound of formula (5) can be mixed with trimethyl orthoformate and formic acid. After stirring at a temperature between 0° C. and 100° C. for between 1 h and 24 h or until reaction is complete, the remaining solvent is removed via distillation. To extract the compound of formula (6), an organic solvent such as dichloromethane may be added, followed by washing with water and brine. The organic phase can be concentrated to obtain the compound of formula (6). The compound of formula (6) may be purified by any suitable methods known in the art such as chromatography on silica gel, trituration, precipitation, crystallization, or washing with organic solvent such as ether including but not limited to methyl t-butyl ether.

Step 5—Preparation of a Compound of Formula (7)

The compounds of formula (7) may be prepared by fluorination of the compounds of formula (6) by methods known in the art. A compound of formula (6) can be mixed with cesium fluoride in a solvent such DMF. After stirring at a temperature between room temperature and 110° C. for between 1 h and 24 h or until reaction is complete, the reaction is cooled to between 0° C. and room temperature by adding ice water or by adding the reaction mixture to ice water. To extract the compound of formula (7), an organic solvent such as ethyl acetate may be added, followed by washing with water and brine. The organic phase can be concentrated to obtain the compound of formula (7). The compound of formula (7) may be purified by any suitable methods known in the art such as chromatography on silica gel, trituration, precipitation, or crystallization.

Step 6—Preparation of a Compound of Formula (9)

The compounds of formula (9) can be made by combining compounds of formulas (6) and (8) or combining compounds of formulas (7) and (8) by methods known in the art. Compounds of formula (8) are commercially available or can be made by methods known in the art. A compound of formula (8) can be mixed with either compounds of formula (6) or (7) in the presence of a base such as sodium hydride in a suitable solvent such as NMP or DMA. After stirring at a temperature between room temperature and 100° C. for between 1 h and 24 h or until reaction is complete, the reaction can be added to water and treated with acid such as 10% citric acid. The compound of formula (7) may be obtained by filtration or precipitation.

Step 7—Preparation of a Compound of Formula (12)

The compounds of formula (12) can be made by combining compounds of formulas (10) and (11) by methods known in the art. Compounds of formulas (10) and (11) are commercially available or can be made by methods known in the art. Compounds of formulas (10) and (11) can be mixed in the presence of a base such as potassium carbonate in a suitable solvent such as DMF. After stirring at a temperature between room temperature and 50° C. for between 1 h and 24 h or until reaction is complete, the reaction is cooled to room temperature. To extract the compound of formula (12), an organic solvent such as ethyl acetate may be added, followed by washing with water and brine. The organic phase can be concentrated to obtain the compound of formula (12). The compound of formula (12) may be purified by any suitable methods known in the art such as chromatography on silica gel, trituration, precipitation, or crystallization.

Step 8—Preparation of a Compound of Formula (13)

The compounds of formula (13) may be prepared by reductive amination of the compounds of formula (12) by methods known in the art. Compounds of formula (12) and amines, that are commercially available or synthesized by methods known in the art, can be mixed with a reducing agent such as sodium triacetoxy borohydride or sodium cyanoborohydride in the presence of acid, such as acetic acid, or Lewis acid, such as zinc chloride, in a suitable solvent such as dichloroethane or methanol. After stirring at a temperature between 0° C. and room temperature for between 1 h and 24 h or until reaction is complete, the reaction may be added to aqueous solution such as saturated aqueous sodium bicarbonate solution. To extract the compound of formula (13), an organic solvent such as methylene chloride may be added, followed by washing with water and brine. The organic phase can be concentrated to obtain the compound of formula (13). The compound of formula (13) may be purified by any suitable methods known in the art such as chromatography on silica gel, trituration, precipitation, or crystallization.

Step 9—Preparation of HPK1 Binder Building Block

An HPK1 Binder building block can be made by combining the compounds of formula (9) and compounds of formula (13) by methods known in the art. Compounds of formulas (9) and (13) can be mixed in the presence of a catalyst such as tetrakis(triphenylphosphine)palladium and a base such as cesium carbonate, sodium carbonate, or potassium phosphate tribasic in a suitable solvent such as a mixture of dimethoxyethane and water, or a mixture of DMAc and water. After stirring at a temperature between 50° C. and 150° C. for between 1 and 24 hours, the reaction is allowed to cool to room temperature. The crude product of may be filtered and concentrated under reduced pressure. To extract the compound, an organic solvent such as methylene chloride may be added, followed by washing with water and brine. The organic phase can be concentrated and the resulting product may be purified by any suitable methods known in the art such as chromatography on silica gel, reverse phase chromatography, trituration, precipitation, or crystallization. The resulting HPK1 Binder building block is used as an intermediate to be further coupled to a linker moiety.

A HPK1 Binder building block prepared according to Reaction Scheme A has at least one reactive site, typically an amine moiety or a carboxyl moiety, that can be further coupled to the remainder of the molecule of Formula (I) or (II) by covalent bond formation. In specific examples of HPK1 Binder building blocks shown below, the —NH— moiety of the spiro[indole-piperidinyl] of Intermediate 1 and the carboxylic acid of Intermediate 2 (structures shown below) represent the respective reactive sites.

These intermediates are described in further detail below:

Intermediate 1: 4-fluoro-N-isopropyl-5-((3-isopropyl-6-(2-oxo-1-((1s,3s)-3-(piperidin-1-yl)cyclobutyl) spiro[indoline-3,4'-piperidin]-6-yl)-3H-imidazo[4,5-c]pyridin-4-yl)amino)-2-methylbenzamide Step 1: Synthesis of tert-butyl 2-oxo-6-(4,4,5,5-tetramethyl-1,3,2-dioxaborolan-2-yl)spiro[indoline-3,4'-piperidine]-1'-carboxylate. In a 100 mL, single necked, round bottomed flask equipped with a reflux condenser were placed tert-butyl 6-bromo-2-oxospiro[indoline-3,4'-piperidine]-1'-carboxylate (1) (0.99 g, 2.6 mmol), bis(pinacolato) boron (0.86 g, 3.4 mmol), potassium acetate (0.76 g, 7.8 mmol), and [1,1'-bis(diphenylphosphino)ferrocene] dichloropalladium (II) complex with dichloromethane (0.21 g, 0.26 mmol) were placed in dioxane (10 mL). After the mixture was degassed by bubbling $N_2$ for 5 min, it was stirred at 80° C. for 16 h. Then, it was cooled to RT, quenched with water, and extracted EtOAc. The combined organic layers were washed with water and brine, dried over $Na_2SO_4$, concentrated, and purified by flash chromatography (0-100% EtOAc/hexanes) to give the title compound product.

Step 2: Synthesis of tert-butyl 2-oxo-1-(3-oxocyclobutyl)-6-(4,4,5,5-tetramethyl-1,3,2-dioxaborolan-2-yl)spiro[indoline-3,4'-piperidine]-1'-carboxylate. In a 100 mL, single necked, round bottomed flask equipped with a reflux condenser were placed tert-butyl 2-oxo-6-(4,4,5,5-tetramethyl-1,3,2-dioxaborolan-2-yl)spiro[indoline-3,4'-piperidine]-1'-carboxylate (2) (0.81 g, 1.9 mmol) and potassium carbonate (0.65 g, 4.7 mmol, 325 mesh), 3-bromocyclobutanone (0.21 mL, 2.53 mmol) in DMF (10 mL). After the mixture was stirred at 50° C. for 1 h, it was cooled to RT and filtered to remove potassium carbonate. The filtrate was diluted with EtOAc, quenched with water, and extracted with EtOAc. The combined organic layers were washed with water and brine, dried over $Na_2SO_4$, filtered, and purified by flash chromatography (0-100% EtOAc/hexanes) to give the title compound.

Step 3: Synthesis of tert-butyl 2-oxo-1-[(1s,3s)-3-(piperidin-1-yl)cyclobutyl]-6-(4,4,5,5-tetramethyl-1,3,2-dioxaborolan-2-yl)spiro[indole-3,4'-piperidine]-1'-carboxylate.

To a stirred solution of tert-butyl 2-oxo-1-(3-oxocyclobutyl)-6-(4,4,5,5-tetramethyl-1,3,2-dioxaborolan-2-yl) spiro[indole-3,4'-piperidine]-1'-carboxylate (2.60 g, 5.24 mmol), acetic acid (0.60 mL, 10.5 mmol), and piperidine (1.55 mL, 15.7 mmol) in DCM (29 mL) was added STAB (3.33 g, 15.7 mmol) in 3 equal portions over 10 minutes. After stirring for 3 h, the reaction was diluted with sodium bicarbonate aq. (100 mL) and the organic layer was separated. The aqueous layer was extracted with DCM (2×75 mL) and the combined organic layers were washed with brine (2×100 mL), dried over sodium sulfate, filtered, and concentrated under reduced pressure to give the title compound (2.9 g, 96%).

Step 4: Synthesis of 5-((6-bromo-3-isopropyl-3H-imidazo[4,5-c]pyridin-4-yl)amino)-4-fluoro-2-methylbenzoic acid. In a 250 mL, round bottomed, single necked flask equipped with a reflux condenser was placed 5-amino-4-fluoro-2-methyl-benzoic acid (2.0 g, 11 mmol) in DMF (40 mL). To this was added NaH (60%, 1.6 g, 39 mmol), and the resulting mixture was stirred at RT for 15 minutes followed by the addition of 6-bromo-4-fluoro-3-isopropyl-imidazo[4,5-c]pyridine (7) (2.0 g, 7.8 mmol). After the mixture was stirred at 60° C. for 16 h, it was cooled to RT and quenched with water followed by the addition of 10% citric acid to adjust to its pH to ~ 5. The precipitates were filtered, washed with water, and dried to give the title compound.

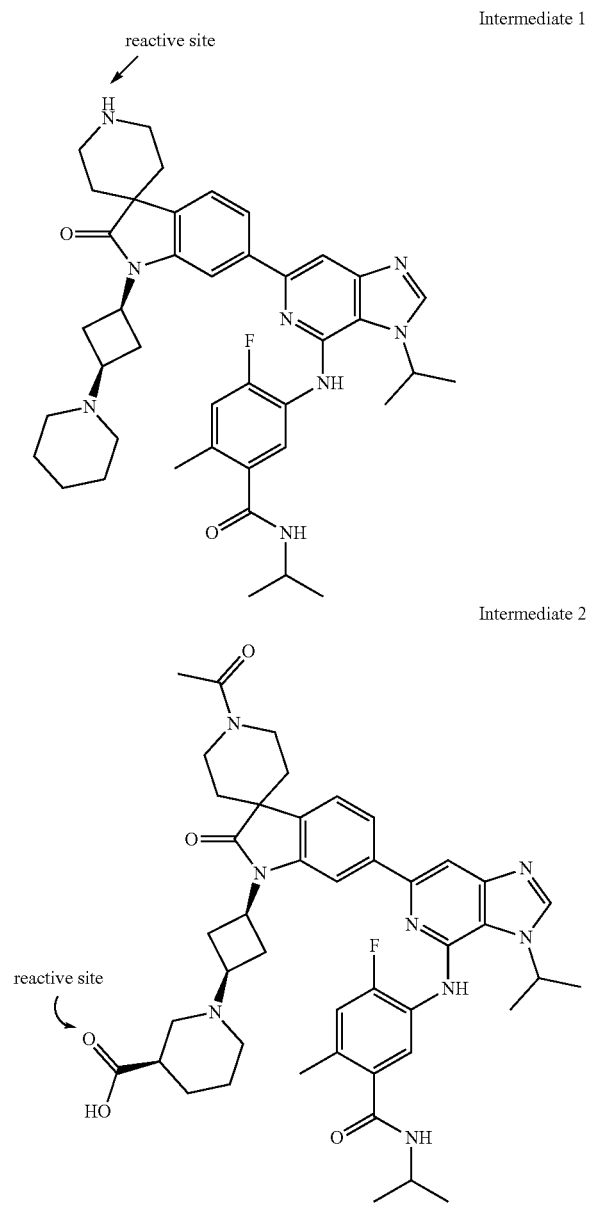

Step 5: Synthesis of 5-({6-bromo-3-isopropylimidazo[4,5-c]pyridin-4-yl}amino)-4-fluoro-N-isopropyl-2-methylbenzamide. To a solution of 5-((6-bromo-3-isopropyl-3H-imidazo[4,5-c]pyridin-4-yl)amino)-4-fluoro-2-methylbenzoic acid (1.0 g, 2.5 mmol), isopropyl amine (0.43 mL, 5.0 mmol) and DIPEA (2.58 mL, 14.8 mmol) in DMF (16 mL) was added HATU (1.91 g, 5.03 mmol) in one portion. The reaction was stirred at RT for 16 h before being cooled to 0° C. and quenched with the addition of water (30 mL). The mixture was stirred at RT for 20 min. before the solids were filtered. The solids were rinsed with water before being dried under reduced pressure over night to provide the title compound (0.95 g, 86%).

Step 6: Synthesis of tert-butyl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate. Combine 5-({6-bromo-3-isopropylimidazo[4,5-c]pyridin-4-yl}amino)-4-fluoro-N-isopropyl-2-methylbenzamide (500 mg, 1.12 mmol), tert-butyl 2-oxo-1-[(1s,3s)-3-(piperidin-1-yl)cyclobutyl]-6-(4,4,5,5-tetramethyl-1,3,2-dioxaborolan-2-yl)spiro[indole-3,4'-piperidine]-1-carboxylate (694 mg, 1.23 mmol), sodium carbonate (438 mg, 4.13 mmol), and tetrakis(triphenylphosphine)palladium(0) (91 mg, 0.08 mmol) in a mixture of 1,2-dimethoxyethane (12 mL) and water (4.1 mL) in a microwave vial equipped with a stir bar. This reaction was then heated at 125° C. in the microwave with stirring for 50 min. After cooling to rt, the reaction was concentrated onto silica gel and purified according to Chromatography B to afford the title compound (650 mg, 72%).

Step 7: Synthesis of 4-fluoro-N-isopropyl-5-((3-isopropyl-6-(2-oxo-1-((1s,3s)-3-(piperidin-1-yl)cyclobutyl)spiro[indoline-3,4'-piperidin]-6-yl)-3H-imidazo[4,5-c]pyridin-4-yl)amino)-2-methylbenzamide. To a solution of tert-butyl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate (900 mg, 1.12 mmol) in DCM (9 mL) was added HCl (4N in dioxane, 4.5 mL). This mixture was stirred for 3 hr before the solvents were removed under reduced pressure. The crude residue was purified according to Chromatography C to afford the title compound (750 mg, 90%).

Intermediate 2: (3R)-1-[(1s,3s)-3-[1'-acetyl-6-(4-{[2-fluoro-5-(isopropylcarbamoyl)-4-methylphenyl]amino}-3-isopropylimidazo[4,5-c]pyridin-6-yl)-2-oxospiro[indole-3,4'-piperidin]-1-yl]cyclobutyl]piperidine-3-carboxylic acid Step 1: Synthesis of tert-butyl 2-oxo-1-[(1s,3s)-3-[(3R)-3-(ethoxycarbonyl)piperidin-1-yl]cyclobutyl]-6-(4,4,5,5-tetramethyl-1,3,2-dioxaborolan-2-yl)spiro[indole-3,4'-piperidine]-1-carboxylate. The reaction was carried out according to General Procedure D using tert-butyl 2-oxo-1-(3-oxocyclobutyl)-6-(4,4,5,5-tetramethyl-1,3,2-dioxaborolan-2-yl)spiro[indole-3,4'-piperidine]-1-carboxylate (1.5 g, 3.0 mmol), ethyl (3R)-piperidine-3-carboxylate hydrochloride (761 mg, 3.93 mmol, 1.3 eq), with the addition of TEA (0.42 mL, 3.02 mmol, 1 eq) to provide the title compound (1.9 g, 3.0 mmol, 99%).

Step 2: Synthesis of tert-butyl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-[(3R)-3-(ethoxycarbonyl)piperidin-1-yl]cyclobutyl]spiro[indole-3,4'-piperidine]-1'-carboxylate. A microwave vial equipped with a stirbar was charged with 5-({6-bromo-3-isopropylimidazo[4,5-c]pyridin-4-yl}amino)-4-fluoro-N-isopropyl-2-methylbenzamide (500 mg, 1.12 mmol, 1 eq), tert-butyl 2-oxo-1-[(1s,3s)-3-[(3R)-3-(ethoxycarbonyl)piperidin-1-yl]cyclobutyl]-6-(4,4,5,5-tetramethyl-1,3,2-dioxaborolan-2-yl)spiro[indole-3,4'-piperidine]-1'-carboxylate (782 mg, 1.1 eq, 1.23 mmol), sodium carbonate (438 mg, 4.13 mmol, 3.7 eq) and tetrakis(triphenylphosphine)palladium (91 mg, 0.08 mmol, 0.07 eq) in a mixture of 1,2-dimethoxyethane (12 mL) and water (4.1 mL). The reaction mixture was heated via microwave at 125° C. for 25 min. The reaction was filtered through celite, and the filter cake was rinsed with a 1:1 mixture of DCM and methanol. The filtrate was concentrated and purified by Chromatography B to afford the title product (0.9 g 1.0 mmol, 92%).

Step 3: Synthesis of ethyl (3R)-1-[(1s,3s)-3-[6-(4-{[2-fluoro-5-(isopropylcarbamoyl)-4-methylphenyl]amino}-3-isopropylimidazo[4,5-c]pyridin-6-yl)-2-oxospiro[indole-3,4'-piperidin]-1-yl]cyclobutyl]piperidine-3-carboxylate. The reaction was carried out according to General Procedure B using tert-butyl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-[(3R)-3-(ethoxycarbonyl)piperidin-1-yl]cyclobutyl]spiro[indole-3,4'-piperidine]-1'-carboxylate (1.8 g, 2.1 mmol) to afford the title compound (1.9 g, quant).

Step 4: Synthesis of ethyl (3R)-1-[(1s,3s)-3-[1'-acetyl-6-(4-{[2-fluoro-5-(isopropylcarbamoyl)-4-methylphenyl]amino}-3-isopropylimidazo[4,5-c]pyridin-6-yl)-2-oxospiro[indole-3,4'-piperidin]-1-yl]cyclobutyl]piperidine-3-carboxylate. To a solution of ethyl (3R)-1-[(1s,3s)-3-[6-(4-{[2-fluoro-5-(isopropylcarbamoyl)-4-methylphenyl]amino}-3-isopropylimidazo[4,5-c]pyridin-6-yl)-2-oxospiro[indole-3,4'-piperidin]-1-yl]cyclobutyl]piperidine-3-carboxylate (1.90 g, 2.44 mmol, 1 eq), HATU (1.95 g, 5.12 mmol, 2.1 eq), and acetic acid (0.35 mL, 6.1 mmol) in dimethylformamide (28.7 mL, 0.85M) was added DIPEA (2.76 mL, 15.9 mmol, 6.5 eq) by slow addition. The reaction mixture was stirred at RT for 1 hour. The reaction mixture was quenched with water (30 mL) and the solid precipitate was removed by filtration and dried under a stream of nitrogen with vacuum overnight to afford the title compound (0.9 g, 1.10 mmol, 45%).

Step 5: (3R)-1-[(1s,3s)-3-[1'-acetyl-6-(4-{[2-fluoro-5-(isopropylcarbamoyl)-4-methylphenyl]amino}-3-isopropylimidazo[4,5-c]pyridin-6-yl)-2-oxospiro[indole-3,4'-piperidin]-1-yl]cyclobutyl]piperidine-3-carboxylic acid. The reaction was carried out according to General Procedure C using ethyl (R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)piperidine-3-carboxylate (900 mg, 1.10 mmol) to afford the title compound (790 mg, 1.0 mmol, 91%).

B. General Schemes for Preparing LHM Building Blocks

CRBN-targeting LHM can be first coupled to a linker precursor, the resulting building block can be further coupled to the HPK1 Binder building blocks (e.g., Intermediate 1 or Intermediate 2).

In certain embodiments, a CRBN-targeting LHM-Linker building block may be generally prepared according to Reaction Scheme B1:

REACTION SCHEME B1

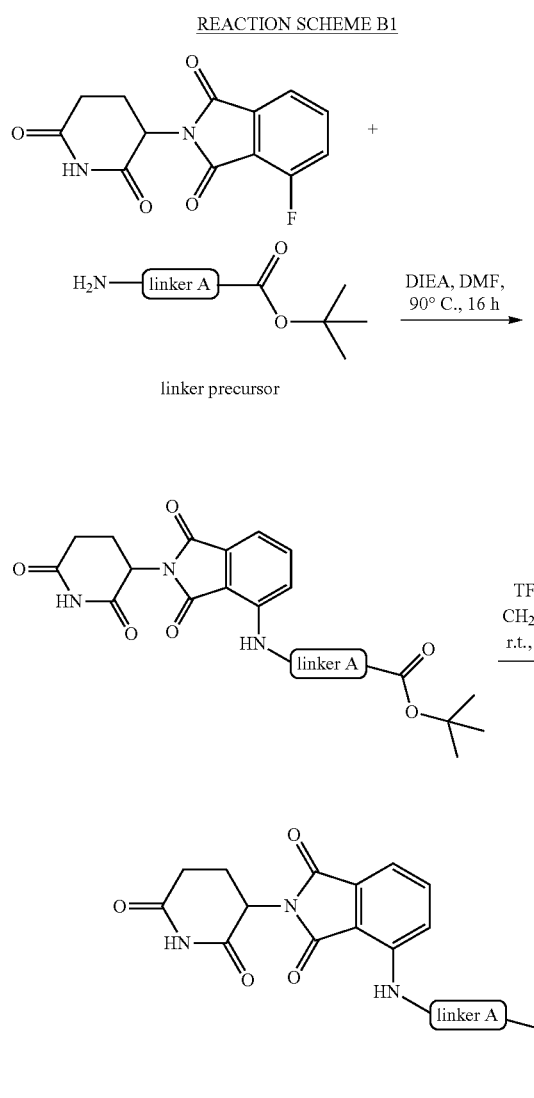

linker precursor

In Reaction Scheme B1, a functionalized thalidomide is first coupled to a linker precursor. The linker precursor (an amino ester) comprises "linker A" (representing one or more linker segments,) and two terminal reactive groups, amine and a protected carboxylic acid in an ester form. Step 1 describes in more detail of the initial coupling step using an exemplary aminoester linker precursor.

Step 1: A mixture of 2-(2,6-dioxopiperidin-3-yl)-4-fluoro-2,3-dihydro-1H-isoindole-1,3-dione (0.26 mmol), aminoester (0.26 mmol), ethylbis(propan-2-yl)amine (0.52 mmol) and DMF (1 mL) was allowed to stir at 90° C. overnight. The mixture was cooled and purified by HPLC (5-95% MeCN in $H_2O$ with 0.1% TFA) to afford the tert-butyl ester intermediate.

The tert-butyl ester intermediate thereafter undergoes hydrolysis (see Step 2) to provide a CRBN-targeting LHM building block having "linker A" terminated in a carboxylic acid group, which may be further reactively coupled to another moiety, e.g., the HPK1 Binder building block, or another linker segment.

Step 2: A mixture of tert-butyl 4-{[2-(2,6-dioxopiperidin-3-yl)-1,3-dioxo-2,3-dihydro-1H-isoindol-4-yl]amino}butanoate (0.10 mmol), $CH_2C_2$ (1 mL), and TFA (1 mL) was allowed to stir at r.t. for 2 h. The mixture was concentrated to afford the carboxylic acid product.

Described below are additional examples of CRBN-targeting LHM building blocks that may be prepared according to Reaction Scheme B1. More detailed description may be found in WO 2020038415, WO 2019207538, WO 2018089736, which references are incorporated by reference in their entireties.

Intermediate 3: 3-(2-((2-(2,6-dioxopiperidin-3-yl)-1,3-dioxoisoindolin-4-yl)amino)ethoxy)propanoic acid

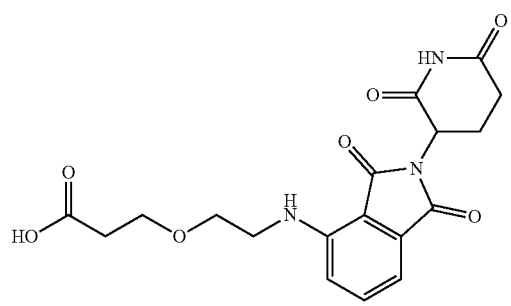 [SMILES: O=C(O)CCOCCNc1cccc2c1C(=O)N(C1CCC(=O)NC1=O)C2=O]

Step 1 product: tert-butyl 3-[2-[[2-(2,6-dioxo-3-piperidyl)-1,3-dioxo-isoindolin-4-yl]amino]ethoxy]propanoate (1.8 g, 52%). LCMS; $C_{22}H_{27}N_3O_7$ requires: 445, found: m/z=468 [M+Na]$^+$.

Step 2 product: 3-[2-[[2-(2,6-dioxo-3-piperidyl)-1,3-dioxo-isoindolin-4-yl]amino]ethoxy]propanoic acid (526 mg, 32%). LCMS; $C_{18}H_{19}N_3O_7$ requires: 389, found: m/z=390 [M+H]$^+$.

Intermediate 4: 3-(2-(2-(2-((2-(2,6-dioxopiperidin-3-yl)-1,3-dioxoisoindolin-5-yl)amino)ethoxy)ethoxy)ethoxy)propanoic acid

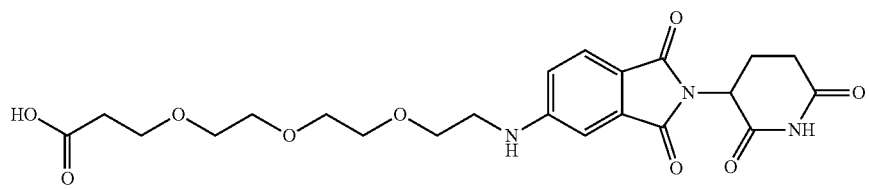 [SMILES: O=C(O)CCOCCOCCOCCNc1ccc2c(c1)C(=O)N(C1CCC(=O)NC1=O)C2=O]

Step 1 product: tert-butyl 3-[2-[2-[2-[[2-(2,6-dioxo-3-piperidyl)-1,3-dioxoisoindolin-5-yl]amino]ethoxy]ethoxy]ethoxy]propanoate.

Step 2 product: 3-[2-[2-[2-[[2-(2,6-dioxo-3-piperidyl)-1,3-dioxo-isoindolin-5-yl]amino]ethoxy]ethoxy]ethoxy]propanoic acid.

Intermediate 5: 6-((2-(2,6-dioxopiperidin-3-yl)-1,3-dioxoisoindolin-5-yl)amino)hexanoic acid

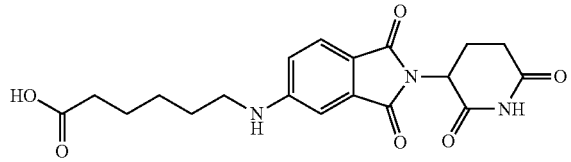 [SMILES: O=C(O)CCCCCNc1ccc2c(c1)C(=O)N(C1CCC(=O)NC1=O)C2=O]

Step 1: tert-butyl 6-{[2-(2,6-dioxopiperidin-3-yl)-1,3-dioxoisoindol-5-yl]amino}hexanoate To a mixture of 2-(2,6-dioxopiperidin-3-yl)-5-fluoroisoindole-1,3-dione (250 mg, 0.91 mmol), tert-butyl 6-aminohexanoate hydrochloride (203 mg, 0.91 mmol) in 3 ml of NMP, was added N,N-diisopropylethylamine (0.6 mL) at heating to 85° C. overnight. The crude reaction mixture was purified by silica gel chromatography using EtOAc/Hexane (0-100%), to give tert-butyl 6-{[2-(2,6-dioxopiperidin-3-yl)-1,3-dioxoisoindol-5-yl]amino}hexanoate (111 mg, 28%). LCMS: $C_{23}H_{29}N_3O_6$, requires: 443.5, found: m/z=444.4 [M+H]$^+$.

Step 2: 6-((2-(2,6-dioxopiperidin-3-yl)-1,3-dioxoisoindolin-5-yl)amino)hexanoic acid To a solution of tert-butyl 6-{[2-(2,6-dioxopiperidin-3-yl)-1,3-dioxoisoindol-5-yl]amino}hexanoate (111 mg, 0.25 mmol) in DCM was added TFA (0.5 mL). The reaction mixture was stirred at room temperature for 30 min, then the reaction mixture was concentrated to give 6-((2-(2,6-dioxopiperidin-3-yl)-1,3-dioxoisoindolin-5-yl)amino) hexanoic acid (78 mg, 78%). $^1$H NMR (500 MHz, DMSO-d6) δ 12.00 (s, 1H), 11.06 (s, 1H), 7.57 (d, J=8.3 Hz, 1H), 7.11 (s, 1H), 6.95 (d, J=2.1 Hz, 1H), 6.85 (dd, J=8.4, 2.1 Hz, 1H), 5.04 (dd, J=12.7, 5.4 Hz, 1H), 3.16 (q, J=6.4 Hz, 2H), 2.23 (t, J=7.4 Hz, 2H), 2.03-1.97 (m, 1H), 1.56 (dq, J=14.8, 7.2 Hz, 4H), 1.39 (q, J=7.9 Hz, 2H). LCMS: $C_{19}H_{21}N_3O_6$, requires: 387.4, found: m/z=388.4 [M+H]$^+$.

Intermediate 6: 8-{[2-(2,6-dioxopiperidin-3-yl)-1,3-dioxoisoindol-5-yl]amino}octanoic acid Intermediate 6 may be prepared in the same manner as Intermediate 5, except that the hexanoic acid was replaced with octanoic acid.

Reaction Scheme B2 shows an alternative approach for preparing a CRBN-targeting LHM building block, which is constructed with a linker precursor having a ring. The linker precursor typically comprises an aldehyde reactive group which can be further coupled to another building block by reductive amination (see, e.g., General Reaction G)

REACTION SCHEME B2

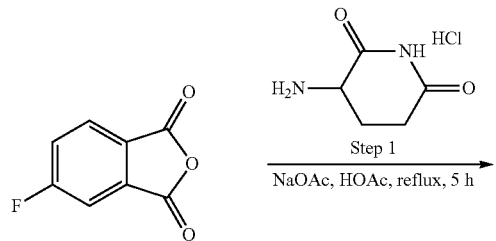

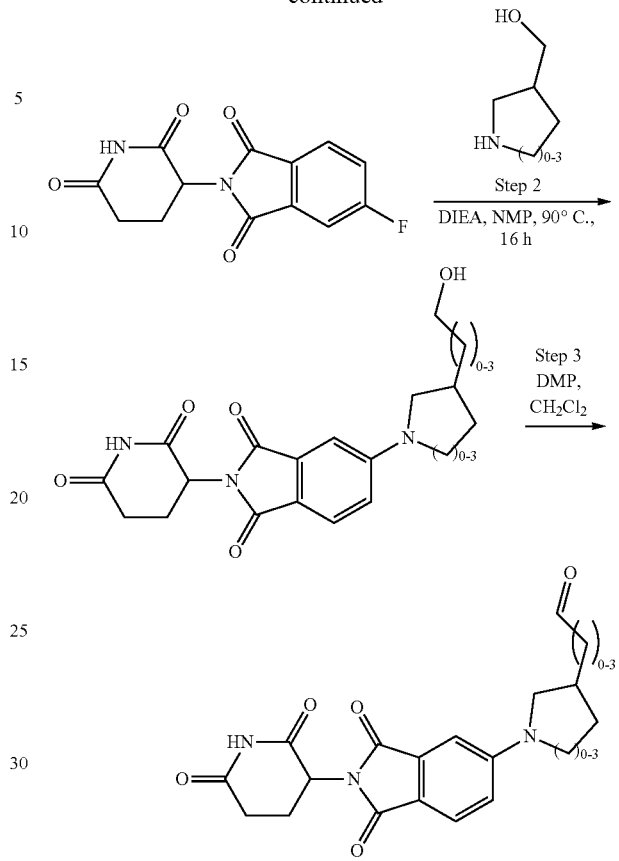

Step 1: 2-(2,6-dioxopiperidin-3-yl)-5-fluoroisoindoline-1,3-dione

A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol) and NaOAc (4.2 g, 51.17 mmol) in HOAc (50 mL) was stirred at 120° C. for 5 h before concentrated under vacuum. The residue was washed with water and the solid was collected by filtration. The crude product was washed with water twice and ethyl acetate twice and dried under oven to afford 2-(2,6-dioxopiperidin-3-yl)-5-fluoroisoindoline-1,3-dione (7.7 g, 92%) as a light brown solid. $^1$H NMR (300 MHz, DMSO-d$_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H).

Step 2: Amine Displacement of Aryl Fluoride

To a solution of 2-(2,6-dioxopiperidin-3-yl)-5-fluoro-2,3-dihydro-1H-isoindole-1,3-dione (1.0 g, 3.62 mmol) in NMP (10 mL) were added the amine (3.60 mmol) and DIPEA (1.4 g, 10.83 mmol). The resulting solution was stirred at 80° C. for 16 h. The reaction mixture was cooled down to room temperature and purified by reverse phase flash chromatography to afford the corresponding final product.

Step 3: Alcohol Oxidation to the Aldehyde

To a mixture of the alcohol (1.06 mmol) in $CH_2Cl_2$ (10 mL) was added Dess-Martin periodinane (2.12 mmol). The mixture was allowed to stir at room temperature for 1 h. The mixture was purified by column chromatography to afford the desired aldehyde.

It is to be understood that using 4-fluoro-1,3-dihydro-2-benzofuran-1,3-dione as a starting material would afford an alternative location for attaching the linker to the thalidomide.

Described below are additional examples of CRBN-targeting LHM building blocks that may be prepared according to Reaction Scheme B2.

Intermediate 7: (3S)-1-(2-(2,6-dioxopiperidin-3-yl)-1,3-dioxoisoindolin-5-yl)pyrrolidine-3-carbaldehyde

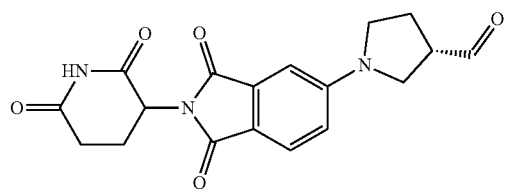 [SMILES: O=C[C@H]1CCN(c2ccc3c(c2)C(=O)N(C2CCC(=O)NC2=O)C3=O)C1]

Step 2: 2-(2,6-dioxopiperidin-3-yl)-5-((S)-3-(hydroxymethyl)pyrrolidin-1-yl)isoindoline-1,3-dione Following Step 1 of Scheme B2, 2-(2,6-dioxopiperidin-3-yl)-5-fluoroisoindoline-1,3-dione was reacted with (S)-pyrrolidin-3-ylmethanol to afford 2-(2,6-dioxopiperidin-3-yl)-5-((S)-3-(hydroxymethyl)pyrrolidin-1-yl)isoindoline-1,3-dione (643.1 mg, 33%) as a yellow solid. $^1$H NMR (300 MHz, DMSO-$d_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (t, J=5.4 Hz, 1H), 3.59-3.41 (m, 5H), 3.22-3.17 (m, 1H), 2.95-2.83 (m, 1H), 2.67-2.44 (m, 3H), 2.12-1.88 (m, 2H), 1.87-1.76 (m, 1H). MS (ESI) calc'd for ($C_{18}H_{19}N_3O_5$) [M+H]$^+$, 358.1; found 358.1.

Step 3: (3S)-1-(2-(2,6-dioxopiperidin-3-yl)-1,3-dioxoisoindolin-5-yl)pyrrolidine-3-carbaldehyde To a mixture of 2-(2,6-dioxopiperidin-3-yl)-5-[(3S)-3-(hydroxymethyl)pyrrolidin-1-yl]isoindole-1,3-dione (258 mg, 0.72 mmol) in DCM (5 mL) was added 1,1-bis(acetyloxy)-3-oxo-1λ$^5$,2-benziodaoxol-1-yl acetate (0.61 g, 1.44 mmol). After 90 minutes, silica gel was added and the mixture was concentrated to dryness. The resulting powder was transferred to a loading cartridge and the mixture was purified by flash chromatography on a 24 g column eluted with 0 to 100% ethyl acetate/hexanes to provide (3S)-1-[2-(2,6-dioxopiperidin-3-yl)-1,3-dioxoisoindol-5-yl]pyrrolidine-3-carbaldehyde (198 mg, 77%). LCMS $C_{18}H_{17}N_3O_5$ requires: 355, found: m/z=356 [M+H]$^+$.

Intermediate 8: (3S)-1-(2-(2,6-dioxopiperidin-3-yl)-1,3-dioxoisoindolin-4-yl)pyrrolidine-3-carbaldehyde

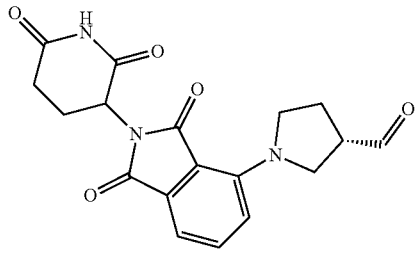 [SMILES: O=C[C@H]1CCN(c2cccc3c2C(=O)N(C2CCC(=O)NC2=O)C3=O)C1]

Intermediate 8 may be prepared in the same manner as Intermediate 7, except that 2-(2,6-dioxopiperidin-3-yl)-5-fluoroisoindoline-1,3-dione was replaced with 2-(2,6-dioxopiperidin-3-yl)-4-fluoroisoindoline-1,3-dione, which was prepared from 4-fluoro-1,3-dihydro-2-benzofuran-1,3-dione.

Intermediate 9: 3-{4-[2-(2,6-dioxopiperidin-3-yl)-1,3-dioxoisoindol-5-yl]piperazin-1-yl}propanoic acid

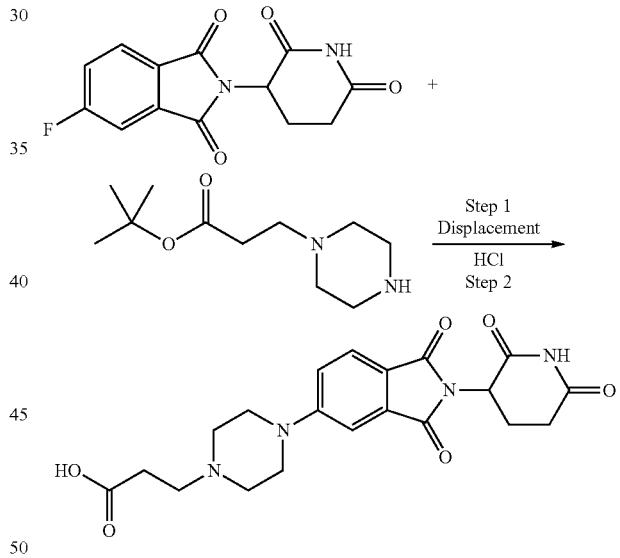

Step 1: tert-butyl 3-(4-(2-(2,6-dioxopiperidin-3-yl)-1,3-dioxoisoindolin-5-yl)piperazin-1-yl)propanoate Tert-butyl 3-(piperazin-1-yl)propanoate (400.00 mg, 1.87 mmol) and 2-(2,6-dioxopiperidin-3-yl)-5-fluoroisoindole-1,3-dione (516 mg, 1.87 mmol) in 10 ml NMP, N,N-diisopropylethylamine (0.65 mL, 0.48 g, 3.73 mmol) was added, followed by heating at 85-90° C. for 16 hr. The resulting reaction mixture was thereafter cooled to rt and partitioned between EtOAc/water. The organic layer was then washed with brine, dried, concentrated. Silica gel column purification using 10-100% EtOAc/Hexanes, obtained 823 mg of the title compound. LCMS: $C_{24}H_{30}N_4O_6$, requires: 470.5, found: m/z=471.8 [M+H]$^+$.

Step 2: 3-{4-[2-(2,6-dioxopiperidin-3-yl)-1,3-dioxoisoindol-5-yl]piperazin-1-yl}propanoic acid Tert-butyl 3-{4-[2-(2,6-dioxopiperidin-3-yl)-1,3-dioxoisoindol-5-yl]piperazin-1-yl}propanoate (820.00 mg, 1.74 mmol) was dissolved in trifluoroacetic acid (9.94 g, 87.14 mmol), after 1 hr, the TFA was evaporated. Lyophilized product to dryness, obtained 3-{4-[2-(2,6-dioxopiperidin-3-yl)-1,3-dioxoisoindol-5-yl]piperazin-1-yl}propanoic acid (722 mg, 100% yield). LCMS: $C_{20}H_{22}N_4O_6$, requires: 414.4, found: m/z=415.4 [M+H]$^+$.

Intermediate 10: 3-{4-[2-(2,6-dioxopiperidin-3-yl)-1,3-dioxoisoindol-5-yl]piperazin-1-yl}acetic acid Intermediate 10 was prepared in a similar manner as Intermediate 9, except that tert-butyl 3-(piperazin-1-yl)propanoate was replaced with tert-butyl 3-(piperazin-1-yl)acetate.

Intermediate 11: 2-(2-(2-(2,6-dioxopiperidin-3-yl)-1,3-dioxoisoindolin-5-yl)-2,7-diazaspiro[3.5]nonan-7-yl)acetic acid

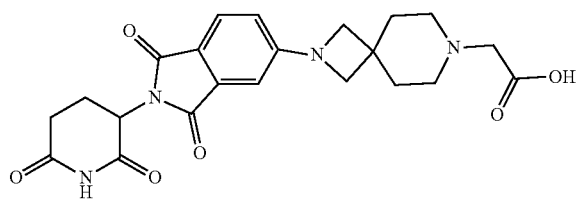 [SMILES: O=C(O)CN1CCC2(CC1)CN(c1ccc3c(c1)C(=O)N(C1CCC(=O)NC1=O)C3=O)C2]

Step 1: benzyl 2-{2-[2-(2,6-dioxopiperidin-3-yl)-1,3-dioxoisoindol-5-yl]-2,7-diazaspiro[3.5]nonan-7-yl}acetate To a mixture of 2-(2,6-dioxopiperidin-3-yl)-5-fluoroisoindole-1,3-dione (70.00 mg, 0.25 mmol) and benzyl 2-{2,7-diazaspiro[3.5]nonan-7-yl}acetate (69.53 mg, 0.25 mmol) in 2 ml of NMP, was added N,N-diisopropylethylamine (0.13 mL), heated to 85° C. overnight. The crude mixture was purified by column chromatography eluting with EtOAc/Hexane (10-100%) to give benzyl 2-{2-[2-(2,6-dioxopiperidin-3-yl)-1,3-dioxoisoindol-5-yl]-2,7-diazaspiro[3.5]nonan-7-yl}acetate (68 mg, 51%). LCMS $C_{29}H_{30}N_4O_6$ requires: 530, found: m/z=532 [M+H]$^+$.

Step 2: 2-(2-(2-(2,6-dioxopiperidin-3-yl)-1,3-dioxoisoindolin-5-yl)-2,7-diazaspiro[3.5]nonan-7-yl)acetic acid To a solution of benzyl 2-{2-[2-(2,6-dioxopiperidin-3-yl)-1,3-dioxoisoindol-5-yl]-2,7-diazaspiro[3.5]nonan-7-yl}acetate (68 mg, 0.13 mmol) in EtOH (5 mL) and DCM (2 mL), was added Palladium on carbon (6 mg, 0.06 mmol). The reaction mixture was sparged with hydrogen and kept under one atmosphere of hydrogen using a balloon, stirred at room temp for 48 hrs. The reaction mixture was filtered through a pad of Celite and concentrated to give benzyl 2-{2-[2-(2,6-dioxopiperidin-3-yl)-1,3-dioxoisoindol-5-yl]-2,7-diazaspiro[3.5]nonan-7-yl}acetate (56 mg, 99%). LCMS $C_{22}H_{24}N_4O_6$ requires: 440, found: m/z=441 [M+H]$^+$.

Intermediate 12: 1-(2-(2,6-dioxopiperidin-3-yl)-1,3-dioxoisoindolin-5-yl)piperidine-4-carbaldehyde

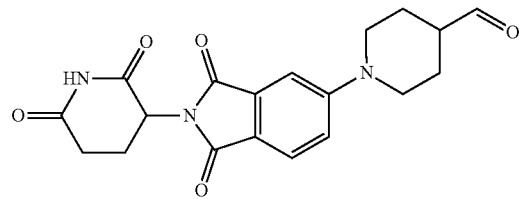 [SMILES: O=CC1CCN(c2ccc3c(c2)C(=O)N(C2CCC(=O)NC2=O)C3=O)CC1]

Step 2: 2-(2,6-dioxopiperidin-3-yl)-5-(4-(hydroxymethyl)piperidin-1-yl)isoindoline-1,3-dione Following Step 1 of Scheme B2, 2-(2,6-dioxopiperidin-3-yl)-5-fluoroisoindoline-1,3-dione was reacted with piperidin-4-ylmethanol to afford 2-(2,6-dioxopiperidin-3-yl)-5-(4-(hydroxymethyl)piperidin-1-yl)isoindoline-1,3-dione (939 mg, 70%) as a yellow solid. $^1$H NMR (300 MHz, DMSO-d$_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.51 (t, J=5.1 Hz, 1H), 4.07 (d, J=13.2 Hz, 2H), 3.27 (t, J=5.7 Hz, 2H), 2.99-2.80 (m, 3H), 2.62-2.55 (m, 2H), 2.17-1.95 (m, 1H), 1.76-1.67 (m, 3H), 1.24-1.12 (m, 2H). MS (ESI) calc'd for ($C_{19}H_{21}N_3O_5$) [M+H]$^+$, 372.1; found 372.2.

Step 3: 1-(2-(2,6-dioxopiperidin-3-yl)-1,3-dioxoisoindolin-5-yl)piperidine-4-carbaldehyde According to Scheme B2, 2-(2,6-dioxopiperidin-3-yl)-5-(4-(hydroxymethyl)piperidin-1-yl)isoindoline-1,3-dione was oxidized to afford 1-(2-(2,6-dioxopiperidin-3-yl)-1,3-dioxoisoindolin-5-yl)piperidine-4-carbaldehyde. LCMS $C_{19}H_{19}N_3O_5$ requires: 369, found: m/z=370 [M+H]$^+$.

VHL-targeting LHM building block can be generally prepared according to Reaction Scheme B3, in which a LHM is first coupled to a linker precursor comprising "linker A" (representing one or more linker segments) and two terminal reactive groups. One of the reactive groups is carboxylic acid or reactive equivalent thereof, the other reactive group X may be, for example, carboxylic acid, hydroxyl or aldehyde group. The resulting LHM building block has a reactive moiety (X), which can be further coupled to another moiety.

REACTION SCHEME B3

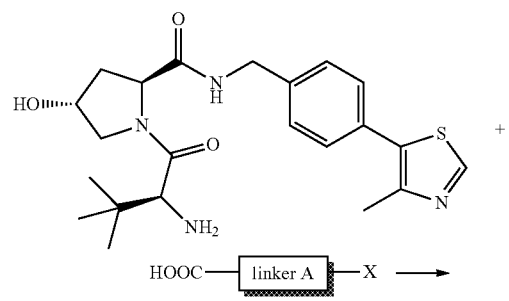

-continued

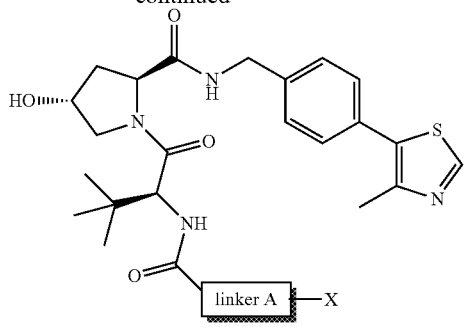

X is a reactive group such as —COOH, OH, CHO

Described below are additional examples of VHL-targeting LHM building blocks that may be prepared according to Reaction Scheme B3.

Intermediate 13: 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid

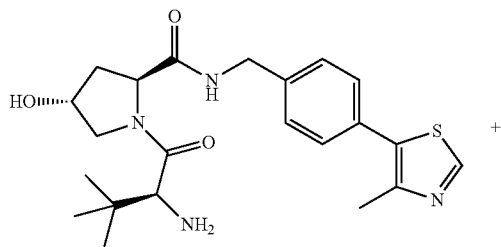

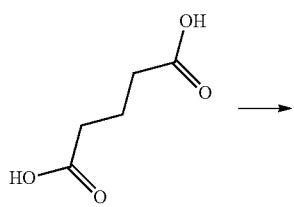

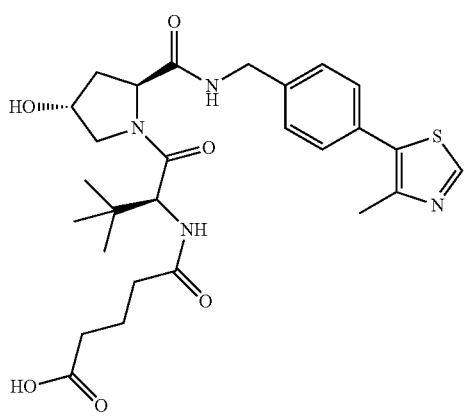

To a solution of glutaric acid (135 mg, 1.0 mmol) in THF (10 mL) and methanol (5 mL) were added HATU (0.39 g, 1.0 mmol) and N,N-diisopropylethylamine (0.33 mL, 1.9 mmol) and the reaction mixture was stirred for 5 minutes, then (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (0.40 g, 0.93 mmol) was added. The reaction mixture was stirred for 16 h, followed by quenching with 4N HCl in dioxane (0.25 mL), then the crude mixture was concentrated onto silica gel and purified by reverse phase chromatography. LCMS $C_{27}H_{36}N_4O_6S$ requires: 544, found: m/z=567.5 [M+Na]+.

$^1$H NMR (500 MHz, DMSO-$d_6$) δ 12.01 (s, 1H), 9.00 (s, 1H), 8.58 (d, J=6.4 Hz, 1H), 7.91 (d, J=9.3 Hz, 1H), 7.43 (p, J=7.8, 6.7 Hz, 4H), 5.14 (d, J=3.7 Hz, 1H), 4.55 (d, J=9.2 Hz, 1H), 4.53-4.43 (m, 2H), 4.37 (s, 1H), 4.23 (dd, J=16.0, 5.2 Hz, 1H), 3.78-3.52 (m, 2H), 2.46 (s, 3H), 2.28 (dt, J=15.7, 7.7 Hz, 1H), 2.25-2.15 (m, 3H), 2.05 (t, J=10.6 Hz, 1H), 1.98-1.83 (m, 1H), 1.72 (h, J=6.4 Hz, 2H), 0.95 (s, 9H).

Intermediate 14: 6-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}hexanoic acid Intermediate 14 may be prepared in the same manner as Intermediate 13, except that the glutaric acid was replaced with hexanoic acid, and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide was replaced with (2S,4R)-1-[(2S)-2-amino-3,3-dimethylbutanoyl]-4-hydroxy-N-{[4-(4-methyl-1,3-thiazol-5-yl)phenyl]ethyl}pyrrolidine-2-carboxamide.

Intermediate 15: 10-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}decanoic acid Intermediate 15 may be prepared in the same manner as Intermediate 13, except that the glutaric acid was replaced with decanoic acid, and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide was replaced with (2S,4R)-1-[(2S)-2-amino-3,3-dimethylbutanoyl]-4-hydroxy-N-{[4-(4-methyl-1,3-thiazol-5-yl)phenyl]ethyl}pyrrolidine-2-carboxamide.

Reaction Scheme B4 shows another approach to generating VHL-targeting LHM building block via a different attachment point to the LHM:

REACTION SCHEME B4
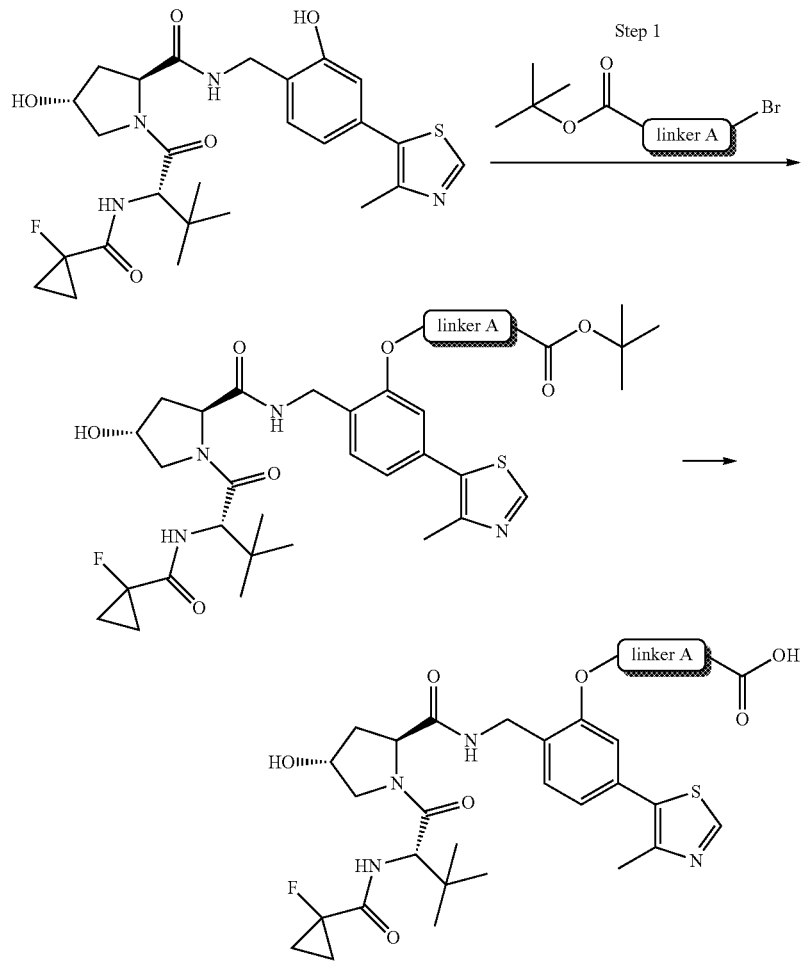
Reaction Scheme B4 begins with coupling a linker precursor to a VHL-targeting LHM, namely, (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide. The VHL-targeting LHM is prepared according to the following steps.
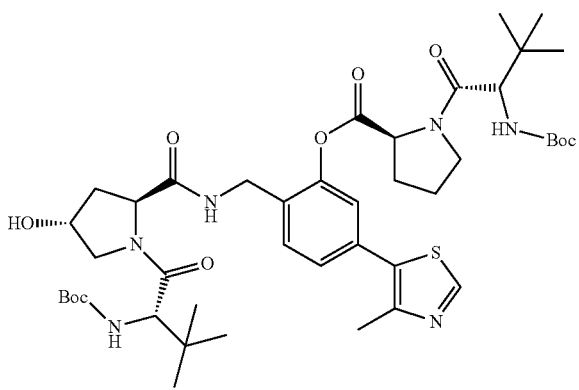
Side product
Step 5a

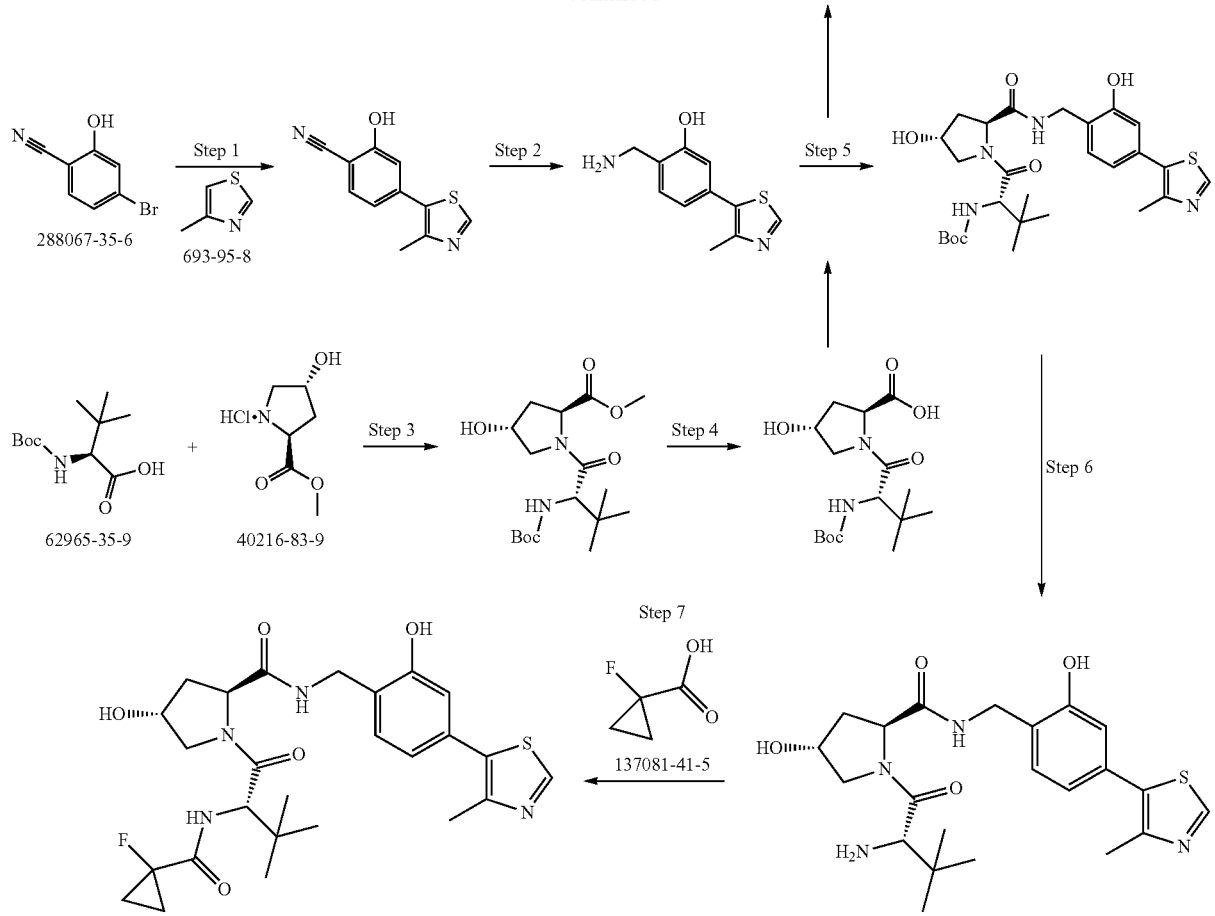

Step 1: 2-Hydroxy-4-(4-methyl-1,3-thiazol-5-yl)benzonitrile

A solution of 4-bromo-2-hydroxybenzonitrile (25.0 g, 126 mmol), 4-methylthiazole (25.0 g, 253 mmol, 2.0 eq) and anhydrous KOAc (24.78 g, 252.5 mmol) in DMF (210.42 mL, 0.6 M) was barbotated with argon on ultra-sonic bath for 10 min. Thereafter Pd(OAc)$_2$ (0.567 g, 2.52 mmol) was added. The resulting mixture was stirred at 110° C. for 5 h under argon, while adding three times an additional amount of Pd(OAc)$_2$ (0.283 g, 1.26 mmol) each hour to the total amount of Pd(OAc)$_2$ (1.417 g, 6.31 mmol). The reaction mixture was cooled down to rt, filtered through Celite, diluted with water and extracted with ethyl acetate. The combined organic layers were washed with brine, dried over anhydrous sodium sulfate and concentrated under reduced pressure. The residue was purified by silica gel column chromatography (DCM/MeOH) to provide 2-hydroxy-4-(4-methyl-1,3-thiazol-5-yl)benzonitrile (17.6 g, 65%) as a yellow solid. LCMS: $C_{11}H_8N_2OS$ requires: 216.3, found: m/z=217.5 [M+H]$^+$ $^1$H NMR (300 MHz, DMSO-d$_6$) δ 11.36 (s, 1H), 9.08 (s, 1H), 7.71 (d, J=8.1 Hz, 1H), 7.14 (d, J=1.6 Hz, 1H), 7.08 (dd, J=8.0, 1.7 Hz, 1H), 2.50 (s, 3H).

Step 2: 2-(Aminomethyl)-5-(4-methyl-1,3-thiazol-5-yl)phenol

To a solution of LAH 1M in THF (203.9 mL, 203.9 mmol) a solution of 2-hydroxy-4-(4-methyl-1,3-thiazol-5-yl)benzonitrile (17.64 g, 81.57 mmol) in THF (203.92 mL, 0.4 M) was added slowly under argon at −10° C. After the complete addition the reaction mixture was allowed slowly to the rt over 5 hours. The reaction was quenched by addition of Na$_2$SO$_4$·10H$_2$O and concentrated under reduced pressure. The residue was purified by silica gel column chromatography (DCM/MeOH) to provide 2-(aminomethyl)-5-(4-methyl-1,3-thiazol-5-yl)phenol (9.18 g, 52%) as an amber oil. LCMS: $C_{11}H_{12}N_2OS$ requires: 220.3, found: m/z=221.5 [M+H]$^+$ $^1$H NMR (300 MHz, DMSO-d$_6$) δ 8.96 (s, 1H), 7.23-7.15 (m, 1H), 6.87-6.81 (m, 2H), 3.88 (s, 2H), 2.45 (s, 3H).

Step 3: Methyl (2S,4R)-1-[(2S)-2-{[(tert-butoxy)carbonyl]amino}-3,3-dimethylbutanoyl]-4-hydroxy-pyrrolidine-2-carboxylate To the solution of methyl (2S)-2-{[(tert-butoxy)carbonyl]amino}-3,3-dimethylbutanoic acid (41.0 g, 0.177 mol) and DIPEA (46.3 mL, 0.266 mol) in anh THF (1770 mL, 0.1 M) HATU (70.8 g, 0.186 mol) was added as a solid in portions at 10° C. to form activated ester within 30 min. In the separate reactor the solution of (2S,4R)-4-hydroxypyrrolidine-2-carboxylate hydrochloride (48.0 g, 1.266 mol) and DIPEA (46.3 mL, 0.266 mol, 1.5 eq) was prepared and cooled down to −45° C. under inert atmosphere. The solution of activated ester was added dropwise at −45 to −40° C. over 0.5 h and RM was left to slowly warm up to RT overnight. Water (~500 mL) was added in single portion to quench the reaction and volatiles were concentrated under vacuum. Oily residue was extracted with EtOAc (3×400 mL), washed with sat. aqueous NaHCO$_3$ (250 mL), 10% aqueous KHSO$_4$ (250 mL), brine (300 mL), dried over MgSO$_4$, filtered and evaporated to give a crude which was purified by FC. Concentration of corresponding fractions gave methyl (2S,4R)-1-[(2S)-2-{[(tert-butoxy)carbonyl]amino}-3,3-dimethylbutanoyl]-4-hydroxypyrrolidine-2-carboxylate as a pale yellow oil (64 g, 99%). LCMS: C$_{17}$H$_{30}$N$_2$O$_6$ requires: 358.4, found: m/z=359.3 [M+H]$^+$ $^1$H NMR (300 MHz, DMSO-d$_6$) δ 6.54 (d, J=9.3 Hz, 1H), 5.23 (d, J=3.8 Hz, 1H), 4.42-4.29 (m, 2H), 4.16 (d, J=9.4 Hz, 1H), 3.71-3.61 (m, 2H), 2.11 (dd, J=12.2, 9.2 Hz, 1H), 1.95-1.85 (m, 1H), 1.38 (s, 10H), 0.94 (s, 9H).

Step 4: (2S,4R)-1-[(2S)-2-{[(Tert-butoxy)carbonyl]amino}-3,3-dimethylbutanoyl]-4-hydroxypyrrolidine-2-carboxylic acid To the solution of methyl (2S,4R)-1-[(2S)-2-{[(tert-butoxy)carbonyl]amino}-3,3-dimethylbutanoyl]-4-hydroxypyrrolidine-2-carboxylate (63.5 g, 0.177 mol) in THF (220 mL, 0.8 M) the LiOH·H$_2$O (14.9 g, 0.355 mol) was added as an aqueous solution (86 mL, 0.2 M) at once at RT. The RM was left to stir at rt for 3 h and monitored by TLC/UPLC. Once reaction was completed, 10% aqueous KHSO$_4$ was added until pH ~3. The THF was concentrated under reduced pressure and the residue was extracted with EtOAc (3×400 mL). Combined organic fractions were washed with 10% aqueous KHSO$_4$ (200 mL), brine (300 mL), dried over MgSO$_4$, filtered and evaporated to dryness. A viscous pale yellow oily residue was sonicated with anh. THF (300 ml) to give off-white precipitate, which was filtered and dried in vacuum at 50° C. yielding 69.6 g of (2S,4R)-1-[(2S)-2-{[(tert-butoxy)carbonyl]amino}-3,3-dimethylbutanoyl]-4-hydroxypyrrolidine-2-carboxylic acid (69.6 g, including THF ~15% by weight). LCMS: C$_{16}$H$_{28}$N$_2$O$_6$ requires: 344.4, found: m/z=345.2 [M+H]+

$^1$H NMR (300 MHz, DMSO-d$_6$) δ 12.43 (s, 1H), 6.49 (d, J=9.4 Hz, 1H), 5.18 (d, J=3.7 Hz, 1H), 4.33 (bs, 1H), 4.26 (t, J=8.4 Hz, 1H), 4.16 (d, J=9.4 Hz, 1H), 3.69-3.52 (m, 2H), 2.18-2.02 (m, 1H), 1.89 (ddd, J=13.2, 9.1, 4.6 Hz, 1H), 1.38 (s, 9H), 0.94 (s, 9H).

Step 5: tert-Butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate To a solution of (2S,4R)-1-[(2S)-2-{[(tert-butoxy)carbonyl]amino}-3,3-dimethylbutanoyl]-4-hydroxypyrrolidine-2-carboxylic acid (14.352 g, 41.67 mmol) in DMF (138.9 mL, 0.3 M) cooled with ice-water bath under argon were added DIPEA (10.89 mL, 62.5 mmol) and HATU (16.64 g, 43.8 mmol). The resulting mixture was allowed to the room temperature during 0.5 h and slowly added dropwise to a solution of 2-(aminomethyl)-5-(4-methyl-1,3-thiazol-5-yl)phenol (9.180 g, 41.7 mmol) and DIPEA (7.26 mL, 42.7 mmol) in DMF (83.3 mL, 0.5 M) at −40° C. under argon. After addition the reaction mixture was left in cooling bath to slowly allow to the room temperature over 5 hours. The reaction was quenched by addition of 5 mL of water and concentrated under reduced pressure. The residue was purified by silica gel flash chromatography (DCM/MeOH) to provide (2S,4R)-1-[(2S)-2-{[(tert-butoxy)carbonyl]amino}-3,3-dimethylbutanoyl]-4-hydroxypyrrolidine-2-carboxylic acid (13.4 g, 58%) as a yellowish solid. LCMS: C$_{27}$H$_{38}$N$_4$O$_6$S requires: 546.7, found: m/z=547.9 [M+H]$^+$.

After purification by flash chromatography was obtained also the double-acylated side product-2-({[(2S,4R)-1-[(2S)-2-{[(tert-butoxy)carbonyl]amino}-3,3-dimethylbutanoyl]-4-hydroxypyrrolidin-2-yl]formamido}methyl)-5-(4-methyl-1,3-thiazol-5-yl)phenyl (2S)-1-(2-{[(tert-butoxy)carbonyl]amino}-3,3-dimethylbutanoyl)pyrrolidine-2-carboxylate. The acyl group can be cleaved according to Step 5a.

$^1$H NMR (300 MHz, Chloroform-d) δ 9.28 (br s, 1H), 8.70 (s, 1H), 8.11 (t, J=6.6 Hz, 1H), 7.13 (d, J=7.8 Hz, 1H), 6.98 (d, J=1.8 Hz, 1H), 6.88 (dd, J=7.7, 1.8 Hz, 1H), 5.19 (d, J=8.9 Hz, 1H), 4.77 (t, J=7.9 Hz, 1H), 4.51 (dd, J=15.0, 6.9 Hz, 2H), 4.12 (td, J=20.4, 8.4 Hz, 3H), 3.57 (dd, J=11.4, 3.6 Hz, 1H), 2.85 (br s, 2H), 2.53 (m, 4H), 2.11 (dd, J=13.5, 8.1 Hz, 1H), 1.56-1.43 (m, 2H), 1.41 (s, 9H), 0.84 (s, 9H).

Step 5a: tert-Butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate To a solution of the 2-({[(2S,4R)-1-[(2S)-2-{[(tert-butoxy)carbonyl]amino}-3,3-dimethylbutanoyl]-4-hydroxypyrrolidin-2-yl]formamido}methyl)-5-(4-methyl-1,3-thiazol-5-yl)phenyl (2S)-1-(2-{[(tert-butoxy)carbonyl]amino}-3,3-dimethylbutanoyl)pyrrolidine-2-carboxylate (3.0 g, 3.5 mmol) in MeOH (70 mL, 0.05 M) was added K$_2$CO$_3$ (0.48 g, 3.5 mmol). The reaction mixture was left to stir at rt for 12 h. The reaction mixture was concentrated, the residue diluted with water, neutralized with KHSO$_4$ and extracted with DCM (×3 times), obtained organic layer were dried under Na$_2$SO$_4$, concentrated under reduced pressure. The obtained residue was purified by silica gel flash chromatography (5% DCM/MeOH) to provide tert-butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate (2.14 g, 99%) as a yellowish solid. LCMS: C$_{27}$H$_{38}$N$_4$O$_6$S requires: 546.7, found: m/z=547.2 [M+H]$^+$ $^1$H NMR (300 MHz, Chloroform-d) δ 9.29 (s, 1H), 8.80 (s, 1H), 8.19 (s, 1H), 7.14 (d, J=7.8 Hz, 1H), 6.98 (d, J=1.8 Hz, 1H), 6.87 (dd, J=7.7, 1.8 Hz, 1H), 5.14 (d, J=8.9 Hz, 1H), 4.81 (t, J=7.9 Hz, 1H), 4.56 (q, J=7.8 Hz, 2H), 4.12 (td, J=13.6, 12.6, 4.7 Hz, 3H), 3.56 (dd, J=11.4, 3.5 Hz, 1H), 2.56 (s, 4H), 2.19-2.05 (m, 1H), 0.83 (s, 10H).

Step 6: (2S,4R)-1-[(2S)-2-Amino-3,3-dimethylbutanoyl]-4-hydroxy-N-{[2-hydroxy-4-(4-methyl-1,3-thiazol-5-yl)phenyl]methyl}pyrrolidine-2-carboxamide To a solution of tert-butyl N-[(2S)-1-[(2S,4R)-4-hydroxy-2-({[2-hydroxy-4-(4-methyl-1,3-thiazol-5-yl)phenyl]methyl}carbamoyl)pyrrolidin-1-yl]-3,3-dimethyl-1-oxobutan-2-yl]carbamate (5.27 g, 9.64 mmol) in DCM (48.2 mL, 0.2 M) cooled with ice-water bath was added 2M HCl in Et$_2$O (38.56 mL, 77.12 mmol). The reaction mixture was stirred at room temperature for 2 hours. The solid was triturated on ultra-sonic bath, filtered off, washed on the filter with DCM and dried under vacuum to provide (2S,4R)-1-[(2S)-2-amino-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, 99%) as a white solid. LCMS: C$_{22}$H$_{30}$N$_4$O$_4$S requires: 446.6, found: m/z=447.7 [M+H]$^+$ $^1$H NMR (300 MHz, D2O) δ 9.50 (d, J=1.0 Hz, 1H), 7.30 (d, J=7.8 Hz, 1H), 7.04-6.89 (m, 2H), 4.58 (dd, J=9.9, 7.6 Hz, 1H), 4.52 (s, 1H), 4.44-4.23 (m, 2H), 4.08 (s, 1H), 3.80 (d, J=11.9 Hz, 1H), 3.68 (dd, J=11.9, 3.4 Hz, 1H), 3.46 (q, J=7.1 Hz, 1H), 2.45 (s, 3H), 2.28 (dd, J=13.9, 7.7 Hz, 1H), 2.01 (ddd, J=14.0, 9.9, 4.2 Hz, 1H), 1.08 (t, J=7.1 Hz, 2H), 0.98 (s, 9H).

Step 7: (2S,4R)-1-[(2S)-2-[(1-Fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide To a solution of 1-fluorocyclopropane-1-carboxylic acid (1.337 g, 12.85 mmol) in DMF (128 mL, 0.1 M) cooled with ice-water bath were added HATU (5.129 g, 13.49 mmol) and DIPEA (3.36 mL, 19.3 mmol). The resulting mixture was allowed to the room temperature during 0.5 h and then added dropwise to the solution of (2S,4R)-1-[(2S)-2-amino-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, quant. yield) (6.674 g, 12.85 mmol) and DIPEA (7.83 mL, 45.0 mmol) in DMF (42 mL, 0.3 M) at −40° C. After addition the reaction mixture was left in cooling bath to slowly allow to the room temperature over 16 hours. The reaction was then diluted with water and extracted with ethyl acetate. The combined organic layers were washed with brine, dried over anhydrous sodium sulfate and concentrated under reduced pressure. The residue was purified by silica gel column chromatography (DCM/MeOH) to provide (2S, 4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (5.05 g, 74%) as a yellow solid. LCMS: $C_{26}H_{33}N_4O_5SF$ requires: 532.6, found: m/z=533.8 [M+H]$^+$ $^1$H NMR (300 MHz, Chloroform-d) δ 9.29 (s, 1H), 8.70 (s, 1H), 8.09 (dd, J=7.5, 5.5 Hz, 1H), 7.13 (d, J=7.8 Hz, 1H), 7.01 (dd, J=8.5, 3.7 Hz, 1H), 6.98 (d, J=1.8 Hz, 1H), 6.88 (dd, J=7.7, 1.8 Hz, 1H), 4.73 (t, J=7.9 Hz, 1H), 4.53 (br s, 1H), 4.51-4.40 (m, 2H), 4.18 (dd, J=14.6, 5.4 Hz, 1H), 3.99 (d, J=11.3 Hz, 1H), 3.63 (dd, J=11.2, 3.7 Hz, 1H), 2.53 (s, 3H), 2.47 (ddd, J=12.9, 7.9, 4.6 Hz, 1H), 2.15-2.01 (m, 1H), 1.36-1.22 (m, 4H), 0.91 (s, 9H).

Described below are additional examples of VHL-targeting LHM building blocks that may be prepared according to Reaction Scheme B4.

Intermediate 16: 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoic acid

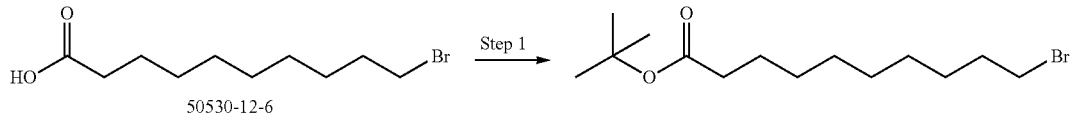

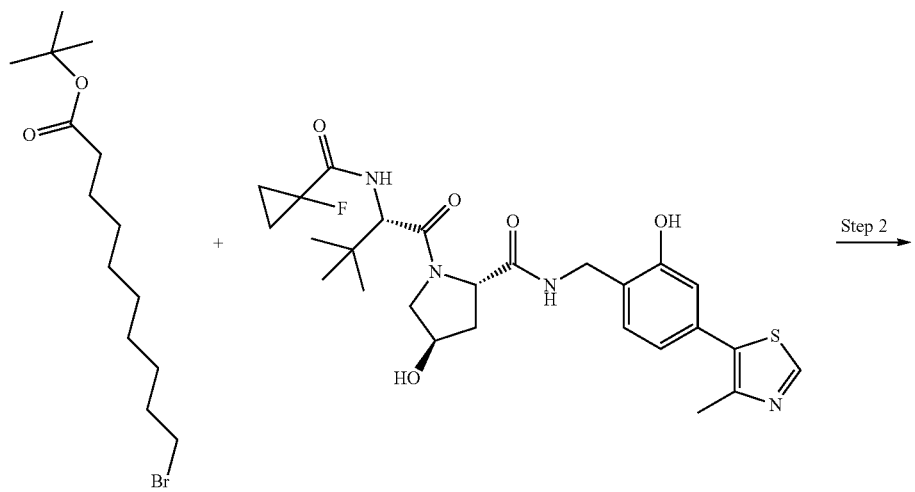

-continued

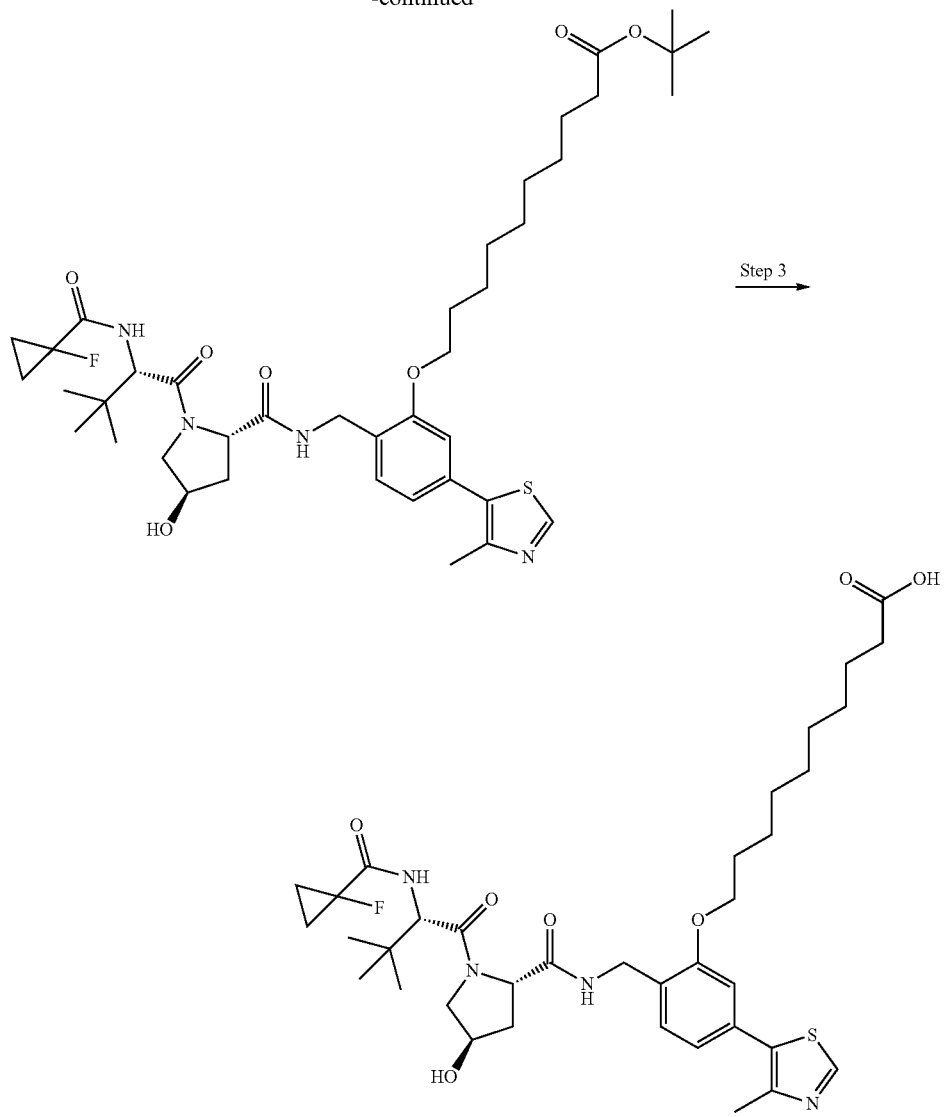

Step 1: tert-butyl 10-bromodecanoate

To solution of 10-bromodecanoic acid (CAS: 50530-12-6, 10.0 g, 39.8 mmol, 1.0 eq) in anh. dichloromethane (0.25 M) was added tert-butyl alcohol (18.9 mL, 199 mmol, 5.0 eq) followed by DMAP (0.96 g, 4.0 mmol, 0.1 equiv) at 0° C. under nitrogen. After 5 min, dicyclohexylcarbodiimide (9.04 g, 44 mmol, 1.1 equiv) was added to this solution at 0° C. The reaction mixture was allowed to warm to room temperature and stirred for 20 h. The volatiles were concentrated and the crude residue was directly loaded onto silica (5-10% EtOAc in hexane). The title compound has been isolated (9.0 g) contaminated with DCC as an impurity. The additional purification was performed by FC (eluent: 10-50% DCM in hexane) to give 5.8 g of tert-butyl 10-bromodecanoate as an colorless oil (47% yield).

$^1$H NMR (300 MHz, Chloroform-d) δ 3.42 (t, J=6.9 Hz, 2H), 2.22 (t, J=7.5 Hz, 2H), 1.87 (p, J=6.9 Hz, 2H), 1.68-1.51 (m, 2H), 1.46 (s, 9H), 1.45-1.37 (m, 2H), 1.31 (s, 8H).

Step 2: tert-butyl 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoate To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (0.8 g, 1.5 mmol, 1.0 eq) in anh. DMF (15 mL, 0.1 M) were added Cs$_2$CO$_3$ (0.734 g, 2.25 mmol, 1.5 eq) and tert-butyl 10-bromodecanoate (0.646 g, 2.10 mmol, 1.4 eq). The reaction mixture was purged with argon, sealed and stirred at 25° C. for 16 hours. The solids were filtered, washed with EtOAc (5 mL) and discarded. Obtained filtrate was diluted with water (60 mL) and extracted with ethyl acetate (3×20 mL). The combined organic layers were washed with brine (20 mL), dried over Na$_2$SO$_4$, filtered and concentrated under reduced pressure to give crude which was by flash chromatography (hexane/ethyl acetate) to give 0.99 g of the title compound as a white solid (87% yield). ESI(+)[M+H]$^+$=782.4

$^1$H NMR (300 MHz, Chloroform-d) δ 8.70 (s, 1H), 7.34 (d, J=7.7 Hz, 1H), 7.25 (t, J=5.9 Hz, 1H), 7.05 (dd, J=8.7, 3.6 Hz, 1H), 6.96 (dd, J=7.6, 1.6 Hz, 1H), 6.89 (d, J=1.6 Hz, 1H), 4.76 (t, J=7.7 Hz, 1H), 4.61-4.49 (m, 3H), 4.44 (dd, J=14.8, 5.4 Hz, 1H), 4.09-3.97 (m, 3H), 3.64 (dd, J=11.3, 3.9 Hz, 1H), 2.65-2.56 (m, 1H), 2.55 (s, 3H), 2.22 (t, J=7.5 Hz, 2H), 2.15 (d, J=2.6 Hz, 1H), 1.87 (p, J=6.6 Hz, 2H), 1.59 (t, J=7.1 Hz, 2H), 1.52 (m, 2H), 1.46 (s, 9H), 1.43-1.32 (m, 10H), 0.96 (s, 9H).

Step 3: 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoic acid To a solution of tert-butyl 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoate (0.993 g, 1.31 mmol, 1.0 eq) in anh. DCM (6.5 mL, 0.2 M) was added TFA (2.00 mL, 26.17 mmol, 20 eq). The reaction was stirred at 25° C. for 3 hours. The reaction was evaporated in vacuo and the resulting oil was treated with aq ammonia (20%, 5 mL). Agitation for 1 hour resulted in formation of an oil. The supernatant was decanted. The oil was dried in vacuo and purified using reverse-phase flash chromatography (20% to 60% acetonitrile/0.1% aqueous solution of formic acid) to give 0.703 g of title compound as a white solid (77% yield). LCMS (254 nm): RT=3.037 min, 100% purity, ESI(+)[M+H]$^+$=703.2

$^1$H NMR (300 MHz, DMSO-d$_6$) δ 12.00 (s, 1H), 8.99 (s, 1H), 8.51 (t, J=5.9 Hz, 1H), 7.41 (d, J=7.8 Hz, 1H), 7.31 (dd, J=9.3, 2.9 Hz, 1H), 7.01 (d, J=1.7 Hz, 1H), 6.96 (dd, J=7.7, 1.6 Hz, 1H), 5.19 (s, 1H), 4.66-4.57 (m, 1H), 4.53 (t, J=8.2 Hz, 1H), 4.36 (s, 1H), 4.25 (qd, J=16.7, 5.9 Hz, 2H), 4.05 (t, J=6.3 Hz, 2H), 3.73-3.56 (m, 2H), 2.47 (s, 3H), 2.19 (t, J=7.3 Hz, 2H), 2.15-2.09 (m, 1H), 1.93 (ddd, J=13.0, 8.9, 4.5 Hz, 1H), 1.76 (p, J=6.4 Hz, 2H), 1.57-1.38 (m, 6H), 1.38-1.15 (m, 12H), 0.97 (s, 9H).

Intermediate 17: 3-{2-[2-({[(2S,4R)-1-[(2S)-2-[(1-fluorocyclopropyl)formamido]-3-methylbutanoyl]-4-hydroxypyrrolidin-2-yl]formamido}methyl)-5-(4-methyl-1,3-thiazol-5-yl)phenoxy]ethoxy}propanoic acid

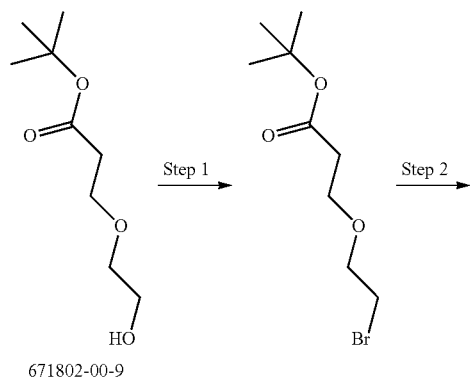

671802-00-9

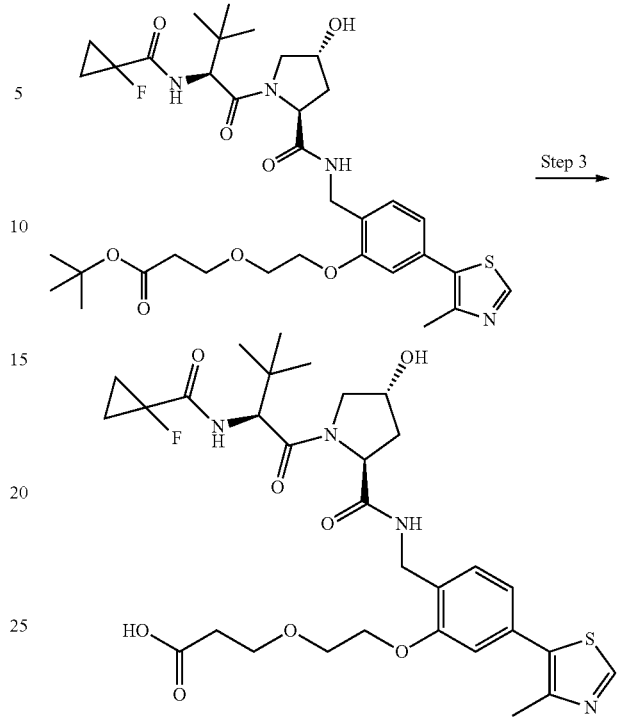

Step 1: tert-butyl 3-(2-bromoethoxy)propanoate

A solution of tert-butyl 3-(2-hydroxyethoxy)propanoate (3.0 g, 16 mmol, 1 eq) and carbon tetrabromide (7.8 g, 24 mmol, 1.5 eq) in dichloromethane (15 mL) was prepared in a 50 mL flask and cooled to 0° C. Triphenyl phosphine (6.2 g, 24 mmol, 1.5 eq) was added via powder funnel in portions over 30 minutes with vigorous stirring. Upon addition of the phosphine, the colorless solution turned a pale brown color and was stirred for an additional 2 h at room temperature. The mixture was concentrated and quickly added to stirring hexane (50 mL). The white precipitate was filtered, the remaining solution was concentrated, obtained residue was purified by FC (eluted DCM/MeOH-9/1 to give 4.1 g of the title compound (yield 62%).

Step 2: tert-butyl 3-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}propanoate To a solution (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (1.5 g, 2.82 mmol, 1.0 eq) in DMF (18.77 mL, 0.15 M) were added Cs$_2$CO$_3$ (1.376 g, 4.22 mmol, 1.5 eq) and tert-butyl 3-(2-bromoethoxy)propanoate (2.18 g, 3.94 mmol, 1.4 eq). The resulting mixture was stirred at room temperature for overnight. The reaction mixture was diluted with water and extracted with EtOAc (3×), organic layers were dried over Na$_2$SO$_4$, concentrated, the resulting residue was purified by FC, eluted with DCM/MeOH-9/1 to give 1.8 g of the title compound as a pale yellow oil (quantitative yield). UPLC (12 min, 254 nm): RT=6.25 min, 100% purity, ESI[M$^+$H$^+$]+=705.6

Step 3: 3-{2-[2-({[(2S,4R)-1-[(2S)-2-[(1-fluorocyclopropyl)formamido]-3-methylbutanoyl]-4-hydroxypyrrolidin-2-yl]formamido}methyl)-5-(4-methyl-1,3-thiazol-5-yl)phenoxy]ethoxy}propanoic acid To a solution of tert-butyl 3-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}propanoate (1.8 g, 2.64 mmol, 1 eq) in DCM (17.6 mL, 0.15 M) at 0° C. was added dropwise TFA (13.2 mL, 0.2 M). The reaction mixture was left to stir at RT for 1 h. The reaction mixture was concentrated, the residue was diluted with 50 mL of aq $NH_4OH$ (till pH=11), left in ultrasonic bath for 0.5 h and then for 1 h just by stirring. The resulting slurry was concentrated and purified by RF twice: First, eluted with $ACN/H_2O$ to give 0.3 g of the title compound; second time, eluted with $ACN/H_2O$ (0.1% formic acid) to give 1 g of the title compound.

After neutralization with $NH_4OH$ the product has been got in form ammonium salt, which was released with formic acid during the second purification. All amount was combined to give 1.3 g of the title compound (yield 76%). LCMS (254 nm): RT=2.29 min, 99% purity, ESI(+)[M+H]$^+$=649.1.

$^1$H NMR (300 MHz, Chloroform-d) δ 8.70 (s, 1H), 7.37 (d, J=7.8 Hz, 2H), 7.09-7.03 (m, 1H), 6.99 (dd, J=7.7, 1.6 Hz, 1H), 6.91 (d, J=1.6 Hz, 1H), 4.76 (t, J=8.1 Hz, 1H), 4.64-4.51 (m, 3H), 4.41 (dd, J=14.3, 5.2 Hz, 1H), 4.20 (t, J=4.2 Hz, 2H), 4.03 (d, J=11.3 Hz, 1H), 3.89 (td, J=8.6, 7.8, 4.4 Hz, 4H), 3.77 (dd, J=11.3, 3.7 Hz, 1H), 2.66 (ddd, J=19.7, 14.9, 5.1 Hz, 2H), 2.54 (s, 3H), 2.33-2.14 (m, 2H), 1.41-1.23 (m, 4H), 1.03 (s, 9H).

Intermediate 18: 1-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)ethoxy}ethoxy)ethoxy]propanoic acid Intermediate 18 was prepared in an analogous manner as Intermediate 17 by substituting tert-butyl 3-(2-hydroxyethoxy)propanoate for tert-butyl 3-{2-[2-(2-bromoethoxy)ethoxy]ethoxy}propanoate in Step 1 to obtain the title compound as a white solid. LCMS (254 nm): RT=2.27 min, 96.35% purity, ESI[M+H]$^+$=736.88.

$^1$H NMR (300 MHz, DMSO-d$_6$) δ 8.98 (s, 1H), 8.51 (t, J=6.0 Hz, 1H), 7.41 (d, J=7.8 Hz, 1H), 7.31 (dd, J=9.2, 2.9 Hz, 1H), 7.04 (d, J=1.7 Hz, 1H), 6.97 (dd, J=7.7, 1.6 Hz, 1H), 5.19 (s, 1H), 4.60 (d, J=9.1 Hz, 1H), 4.51 (t, J=8.2 Hz, 1H), 4.35 (s, 1H), 4.28 (d, J=6.1 Hz, 1H), 4.25-4.14 (m, 3H), 3.79 (dd, J=5.8, 3.4 Hz, 2H), 3.66-3.46 (m, 12H), 2.46 (s, 3H), 2.42 (t, J=6.3 Hz, 2H), 2.10 (dd, J=13.0, 8.0 Hz, 1H), 1.92 (ddd, J=13.1, 9.0, 4.4 Hz, 1H), 1.49-1.28 (m, 2H), 1.21 (tq, J=8.4, 4.6, 3.8 Hz, 2H), 0.96 (s, 9H).

C. General Schemes for Coupling the HPK1 Binder and LHM Building Blocks

The following General Methods A-F illustrate the bond formations by which the building blocks may be coupled to afford the compounds of Formula (I) or Formula (II), and their respective substructures.

General Procedure A: SNAR Attachment to Harness

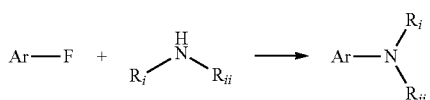

Substituted anilines were prepared as follows. To a solution of primary or secondary amine (1 eq.) and DIPEA (4.0 eq.) in NMP (0.4M) was added aryl fluoride (1 eq.). The reaction mixture was stirred at 120° C. for 4 h. At this time, LCMS showed loss of starting material. The reaction mixture was cooled to rt and water (half the volume of NMP) was added. This crude mixture was injected directly onto reverse-phase ISCO and purified via Chromatography C to provide the desired product.

General Procedure B: BOC Deprotection (and t-Butyl Ester Hydrolysis)

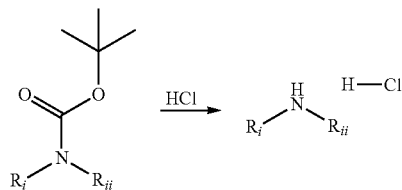

tert-Butyl carbamates were deprotected following the General Procedure to generate primary and secondary amines; tert-butyl esters were deprotected following the General Procedure to generate carboxylic acids: To a stirred rt solution of tert-butyl carbamate (or tert-butyl ester) substrate (1 eq.) in DCM (0.23M) was added HCl (4N in dioxane, 18 eq.) dropwise. The reaction mixture was stirred for 16 hr. before being concentrated to dryness. The resulting product was then used without further purification unless otherwise noted.

General Procedure C: Ester Saponification

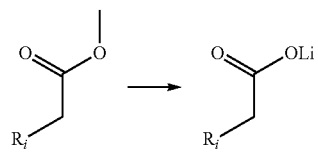

Methyl and ethyl ester saponification reactions were performed according to the following General Procedure: The ester starting material (1 eq.) was dissolved in THF (0.25M) at rt. To this solution was added lithium hydroxide (aqueous solution, 0.55M, 1.1 eq.) and the resulting mixture was stirred vigorously overnight. LCMS at this point showed loss of starting material, and the reaction was concentrated to dryness to provide the product as a lithium salt.

General Procedure D: Reductive Amination

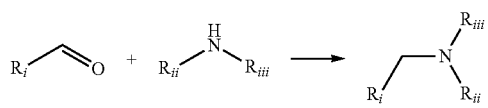

To a solution of aldehyde (1 eq.) and amine (1 eq.) in DCM (0.25M) was added STAB (3 eq.) and the reaction mixture was stirred at rt for 30 min to 24 hours, until LCMS shows conversion to the desired product. The reaction mixture was quenched by addition of saturated sodium bicarbonate. The reaction mixture was extracted with DCM (2×), and the combined organics were washed with brine, dried over anhydrous sodium sulfate, filtered, and concentrated in vacuo.

General Procedure E: Amine Alkylation

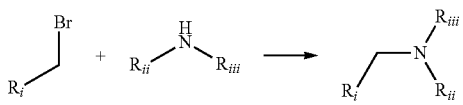

To a stirred solution of amine in DMF (0.2M) was added potassium carbonate (2 eq.) followed by dropwise addition of the alkyl bromide (1.1 eq., in a 0.57M DMF solution). The reaction mixture was stirred at RT overnight. The reaction mixture was diluted with DCM and the organic phase was washed water (2×), brine (1×), and dried over sodium sulfate before filtration and concentration in vacuo. The crude residue was purified by Chromatography B to afford the desired product.

General Procedure F: BOP Amide Coupling

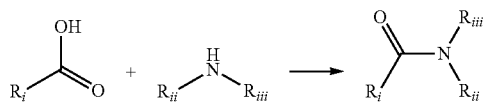

To a solution of acid in DMF (0.1M) was added amine (1 eq.) and DIPEA (5 eq.). BOP (1.3 eq.) was added last and the reaction mixture was let stir at rt for 16 h. The reaction mixture was diluted with DMF, filtered using syringe filter, and further purified by RP-HPLC to afford the desired product.

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an or branched saturated hydrocarbon chain containing no unsaturation. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH (CH$_3$)$_2$) and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkylene" or "alkylene chain" refers to a unbranched or branched divalent hydrocarbon chain, linking the rest of the molecule to a radical group, containing no unsaturation and having from 1 to 20 carbon atoms, or more typically 1 to 12 carbon atoms ($C_{1-12}$ alkylene), or 1 to 8 carbon atoms ($C_{1-8}$ alkylene), or 1 to 3 carbon atoms ($C_{1-3}$ alkylene) e.g., methylene, ethylene, propylene, n-butylene, and the like. The alkylene chain may be attached to the rest of the molecule and to the radical group through one carbon within the chain or through any two carbons within the chain.

"Alkenyl" refers to an alkyl group containing at least one carbon-carbon double bond and having from 2 to 20 carbon atoms (i.e., $C_{2-20}$ alkenyl), or more typically 2 to 12 carbon atoms (i.e., $C_{2-12}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkenylene" and "alkenylene chain" refer to a unbranched or branched divalent hydrocarbon chain linking the rest of the molecule to a radical group, containing at least one double bond and having from 2 to 20 carbon atoms, or more typically 2 to 12 carbon atoms, or 2 to 8 carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

"Alkynyl" refers to an alkyl group containing at least one carbon-carbon triple bond and having from 2 to 20 carbon atoms (i.e., $C_{2-20}$ alkynyl), or more typically 2 to 12 carbon atoms (i.e., $C_{2-12}$ alkynyl), or more typically 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkynylene" and "alkynylene chain" refer to a unbranched or branched divalent hydrocarbon chain linking the rest of the molecule to a radical group, containing at least one triple bond and having from 2 to 20 carbon atoms, or more typically 2 to 12 carbon atoms, or 2 to 8 carbon atoms. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S-".

"Amino" refers to the group —NR$^y$R$^y$ wherein each R$^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 15 carbon ring atoms (i.e., $C_{6-15}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" or "carboxylic acid" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond). As used herein, cycloalkyl has from 3 to 15 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, cyclohexyl, and bicyclo[2.2.2]octan-1-yl. Cycloalkyl may be attached to the remainder of a molecule by a single ring atom (e.g., as a substituent) or by two ring atoms (e.g., as a linker).

"Ethylene glycol unit" refers to a bivalent monomer having the structure of —CH$_2$CH$_2$O—, which may be repeated and extended into a longer chain. A linker segment may have up to 12 ethylene glycol units, or more typically up to 6 ethylene glycol units.

"Propylene glycol unit" refers to a bivalent monomer having the structure of —CH(CH$_3$)—CH$_2$O—, which may be repeated and extended into a longer chain. A linker segment may have up to 12 propylene glycol units, or more typically up to 6 propylene glycol units.

"Halogen" or "halo" includes fluoro, chloro, bromo, and iodo.

"Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatoms such as N, O, S, and the likes. The term "heteroalkyl" includes unbranched or branched saturated chain having carbon and heteroatoms. By way of example, 1, 2 or 3 carbon atoms may be independently replaced with the same or different heteroatoms. Heteroatomic groups include, but are not limited to, —N(R)—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to a 5-15 membered, or more typically, 5-12 membered aromatic group having a single ring, multiple rings, or multiple fused rings, with 1-3 ring heteroatoms independently selected from nitrogen, oxygen, and sulfur. As used herein, heteroaryl includes 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above. Heteroaryl may be attached to the remainder of a molecule by a single ring atom (e.g., as a substituent) or by two ring atoms (e.g., as a linker).

"Heterocyclyl" refers to a 3-15 membered, or more typically, 5-12 membered, saturated or unsaturated cyclic alkyl group, with 1-3 ring heteroatoms independently selected from nitrogen, oxygen and sulfur. The term "heterocyclyl" includes heterocycloalkenyl groups (i.e., the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 3 to 15 ring atoms (e.g., 3-15 membered heterocyclyl, 3-12 membered heterocyclyl, 4 to 10 membered heterocyclyl, 4-8 membered heterocyclyl or 4-6 membered heterocyclyl; having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, heterocyclyl may include a bridged structure (i.e., "bridged heterocyclyl), in which a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiroheterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group. Heteroaryl may be attached to the remainder of a molecule by a single ring atom (e.g., as a substituent) or by two ring atoms (e.g., as a linker).

"Fused" refers to a ring which is joint to an adjacent ring and share two adjacent ring atoms that form a covalent bond.

"Bridged" refers to a ring fusion wherein non-adjacent atoms on a ring are joined by a divalent substituent, such as alkylenyl group, an alkylenyl group containing one or two heteroatoms, or a single heteroatom. Quinuclidinyl and admantanyl are examples of bridged ring systems.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group —$NO_2$.

"Imino" refers to a group that contains a C=N double bond, such as C=N—$R^y$, or =N—C(O)$R^y$, wherein $R^y$ is selected from the group consisting of hydrogen, alkyl, aryl, cyano, haloalkyl, or heteroaryl; each of which may be optionally substituted. Imino may be a linker segment by attaching to the remainder molecule at the carbon and nitrogen respectively.

"Sulfonyl" refers to the group —S(O)$_2$R, where R is a substituent, or a defined group.

"Alkylsulfonyl" refers to the group —S(O)$_2$R, where R is a substituent, or a defined group.

"Alkylsulfinyl" refers to the group —S(O)R, where R is a substituent, or a defined group.

"Thiocyanate"-SCN.

"Thiol" refers to the group —SR, where R is a substituent, or a defined group.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g., arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl) as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some compounds of Formula (I) or Formula (II) may exist as a "stereoisomer" or a mixture of stereoisomers. Stereoisomer refers to a compound made up of the same atoms bonded by the same bonds but having different three-dimensional structures, which are not interchangeable. The compounds of the disclosure, or their pharmaceutically acceptable salts may contain one or more asymmetric centers and may thus give rise to enantiomers (two stereoisomers whose molecules are non-superimposable mirror images of one another), diastereomers, and other stereoisomeric forms that may be defined, in terms of absolute stereochemistry, as (R)- or (S)-. The present disclosure is meant to include all such possible isomers, as well as their racemic mixture (i.e., equal amounts of (R) and (S) enantiomers) and optically pure forms. Optically active (+) and (−), (R)- and (S)-isomers may be prepared using chiral synthons or chiral reagents, or resolved using conventional techniques, such as HPLC using a chiral column.

The disclosure also includes "deuterated analogues" of compounds of Formula (I) or Formula (II) in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula (I) or Formula (II) when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula (I) or Formula (II).

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, or solvates of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical uses.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN$(substituted $alkyl)_2$), tri (substituted alkyl) amines (i.e., $N$(substituted $alkyl)_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN$(substituted $alkenyl)_2$), tri(substituted alkenyl) amines (i.e., $N$(substituted $alkenyl)_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2$(aryl), $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Targeted HPK1 Degradation

The compounds of the present disclosure are demonstrated by cell-based profiling to degrade HPK1.

HiBiT HPK1 Jurkat cell lines were used to evaluate the total protein levels of HPK1 in a robust human cellular high throughput format. The level of HPK1 remaining following treatment with HPK1 CTMs is reported as $D_{max}$ (maximum degradation) achieved at 24 hours when compared to vehicle treated controls. As further described in the Biological Example, the results indicate that HPK1 CTMs are able to degrade HPK1. These decreases were not a result of cytotoxicity measured by a parallel viability assessment (CTG). See also Table 1.

Pharmaceutical Composition and Use of the Bifunctional Compounds of Formulae (I) and (II)

The bifunctional compounds of Formula (I) or Formula (II) are demonstrated to degrade HPK1 and are therefore useful for treating disease indications or disorders involving the function of HPK1, such as signaling or scaffolding.

Various embodiments provide pharmaceutical compositions of a compound of Formula (I) or Formula (II), or any one of the substructures or specific compounds of Examples 1-97, and a pharmaceutically acceptable carrier.

Further embodiments provide methods for treating a disease or disorder associated with increased hematopoietic progenitor kinase 1 (HPK1) activity, for increasing T-cell activation, for treating cancer, for inhibiting the growth or proliferation of cancer cells, for treating or preventing a hepatitis B virus (HBV) infection, or for treating or preventing a human immunodeficiency virus (HIV) infection, the method comprising administering to a subject in need thereof a therapeutically effective amount of a compound of Formula (I) or Formula (II), any one of the substructures or compounds of Examples 1-97.

In more specific embodiments, cancer is selected from the group consisting of bladder cancer, breast cancer, colorectal cancer, gastric cancer, head and neck squamous cell carcinoma, Hodgkin lymphoma, Merkel-cell carcinoma, mesothelioma, melanoma, non-small cell lung cancer, lung cancer, ovarian cancer, pancreatic cancer, prostate cancer, renal cell carcinoma, small cell lung cancer, transitional cell carcinoma, and urothelial cancer.

In some embodiments, a compound of Formula (I) or Formula (II), or any one of the substructures or a compound of Examples 1-97 may be administered with a therapeutically effective amount of one or more additional therapeutic agents, or a pharmaceutically acceptable salt thereof.

In further embodiments, the one or more additional therapeutic agents is selected from the group consisting of: Inducible T-cell costimulator (ICOS) agonists, cytotoxic T-lymphocyte antigen 4 (CTLA-4)-blocking antibodies, PD1 and/or PD-L1 inhibitors, Cluster of Differentiation 47 (CD47) inhibitors, OX40 agonists, GITR agonists, CD27 agonists, CD28 agonists, CD40 agonists, CD137 agonists, Toll-like receptor 8 (TLR8) agonists, T cell immunoglobulin and mucin domain-3 (TIM-3) inhibitors, lymphocyte activation gene 3 (LAG-3) inhibitors, CEACAM1 inhibitors, T cell immunoreceptor with Ig and ITIM domains (TIGIT) inhibitors, V-domain immunoglobulin (Ig)-containing suppressor of T-cell activation (VISTA) inhibitors, anti-Killer IgG-like receptors (KIR) inhibitors, STING agonists, C-X-C chemokine receptor type 4 (CXCR-4) inhibitors, B7-H3 inhibitors, CD73 inhibitors, inhibitory RNA, IL2/15/17 fusion proteins, MKNK1/2 inhibitors, JAK inhibitors, and PI3K inhibitors, or a pharmaceutically acceptable salt of any of the foregoing, or any combinations thereof.

In more specific embodiments, the one or more additional therapeutic agents is selected from the group consisting of: rituxan, doxorubicin, gemcitabine, nivolumab, pembrolizumab, pidilizumab, PDR001, TSR-001, atezolizumab, durvalumab, avelumab, pidilizumab, TSR-042, BMS-986016, ruxolitinib, N-(cyanomethyl)-4-[2-(4-morpholinoanilino) pyrimidin-4-yl]benzamide, XL147, BKM120, GDC-0941, BAY80-6946, PX-866, CH5132799, XL756, BEZ235, and GDC-0980, wortmannin, LY294002, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, IPI-549, INCB050465, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2-(1-((9H-purin-6-yl)amino)ethyl)-3-(2,6-difluorophenyl)quinazolin-4 (3H)-one, (S)-4-amino-6-((1-(5-chloro-4-oxo-3-phenyl-3,4-dihydroquinazolin-2-yl)ethyl)amino)pyrimidine-5-carbonitrile, and ipilimumab, or a pharmaceutically acceptable salt of any of the foregoing, or any combinations thereof.

In more specific embodiments, wherein the one or more additional therapeutic agents is selected from the group consisting of idelalisib, tirabrutinib, momelotinib, and entospletinib, or a pharmaceutically acceptable salt of any of the foregoing, or any combinations thereof.

In further embodiments, the one or more additional therapeutic agents is selected from the group consisting of HBV combination drugs, HBV vaccines, HBV DNA polymerase inhibitors, immunomodulators, toll-like receptor (TLR) modulators, interferon alpha receptor ligands, hyaluronidase inhibitors, hepatitis b surface antigen (HBsAg) inhibitors, cytotoxic T-lymphocyte-associated protein 4 (ipi4) inhibitors, cyclophilin inhibitors, HBV viral entry inhibitors, antisense oligonucleotide targeting viral mRNA, short interfering RNAs (siRNA) and ddRNAi endonuclease modulators, ribonucelotide reductase inhibitors, HBV E antigen inhibitors, covalently closed circular DNA (cccDNA) inhibitors, farnesoid X receptor agonists, HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1 agonists, Bruton's tyrosine kinase (BTK) inhibitors, KDM inhibitors, HBV replication inhibitors, arginase inhibitors, and other HBV drugs, or a pharmaceutically acceptable salt of any of the foregoing, or any combinations thereof.

In more specific embodiments, the one or more additional therapeutic agents is selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b, Feron, interferon-alpha 2 (CJ), Bevac, Laferonum, Vipeg, Blauferon-B, Blauferon-A, Intermax Alpha, Realdiron, Lanstion, Pegaferon, PDferon-B, alfainterferona 2b, Kalferon, Pegnano, Feronsure, PegiHep, Optipeg A, Realfa 2B, Reliferon, peginterferon alfa-2b, Reaferon-EC, Proquiferon, Uniferon, Urifron, interferon alfa-2b, Anterferon, Shanferon, MOR-22, interleukin-2 (IL-2), recombinant human interleukin-2 (Shenzhen Neptunus), Layfferon, Ka Shu Ning, Shang Sheng Lei Tai, Intefen, Sinogen, Fukangtai, Alloferon and celmoleukin, or a pharmaceutically acceptable salt of any of the foregoing, or any combinations thereof.

In more specific embodiments, the one or more additional therapeutic agents is selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine, or a pharmaceutically acceptable salt of any of the foregoing, or any combinations thereof.

In more specific embodiments, the one or more additional therapeutic agents is selected from the group consisting of tenofovir alafenamide, tenofovir alafenamide fumarate, and tenofovir alafenamide hemifumarate, or a pharmaceutically acceptable salt of any of the foregoing, or any combinations thereof.

In further embodiments, the one or more additional therapeutic agents is selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MILK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In more specific embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir, tenofovir alafenamide, tenofovir alafenamide fumarate or tenofovir alafenamide hemifumarate, or a pharmaceutically acceptable salt of any of the foregoing, or any combinations thereof.

In more specific embodiments, the one or more additional therapeutic agents is selected from the group consisting of 4'-ethynyl-2-fluoro-2'-deoxyadenosine, bictegravir or a pharmaceutically acceptable salt thereof, tenofovir disoproxil, tenofovir disoproxil hemifumarate or tenofovir disoproxil fumarate, or a pharmaceutically acceptable salt of any of the foregoing, or any combinations thereof.

EXAMPLES

Purification Procedures

Preparative-scale HPLC was performed using columns such as SunFire Prep C18 OBD, XBridge Prep OBD C18 and Xbridge Shield RP18 OBD, using solvent systems such as (water-0.1% formic acid)/acetonitrile, (water-10 mmol/L NH₄HCO₃)/acetonitrile, or (water-10 mmol/L NH₄HCO₃)/acetonitrile. Chromatography A refers to purification over silica gel, typically in pre-packed cartridges, eluting with mixtures of EtOAc in hexanes or petroleum ether; Chromatography B refers to elution with mixtures of MeOH in DCM; Chromatography C refers to use of C18 reverse-phase silica gel, eluting with mixtures of acetonitrile in water. Compounds drawn without stereochemistry were tested as racemic or diasteromeric mixtures in the Biological Examples.

Abbreviations

Abbreviations used in the Examples include the following: BOP (Benzotriazol-1-yloxy)tris(dimethylamino)phosphonium hexafluorophosphate; HATU (N-[(Dimethylamino)-1H-1,2,3-triazolo-[4,5-b]pyridin-1-ylmethylene]-N-methylmethanaminium hexafluorophosphate N-oxide); DMSO (dimethyl sulfoxide); THE (tetrahydrofuran); EtOAc (ethyl acetate); ACN (acetonitrile); Et₂O (diethyl ether); DCM (dichloromethane); MeOH (methanol); EtOH (ethanol); DCE (1,2-dichloroethane); TEA (trimethylamine); DIPEA (N,N-Diisopropylethylamine); DMF (N,N-dimethylformamide); NMP (N-methyl-2-pyrrolidone); STAB (sodium triacetoxyborohydride); DMP (Dess-Martin periodinane); TFA (trifluoroacetic acid); rt or RT (room temperature); anh (anhydrous); eq. or equiv. (equivalent).

Example 1

5-((6-(1'-(10-((2-(2,6-dioxopiperidin-3-yl)-1,3-dioxoisoindolin-4-yl)amino)decanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

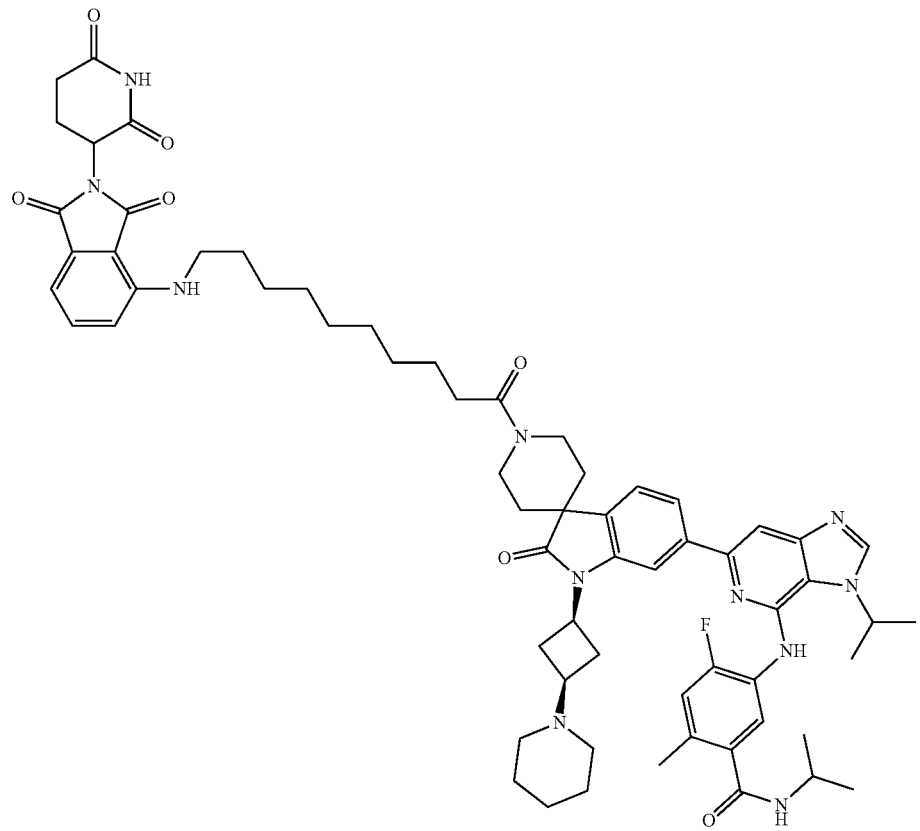 [SMILES: Cc1cc(F)c(Nc2nc(-c3ccc4c(c3)N([C@H]3C[C@@H](N5CCCCC5)C3)C(=O)C43CCN(C(=O)CCCCCCCCCNc4cccc5c4C(=O)N(C4CCC(=O)NC4=O)C5=O)CC3)cc3ncn(C(C)C)c23)cc1C(=O)NC(C)C]

The title compound was synthesized according to General Procedure F, using Intermediate 1 (10 mg), 10-{[2-(2,6-dioxopiperidin-3-yl)-1,3-dioxoisoindol-4-yl]amino}decanoic acid (6.3 mg) as starting materials. Crude material was purified by reverse phase HPLC to provide the title compound (4.0 mg, 24%); LCMS: $C_{64}H_{78}FN_{11}O_7$ requires 1132.4, found 1133.2 $[M+H]^+$.

Example 2

5-((6-(1'-(1-((2-(2,6-dioxopiperidin-3-yl)-1,3-dioxoisoindolin-4-yl)amino)-3,6,9,12-tetraoxapentadecan-15-oyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

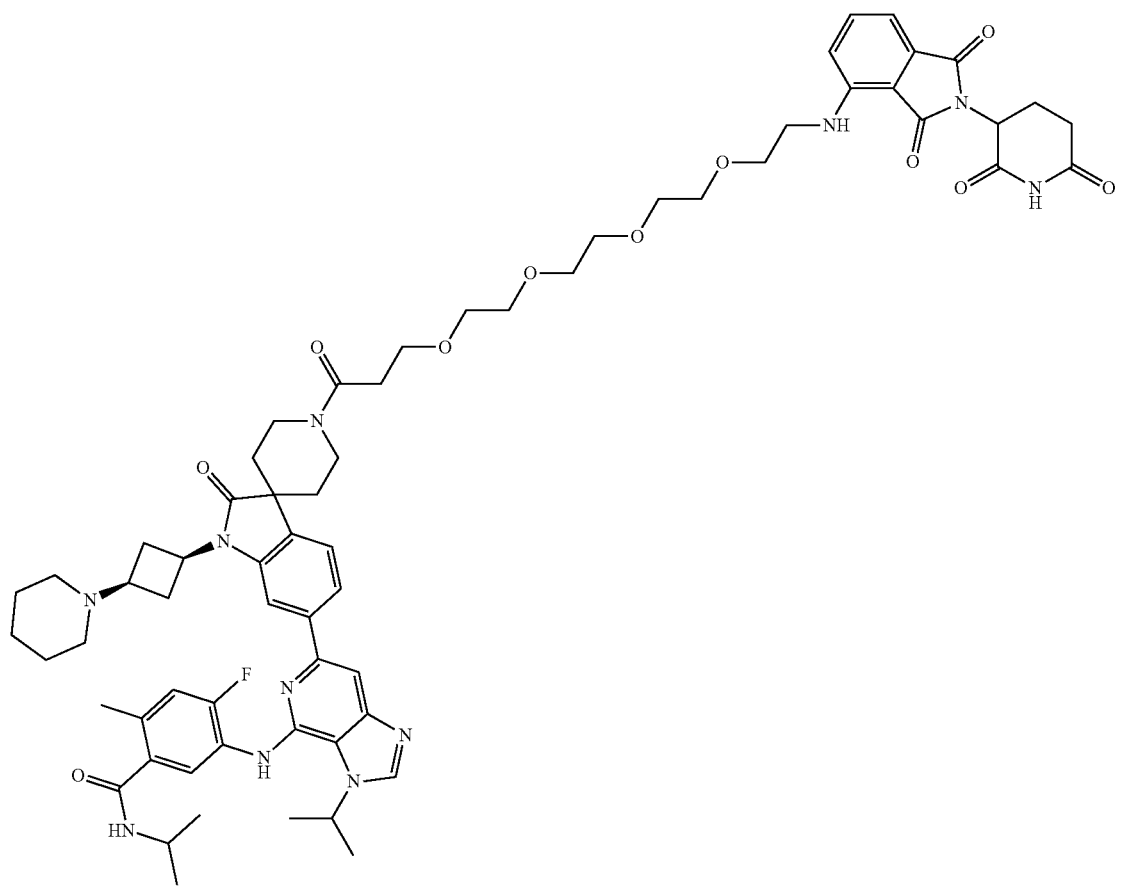 [SMILES: Cc1cc(F)c(Nc2nc(-c3ccc4c(c3)N([C@H]3C[C@@H](N5CCCCC5)C3)C(=O)C43CCN(C(=O)CCOCCOCCOCCOCCNc4cccc5c4C(=O)N(C4CCC(=O)NC4=O)C5=O)CC3)cc3ncn(C(C)C)c23)cc1C(=O)NC(C)C]

The title compound was synthesized according to General Procedure F, using Intermediate 1 (10 mg), 1-{[2-(2,6-dioxopiperidin-3-yl)-1,3-dioxoisoindol-4-yl]amino}-3,6,9,12-tetraoxapentadecan-15-oic acid (7.4 mg) as starting materials. Crude material was purified by reverse phase HPLC to provide the title compound (4.3 mg, 25%); LCMS: $C_{65}H_{80}FN_{11}O_{11}$ requires 1209.6, found 1233.1 $[M+Na]^+$.

Example 3

5-((6-(1'-(8-((2-(2,6-dioxopiperidin-3-yl)-1,3-dioxoisoindolin-5-yl)amino)octanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide The title compound was synthesized according to General Procedure F, using Intermediate 1 (10 mg), 8-{[2-(2,6-dioxopiperidin-3-yl)-1,3-dioxoisoindol-5-yl]amino}octanoic acid (5.9 mg, WO 2018089736 A1) as starting materials. Crude material was purified by reverse phase HPLC to provide the title compound (5.1 mg, 32%); LCMS: $C_{62}H_{74}FN_{11}O_7$ requires 1103.6, found 1105.3 [M+H]; $^1$H NMR (500 MHz, DMSO-$d_6$) δ 11.05 (s, 1H), 9.31 (d, J=9.3 Hz, 1H), 8.57 (s, 1H), 8.35 (s, 1H), 8.13 (d, J=7.9 Hz, 1H), 7.87 (s, 1H), 7.66 (d, J=7.7 Hz, 1H), 7.61 (d, J=8.3 Hz, 1H), 7.56 (d, J=8.4 Hz, 1H), 7.50 (d, J=9.7 Hz, 2H), 7.22-6.99 (m, 2H), 6.95 (s, 1H), 6.85 (d, J=8.6 Hz, 1H), 5.32-5.20 (m, 1H), 5.02 (dd, J=12.6, 5.3 Hz, 1H), 4.26-4.17 (m, 1H), 4.07-3.99 (m, 1H), 3.89-3.67 (m, 6H), 3.20-3.12 (m, 3H), 3.02-2.72 (m, 9H), 2.66-2.53 (m, 2H), 2.35 (s, 6H), 2.06-1.94 (m, 1H), 1.87-1.48 (m, 22H), 1.09 (d, J=6.6 Hz, 6H).

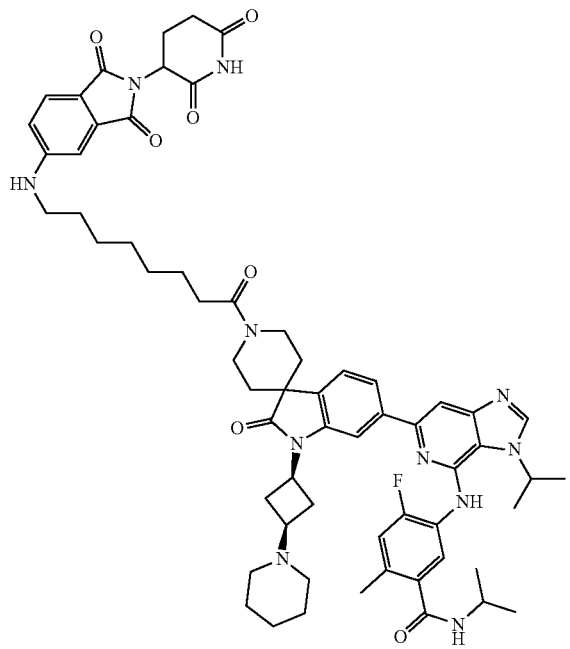 [SMILES: Cc1cc(F)c(Nc2nc(-c3ccc4c(c3)N([C@H]3C[C@@H](N5CCCCC5)C3)C(=O)C43CCN(C(=O)CCCCCCCNc4ccc5c(c4)C(=O)N(C4CCC(=O)NC4=O)C5=O)CC3)cc3ncn(C(C)C)c23)cc1C(=O)NC(C)C]

Example 4

5-((6-(1'-(10-((2-(2,6-dioxopiperidin-3-yl)-1,3-dioxoisoindolin-5-yl)amino)decanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

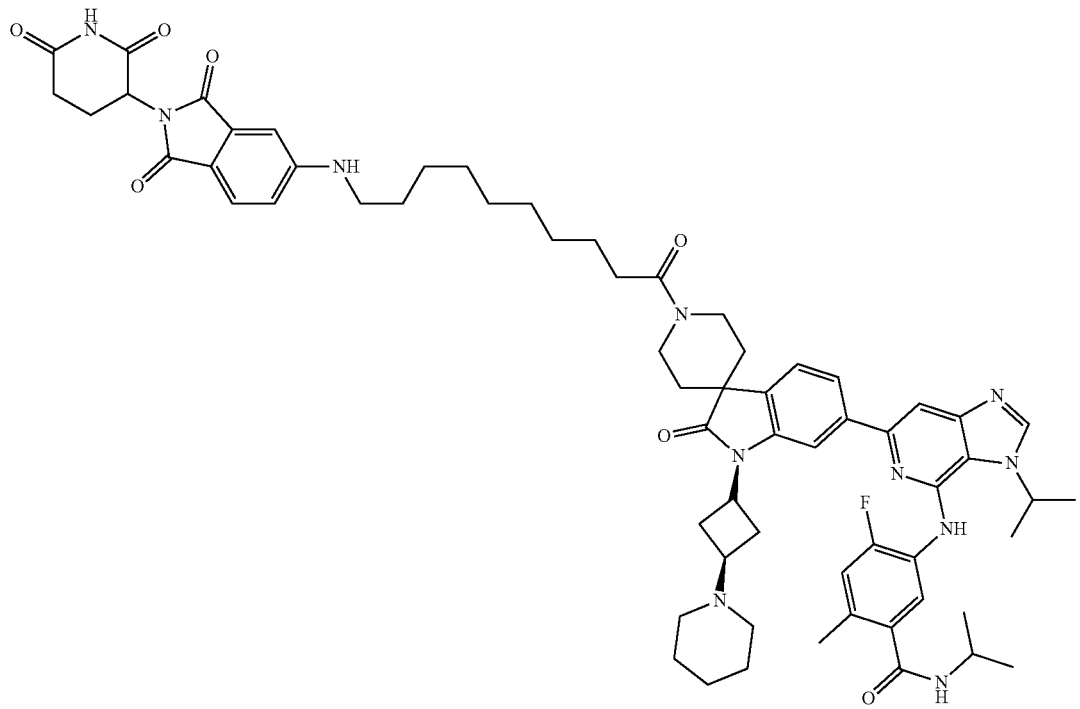

Step 1: Synthesis of benzyl 10-((2-(2,6-dioxopiperidin-3-yl)-1, 3-dioxoisoindolin-5-yl)amino)decanoate. The reaction was carried out according to General Procedure A using benzyl 10-aminodecanoate (11.0 g, 39.7 mmol) and 2-(2,6-dioxopiperidin-3-yl)-5-fluoro-2,3-dihydro-1H-isoindole-1,3-dione (9.86 g, 35.7 mmol) followed by Chromatography B to afford the title compound (4.8 g, 250%).

Step 2: Synthesis of 10-({2-[2,6-dioxopiperidin-3-yl]-1,3-dioxo-2,3-dihydro-1H-isoindol-5-yl}amino)decanoic acid. A mixture of benzyl 10-((2-(2,6-dioxopiperidin-3-yl)-1,3-dioxoisoindolin-5-yl)amino)decanoate (4.8 g, 9.0 mmol), HCl (2M in diethyl ether, 5.0 eq), and 10% Pd/C (20% by weight) in THF (0.03M) was stirred under a hydrogen balloon for 2 hr. After this time, the reaction was sparged with nitrogen for 15 min, before filtration over a pad of celite. The filter cake was then washed with a mixture of TFA:DCM (9:1) and the filtrate was concentrated under reduced pressure to afford the product (3.3 g, 830%).

Step 3: Synthesis of 5-((6-(1'-(10-((2-(2,6-dioxopiperidin-3-yl)-1,3-dioxoisoindolin-5-yl)amino)decanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (10 mg), 10-({2-[2,6-dioxopiperidin-3-yl]-1,3-dioxo-2,3-dihydro-1H-isoindol-5-yl}amino)decanoic acid (6.3 mg) as starting materials. Crude material was purified by reverse phase HPLC to provide the title compound (3.7 mg, 230%); LCMS: $C_{64}H_{78}FN_{11}O_7$ requires 1131.6, found 1132.9 [M+H]$^+$.

Example 5

5-((6-(1'-(3-(2-(2-(2-((2-(2,6-dioxopiperidin-3-yl)-1,3-dioxoisoindolin-5-yl)amino)ethoxy)ethoxy)ethoxy)propanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

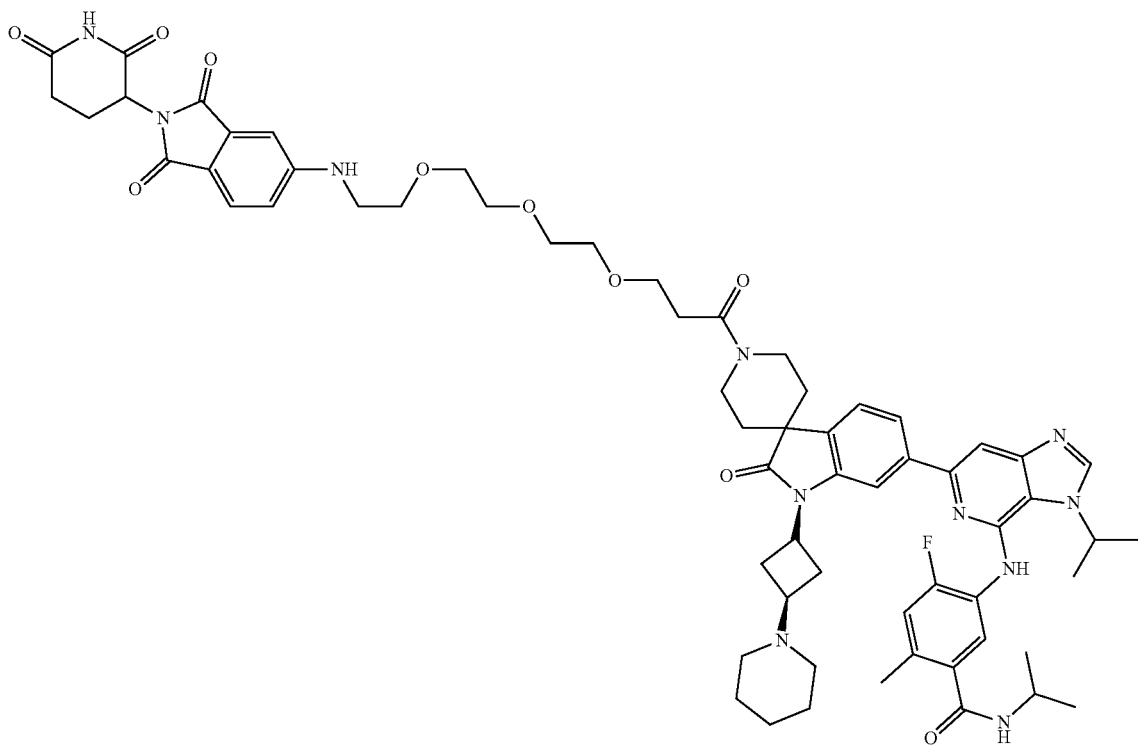

The title compound was synthesized according to General Procedure F, using Intermediate 1 (10 mg), 3-{2-[2-(2-{[2-(2,6-dioxopiperidin-3-yl)-1,3-dioxoisoindol-5-yl]amino}ethoxy)ethoxy]ethoxy}propanoic acid (6.8 mg, WO 2020038415 A1) as starting materials. Crude material was purified by reverse phase HPLC to provide the title compound (5.0 mg, 30%); LCMS: $C_{63}H_{76}FN_{11}O_{10}$ requires 1165.6, found 1167.3 $[M+H]^+$.

Example 6

(2S,4R)—N-(2-((10-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-10-oxodecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide

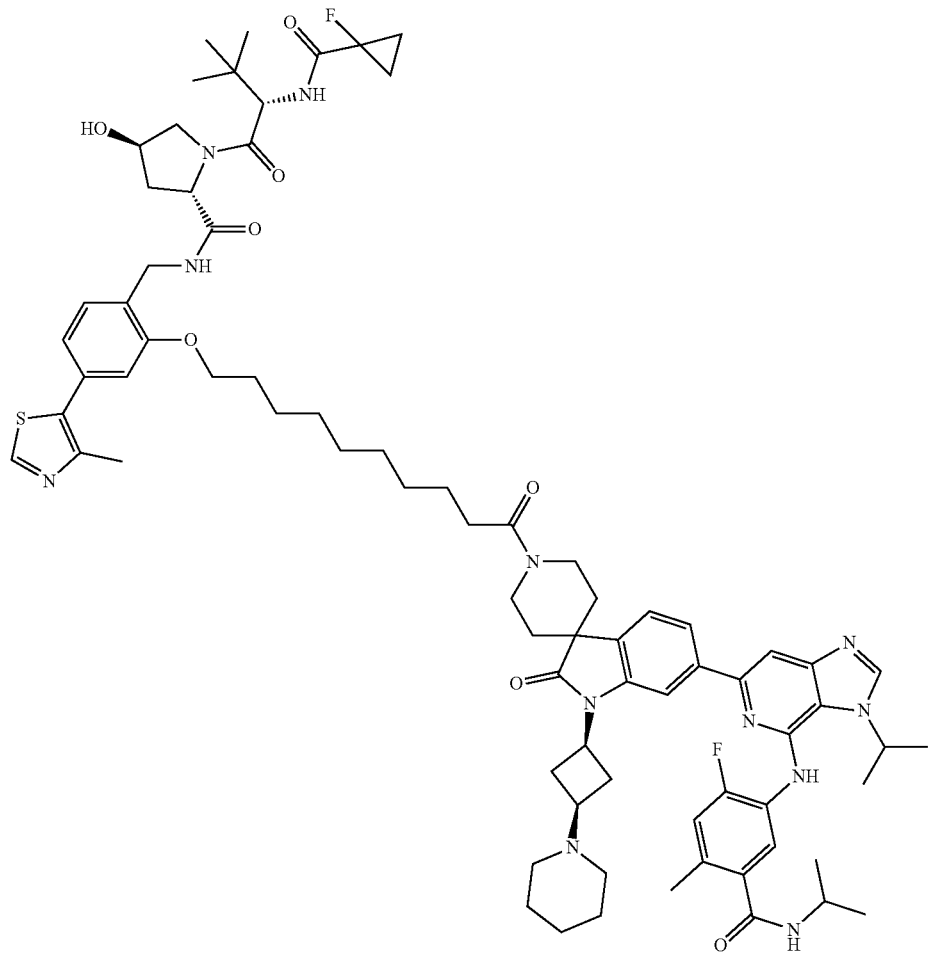 [SMILES: Cc1cc(F)c(Nc2nc(-c3ccc4c(c3)N([C@H]3C[C@@H](N5CCCCC5)C3)C(=O)C43CCN(C(=O)CCCCCCCCCOc4cc(-c5scnc5C)ccc4CNC(=O)[C@@H]4C[C@@H](O)CN4C(=O)[C@@H](NC(=O)C4(F)CC4)C(C)(C)C)CC3)cc3ncn(C(C)C)c23)cc1C(=O)NC(C)C]

Step 1: Synthesis of tert-butyl 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoate. To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (0.8 g, 1.5 mmol, 1.0 eq) in anh. DMF (15 mL, 0.1 M) were added $Cs_2CO_3$ (0.734 g, 2.25 mmol, 1.5 eq) and tert-butyl 10-bromodecanoate (0.646 g, 2.10 mmol, 1.4 eq). The reaction mixture was purged with argon, sealed and stirred at 25° C. for 16 hours. The solids were filtered, washed with EtOAc (5 mL) and discarded. Obtained filtrate was diluted with water (60 mL) and extracted with ethyl acetate (3×20 mL). The combined organic layers were washed with brine (20 mL), dried over $Na_2SO_4$, filtered and concentrated under reduced pressure to give crude which was by purified according to Chromatography A to give the title compound (0.99 g, 8700 yield).

Step 2: Synthesis of 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoic acid. To a solution of tert-butyl 10-[2-({[(2S,4R)-1-[(2S)-2-[(1-fluorocyclopropyl)formamido]-3, 3-dimethylbutanoyl]-4-hydroxypyrrolidin-2-yl]formamido}methyl)-5-(4-methyl-1,3-thiazol-5-yl) phenoxy]decanoate (0.993 g, 1.31 mmol, 1.0 eq) in anh. DCM (6.5 mL, 0.2 M) was added TFA (2.00 mL, 26.2 mmol, 20 eq). The reaction was stirred at 25° C. for 3 hours. The reaction was evaporated in vacuo and the resulting oil was treated with aq ammonia (20%, 5 mL). Agitation for 1 hour resulted in formation of an oil. The supernatant was decantated. The oil was dried in vacuo and purified using Chromatography C (20% to 60% acetonitrile/0.1% aqueous solution of formic acid) to give the title compound as a solid (0.703 g, 76% yield).

Step 3: Synthesis of (2S,4R)—N-(2-((10-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-10-oxodecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide.
The title compound was synthesized according to General Procedure F, using Intermediate 1 (11 mg), 10-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]decanoic acid (11 mg) as starting materials. Crude material was purified by reverse phase HPLC to provide the title compound (3.6 mg, 16%); LCMS: $C_{77}H_{100}F_2N_{12}O_8S$ requires 1390.7, found 1393.2 $[M+H]^+$.

Example 7

(2S,4R)-1-((S)-2-(7-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-7-oxoheptanamido)-3,3-dimethylbutanoyl)-4-hydroxy-N—((S)-1-(4-(4-methylthiazol-5-yl)phenyl)ethyl)pyrrolidine-2-carboxamide

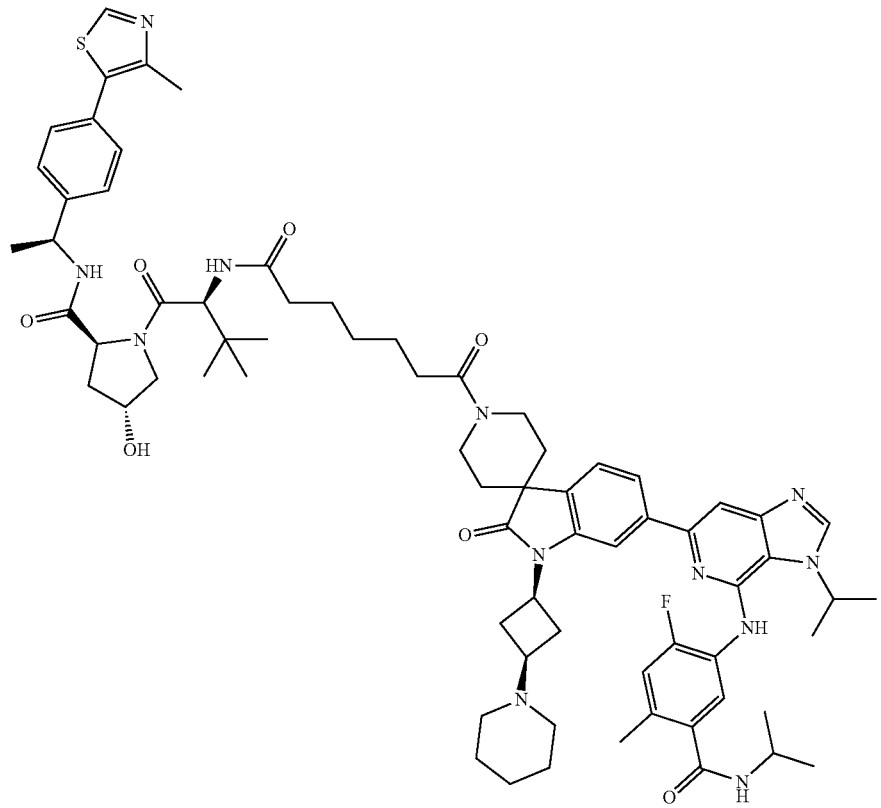 [SMILES: Cc1cc(F)c(Nc2nc(-c3ccc4c(c3)N([C@H]3C[C@@H](N5CCCCC5)C3)C(=O)C43CCN(C(=O)CCCCCC(=O)N[C@H](C(=O)N4C[C@H](O)C[C@H]4C(=O)N[C@@H](C)c4ccc(-c5scnc5C)cc4)C(C)(C)C)CC3)cc3ncn(C(C)C)c23)cc1C(=O)NC(C)C]

The title compound was synthesized according to General Procedure F, using Intermediate 1 (11 mg), 6-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}hexanoic acid (8.9 mg) as starting materials. Crude material was purified by reverse phase HPLC to provide the title compound (5.2 mg, 28%); LCMS: $C_{71}H_{91}FN_{12}O_7S$ requires 1274.7, found 1277.3 $[M+2H]^+$.

Example 8

(2S,4R)-1-((S)-2-(11-(6-(4-((2-fluoro-5-(isopropyl-carbamoyl)-4-methylphenyl)amino)-3-isopropyl-3H-imidazo[4,5-c]pyridin-6-yl)-2-oxo-1-((1s,3s)-3-(pip-eridin-1-yl)cyclobutyl)spiro[indoline-3,4'-piperidin]-1'-yl)-11-oxoundecanamido)-3,3-dimethylbutanoyl)-4-hydroxy-N—((S)-1-(4-(4-methylthiazol-5-yl)phenyl)ethyl)pyrrolidine-2-carboxamide

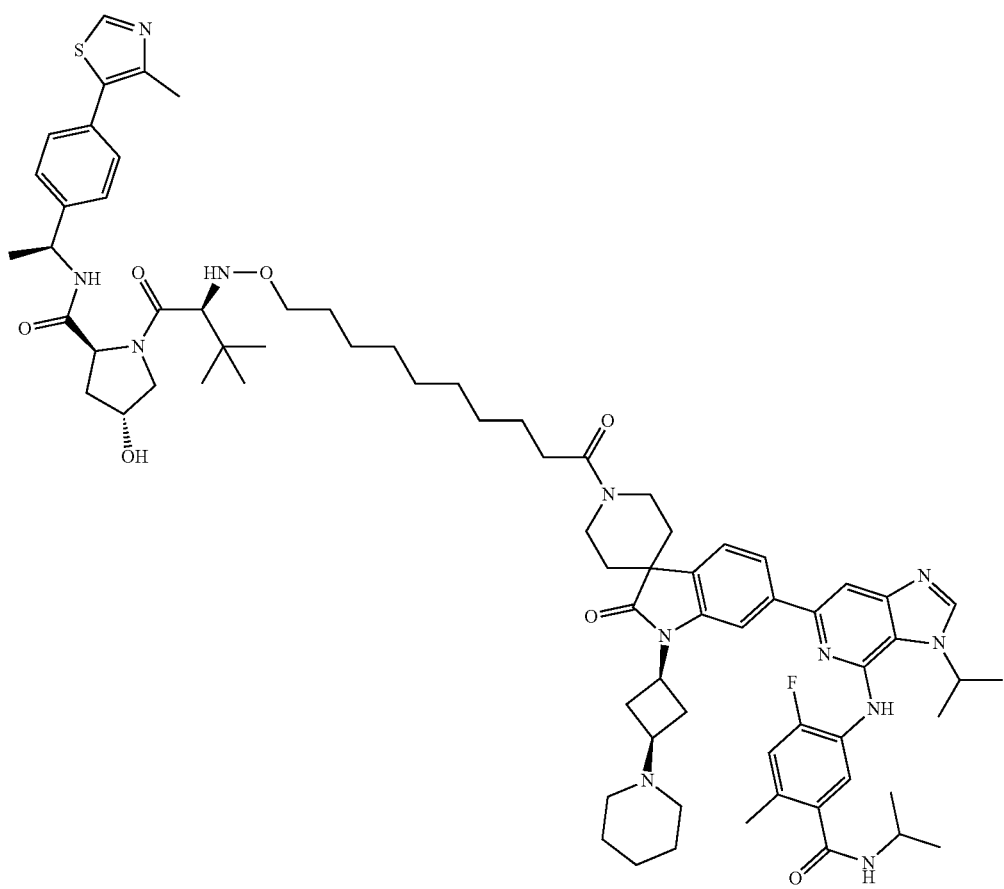 [SMILES: Cc1cc(F)c(Nc2nc(-c3ccc4c(c3)N([C@H]3C[C@@H](N5CCCCC5)C3)C(=O)C43CCN(C(=O)CCCCCCCCCON[C@H](C(=O)N4C[C@H](O)C[C@H]4C(=O)N[C@@H](C)c4ccc(-c5scnc5C)cc4)C(C)(C)C)CC3)cc3ncn(C(C)C)c23)cc1C(=O)NC(C)C]

The title compound was synthesized according to General Procedure F, using Intermediate 1 (11 mg), 10-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}decanoic acid (9.5 mg, WO 2019207538 A1) as starting materials. Crude material was purified by reverse phase HPLC to provide the title compound (5.6 mg, 28%); LCMS: $C_{75}H_{99}FN_{12}O_7S$ requires 1330.7, found 1333.3 $[M+2H]^+$.

Example 9

(2S,4R)—N-(2-(2-(2-(2-(3-(6-(4-((2-fluoro-5-(iso-propylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropoxy)ethoxy)ethoxy)ethoxy)-4-(4-methylthiazol-5-yl)benzyl)-1-((S)-2-(1-Fluorocyclopropane-1-carboxamido)-3,3-dimethylbutanoyl)-4-hydroxypyrrolidine-2-carboxamide

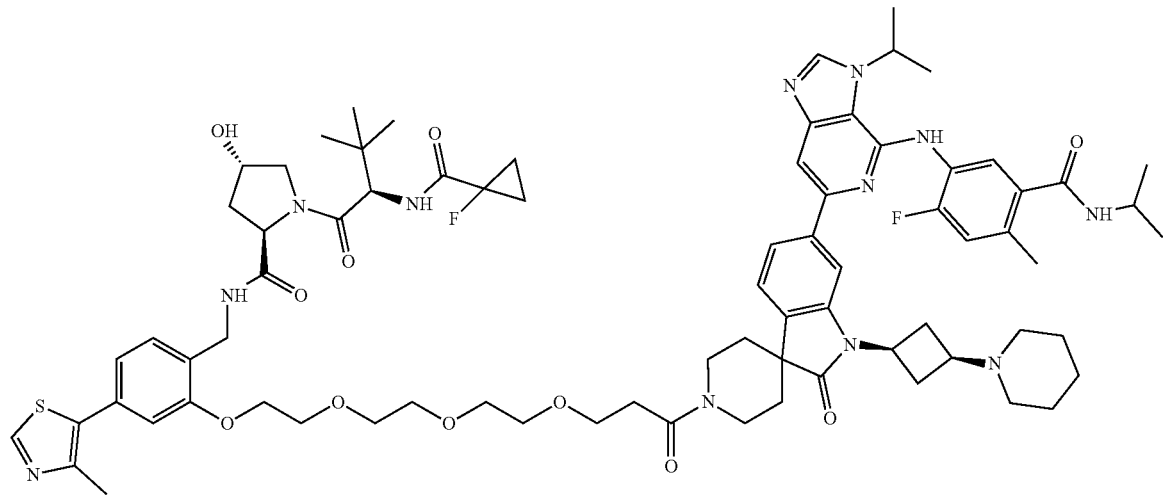 [SMILES: Cc1cc(F)c(Nc2nc(-c3ccc4c(c3)N([C@H]3C[C@@H](N5CCCCC5)C3)C(=O)C43CCN(C(=O)CCOCCOCCOCCOc4cc(-c5scnc5C)ccc4CNC(=O)[C@H]4C[C@H](O)CN4C(=O)[C@H](NC(=O)C4(F)CC4)C(C)(C)C)CC3)cc3ncn(C(C)C)c23)cc1C(=O)NC(C)C]

Step 1: Synthesis of tert-butyl 3-[2-(2-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}ethoxy)ethoxy]propanoate. To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (0.7 g, 1.31 mmol, 1.0 eq) in anh. DMF (13 mL, 0.1 M) were added $Cs_2CO_3$ (0.642 g, 1.97 mmol, 1.5 eq) and tert-butyl 3-{2-[2-(2-bromoethoxy)ethoxy]ethoxy}propanoate (0.897 g, 2.63 mmol, 2.0 eq). The reaction mixture was purged with argon and stirred at 25° C. for 16 hours. The solids were filtered, washed with EtOAc (5 mL) and discarded. Obtained filtrate was diluted with water (60 mL) and extracted with ethyl acetate (3×20 mL). The combined organic layers were washed with brine (20 mL), dried over $Na_2SO_4$, filtered and concentrated under reduced pressure to give crude which was purified by flash chromatography to give the title compound as a white foam (0.63 g, 61% yield).

Step 2: Synthesis of 3-[2-(2-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}ethoxy)ethoxy]propanoic acid. To a solution of tert-butyl 3-[2-(2-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}ethoxy)ethoxy]propanoate (0.63 g, 1.3 mmol, 1.0 eq) in anh. DCM (6.5 mL, 0.2 M) was added TFA (1.81 g, 15.9 mmol, 20 eq). The reaction was stirred at 25° C. for 2 hours. The reaction was evaporated in vacuo and the resulting oil was treated with aq ammonia (20%, 5 mL). Stirring for 1 hour resulted in formation of an oil. The supernatant was decantated and the oil was dried in vacuo and purified using Chromatography C (20% to 60% acetonitrile/0.1% aqueous solution of formic acid) to give of title compound as a white solid (0.502 g, 87% yield).

Step 3: Synthesis of (2S,4R)—N-(2-(2-(2-(2-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropoxy)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide. The title compound was synthesized according to General Procedure F, using Intermediate 1 (15 mg), 3-[2-(2-{2-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]ethoxy}ethoxy)ethoxy]propanoic acid (15 mg) as starting materials. Crude material was purified by reverse phase HPLC to provide the title compound (8.3 mg, 29%); LCMS: $C_{76}H_{98}F_2N_{12}O_{11}S$ requires 1424.7, found 1425.1 $[M+H]^+$.

Example 10

(2S,4R)-1-((S)-2-(9-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-9-oxononanamido)-3,3-dimethylbutanoyl)-4-hydroxy-N—((S)-1-(4-(4-methylthiazol-5-yl)phenyl)ethyl)pyrrolidine-2-carboxamide

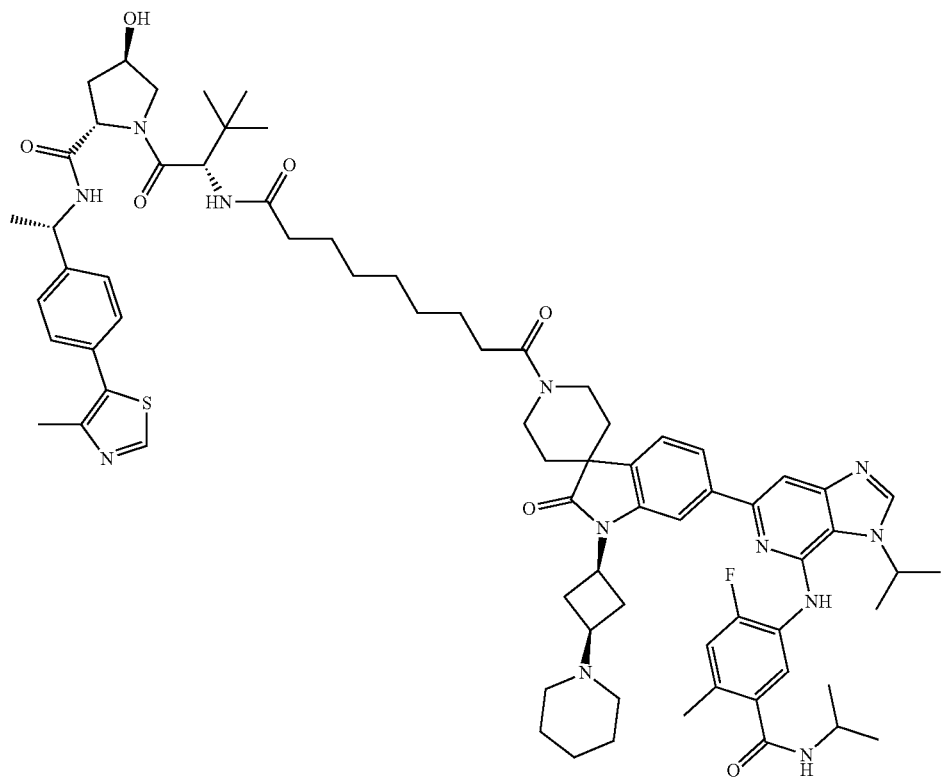 [SMILES: Cc1cc(F)c(Nc2nc(-c3ccc4c(c3)N([C@H]3C[C@@H](N5CCCCC5)C3)C(=O)C43CCN(C(=O)CCCCCCCC(=O)N[C@H](C(=O)N4C[C@H](O)C[C@H]4C(=O)N[C@@H](C)c4ccc(-c5scnc5C)cc4)C(C)(C)C)CC3)cc3ncn(C(C)C)c23)cc1C(=O)NC(C)C]

The title compound was synthesized according to General Procedure F, using Intermediate 1 (13 mg), 9-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-9-oxononanoic acid (11 mg, WO 2019207538 A1) as starting materials. Crude material was purified by reverse phase HPLC to provide the title compound (11.9 mg, 50%); LCMS: $C_{73}H_{95}FN_{12}O_7S$ requires 1302.7, found 1303.9 [M+H]$^+$. $^1$H NMR (500 MHz, DMSO-d$_6$) δ 9.36 (d, J=9.9 Hz, 1H), 8.98 (s, 1H), 8.70 (s, 1H), 8.41 (s, 1H), 8.37 (d, J=7.8 Hz, 1H), 8.14 (d, J=7.8 Hz, 1H), 7.87 (s, 1H), 7.78 (d, J=9.3 Hz, 1H), 7.66 (d, J=7.9 Hz, 1H), 7.60 (d, J=8.2 Hz, 1H), 7.51 (d, J=8.4 Hz, 2H), 7.46-7.42 (m, 2H), 7.42-7.33 (m, 2H), 7.18 (d, J=12.1 Hz, 1H), 5.30 (t, J=6.7 Hz, 1H), 4.92 (q, J=7.1 Hz, 1H), 4.54-3.32 (m, 13H), 3.04-2.71 (m, 6H), 2.45 (s, 3H), 2.36 (s, 5H), 2.26 (dt, J=14.7, 7.5 Hz, 1H), 2.12 (dt, J=14.1, 7.2 Hz, 1H), 2.01 (t, J=10.5 Hz, 1H), 1.91-1.20 (m, 31H), 1.09 (d, J=6.6 Hz, 6H), 0.94 (s, 9H).

Example 11

5-((6-(1'-(3-(2-((2-(2,6-dioxopiperidin-3-yl)-1,3-dioxoisoindolin-4-yl)amino)ethoxy)propanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

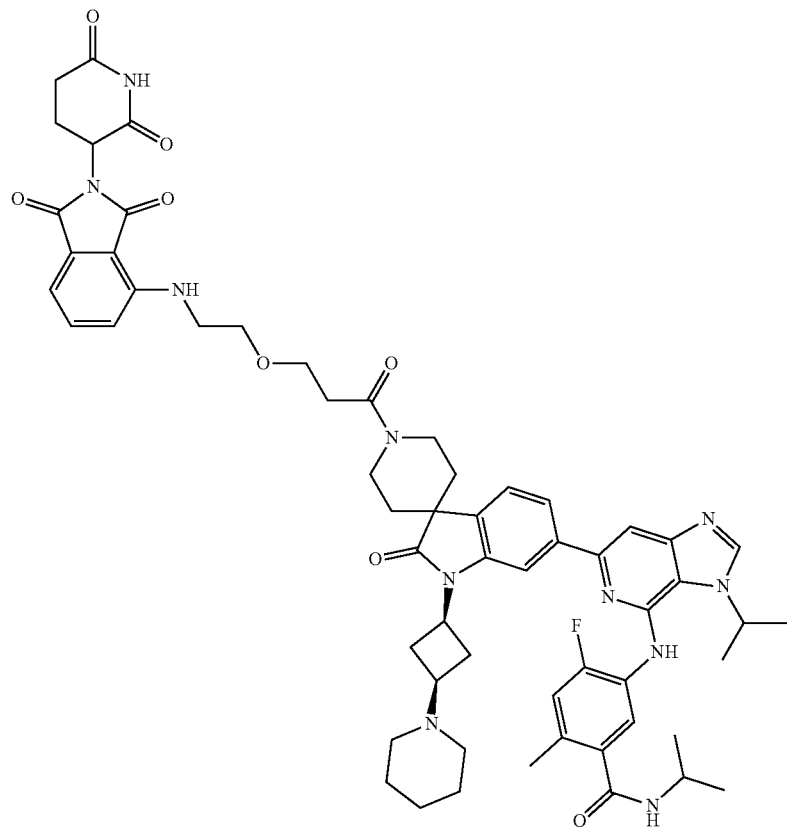 [SMILES: Cc1cc(F)c(Nc2nc(-c3ccc4c(c3)N([C@H]3C[C@@H](N5CCCCC5)C3)C(=O)C43CCN(C(=O)CCOCCNc4cccc5c4C(=O)N(C4CCC(=O)NC4=O)C5=O)CC3)cc3ncn(C(C)C)c23)cc1C(=O)NC(C)C]

The title compound was synthesized according to General Procedure F, using Intermediate 1 (15 mg), 3-(2-((2-(2,6-dioxopiperidin-3-yl)-1,3-dioxoisoindolin-4-yl)amino)ethoxy)propanoic acid (9 mg) as starting materials. Crude material was purified by reverse phase HPLC to provide the title compound (15.5 mg, 70%); LCMS: $C_{59}H_{68}FN_{11}O_8$ requires 1077.5, found 1078.9 [M+H]$^+$; $^1$H NMR (500 MHz, DMSO-$d_6$) δ 11.07 (s, 1H), 9.36 (d, J=9.1 Hz, 1H), 8.76 (s, 1H), 8.44 (s, 1H), 8.13 (d, J=7.8 Hz, 1H), 7.86 (s, 1H), 7.61 (dd, J=26.4, 7.9 Hz, 4H), 7.48 (d, J=8.8 Hz, 2H), 7.17 (t, J=10.9 Hz, 2H), 7.04 (d, J=7.0 Hz, 1H), 6.61 (s, 1H), 5.36-5.29 (m, 1H), 5.04 (dd, J=12.9, 5.4 Hz, 1H), 4.19 (dd, J=16.6, 8.4 Hz, 1H), 4.08-3.97 (m, 1H), 3.94-3.81 (m, 2H), 3.74 (t, J=6.7 Hz, 4H), 3.64 (t, J=5.4 Hz, 2H), 3.56-3.32 (m, 4H), 3.04-2.60 (m, 6H), 2.36 (s, 3H), 2.07-1.92 (m, 1H), 1.92-1.29 (m, 18H), 1.09 (d, J=6.5 Hz, 9H).

Example 12

5-((6-(1'-(1-((2-(2,6-dioxopiperidin-3-yl)-1,3-dioxoi-
soindolin-4-yl)amino)-3,6,9,12,15-pentaoxaoctade-
can-18-oyl)-2-oxo-1-((1s,3s)-3-(piperidin-1-yl)cy-
clobutyl)spiro[indoline-3,4'-piperidin]-6-yl)-3-
isopropyl-3H-imidazo[4,5-c]pyridin-4-yl)amino)-4-
fluoro-N-isopropyl-2-methylbenzamide

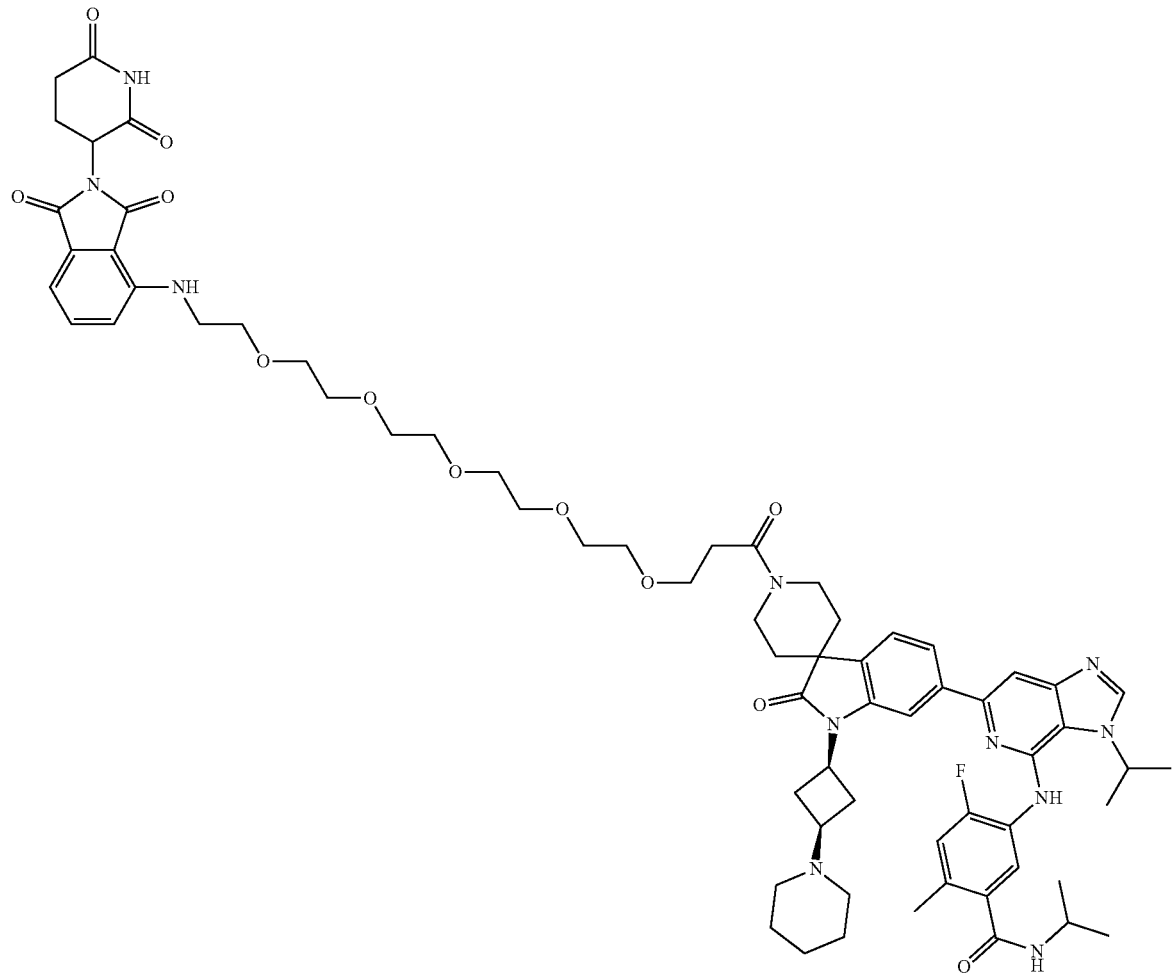 [SMILES: Cc1cc(F)c(Nc2nc(-c3ccc4c(c3)N([C@H]3C[C@@H](N5CCCCC5)C3)C(=O)C43CCN(C(=O)CCOCCOCCOCCOCCOCCNc4cccc5c4C(=O)N(C4CCC(=O)NC4=O)C5=O)CC3)cc3ncn(C(C)C)c23)cc1C(=O)NC(C)C]

The title compound was synthesized according to General Procedure F, using Intermediate 1 (15 mg), 1-((2-(2,6-dioxopiperidin-3-yl)-1,3-dioxoisoindolin-4-yl)amino)-3,6,9,12,15-pentaoxaoctadecan-18-oic acid (11 mg) as starting materials. Crude material was purified by reverse phase HPLC to provide the title compound (19 mg, 52%); LCMS: $C_{67}H_{84}FN_{11}O_{12}$ requires 1253.6, found 1255.0 [M+H]$^+$; $^1$H NMR (500 MHz, DMSO-d$_6$) δ 11.09 (s, 1H), 9.35 (s, 1H), 8.65 (d, J=10.3 Hz, 1H), 8.39 (s, 1H), 8.13 (d, J=7.8 Hz, 1H), 7.86 (s, 1H), 7.74-7.43 (m, 5H), 7.16 (dd, J=21.5, 10.4 Hz, 2H), 7.09-6.98 (m, 1H), 6.60 (s, 1H), 5.36-5.24 (m, 1H), 5.05 (dd, J=12.8, 5.5 Hz, 1H), 4.24-4.16 (m, 1H), 4.02 (dd, J=13.6, 6.8 Hz, 1H), 3.91-3.80 (m, 4H), 3.79-3.58 (m, 8H), 3.58-3.35 (m, 16H), 3.01-2.54 (m, 9H), 2.36 (s, 3H), 2.06-1.98 (m, 1H), 1.88-1.31 (m, 18H), 1.09 (d, J=6.5 Hz, 6H).

Example 13

(2S,4R)—N-(2-((8-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-8-oxooctyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide

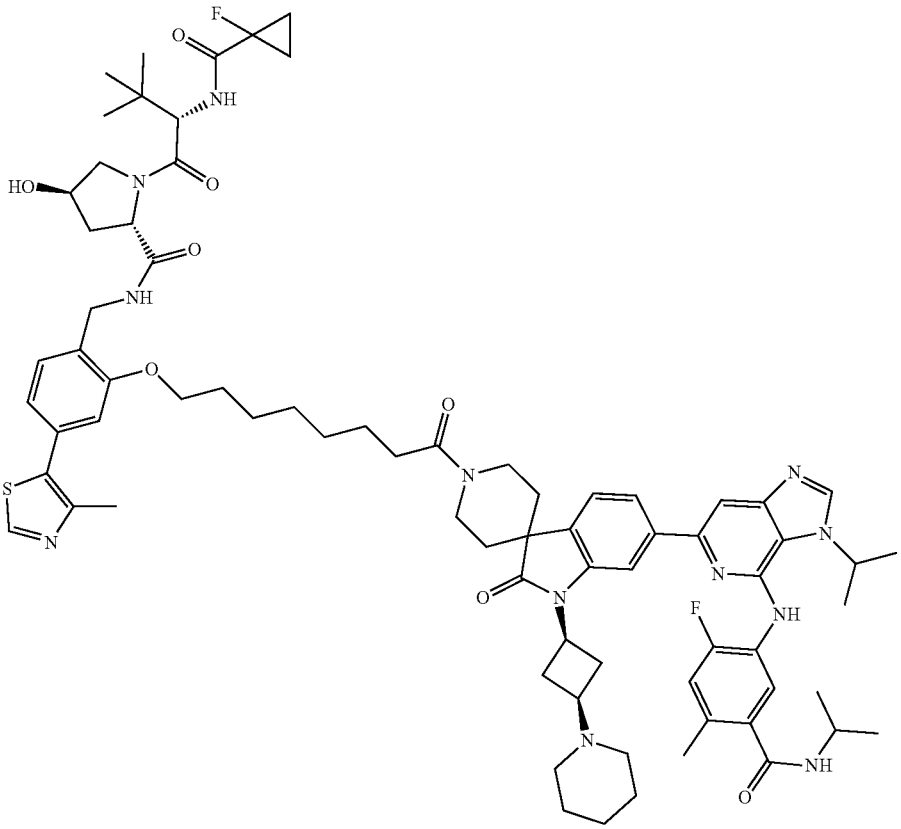 [SMILES: Cc1cc(F)c(Nc2nc(-c3ccc4c(c3)N([C@H]3C[C@@H](N5CCCCC5)C3)C(=O)C43CCN(C(=O)CCCCCCCOc4cc(-c5scnc5C)ccc4CNC(=O)[C@@H]4C[C@@H](O)CN4C(=O)[C@@H](NC(=O)C4(F)CC4)C(C)(C)C)CC3)cc3ncn(C(C)C)c23)cc1C(=O)NC(C)C]

Step 1: Synthesis of tert-butyl 8-[2-({[(2S,4R)-1-[(2S)-2-[(1-fluorocyclopropyl)formamido]-3,3-dimethyl butanoyl]-4-hydroxypyrrolidin-2-yl]formamido}methyl)-5-(4-methyl-1,3-thiazol-5-yl)phenoxy] octanoate. To a solution of (2S,4R)-1-[(2S)-2-[(1-fluorocyclopropyl)formamido]-3,3-dimethylbutanoyl]-4-hydroxy-N-{[2-hydroxy-4-(4-methyl-1,3-thiazol-5-yl)phenyl]methyl}pyrrolidine-2-carboxamide (1.4 g, 2.6 mmol, 1.0 eq) in anh DMF (17.5 mL, 0.15M) were added tert-butyl 8-bromooctanoate (1.03 g, 3.68 mmol, 1.4 eq) and $Cs_2CO_3$ (1.29 g, 3.94 mmol, 1.5 eq). The reaction mixture was sealed and stirred at room temperature overnight. The reaction mixture was then diluted with EtOAc (20 mL) and filtered. Obtained filtrate was diluted with water (60 mL) and extracted with ethyl acetate (3×20 mL). The combined organic layers were washed with brine (20 mL), dried over $Na_2SO_4$, filtered and concentrated under reduced pressure to give crude which was purified by Chromatography B to give the title compound as a solid (1.84 g, 96%).

Step 2: Synthesis of 8-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]octanoic acid. To a solution of tert-butyl 8-[2-({[(2S,4R)-1-[(2S)-2-[(1-fluorocyclopropyl)formamido]-3,3-dimethylbutanoyl]-4-hydroxypyrrolidin-2-yl]formamido}methyl)-5-(4-methyl-1,3-thiazol-5-yl)phenoxy]octanoate (1.84 g, 2.51 mmol, 1.0 eq) in anh DCM (12.6 mL, 0.2M) was added TFA (1.29 g, 3.94 mmol, 1.5 eq) under argon atmosphere. The reaction mixture was stirred for 2 h at room temperature and evaporated to dryness. The crude residue was triturated with aq. ammonia (10 mL) for 1 h. The water phase was decantated, the oil was dried in vacuo and purified using Chromatography C (20% to 60% acetonitrile/0.1% aqueous solution of formic acid) to give title compound (1.32 g, 78%).

Step 3: Synthesis of (2S,4R)—N-(2-((8-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-8-oxooctyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide.

The title compound was synthesized according to General Procedure F, using Intermediate 1 (11 mg), 8-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)octanoic acid (11 mg) as starting materials. Crude material was purified by reverse phase HPLC to provide the title compound (10.7 mg, 53%); LCMS: $C_{75}H_{96}F_2N_{12}O_8S$ requires 1362.7, found 1364.5 $[M+2H]^+$; $^1H$ NMR (500 MHz, DMSO-$d_6$) δ 9.33 (d, J=9.5 Hz, 1H), 8.98 (s, 1H), 8.62 (s, 1H), 8.49 (t, J=6.0 Hz, 1H), 8.37 (s, 1H), 8.13 (d, J=7.8 Hz, 1H), 7.87 (s, 1H), 7.66 (d, J=7.9 Hz, 1H), 7.61 (d, J=8.3 Hz, 1H), 7.53-7.45 (m, 2H), 7.40 (d, J=7.8 Hz, 1H), 7.28 (dd, J=9.2, 2.8 Hz, 1H), 7.17 (d, J=12.2 Hz, 1H), 7.04-6.98 (m, 1H), 6.95 (dd, J=7.8, 1.6 Hz, 1H), 5.28 (p, J=6.5 Hz, 1H), 4.59 (d, J=9.2 Hz, 1H), 4.52 (t, J=8.2 Hz, 1H), 4.38-4.16 (m, 4H), 4.10-3.98 (m, 4H), 3.89-3.59 (m, 5H), 3.02-2.73 (m, 7H), 2.46 (s, 3H), 2.36 (s, 5H), 2.08 (t, J=10.3 Hz, 1H), 1.96-1.88 (m, 1H), 1.88-1.29 (m, 29H), 1.26-1.15 (m, 3H), 1.09 (d, J=6.6 Hz, 6H), 0.95 (s, 9H).

Example 14

(2S,4R)-1-((S)-2-(2-(4-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

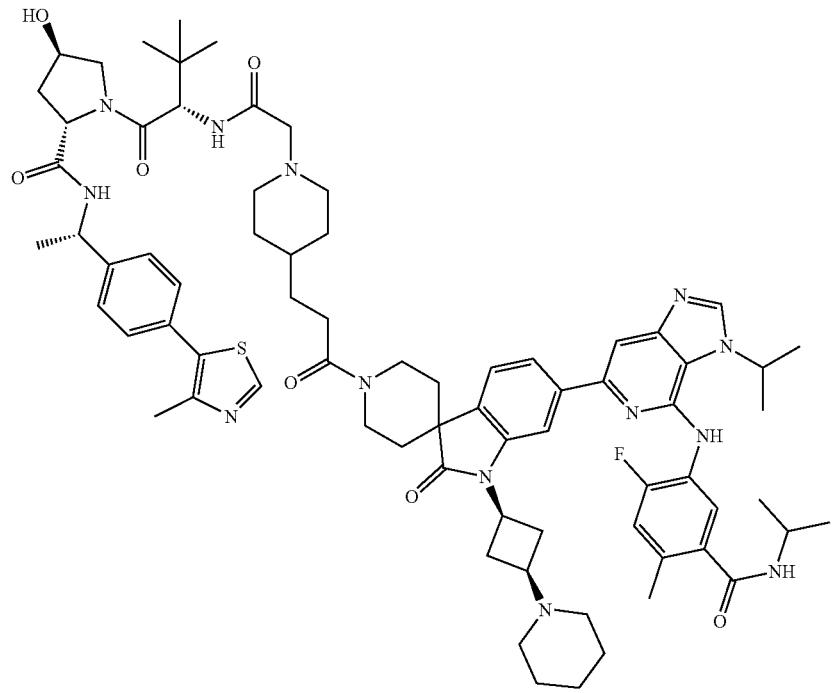 [SMILES: Cc1cc(F)c(Nc2nc(-c3ccc4c(c3)N([C@H]3C[C@@H](N5CCCCC5)C3)C(=O)C43CCN(C(=O)CCC4CCN(CC(=O)N[C@H](C(=O)N5C[C@H](O)C[C@H]5C(=O)N[C@@H](C)c5ccc(-c6scnc6C)cc5)C(C)(C)C)CC4)CC3)cc3ncn(C(C)C)c23)cc1C(=O)NC(C)C]

Step 1: Synthesis of tert-butyl 3-[1-(2-methoxy-2-oxoethyl)piperidin-4-yl]propanoate. The title compound was synthesized according to General Procedure E, using tert-butyl 3-(piperidin-4-yl)propanoate (300 mg, 1.4 mmol) and methyl 2-bromoacetate (230 mg, 1.5 mmol) as starting materials. The title compound was obtained Following Chromatography C (400 mg, 99%).

Step 2: Synthesis of {4-[3-(tert-butoxy)-3-oxopropyl]piperidin-1-yl}acetic acid. The title compound was synthesized according to General Procedure C using tert-butyl 3-[1-(2-methoxy-2-oxoethyl)piperidin-4-yl]propanoate (400 mg, 1.4 mmol) as the starting material. The title compound was obtained and used without purification (370 mg, 97%)

Step 3: Synthesis of tert-butyl 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-4-yl]propanoate. The title compound was synthesized according to General Procedure F using {4-[3-(tert-butoxy)-3-oxopropyl]piperidin-1-yl}acetic acid (113 mg, 0.42 mmol) and (1R,4S)-2-[(2S)-2-amino-3,3-dimethylbutanoyl]-4-hydroxy-N-[(1S)-1-[4-(4-methyl-1,3-thiazol-5-yl)phenyl]ethyl]cyclopentane-1-carboxamide hydrochloride (200 mg, 0.42 mmol) as starting materials. The crude material was purified via Chromatography B to give the title compound (280 mg, 96%).

Step 4: Synthesis of 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-4-yl]propanoic acid. The title compound was synthesized according to General Procedure B using tert-butyl 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-4-yl]propanoate (270 mg, 0.39 mmol) as the starting material. The title compound was obtained and used without purification (220 mg, 89%).

Step 5: Synthesis of (2S,4R)-1-((S)-2-(2-(4-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-1-yl)acetamido)-3,3- dimethylbutanoyl)-4-hydroxy-N—((S)-1-(4-(4-methylthiazol-5-yl)phenyl)ethyl)pyrrolidine-2-carboxamide. The title compound was synthesized according to General Procedure F, using Intermediate 1 (12 mg), 3-(1-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethyl)piperidin-4-yl)propanoic acid (10 mg) as starting materials. Crude material was purified by reverse phase HPLC to provide the title compound (8.1 mg, 28%); LCMS: $C_{74}H_{96}FN_{13}O_7S$ requires 1329.7, found 1331.5 $[M+2H]^+$; $^1H$ NMR (500 MHz, DMSO-$d_6$) δ 9.49 (s, 2H), 8.99 (s, 1H), 8.73 (d, J=9.1 Hz, 1H), 8.67 (s, 1H), 8.39 (d, J=9.3 Hz, 2H), 8.14 (d, J=7.9 Hz, 1H), 7.87 (s, 1H), 7.66 (d, J=7.8 Hz, 1H), 7.60 (d, J=8.2 Hz, 1H), 7.54-7.41 (m, 5H), 7.41-7.27 (m, 2H), 7.18 (d, J=12.2 Hz, 1H), 5.33-5.25 (m, 1H), 4.92 (t, J=7.2 Hz, 1H), 4.57 (d, J=9.1 Hz, 1H), 4.43 (t, J=8.2 Hz, 1H), 4.31 (s, 1H), 4.24-4.16 (m, 1H), 4.07-3.93 (m, 1H), 3.67-3.28 (m, 4H), 3.08-2.71 (m, 9H), 2.47-2.32 (m, 8H), 2.08-1.99 (m, 1H), 1.93-1.32 (m, 33H), 1.15-1.04 (m, 6H), 0.96 (d, J=13.7 Hz, 9H).

Example 15

(3R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(9-((2-(2,6-dioxopiperidin-3-yl)-1,3-dioxoisoindolin-5-yl)amino)nonyl)piperidine-3-carboxamide

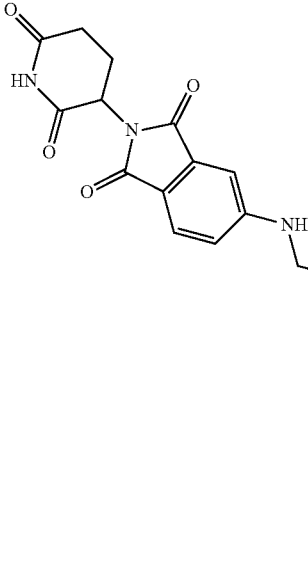
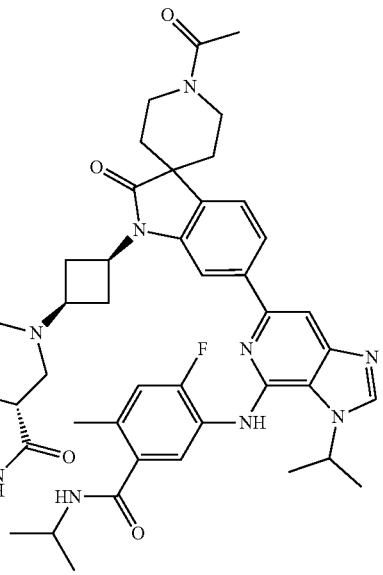

Step 1: Synthesis of 5-((9-aminononyl)amino)-2-(2,6-dioxopiperidin-3-yl)isoindoline-1,3-dione. The reaction was run according to General Procedure A using tert-butyl 9-aminononylcarbamate (8.2 g, 32 mmol) and 2-(2,6-dioxopiperidin-3-yl)-5-fluoro-2,3-dihydro-1H-isoindole-1,3-dione (8.0 g, 29 mmol). The product of this reaction was subjected to General Procedure B to provide the title compound (3.25 g, 23% over two steps).

Step 2: Synthesis of (3R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(9-((2-(2,6-dioxopiperidin-3-yl)-1,3-dioxoisoindolin-5-yl)amino)nonyl)piperidine-3-carboxamide. The title compound was synthesized according to General Procedure F, using Intermediate 2 (12 mg), 5-((9-aminononyl)amino)-2-(2,6-dioxopiperidin-3-yl)isoindoline-1,3-dione (10 mg) as starting materials. Crude material was purified by reverse phase HPLC to provide the title compound (10.6 mg, 45%); LCMS: $C_{66}H_{81}FN_{12}O_8$ requires 1188.6, found 1191.2 $[M+2H]^+$; $^1H$ NMR (500 MHz, DMSO-$d_6$) δ 11.05 (s, 1H), 9.56 (s, 1H), 8.64 (s, 1H), 8.38 (s, 1H), 8.22-8.09 (m, 1H), 8.05 (t, J=5.5 Hz, 1H), 7.87 (d, J=7.5 Hz, 1H), 7.71-7.44 (m, 6H), 7.17 (dd, J=12.1, 6.5 Hz, 2H), 6.93 (s, 2H), 6.84 (dt, J=8.4, 2.8 Hz, 2H), 5.29 (p, J=6.7 Hz, 1H), 5.07-4.97 (m, 1H), 4.20 (t, J=8.3 Hz, 1H), 4.03 (dq, J=13.1, 6.6 Hz, 1H), 3.93-3.45 (m, 4H), 3.20-2.97 (m, 8H), 2.57 (d, J=18.8 Hz, 3H), 2.36 (s, 3H), 2.07 (s, 3H), 2.02-1.19 (m, 30H), 1.09 (d, J=6.6 Hz, 6H).

Example 16

(R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(7-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)heptyl)piperidine-3-carboxamide

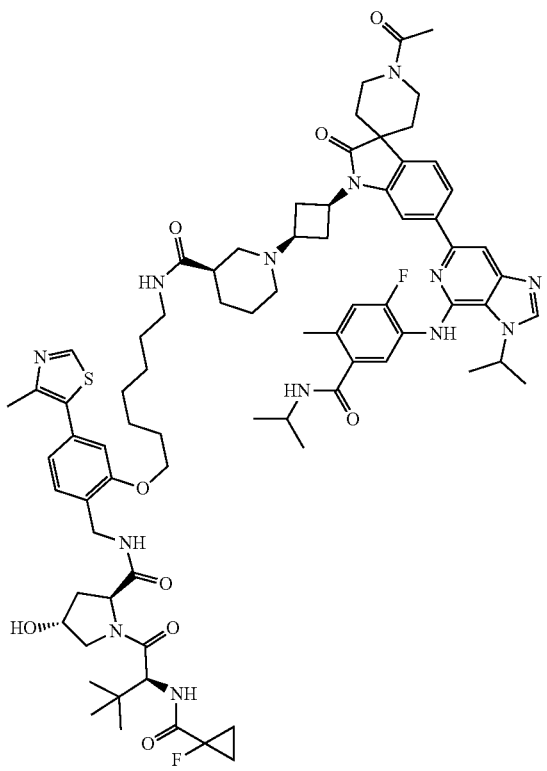 [SMILES: CC(=O)N1CCC2(CC1)C(=O)N([C@H]1C[C@@H](N3CCC[C@@H](C(=O)NCCCCCCCOc4cc(-c5scnc5C)ccc4CNC(=O)[C@@H]4C[C@@H](O)CN4C(=O)[C@@H](NC(=O)C4(F)CC4)C(C)(C)C)C3)C1)c1cc(-c3cc4ncn(C(C)C)c4c(Nc4cc(C(=O)NC(C)C)c(C)cc4F)n3)ccc12]

Step 1: Synthesis of (2S,4R)—N-(2-((7-aminoheptyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide. The title compound was synthesized according to the procedures outlined in Example 9, Steps 1-2 using tert-butyl (7-bromoheptyl)carbamate as the starting material in Step 1.

Step 2: Synthesis of (R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(7-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)heptyl)piperidine-3-carboxamide. The title compound was synthesized according to General Procedure F, using Intermediate 2 (12 mg), (2S,4R)—N-(2-((7-aminoheptyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (7.7 mg) as starting materials. Crude material was purified by reverse phase HPLC to provide the title compound (6.2 mg, 34%); LCMS: $C_{77}H_{99}F_2N_{13}O_9S$ requires 1419.7, found 1422.4 [M+2H]$^+$; $^1$H NMR (500 MHz, DMSO-d$_6$) δ 9.55 (s, 1H), 8.98 (s, 1H), 8.76 (s, 1H), 8.50 (t, J=6.0 Hz, 1H), 8.43 (s, 1H), 8.13 (d, J=8.0 Hz, 1H), 8.10-8.05 (m, 1H), 7.86 (d, J=6.5 Hz, 1H), 7.67-7.44 (m, 4H), 7.40 (d, J=7.8 Hz, 1H), 7.28 (dd, J=9.6, 2.7 Hz, 1H), 7.18 (dd, J=12.0, 6.7 Hz, 1H), 6.99 (t, J=2.7 Hz, 1H), 6.95 (dd, J=7.8, 1.6 Hz, 1H), 5.31 (p, J=6.6 Hz, 1H), 4.59 (d, J=9.2 Hz, 1H), 4.51 (t, J=8.2 Hz, 1H), 4.37-4.14 (m, 4H), 4.07-3.99 (m, 4H), 3.91-3.34 (m, 6H), 3.13-2.73 (m, 8H), 2.65-2.57 (m, 1H), 2.45 (s, 3H), 2.37 (d, J=2.2 Hz, 3H), 2.07 (s, 4H), 1.91 (ddd, J=13.2, 9.2, 4.5 Hz, 3H), 1.86-1.56 (m, 14H), 1.56-1.15 (m, 14H), 1.09 (d, J=6.6 Hz, 6H), 0.95 (s, 9H).

Example 17

(R)-1-((1s,3s)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(9-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)nonyl)piperidine-3-carboxamide

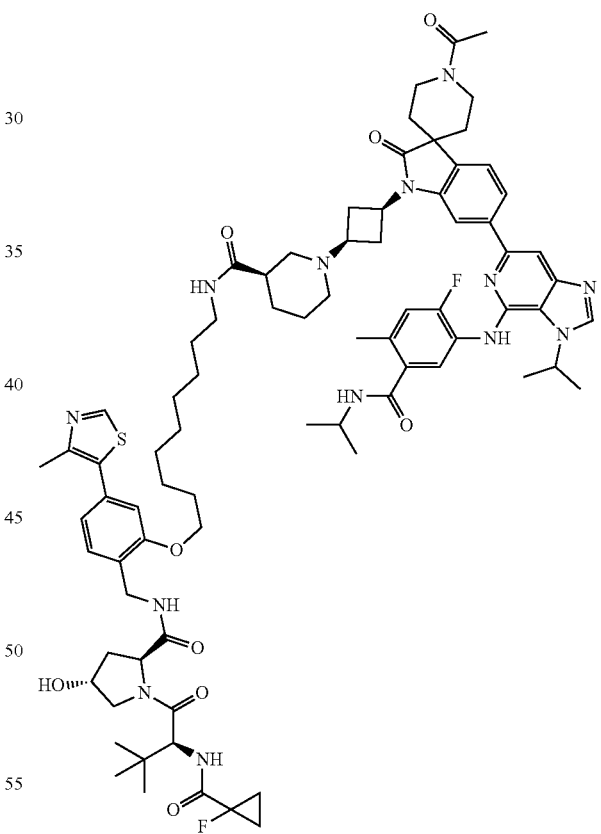

Step 1: Synthesis of (2S,4R)—N-(2-((9-aminononyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide. The title compound was synthesized according to the procedures outlined in Example 9, Steps 1-2 using tert-butyl (9-bromononyl)carbamate as the starting material in Step 1.

Step 2: Synthesis of (R)-1-((1s,3s)-3-(1'-acetyl-6-(4-((2-fluoro-5-(isopropylcarbamoyl)-4-methylphenyl)amino)-3- isopropyl-3H-imidazo[4,5-c]pyridin-6-yl)-2-oxospiro[indoline-3,4'-piperidin]-1-yl)cyclobutyl)-N-(9-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)nonyl)piperidine-3-carboxamide The title compound was synthesized according to General Procedure F, using Intermediate 2 (12 mg), (2S,4R)—N-(2-((9-aminononyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide (7.7 mg) as starting materials. Crude material was purified by reverse phase HPLC to provide the title compound (5.3 mg, 28%); LCMS: $C_{79}H_{103}F_2N_{13}O_9S$ requires 1447.8, found 1449.5 [M+2H]$^+$; $^1$H NMR (500 MHz, DMSO-d$_6$) δ 8.98 (s, 1H), 8.68 (s, 1H), 8.49 (t, J=6.0 Hz, 1H), 8.39 (s, 1H), 8.12 (d, J=8.1 Hz, 1H), 8.05 (t, J=5.9 Hz, 1H), 7.86 (d, J=7.8 Hz, 1H), 7.65 (d, J=8.0 Hz, 1H), 7.58 (dd, J=8.3, 4.7 Hz, 1H), 7.50 (d, J=8.6 Hz, 2H), 7.40 (d, J=7.8 Hz, 1H), 7.28 (dd, J=9.2, 2.8 Hz, 1H), 7.18 (dd, J=12.1, 6.7 Hz, 1H), 7.02-6.97 (m, 1H), 6.95 (d, J=7.8 Hz, 1H), 5.29 (p, J=6.6 Hz, 1H), 4.59 (d, J=9.2 Hz, 1H), 4.51 (t, J=8.2 Hz, 1H), 4.35 (s, 1H), 4.28 (dd, J=16.5, 6.0 Hz, 1H), 4.19 (dd, J=16.6, 5.2 Hz, 2H), 4.09-3.98 (m, 5H), 3.86 (s, 2H), 3.77-3.68 (m, 2H), 3.66-3.55 (m, 3H), 3.41 (s, 1H), 3.12-2.78 (m, 8H), 2.59 (s, 1H), 2.45 (s, 3H), 2.36 (d, J=2.4 Hz, 3H), 2.07 (s, 3H), 1.96-1.87 (m, 3H), 1.86-1.63 (m, 8H), 1.59 (dd, J=6.6, 4.0 Hz, 6H), 1.46-1.16 (m, 17H), 1.09 (dd, J=6.6, 2.0 Hz, 6H), 0.95 (s, 9H).

Example 18

(2S,4R)-1-((S)-2-(2-(4-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide Step 1: Synthesis of tert-butyl 4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazine-1-carboxylate. The title compound was synthesized according to General Procedure F using [4-(tert-butoxycarbonyl)piperazin-1-yl]acetic acid (900 mg, 3.68 mmol) and (1R,4S)-2-[(2S)-2-amino-3,3-dimethylbutanoyl]-4-hydroxy-N-[(1S)-1-[4-(4-methyl-1,3-thiazol-5-yl)phenyl]ethyl]cyclopentane-1-carboxamide hydrochloride (1.77 g, 3.68 mmol). Chromatography B afforded the title compound (2.1 g, 85%).

Step 2: Synthesis of (2S,4R)-1-[(2S)-3,3-dimethyl-2-[2-(piperazin-1-yl)acetamido]butanoyl]-4-hydroxy-N-[(1S)-1-[4-(4-methyl-1,3-thiazol-5-yl)phenyl]ethyl]pyrrolidine-2-carboxamide dihydrochloride. The reaction was carried out according to General Procedure B using tert-butyl 4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazine-1-carboxylate (2.1 g, 3.13 mmol) to provide the title compound (2.0 g, 99%).

Step 3: Synthesis of methyl 2-[4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]acetate. The title compound was synthesized according to General Procedure E using (2S,4R)-1-[(2S)-3,3-dimethyl-2-[2-(piperazin-1-yl)acetamido]butanoyl]-4-hydroxy-N-[(1S)-1-[4-(4-methyl-1,3-thiazol-5-yl)phenyl]ethyl]pyrrolidine-2-carboxamide dihydrochloride (1.34 g, 1.57 mmol) and methyl 2-bromoacetate (264 mg, 1.72 mmol) as starting materials. Chromatography B afforded the title compound (0.590 g, 59%).

Step 4: Synthesis of [4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]acetic acid. The reaction was carried out according to General Procedure C using methyl 2-[4-({[(2S)-1-[(2S,4R)-4-hydroxy-2-{[(1S)-1-[4-(4-methyl-1,3-thiazol-5-yl)phenyl]ethyl]

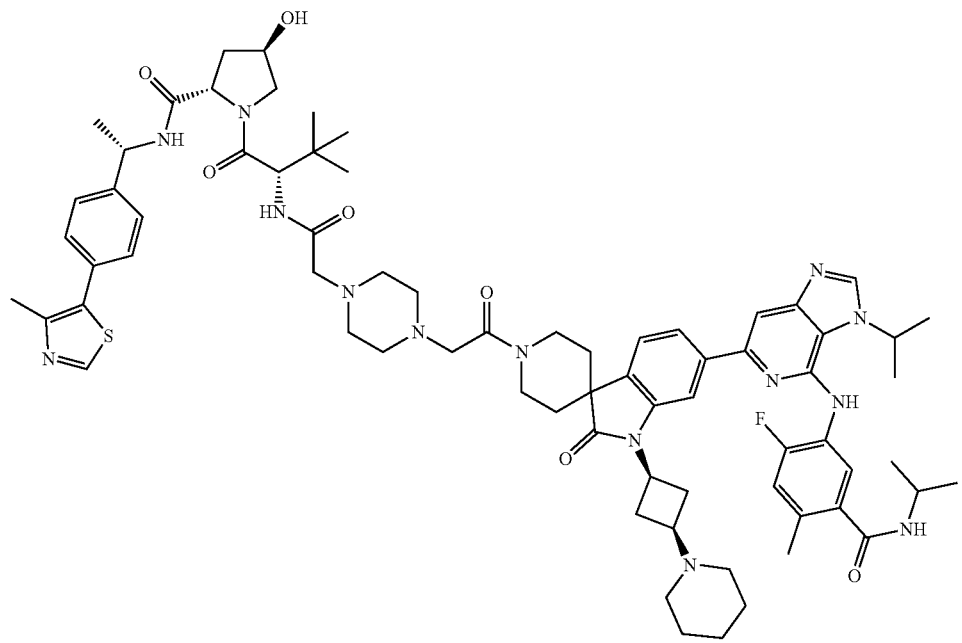 [SMILES: Cc1cc(F)c(Nc2nc(-c3ccc4c(c3)N([C@H]3C[C@@H](N5CCCCC5)C3)C(=O)C43CCN(C(=O)CN4CCN(CC(=O)N[C@H](C(=O)N5C[C@H](O)C[C@H]5C(=O)N[C@@H](C)c5ccc(-c6scnc6C)cc5)C(C)(C)C)CC4)CC3)cc3ncn(C(C)C)c23)cc1C(=O)NC(C)C]

carbamoyl}pyrrolidin-1-yl]-3,3-dimethyl-1-oxobutan-2-yl]carbamoyl}methyl)piperazin-1-yl]acetate (589 mg, 0.92 mmol) to provide the title compound (0.566 g, 98%).

Step 5: Synthesis of (2S,4R)-1-((S)-2-(2-(4-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide. The title compound was synthesized according to General Procedure F, using Intermediate 1 (11.5 mg), [4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]acetic acid (10 mg) as starting materials. Crude material was purified by reverse phase HPLC to provide the title compound (8.2 mg, 36%); LCMS: $C_{72}H_{93}FN_{14}O_7S$ requires 1316.6, found 1317.6 [M+2H]$^+$; $^1$H NMR (500 MHz, DMSO-$d_6$) δ 9.52 (d, J=9.5 Hz, 1H), 8.99 (s, 1H), 8.66 (s, 1H), 8.40 (d, J=8.5 Hz, 2H), 8.14 (d, J=7.8 Hz, 1H), 7.88 (s, 1H), 7.68 (d, J=7.7 Hz, 1H), 7.59 (d, J=8.3 Hz, 1H), 7.53-7.40 (m, 4H), 7.37 (d, J=8.1 Hz, 2H), 7.18 (d, J=12.1 Hz, 1H), 5.29 (q, J=6.6 Hz, 1H), 4.91 (t, J=7.2 Hz, 1H), 4.54 (d, J=9.4 Hz, 1H), 4.43 (t, J=8.2 Hz, 1H), 4.33-3.32 (m, 22H), 3.03-2.92 (m, 1H), 2.92-2.76 (m, 6H), 2.45 (s, 3H), 2.36 (s, 3H), 2.05 (t, J=10.3 Hz, 1H), 1.92-1.52 (m, 18H), 1.43 (dd, J=53.2, 7.0 Hz, 4H), 1.09 (d, J=6.6 Hz, 6H), 0.97 (s, 9H).

Example 19

(2S,4R)-1-((S)-2-(5-(1-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperidin-4-yl)pentanamido)-3,3-dimethylbutanoyl)-4-hydroxy-N—((S)-1-(4-(4-methylthiazol-5-yl)phenyl)ethyl)pyrrolidine-2-carboxamide Step 1: Synthesis of tert-butyl 4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidine-1-carboxylate. The title compound was synthesized according to General Procedure F using 5-[1-(tert-butoxycarbonyl)piperidin-4-yl]pentanoic acid (107 mg, 0.37 mmol) and (1R,4S)-2-[(2S)-2-amino-3,3-dimethylbutanoyl]-4-hydroxy-N-[(1S)-1-[4-(4-methyl-1,3-thiazol-5-yl)phenyl]ethyl]cyclopentane-1-carboxamide hydrochloride (150 mg, 0.31 mmol) as starting materials. Chromatography C provided the title compound (0.220 g, 99%).

Step 2: Synthesis of (2S,4R)-1-[(2S)-3,3-dimethyl-2-[5-(piperidin-4-yl)pentanamido]butanoyl]-4-hydroxy-N-[(1S)-1-[4-(4-methyl-1,3-thiazol-5-yl)phenyl]ethyl]pyrrolidine-2-carboxamide hydrochloride. The reaction was carried out according to General Procedure B using tert-butyl 4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidine-1-carboxylate (0.220 g, 0.31 mmol) to provide the title compound (0.194 g, 99%).

Step 3: Synthesis of methyl 2-[4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]acetate. The reaction was carried out according to General Procedure E, using (2S,4R)-1-[(2S)-3,3-dimethyl-2-[5-(piperidin-4-yl)pentanamido]butanoyl]-4-hydroxy-N-[(1S)-1-[4-(4-methyl-1,3-thiazol-5-yl)phenyl]ethyl]pyrrolidine-2-carboxamide hydrochloride (168 mg, 0.26 mmol) and methyl 2-bromoacetate (40 mg, 0.26 mmol). Chromatography B provided the title compound (69.9 mg, 39%).

Step 4: Synthesis of [4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]acetic acid. The reaction was carried out according to General Procedure C using methyl 2-[4-(4-{[(2S)-1-[(2S,4R)-4-hydroxy-2-{[(1S)-1-[4-

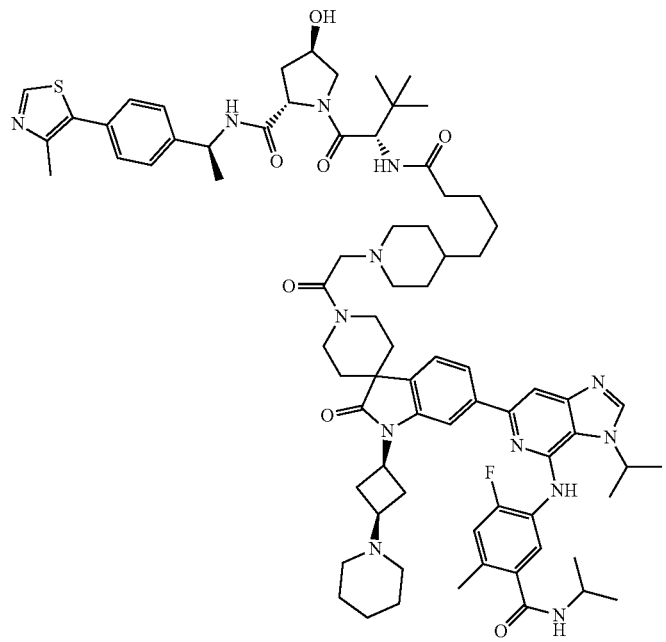 [SMILES: Cc1cc(F)c(Nc2nc(-c3ccc4c(c3)N([C@H]3C[C@@H](N5CCCCC5)C3)C(=O)C43CCN(C(=O)CN4CCC(CCCCC(=O)N[C@H](C(=O)N5C[C@H](O)C[C@H]5C(=O)N[C@@H](C)c5ccc(-c6scnc6C)cc5)C(C)(C)C)CC4)CC3)cc3ncn(C(C)C)c23)cc1C(=O)NC(C)C]

(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]acetate (69.9 mg, 0.10 mmol) to provide the title compound (67 mg, 98%).

Step 5: Synthesis of (2S,4R)-1-((S)-2-(5-(1-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperidin-4-yl)pentanamido)-3,3-dimethylbutanoyl)-4-hydroxy-N—(S)-1-(4-(4-methylthiazol-5-yl)phenyl)ethyl)pyrrolidine-2-carboxamide. The title compound was synthesized according to General Procedure F, using Intermediate 1 (11.5 mg), [4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]acetic acid (10 mg) as starting materials. Crude material was purified by reverse phase HPLC to provide the title compound (8.2 mg, 46%); LCMS: $C_{76}H_{100}FN_{13}O_7S$ requires 1357.8, found 1359.5 [M+2H]$^+$; $^1$H NMR (500 MHz, DMSO-d$_6$) δ 9.42 (s, 1H), 8.99 (s, 1H), 8.61 (s, 1H), 8.40-8.33 (m, 2H), 8.13 (d, J=7.8 Hz, 1H), 7.88 (s, 1H), 7.80 (d, J=9.2 Hz, 1H), 7.68 (d, J=7.7 Hz, 1H), 7.60 (d, J=8.2 Hz, 1H), 7.52 (s, 1H), 7.49-7.32 (m, 6H), 7.17 (d, J=12.1 Hz, 1H), 5.31-5.25 (m, 1H), 4.92 (t, J=7.2 Hz, 1H), 4.53 (d, J=9.2 Hz, 1H), 4.45-4.27 (m, 6H), 4.24-3.30 (m, 17H), 3.22 (s, 1H), 3.02-2.73 (m, 10H), 2.45 (s, 4H), 2.36 (s, 3H), 2.31-2.23 (m, 1H), 2.13 (d, J=8.3 Hz, 1H), 2.01 (s, 1H), 1.93-1.35 (m, 30H), 1.09 (d, J=6.6 Hz, 6H), 0.94 (s, 9H).

Example 20

(2S,4R)-1-((S)-2-(5-(1-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-4-yl)pentanamido)-3,3-dimethylbutanoyl)-4-hydroxy-N—((S)-1-(4-(4-methylthiazol-5-yl)phenyl)ethyl)pyrrolidine-2-carboxamide Step 1: Synthesis of methyl 3-[4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]propanoate. The reaction was carried out according to General Procedure E, using (2S,4R)-1-[(2S)-3,3-dimethyl-2-[5-(piperidin-4-yl)pentanamido]butanoyl]-4-hydroxy-N-[(1S)-1-[4-(4-methyl-1,3-thiazol-5-yl)phenyl]ethyl]pyrrolidine-2-carboxamide hydrochloride (168 mg, 0.26 mmol) and methyl 3-bromopropanoate (43 mg, 0.26 mmol). Chromatography B provided the title compound (47 mg, 26%).

Step 2: Synthesis of 3-[4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]propanoic acid. The reaction was carried out according to General Procedure C using methyl 3-[4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]propanoate (47 mg, 0.07 mmol) to provide the title compound (46 mg, 98%).

Step 3: Synthesis of (2S,4R)-1-((S)-2-(5-(1-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-4-yl)pentanamido)-3,3-dimethylbutanoyl)-4-hydroxy-N—((S)-1-(4-(4-methylthiazol-5-yl)phenyl)ethyl)pyrrolidine-2-carboxamide. The title compound was synthesized according to General Procedure F, using Intermediate 1 (5.2 mg), 3-[4-(4-{[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}butyl)piperidin-1-yl]propanoic acid (5 mg) as starting materials. Crude material was purified by reverse phase HPLC to provide the title compound (2.5 mg, 24%); LCMS: $C_{77}H_{102}FN_{13}O_7S$ requires 1371.8, found 1374.9 [M+3H]$^+$; $^1$H NMR (500 MHz, DMSO-d$_6$) δ 9.40 (s, 1H), 8.99 (s, 1H), 8.59 (s, 1H), 8.36 (d, J=9.3 Hz, 2H), 8.13 (d, J=7.8 Hz, 1H), 7.88 (s, 1H), 7.80 (d, J=9.3 Hz, 1H), 7.68 (d,

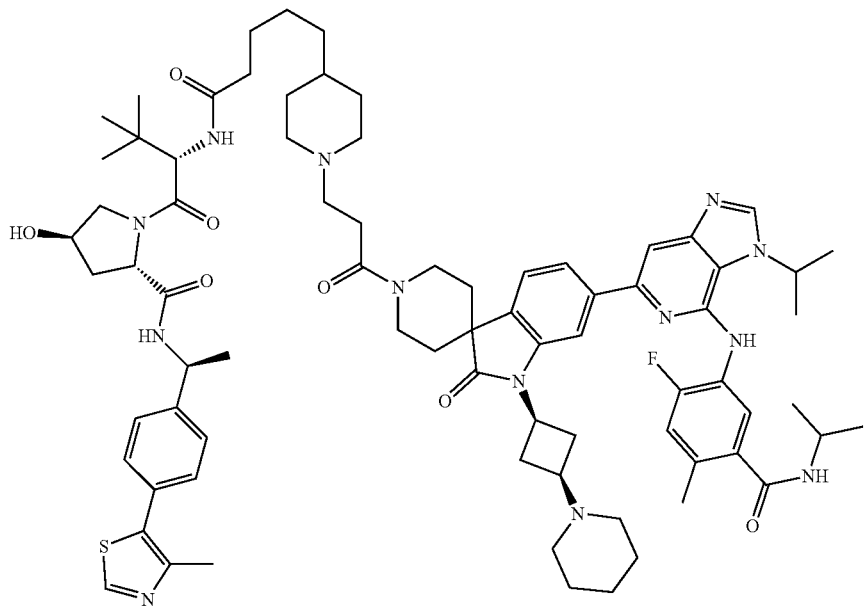 [SMILES: Cc1cc(F)c(Nc2nc(-c3ccc4c(c3)N([C@H]3C[C@@H](N5CCCCC5)C3)C(=O)C43CCN(C(=O)CCN4CCC(CCCCC(=O)N[C@H](C(=O)N5C[C@H](O)C[C@H]5C(=O)N[C@@H](C)c5ccc(-c6scnc6C)cc5)C(C)(C)C)CC4)CC3)cc3ncn(C(C)C)c23)cc1C(=O)NC(C)C]

J=7.8 Hz, 1H), 7.61 (d, J=8.3 Hz, 1H), 7.52 (s, 1H), 7.50-7.41 (m, 3H), 7.38 (d, J=8.2 Hz, 2H), 7.17 (d, J=12.1 Hz, 1H), 5.31-5.25 (m, 1H), 4.95-4.88 (m, 1H), 4.53 (d, J=9.3 Hz, 1H), 4.41 (t, J=8.0 Hz, 1H), 4.29 (s, 1H), 4.20 (t, J=8.2 Hz, 1H), 4.07-3.99 (m, 1H), 3.96-3.30 (m, 12H), 3.02-2.73 (m, 11H), 2.45 (s, 3H), 2.36 (s, 3H), 2.31-2.23 (m, 1H), 2.12 (dt, J=13.9, 6.4 Hz, 1H), 2.01 (t, J=10.4 Hz, 1H), 1.88-1.44 (m, 22H), 1.38 (d, J=7.0 Hz, 3H), 1.34-1.18 (m, 6H), 1.09 (d, J=6.6 Hz, 6H), 0.94 (s, 9H).

Example 21

5-{[6-(1'-{2-[4-(3-{2-[2,6-dioxopiperidin-3-yl]-1,3-dioxo-2,3-dihydro-1H-isoindol-4-yl}propyl)piperazin-1-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

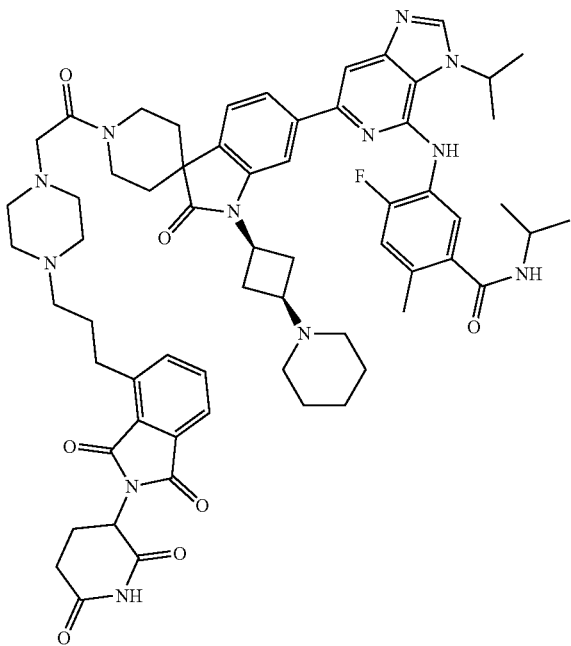 [SMILES: Cc1cc(F)c(Nc2nc(-c3ccc4c(c3)N([C@H]3C[C@@H](N5CCCCC5)C3)C(=O)C43CCN(C(=O)CN4CCN(CCCc5cccc6c5C(=O)N(C5CCC(=O)NC5=O)C6=O)CC4)CC3)cc3ncn(C(C)C)c23)cc1C(=O)NC(C)C]

Step 1: Synthesis of tert-butyl 2-[4-(prop-2-yn-1-yl)piperazin-1-yl]acetate. To a solution of tert-butyl 2-(piperazin-1-yl)acetate (1.5 g, 7.5 mmol) in ACN (50.0 mL) was added 3-bromoprop-1-yne (893 mg, 7.50 mmol) and Cs$_2$CO$_3$ (2.4 g, 7.50 mmol). The resulting mixture was stirred at room temperature for 3 h. After the reaction was completed, the mixture was filtered. The filtrate was concentrated under vacuum. The residue was purified by Chromatography A to afford tert-butyl 2-[4-(prop-2-yn-1-yl)piperazin-1-yl]acetate (1.1 g, 62%) as a yellow oil.

Step 2: Synthesis of tert-butyl 2-(4-(3-(2-(2,6-dioxopiperidin-3-yl)-1,3-dioxoisoindolin-4-yl)prop-2-ynyl)piperazin-1-yl)acetate. To a solution of 4-bromo-2-(2,6-dioxopiperidin-3-yl)isoindoline-1,3-dione (1.3 g, 3.86 mmol) in DMF (18.0 mL) was added tert-butyl 2-(4-(prop-2-ynyl) piperazin-1-yl)acetate (1.4 g, 5.6 mmol), Pd(PPh$_3$)$_2$Cl$_2$ (423 mg, 0.60 mmol), DIPEA (12.0 mL) and CuI (251 mg, 1.32 mmol). The resulting mixture was stirred at 75° C. for 4 h. After the reaction was completed, the resulting mixture was diluted with water and extracted with ethyl acetate. The combined organic layer was washed with brine, dried over anhydrous sodium sulfate, and filtered. The filtrate was evaporated in vacuo. The residue was purified by Chromatography B to afford tert-butyl 2-(4-(3-(2-(2,6-dioxopiperidin-3-yl)-1,3-dioxoisoindolin-4-yl)prop-2-ynyl)piperazin-1-yl)acetate (2.5 g, 70%) as a solid.

Step 3: Synthesis of tert-butyl 2-(4-(3-(2-(2,6-dioxopiperidin-3-yl)-1,3-dioxoisoindolin-4-yl)propyl)piperazin-1-yl)acetate. To a solution of tert-butyl 2-(4-(3-(2-(2,6-dioxopiperidin-3-yl)-1,3-dioxoisoindolin-4-yl)prop-2-ynyl)piperazin-1-yl)acetate (2.1 g, 4.25 mmol) in ethanol (50.0 mL) was added 10% Pd/C (0.42 g, dry). The resulting mixture was stirred at room temperature for 16 h under H$_2$. After the reaction was completed, the reaction mixture was filtered. The filtrate was evaporated in vacuo to afford tert-butyl 2-(4-(3-(2-(2,6-dioxopiperidin-3-yl)-1,3-dioxoisoindolin-4-yl)propyl)piperazin-1-yl)acetate (1.6 g, crude) as a solid.

Step 4: Synthesis of 2-(4-(3-(2-(2,6-dioxopiperidin-3-yl)-1,3-dioxoisoindolin-4-yl)propyl)piperazin-1-yl)acetic acid 2,2,2-trifluoroacetic acid. To a solution of tert-butyl 2-(4-(3-(2-(2,6-dioxopiperidin-3-yl)-1,3-dioxoisoindolin-4-yl)propyl)piperazin-1-yl)acetate (2.1 g, 4.2 mmol) in dichloromethane (20.0 mL) was added trifluoroacetic acid (20.0 mL). The resulting mixture was stirred at room temperature for 4 h. The resulting mixture was concentrated under vacuum. The residue was purified by Pre-HPLC with the following conditions: Column: XSelect CSH Prep C18 OBD Column, 5 um, 19×150 mm; Mobile Phase A: Water (0.05% TFA), Mobile Phase B: ACN; Flow rate: 25 mL/min; Gradient: 5% B to 20% B in 7 min; 254/220 nm; Rt: 6.05 min to afford 2-(4-(3-(2-(2,6-dioxopiperidin-3-yl)-1,3-dioxoisoindolin-4-yl)propyl)piperazin-1-yl)acetic acid 2,2,2-trifluoroacetic acid (398 mg, 21%) as a solid.

Step 5: Synthesis of 5-{[6-(1'-{2-[4-(3-{2-[2,6-dioxopiperidin-3-yl]-1,3-dioxo-2,3-dihydro-1H-isoindol-4-yl}propyl)piperazin-1-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide
The title compound was synthesized according to General Procedure F, using Intermediate 1 (17.9 mg), 2-(4-(3-(2-(2,6-dioxopiperidin-3-yl)-1,3-dioxoisoindolin-4-yl)propyl) piperazin-1-yl)acetic acid 2,2,2-trifluoroacetic acid (10 mg) as starting materials. Crude material was purified by reverse phase HPLC to provide the title compound (12.4 mg, 46%); LCMS: C$_{63}$H$_{75}$FN$_{12}$O$_7$ requires 1130.6, found 1133.3 [M+2H]$^+$; $^1$H NMR (500 MHz, DMSO-d$_6$) δ 11.14 (s, 1H), 9.49 (s, 1H), 8.63 (s, 1H), 8.39 (s, 1H), 8.13 (d, J=7.8 Hz, 1H), 7.88 (s, 1H), 7.82 (d, J=6.7 Hz, 2H), 7.75 (dd, J=6.6, 2.2 Hz, 1H), 7.67 (d, J=7.6 Hz, 1H), 7.60 (d, J=8.2 Hz, 1H), 7.51 (s, 1H), 7.47 (d, J=7.8 Hz, 1H), 7.17 (d, J=12.2 Hz, 1H), 5.34-5.24 (m, 1H), 5.14 (dd, J=12.8, 5.5 Hz, 1H), 4.24-4.14 (m, 1H), 4.04 (dt, J=13.8, 6.7 Hz, 1H), 3.96-3.07 (m, 10H), 3.01-2.72 (m, 13H), 2.65-2.52 (m, 3H), 2.36 (s, 4H), 2.10-1.92 (m, 4H), 1.91-1.50 (m, 16H), 1.48-1.38 (m, 1H), 1.09 (d, J=6.5 Hz, 6H).

Example 22

5-[(6-{1'-[2-(2-{2-[2,6-dioxopiperidin-3-yl]-1,3-dioxo-2,3-dihydro-1H-isoindol-5-yl}-2,7-diazaspiro[3.5]nonan-7-yl)acetyl]-2-oxo-1-[(1s,3s)-3-(piperidin-1-yl)cyclo butyl]-1,2-dihydrospiro[indole-3,4'-piperidin]-6-yl}-3-(propan-2-yl)-3H-imidazo[4,5-c]pyridine-4-yl)amino]-4-fluoro-2-methyl-N-(propan-2-yl)benzamide

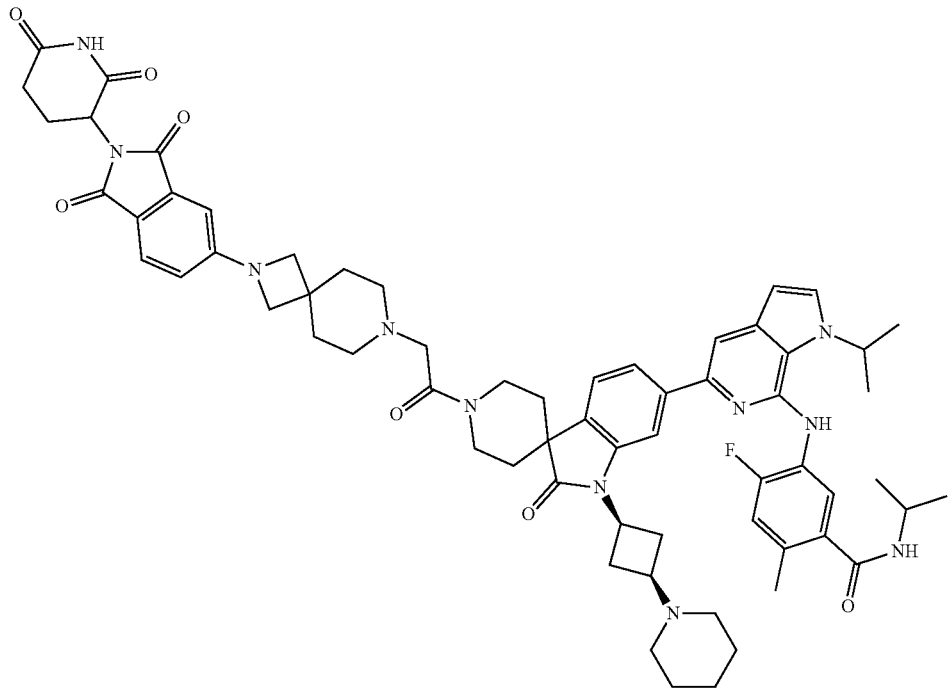 [SMILES: Cc1cc(F)c(Nc2nc(-c3ccc4c(c3)N([C@H]3C[C@@H](N5CCCCC5)C3)C(=O)C43CCN(C(=O)CN4CCC5(CC4)CN(c4ccc6c(c4)C(=O)N(C4CCC(=O)NC4=O)C6=O)C5)CC3)cc3ccn(C(C)C)c23)cc1C(=O)NC(C)C]

Step 1: Synthesis of tert-butyl 7-[2-(benzyloxy)-2-oxoethyl]-2,7-diazaspiro[3.5]nonane-2-carboxylate. To a solution of tert-butyl 2,7-diazaspiro[3.5]nonane-2-carboxylate (5.0 g, 22 mmol, 1.0 eq) in DMF (85 mL, 0.26 M) were added $Cs_2CO_3$ (14.4 g, 44.2 mmol, 2.0 eq) and benzyl 2-bromoacetate (5.06 g, 22.1 mmol, 1.0 eq). The reaction mixture was stirred at rt for 3 h. At this time, DMF was evaporated to dryness and the crude was dissolved in water and extracted with $Et_2O$ (350 mL x 2), washed with brine, and evaporated to dryness to give a crude residue which was then purified by Chromatography A to afford the title compound (6.25 g, 760%).

Step 2: Synthesis of benzyl 2-{2,7-diazaspiro[3.5]nonan-7-yl}acetate trifluoroacetate. To a solution of tert-butyl 7-[2-(benzyloxy)-2-oxoethyl]-2,7-diazaspiro[3.5]nonane-2-carboxylate (6.25 g, 16.7 mmol, 1.0 eq) in DCM (56 mL, 0.3 M) was added trifluoroacetic acid (25.5 mL, 114 mmol, 20.0 eq). The reaction mixture was stirred at RT overnight. Volatiles were then evaporated to dryness, and the crude was triturated with $Et_2O$ to give 8.23 g of the title compound as a TFA salt (quantitative yield).

Step 3: Synthesis of benzyl 2-{2-[2-(2,6-dioxopiperidin-3-yl)-1,3-dioxo-2,3-dihydro-1H-isoindol-5-yl]-2,7-diazaspiro[3.5]nonan-7-yl}acetate. To a solution of 2-(2,6-dioxopiperidin-3-yl)-5-fluoro-2,3-dihydro-1H-isoindole-1,3-dione (7.5 g, 27.1 mmol, 1 eq) in DMSO (54.3 mL, 0.5 M) were added benzyl 2-{2,7-diazaspiro[3.5]nonan-7-yl}acetate trifluoroacetate (7.7 g, 30 mmol, 1.1 eq) and DIPEA (10.7 mL, 81.4 mmol, 3 eq) under anhydrous conditions. The reaction mixture was stirred at 70° C. for 48 h. Reaction mixture was poured in ice-cold water (250 mL) and extracted with ethyl acetate. Organic layers were combined, washed with ice water (200 mL×2), dried over $Na_2SO_4$ and concentrated under reduced. The crude residue was purified by Chromatography A to give 3.6 g of titled compound (25% yield).

Step 4: Synthesis of 2-{2-[2-(2,6-dioxopiperidin-3-yl)-1,3-dioxo-2,3-dihydro-1H-isoindol-5-yl]-2,7-diazaspiro[3.5]nonan-7-yl}acetic acid trifluoroacetate. To a solution of benzyl 2-{2-[2-(2,6-dioxopiperidin-3-yl)-1,3-dioxo-2,3-dihydro-1H-isoindol-5-yl]-2,7-diazaspiro[3.5]nonan-7-yl}acetate (2.5 g, 4.7 mmol) in 5% trifluoroacetic acid in DCM (47 mL, 0.1 M) were added Pd/C 10% (500 mg, 20% by wt). Reaction mixture was purged with argon, followed by hydrogen, repeated three times and the mixture was stirred under hydrogen atmosphere (balloon) for one hour. The reaction mixture was filtered through celite and evaporated to dryness to give 2.08 g of the title compound (80% yield).

Step 5: Synthesis of 5-[(6-{1'-[2-(2-{2-[2,6-dioxopiperidin-3-yl]-1,3-dioxo-2,3-dihydro-1H-isoindol-5-yl}-2,7-diazaspiro[3.5]nonan-7-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridine-4-yl)amino]-4-fluoro-2-methyl-N-(propan-2-yl)benzamide. The title compound was synthesized according to General Procedure F, using Intermediate 1 (10 mg), 2-(2-(2-(2,6-dioxopiperidin-3-yl)-1,3-dioxoisoindolin-5-yl)-2,7-diazaspiro[3.5]nonan-7-yl)acetic acid (10 mg) as starting materials. Crude material was purified by reverse phase HPLC to provide the title compound (11.8 mg, 62%); LCMS: $C_{63}H_{73}FN_{12}O_7$ requires 1128.6, found 1131.3 $[M+2H]^+$; $^1H$ NMR (500 MHz, DMSO-$d_6$) δ 11.07 (s, 1H), 9.63 (s, 1H), 9.52 (s, 1H), 8.61 (s, 1H), 8.39 (s, 1H), 8.13 (d, J=7.8 Hz, 1H), 7.89 (s, 1H), 7.69 (d, J=8.1 Hz, 2H), 7.60 (d, J=8.2 Hz, 1H), 7.52 (s, 1H), 7.47 (d, J=7.8 Hz, 1H), 7.17 (d, J=12.1 Hz, 1H), 6.81 (d, J=2.0 Hz, 1H), 6.69 (dd, J=8.4, 2.1 Hz, 1H), 5.28 (p, J=6.6 Hz, 1H), 5.06 (dd, J=12.8, 5.5 Hz, 1H), 4.39 (s, 1H), 4.20 (p, J=8.4 Hz, 1H), 4.08-3.57 (m, 10H), 3.57-3.34 (m, 2H), 3.17-2.77 (m, 8H), 2.59 (d, J=17.3 Hz, 1H), 2.54 (s, 3H), 2.36 (s, 3H), 2.23-1.95 (m, 4H), 1.94-1.53 (m, 15H), 1.42 (q, J=11.6 Hz, 1H), 1.10 (d, J=6.6 Hz, 6H).

Example 23

5-[(6-{1'-[2-(4-{2-[(3RS)-2,6-dioxopiperidin-3-yl]-1,3-dioxo-2,3-dihydro-1H-isoindol-5-yl}piperazin-1-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

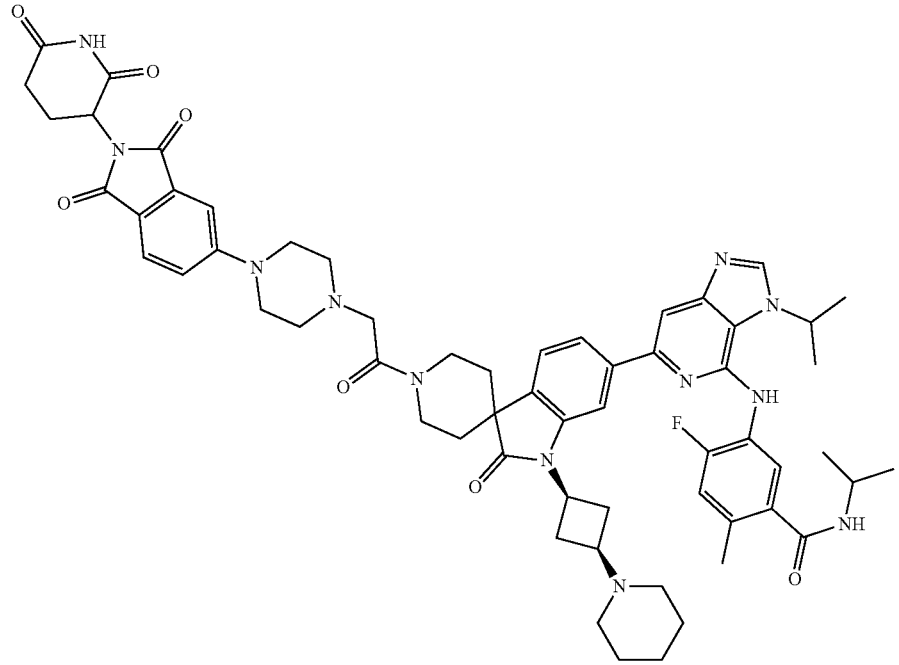 [SMILES: Cc1cc(F)c(Nc2nc(-c3ccc4c(c3)N([C@H]3C[C@@H](N5CCCCC5)C3)C(=O)C43CCN(C(=O)CN4CCN(c5ccc6c(c5)C(=O)N(C5CCC(=O)NC5=O)C6=O)CC4)CC3)cc3ncn(C(C)C)c23)cc1C(=O)NC(C)C]

Step 1: Synthesis of tert-butyl 2-{4-[2-(2,6-dioxopiperidin-3-yl)-1,3-dioxo-2,3-dihydro-1H-isoindol-5-yl]piperazin-1-yl}acetate. To a solution of tert-butyl piperazin-1-yl-acetate dihydrochloride (4.46 g, 16.3 mmol, 1.1 eq) in DMSO (29.7 mL, 0.5 M) were added DIPEA (3.93 mL, 22.5 mmol, 2 eq) and 2-(2,6-dioxopiperidin-3-yl)-5-fluoroisoindoline-1,3-dione (4.1 g, 14.8 mmol, 1 eq). The reaction mixture was heated at 90° C. under argon for 40 h. The reaction mixture was cooled down to rt and 5 mL of water was added dropwise. A bright-yellow precipitate was formed and was filtered off. The filter cake was then washed 2 times with water. The filtrate was extracted 2 times with DCM. The combined DCM layers were concentrated in vacuo and combined with the precipitate. The crude was purified by Chromatography B to give the title compound as a yellow solid (5.49 g, 81% yield).

Step 2: Synthesis of 2-{4-[2-(2,6-dioxopiperidin-3-yl)-1,3-dioxo-2,3-dihydro-1H-isoindol-5-yl]piperazin-1-yl}acetic acid trifluoroacetate. To a solution of tert-butyl 2-{4-[2-(2,6-dioxopiperidin-3-yl)-1,3-dioxo-2,3-dihydro-1H-isoindol-5-yl]piperazin-1-yl}acetate (5.49 g, 12.0 mmol, 1 eq) in DCM (100 mL, 0.12 M) TFA (50.6 mL, 661 mmol, 55 eq) was added. The reaction mixture was stirred 16 h at rt and then concentrated under reduced pressure. The resulting bright-yellow sticky solid was sonicated with 200 mL of anhydrous diethyl ether and stirred for 1 hour. The resulting precipitate was filtered, washed twice with anh Et$_2$O, and dried under reduced pressure to give a bright-yellow solid (6.55 g, quant).

Step 3: Synthesis of 5-[(6-{1'-[2-(4-{2-[(3RS)-2,6-dioxopiperidin-3-yl]-1,3-dioxo-2,3-dihydro-1H-isoindol-5-yl}piperazin-1-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide.

The title compound was synthesized according to General Procedure F, using Intermediate 1 (10 mg), 2-(4-(2-(2,6-dioxopiperidin-3-yl)-1,3-dioxoisoindolin-5-yl)piperazin-1-yl)acetic acid (10 mg) as starting materials. Crude material was purified by reverse phase HPLC to provide the title compound (13 mg, 70%); LCMS: $C_{60}H_{69}FN_{12}O_7$ requires 1088.5, found 1090.4 [M+2H]$^+$; $^1$H NMR (500 MHz, DMSO-d$_6$) δ 11.10 (s, 1H), 10.18 (s, 1H), 9.53 (s, 1H), 8.62 (s, 1H), 8.39 (s, 1H), 8.14 (d, J=7.8 Hz, 1H), 7.89 (s, 1H), 7.79 (d, J=8.5 Hz, 1H), 7.72-7.65 (m, 1H), 7.60 (d, J=8.2 Hz, 1H), 7.53-7.44 (m, 3H), 7.36 (dd, J=8.7, 2.3 Hz, 1H), 7.17 (d, J=12.1 Hz, 1H), 5.28 (p, J=6.7 Hz, 1H), 5.10 (dd, J=12.7, 5.5 Hz, 1H), 4.46 (s, 1H), 4.26-4.11 (m, 1H), 4.08-3.18 (m, 10H), 3.04-2.73 (m, 8H), 2.64-2.54 (s, 4H), 2.36 (s, 3H), 2.10-1.99 (m, 1H), 1.92-1.52 (m, 17H), 1.41 (d, J=13.0 Hz, 1H), 1.09 (d, J=6.5 Hz, 6H).

Example 24

5-[(6-{1'-[1-(1-{2-[2,6-dioxopiperidin-3-yl]-1,3-dioxo-2,3-dihydro-1H-isoindol-5-yl}piperidin-4-yl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

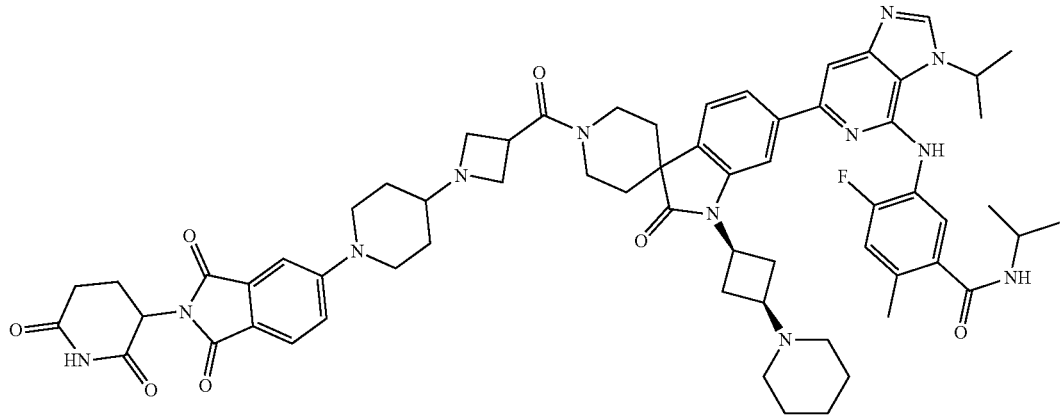 [SMILES: Cc1cc(F)c(Nc2nc(-c3ccc4c(c3)N([C@H]3C[C@@H](N5CCCCC5)C3)C(=O)C43CCN(C(=O)C4CN(C5CCN(c6ccc7c(c6)C(=O)N(C6CCC(=O)NC6=O)C7=O)CC5)C4)CC3)cc3ncn(C(C)C)c23)cc1C(=O)NC(C)C]

Step 1: Synthesis of benzyl 4-{3-[(tert-butoxy)carbonyl]azetidin-1-yl}piperidine-1-carboxylate. To a solution of tert-butyl azetidine-3-carboxylate (4.5 g, 29 mmol, 1.0 eq) and 1-(benzyloxycarbonyl)-4-piperidinone (7.35 g, 31.5 mmol, 1.10 eq) in DCE (136 mL, 0.2 M) was added acetic acid (2.46 mL, 42.9 mmol, 1.5 eq) and the reaction mixture was stirred at RT for 1 h. Next, NaBH(OAc)$_3$ (9.71 g, 45.8 mmol, 1.6 eq) was added and the mixture was stirred at RT overnight. The reaction mixture was then quenched with aqueous NaHCO$_3$, extracted with DCM (3×), washed with brine, dried over Na$_2$SO$_4$ and concentrated to dryness. The colorless oil was purified by Chromatography B to give 9.39 g (88% yield) of the title compound.

Step 2: Synthesis of tert-butyl 1-(piperidin-4-yl)azetidine-3-carboxylate. A solution of benzyl 4-{3-[(tert-butoxy)carbonyl]azetidin-1-yl}piperidine-1-carboxylate (9.39 g, 25.1 mmol, 1.0 eq) in MeOH (250 mL, 0.1 M) was degassed and filled with argon 3 times. Then Pd(OH)$_2$ (0.7 g, 5.0 mmol, 0.2 eq) was added and the mixture was again degassed and filled with argon 3 times. After that, the reaction mixture was degassed and charged with H$_2$ balloon and stirred at RT overnight. The reaction mixture was filtrated through a celite pad and filtrate was concentrated to afford 5.81 g (96% yield) of the title compound.

Step 3: Synthesis of tert-butyl 1-{1-[2-(2,6-dioxopiperidin-3-yl)-1,3-dioxo-2,3-dihydro-1H-isoindol-5-yl]piperidin-4-yl}azetidine-3-carboxylate. To a solution of 2-(2,6-dioxopiperidin-3-yl)-5-fluoro-2,3-dihydro-1H-isoindole-1,3-dione (6.05 g, 21.9 mmol, 1.0 eq) in DMSO (43.8 mL, 0.5 M) were added tert-butyl 1-(piperidin-4-yl)azetidine-3-carboxylate (5.79 g, 24.1 mmol, 1.1 eq) and DIPEA (7.63 mL, 43.8 mmol, 2.0 eq). The reaction mixture was then moved to pre-heated bath to 90° C., and stirred overnight under an argon atmosphere. The reaction was quenched with water, extracted with DCM (3×), and the organic phase was washed with ice-cold water. The crude was purified by FC eluted by DCM: Acetone (0-10%) to acquire 6.95 g (64% yield) of the title compound.

Step 4: Synthesis of 1-{1-[2-(2,6-dioxopiperidin-3-yl)-1,3-dioxo-2,3-dihydro-1H-isoindol-5-yl]piperidin-4-yl}azetidine-3-carboxylic acid hydrochloride. To a solution of tert-butyl 1-{1-[2-(2,6-dioxopiperidin-3-yl)-1,3-dioxo-2,3-dihydro-1H-isoindol-5-yl]piperidin-4-yl}azetidine-3-carboxylate (4.95 g, 9.97 mmol, 1.0 eq) in anh DCM (100 mL, 0.1 M) was added 2M HCl in Et$_2$O (50 mL, 100 mmol, 10.0 eq). The reaction mixture was then stirred at RT for 2 h. Another portion of HCl in Et$_2$O (50 mL, 100 mmol, 10.0 eq) was added and the reaction was left stirring for another 3 h. The precipitate was filtrated out and again dissolved in DCM, followed by the addition of 2M HCl in Et$_2$O (50 mL, 100 mmol, 10.0 eq) and the reaction mixture was sonicated for 45 min. The precipitated solid was filtrated off, washed with Et$_2$O, and dried under vacuum resulting in 4.83 g (quant yield) of the title compound as HCl salt.

Step 5: Synthesis of 5-[(6-{1'-[1-(1-{2-[2,6-dioxopiperidin-3-yl]-1,3-dioxo-2,3-dihydro-1H-isoindol-5-yl}piperidin-4-yl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (11.8 mg), rac-1-(1-{2-[(3R)-2,6-dioxopiperidin-3-yl]-1,3-dioxoisoindol-5-yl}piperidin-4-yl)azetidine-3-carboxylic acid (7 mg) as starting materials. Crude material was purified by reverse phase HPLC to provide the title compound (6.5 mg, 36%); LCMS: $C_{63}H_{73}FN_{12}O_7$ requires 1128.6, found 1130.7 [M+2H]$^+$; $^1$H NMR (500 MHz, DMSO-d$_6$) δ 11.08 (s, 1H), 9.49 (s, 1H), 8.61 (s, 1H), 8.38 (s, 1H), 8.13 (d, J=7.8 Hz, 1H), 7.88 (s, 1H), 7.76-7.65 (m, 2H), 7.60 (dd, J=8.2, 3.6 Hz, 1H), 7.53-7.45 (m, 2H), 7.42 (s, 1H), 7.32 (d, J=8.2 Hz, 1H), 7.17 (d, J=12.0 Hz, 1H), 5.37-5.20 (m, 1H), 5.08 (dd, J=12.7, 5.5 Hz, 1H), 4.46-4.20 (m, 2H), 4.22-4.14 (m, 4H), 4.06-3.32 (m, 11H), 3.05-2.73 (m, 8H), 2.65-2.53 (m, 2H), 2.36 (s, 3H), 2.15-1.98 (m, 3H), 1.92-1.50 (m, 17H), 1.50-1.34 (m, 3H), 1.09 (d, J=6.6 Hz, 6H).

Example 25

5-[(6-{1'-[1-(1-{2-[(3RS)-2,6-dioxopiperidin-3-yl]-1,3-dioxo-2,3-dihydro-1H-isoindol-4-yl}piperidine-4-carbonyl)pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

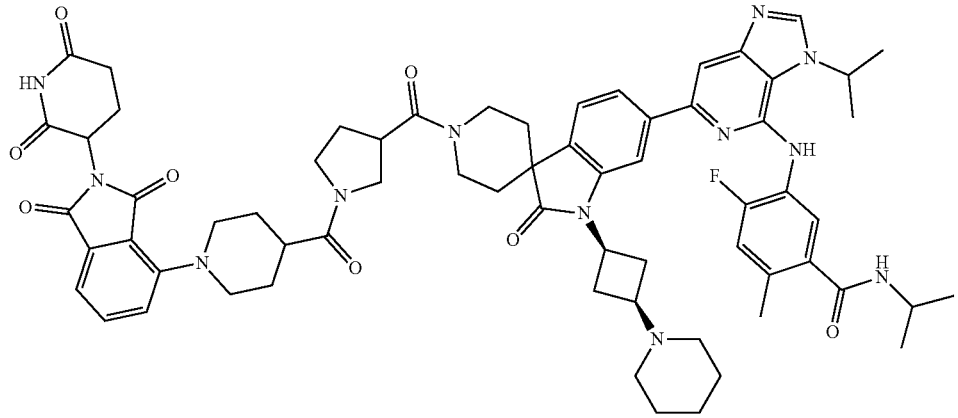 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)C5CCN(c6cccc7c6C(=O)N(C6CCC(=O)NC6=O)C7=O)CC5)C4)CC3)cc3ncn(C(C)C)c23)cc1C(=O)NC(C)C]

Step 1: Synthesis of 1-[2-(2,6-dioxopiperidin-3-yl)-1,3-dioxoisoindol-4-yl]piperidine-4-carboxylic acid. The reaction was carried out according to General Procedure A using 2-(2,6-dioxopiperidin-3-yl)-4-fluoroisoindole-1,3-dione (400 mg, 1.45 mmol) and tert-butyl piperidine-4-carboxylate (350 mg, 1.89 mmol) as starting materials. The crude material was purified with Chromatography B. Using this material, General Procedure B was followed to yield the title compound (0.378 mg, 680%) after Chromatography C.

Step 2: Synthesis of 1-(1-{2-[-2,6-dioxopiperidin-3-yl]-1,3-dioxoisoindol-4-yl}piperidine-4-carbonyl)pyrrolidine-3-carboxylic acid. The reaction was carried out according to General Procedure F using 1-[2-(2,6-dioxopiperidin-3-yl)-1,3-dioxoisoindol-4-yl]piperidine-4-carboxylic acid (50 mg, 0.13 mmol) and tert-butyl pyrrolidine-3-carboxylate (27 mg, 0.16 mmol) and purified using Chromatography B. This material was then treated according to General Procedure B, and the title compound (40 mg, 64%) was isolated after Chromatography C.

Step 3: Synthesis of 5-[(1-(1-{2-[(3R)-2,6-dioxopiperidin-3-yl]-1,3-dioxoisoindol-4-yl}piperidine-4-carbonyl)pyrrolidine-3-carboxylic acid 6-{1'-[1-(1-{2-[(3RS)-2,6-dioxopiperidin-3-yl]-1,3-dioxo-2,3-dihydro-1H-isoindol-4-yl}piperidine-4-carbonyl)pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (10.5 mg), 1-(1-(2-(2,6-dioxopiperidin-3-yl)-1,3-dioxoisoindolin-4-yl)piperidine-4-carbonyl)pyrrolidine-3-carboxylic acid (7 mg) as starting materials. Crude material was purified by reverse phase HPLC to provide the title compound (5.1 mg, 31%); LCMS: $C_{65}H_{75}FN_{12}O_8$ requires 1170.6, found 1172.5 [M+2H]$^+$; $^1$H NMR (500 MHz, DMSO-$d_6$) δ 11.08 (s, 1H), 9.34 (s, 1H), 8.68 (s, 1H), 8.40 (s, 1H), 8.13 (dd, J=7.8, 4.5 Hz, 1H), 7.87 (d, J=2.9 Hz, 1H), 7.74-7.63 (m, 2H), 7.63-7.47 (m, 3H), 7.35 (dd, J=10.7, 6.8 Hz, 2H), 7.18 (d, J=12.0 Hz, 1H), 5.37-5.23 (m, 1H), 5.10 (dd, J=12.9, 5.3 Hz, 1H), 4.26-3.26 (m, 8H), 3.03-2.73 (m, 8H), 2.71-2.54 (m, 8H), 2.36 (d, J=6.0 Hz, 4H), 2.22-1.98 (m, 3H), 1.92-1.50 (m, 21H), 1.50-1.36 (m, 1H), 1.09 (dd, J=6.6, 4.1 Hz, 6H).

Example 26

4-fluoro-2-methyl-5-[(6-{2-oxo-1'-[1-[(1R,4R)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

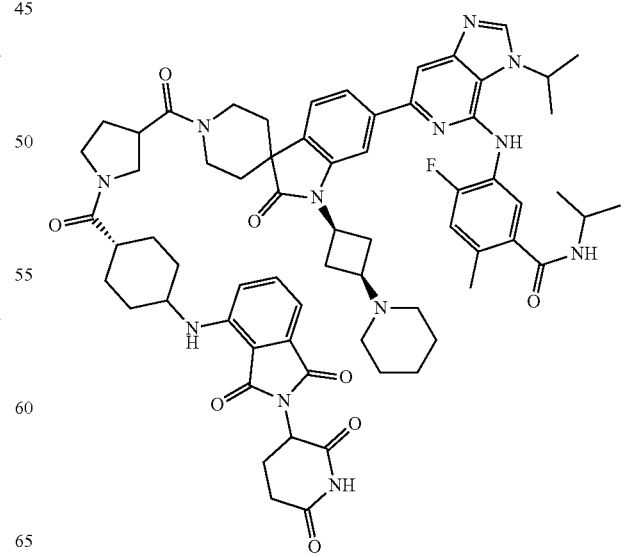

Step 1: Synthesis of (trans)-4-{[2-(2,6-dioxopiperidin-3-yl)-1,3-dioxoisoindol-4-yl]amino}cyclohexane-1-carboxylic acid. The reaction was carried out according to General Procedure A using 2-(2,6-dioxopiperidin-3-yl)-4-fluoroisoindole-1,3-dione (100 mg, 0.36 mmol) and (trans)-4-aminocyclohexane-1-carboxylic acid (104 mg, 0.72 mmol) as starting materials. Chromatography C afforded the title compound (40 mg, 28%).

Step 2: Synthesis of 1-[(trans)-4-({2-[2,6-dioxopiperidin-3-yl]-1,3-dioxoisoindol-4-yl}amino)cyclohexanecarbonyl]pyrrolidine-3-carboxylic acid. The reaction was carried out according to General Procedure F using (trans)-4-{[2-(2,6-dioxopiperidin-3-yl)-1,3-dioxoisoindol-4-yl]amino}cyclohexane-1-carboxylic acid (32 mg, 0.08 mmol) and tert-butyl pyrrolidine-3-carboxylate (16.5 mg, 0.10 mmol) and purified using Chromatography C. This material was then treated according to General Procedure B, and the title compound (23 mg, 58%) was isolated after Chromatography C.

Step 3: Synthesis of 4-fluoro-2-methyl-5-[(6-{2-oxo-1'-[1-[(1r,4r)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F, using Intermediate 1 (10.5 mg), 1-[(trans)-4-({2-[2,6-dioxopiperidin-3-yl]-1,3-dioxoisoindol-4-yl}amino)cyclohexanecarbonyl]pyrrolidine-3-carboxylic acid (7 mg) as starting materials. Crude material was purified by reverse phase HPLC to provide the title compound (5.9 mg, 34%); LCMS: $C_{66}H_{77}FN_{12}O_8$ requires 1184.6, found 1185.9 [M+H]$^+$; $^1$H NMR (500 MHz, DMSO-d$_6$) δ 11.11 (s, 1H), 9.34 (s, 1H), 8.67 (s, 1H), 8.41 (s, 1H), 8.15 (d, J=8.0 Hz, 1H), 7.89 (d, J=2.5 Hz, 1H), 7.78-7.48 (m, 5H), 7.33-7.14 (m, 2H), 7.05 (d, J=7.0 Hz, 1H), 6.18 (d, J=8.1 Hz, 1H), 5.38-5.25 (m, 1H), 5.06 (dd, J=12.8, 5.5 Hz, 1H), 4.22-3.24 (m, 8H), 3.09-2.69 (m, 8H), 2.69-2.54 (m, 4H), 2.37 (s, 3H), 2.21-1.94 (m, 6H), 1.91-1.48 (m, 22H), 1.48-1.29 (m, 3H), 1.11 (d, J=6.4 Hz, 6H).

Example 27

4-fluoro-2-methyl-5-[(6-{2-oxo-1-[(1s,3s)-3-(piperidin-1-yl)cyclobutyl]-1'-[1-[(1S,4S)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

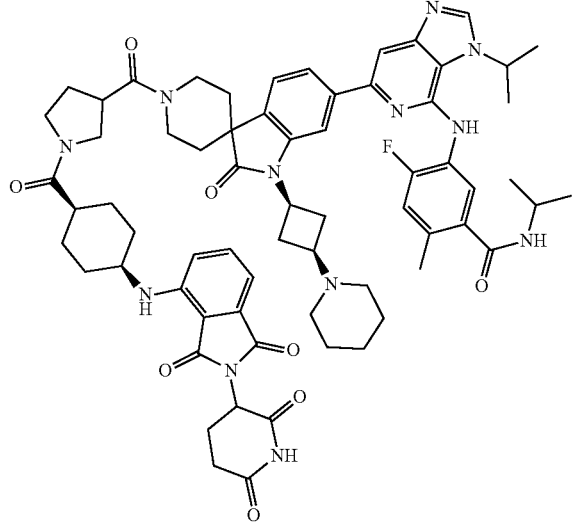 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)[C@H]5CC[C@@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of 1-[(cis)-4-({2-[2,6-dioxopiperidin-3-yl]-1,3-dioxoisoindol-4-yl}amino)cyclohexanecarbonyl]pyrrolidine-3-carboxylic acid. The synthesis was done analogously to Example 26, Steps 1 and 2, starting with (cis)-4-aminocyclohexane-1-carboxylic acid to afford the title compound.

Step 2: Synthesis of 4-fluoro-2-methyl-5-[(6-{2-oxo-1-[(1s,3s)-3-(piperidin-1-yl)cyclobutyl]-1'-[1-[(1s,4s)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F, using Intermediate 1 (10 mg), 1-[(cis)-4-({2-[(3RS)-2,6-dioxopiperidin-3-yl]-1,3-dioxoisoindol-4-yl}amino)cyclohexanecarbonyl]pyrrolidine-3-carboxylic acid (7 mg) as starting materials. Crude material was purified by reverse phase HPLC to provide the title compound (9.7 mg, 58%); LCMS: $C_{66}H_{77}FN_{12}O_8$ requires 1184.6, found 1185.9 [M+H]$^+$; $^1$H NMR (500 MHz, DMSO-d$_6$) δ 11.10 (s, 1H), 9.36 (s, 1H), 8.69 (s, 1H), 8.41 (s, 1H), 8.14 (d, J=7.8 Hz, 1H), 7.87 (d, J=4.5 Hz, 1H), 7.75-7.47 (m, 5H), 7.16 (dd, J=18.2, 10.4 Hz, 2H), 7.05 (d, J=7.0 Hz, 1H), 6.53 (s, 1H), 5.39-5.20 (m, 1H), 5.07 (dd, J=12.9, 5.4 Hz, 1H), 4.24-3.21 (m, 9H), 3.03-2.73 (m, 8H), 2.65-2.52 (m, 5H), 2.36 (s, 3H), 2.16-2.02 (m, 2H), 1.90-1.50 (m, 26H), 1.41 (q, J=14.2, 13.6 Hz, 1H), 1.10 (d, J=6.6 Hz, 6H).

Example 28

5-[(6-{1'-[2-(7-{2-[2,6-dioxopiperidin-3-yl]-1,3-dioxo-2,3-dihydro-1H-isoindol-5-yl}-2,7-diazaspiro[3.5]nonan-2-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

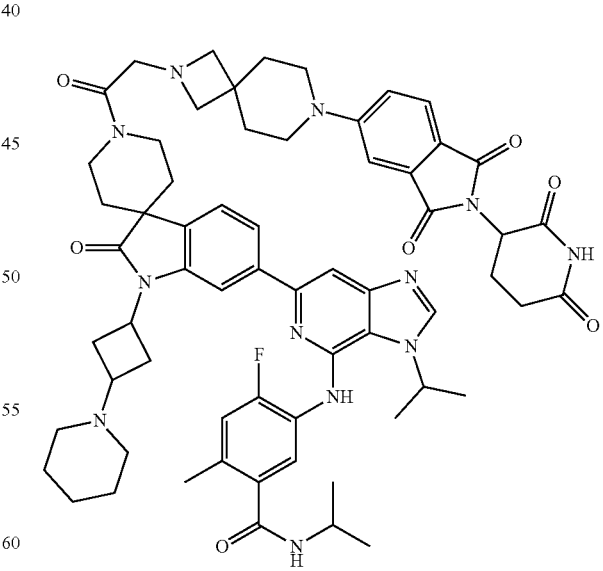

Step 1: Synthesis of 2,7-diazaspiro[3.5]nonan-2-ylacetic acid hydrochloride. The synthesis was carried out according to General Procedure E followed by General Procedure B using tert-butyl 2,7-diazaspiro[3.5]nonane-7-carboxylate (400 mg, 1.77 mmol) and tert-butyl 2-bromoacetate (379 mg, 1.94 mmol) as starting materials. The title compound (331 mg, 84% over two steps) was isolated without further purification.

Step 2: Synthesis of (7-[2-(2,6-dioxopiperidin-3-yl)-1,3-dioxoisoindol-5-yl]-2,7-diazaspiro[3.5]nonan-2-yl)acetic acid. The reaction was carried out according to General Procedure A using 2,7-diazaspiro[3.5]nonan-2-ylacetic acid hydrochloride (331 mg, 1.50 mmol) and 2-(2,6-dioxopiperidin-3-yl)-5-fluoroisoindole-1,3-dione (414 mg, 1.50 mmol) as starting materials. Chromatography C afforded the title compound (50 mg, 8%).

Step 3: Synthesis of 5-[(6-{1'-[2-(7-{2-[2,6-dioxopiperidin-3-yl]-1,3-dioxo-2,3-dihydro-1H-isoindol-5-yl}-2,7-diazaspiro[3.5]nonan-2-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (13.5 mg), (7-[2-(2,6-dioxopiperidin-3-yl)-1,3-dioxoisoindol-5-yl]-2,7-diazaspiro[3.5]nonan-2-yl)acetic acid (8 mg) as starting materials. Crude material was purified by reverse phase HPLC to provide the title compound (6.2 mg, 30%); LCMS: $C_{63}H_{73}FN_{12}O_7$ requires 1128.6, found 1129.9 [M+H]$^+$; $^1$H NMR (500 MHz, DMSO-$d_6$) δ 11.07 (d, J=4.3 Hz, 1H), 10.30 (d, J=37.2 Hz, 1H), 9.48 (s, 1H), 8.59 (s, 1H), 8.37 (s, 1H), 8.13 (d, J=7.8 Hz, 1H), 7.89 (s, 1H), 7.70 (t, J=7.9 Hz, 2H), 7.61 (d, J=8.3 Hz, 1H), 7.52 (s, 1H), 7.46 (d, J=7.9 Hz, 1H), 7.17 (d, J=12.2 Hz, 1H), 6.97-6.80 (m, 1H), 5.35-5.20 (m, 1H), 5.10-5.01 (m, 1H), 4.54 (d, J=17.4 Hz, 1H), 4.25-3.13 (m, 9H), 3.04-2.68 (m, 9H), 2.65-2.52 (m, 6H), 2.36 (s, 3H), 2.23-1.52 (m, 22H), 1.41 (d, J=13.6 Hz, 1H), 1.09 (d, J=6.4 Hz, 6H).

Example 29

5-{[6-(1'-{2-[(3S)-1-({1-[2-(2,6-dioxopiperidin-3-yl)-1,3-dioxo-2,3-dihydro-1H-isoindol-5-yl]pyrrolidin-3-yl}Methyl)piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

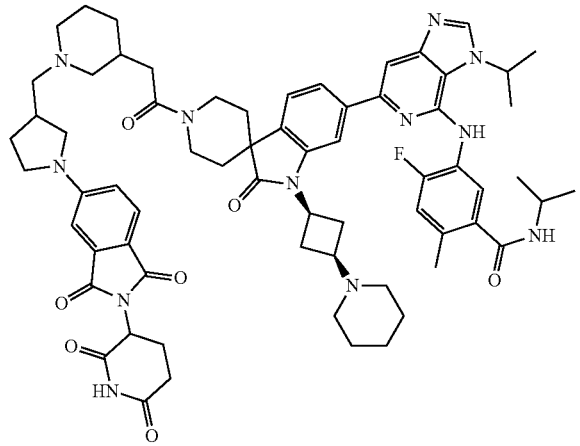 [SMILES: Cc1cc(F)c(Nc2nc(-c3ccc4c(c3)N([C@H]3C[C@@H](N5CCCCC5)C3)C(=O)C43CCN(C(=O)CC4CCCN(CC5CCN(c6ccc7c(c6)C(=O)N(C6CCC(=O)NC6=O)C7=O)C5)C4)CC3)cc3ncn(C(C)C)c23)cc1C(=O)NC(C)C]

Step 1: Synthesis of tert-butyl 3-{[(3S)-3-(2-methoxy-2-oxoethyl)piperidin-1-yl]methyl}pyrrolidine-1-carboxylate. The reaction was carried out according to General Procedure D, using tert-butyl 3-formylpyrrolidine-1-carboxylate (1.00 g, 5.02 mmol), methyl 2-[(3S)-piperidin-3-yl]acetate hydrochloride (972 mg, 5.02 mmol), and TEA (1.54 mL, 11.0 mmol) as reagents. Following the procedure, the title compound (1.6 g, 94%) was used without further purification.

Step 2: Synthesis of [(3S)-1-(pyrrolidin-3-ylmethyl)piperidin-3-yl]acetic acid. The saponification reaction was carried out according to General Procedure C using tert-butyl 3-{[(3S)-3-(2-methoxy-2-oxoethyl)piperidin-1-yl]methyl}pyrrolidine-1-carboxylate (1.60 g, 4.70 mmol) as the starting material. The product of this reaction was directly subjected to General Procedure B to yield the title compound (1.06 g, quant).

Step 3: Synthesis of 2-((3S)-1-((1-(2-(2,6-dioxopiperidin-3-yl)-1,3-dioxoisoindolin-5-yl)pyrrolidin-3-yl)methyl)piperidin-3-yl)acetic acid. The reaction was carried out according to General Procedure A, using [(3S)-1-(pyrrolidin-3-ylmethyl)piperidin-3-yl]acetic acid (328 mg, 0.72 mmol) and 2-(2,6-dioxopiperidin-3-yl)-5-fluoroisoindole-1,3-dione (200 mg, 0.72 mmol) as starting materials. Chromatography C provided the title compound (214 mg, 61%).

Step 4: Synthesis of 5-{[6-(1'-{2-[(3S)-1-({1-[2-(2,6-dioxopiperidin-3-yl)-1,3-dioxo-2,3-dihydro-1H-isoindol-5-yl]pyrrolidin-3-yl}methyl)piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (7.3 mg), 2-((3S)-1-((1-(2-(2,6-dioxopiperidin-3-yl)-1,3-dioxoisoindolin-5-yl)pyrrolidin-3-yl)methyl)piperidin-3-yl)acetic acid (5 mg) as starting materials. Crude material was purified by reverse phase HPLC to provide the title compound (2.8 mg, 23%); LCMS: $C_{66}H_{79}FN_{12}O_7$ requires 1170.6, found 1172.1 [M+H]$^+$; $^1$H NMR (500 MHz, DMSO-$d_6$) δ 10.99 (s, 1H), 8.49 (s, 1H), 8.27 (s, 1H), 8.05 (d, J=7.9 Hz, 1H), 7.79 (s, 1H), 7.60 (dd, J=14.7, 8.1 Hz, 2H), 7.52 (d, J=8.1 Hz, 1H), 7.46-7.37 (m, 2H), 7.09 (d, J=12.2 Hz, 1H), 6.87 (s, 1H), 6.76 (d, J=8.2 Hz, 1H), 5.23-5.11 (m, 1H), 4.98 (dd, J=13.0, 5.4 Hz, 1H), 4.16-4.07 (m, 1H), 4.01-3.91 (m, 1H), 3.81-3.05 (m, 8H), 2.99-2.65 (m, 14H), 2.57-2.46 (m, 4H), 2.36-2.12 (m, 10H), 2.03-1.28 (m, 30H), 1.01 (d, J=6.6 Hz, 6H).

Example 30

4-fluoro-2-methyl-5-[(6-{2-oxo-1-[(1s,3s)-3-(piperidin-1-yl)cyclobutyl]-1'-[1-[(1s,3s)-3-({2-[2,6-dioxopiperidin-3-yl]-1,3-dioxo-2,3-dihydro-1H-isoindol-4-yl}amino)cyclobutanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

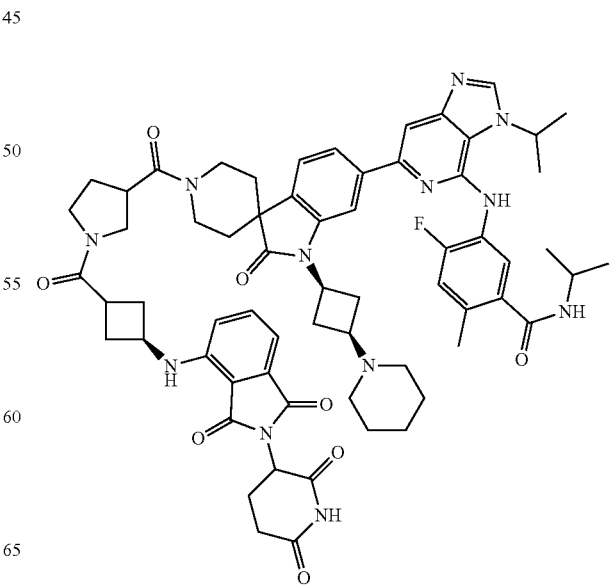

Step 1: Synthesis of (cis)-3-{[2-(2,6-dioxopiperidin-3-yl)-1,3-dioxoisoindol-4-yl]amino}cyclobutane-1-carboxylic acid. The reaction was carried out according to General Procedure A using 2-(2,6-dioxopiperidin-3-yl)-4-fluoroisoindole-1,3-dione (150 mg, 0.54 mmol) and (cis)-3-aminocyclobutane-1-carboxylic acid hydrochloride (82 mg, 0.54 mmol) as staring materials. Chromatography C afforded the title compound (50 mg, 25%).

Step 2: Synthesis of 1-[(cis)-3-({2-[2,6-dioxopiperidin-3-yl]-1,3-dioxoisoindol-4-yl}amino)cyclobutanecarbonyl]pyrrolidine-3-carboxylic acid. The reaction was carried out according to General Procedure F, using (cis)-3-{[2-(2,6-dioxopiperidin-3-yl)-1,3-dioxoisoindol-4-yl]amino}cyclobutane-1-carboxylic acid (18 mg, 0.05 mmol) and tert-butyl pyrrolidine-3-carboxylate (10 mg, 0.06 mmol) as starting materials. The product of this reaction was then subjected to General Procedure B which provided the title compound (8 mg, 40%) after Chromatography C.

Step 3: Synthesis of 4-fluoro-2-methyl-5-[(6-{2-oxo-1-[(1s,3s)-3-(piperidin-1-yl)cyclobutyl]-1'-[1-[(1s,3s)-3-({2-[2,6-dioxopiperidin-3-yl]-1,3-dioxo-2,3-dihydro-1H-isoindol-4-yl}amino)cyclobutanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F, using Intermediate 1 (12.7 mg), 1-((cis)-3-((2-(2,6-dioxopiperidin-3-yl)-1,3-dioxoisoindolin-4-yl)amino)cyclobutane-1-carbonyl)pyrrolidine-3-carboxylic acid (8 mg, 0.02 mmol) as starting materials. Crude material was purified by reverse phase HPLC to provide the title compound (9.3 mg, 45%); LCMS: $C_{64}H_{73}FN_{12}O_8$ requires 1156.6, found 1157.9 [M+H]$^+$; $^1$H NMR (500 MHz, DMSO-d$_6$) δ 11.10 (s, 1H), 9.35 (s, 1H), 8.66 (s, 1H), 8.40 (s, 1H), 8.13 (d, J=7.8 Hz, 1H), 7.87 (d, J=3.6 Hz, 1H), 7.71-7.63 (m, 1H), 7.63-7.47 (m, 4H), 7.18 (d, J=12.1 Hz, 1H), 7.10-7.03 (m, 2H), 6.45 (s, 1H), 5.29 (p, J=6.6 Hz, 1H), 5.06 (dd, J=12.7, 5.4 Hz, 1H), 4.25-3.19 (m, 8H), 3.08-2.74 (m, 8H), 2.72-2.56 (m, 4H), 2.54 (s, 3H), 2.36 (s, 3H), 2.18-2.01 (m, 5H), 1.91-1.53 (m, 18H), 1.41 (d, J=12.9 Hz, 1H), 1.10 (d, J=6.6 Hz, 6H).

Example 31

5-{[6-(1'-{2-[(3S)-1-{[1-{2-[2,6-dioxopiperidin-3-yl]-1,3-dioxo-2,3-dihydro-1H-isoindol-4-yl}pyrrolidin-3-yl]methyl}piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide Step 1: Synthesis of tert-butyl 3-{[(3S)-3-(2-methoxy-2-oxoethyl)piperidin-1-yl]methyl}pyrrolidine-1-carboxylate. The reaction was carried out according to General Procedure D, using tert-butyl 3-formylpyrrolidine-1-carboxylate (1.00 g, 5.02 mmol), methyl 2-[(3S)-piperidin-3-yl]acetate hydrochloride (972 mg, 5.02 mmol), and methyl 2-[(3S)-piperidin-3-yl]acetate hydrochloride (972 mg, 5.02 mmol) as reagents. Following the procedure, the title compound (1.6 g, 94%) was used without further purification.

Step 2: Synthesis of [(3S)-1-(pyrrolidin-3-ylmethyl)piperidin-3-yl]acetic acid. The saponification reaction was carried out according to General Procedure C using tert-butyl 3-{[(3S)-3-(2-methoxy-2-oxoethyl)piperidin-1-yl]methyl}pyrrolidine-1-carboxylate (1.60 g, 4.70 mmol) as the starting material. The product of this reaction was directly subjected to General Procedure B to yield the title compound (1.06 g, quant).

Step 3: Synthesis of 2-((3S)-1-((1-(2-(2,6-dioxopiperidin-3-yl)-1,3-dioxoisoindolin-4-yl)pyrrolidin-3-yl)methyl)piperidin-3-yl)acetic acid. The reaction was carried out according to General Procedure A, using [(3S)-1-(pyrrolidin-3-ylmethyl)piperidin-3-yl]acetic acid (819 mg, 1.81 mmol) and 2-(2,6-dioxopiperidin-3-yl)-4-fluoroisoindole-1,3-dione (500 mg, 1.81 mmol) as starting materials. Chromatography C provided the title compound (490 mg, 48%).

Step 4: Synthesis of 5-{[6-(1'-{2-[(3S)-1-{[1-{2-[2,6-dioxopiperidin-3-yl]-1,3-dioxo-2,3-dihydro-1H-isoindol-4-yl}pyrrolidin-3-yl]methyl}piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (14 mg), 2-((3S)-1-((1-(2-(2,6-dioxopiperidin-3-yl)-1,3-dioxoisoindolin-4-yl)pyrrolidin-3-yl)methyl)piperidin-3-yl)acetic acid (10 mg) as starting materials. Crude material was purified by reverse phase HPLC to provide the title compound (8.1 mg, 29%); LCMS: $C_{66}H_{79}FN_{12}O_7$ requires 1170.6, found 1171.8 [M+H]$^+$; $^1$H NMR (500 MHz, DMSO-d$_6$) δ 11.07 (s, 1H), 9.49 (s, 1H), 9.17 (s, 1H), 8.65 (s, 1H), 8.40 (s, 1H), 8.14 (d, J=7.8 Hz, 1H), 7.87 (s, 1H), 7.69-7.54 (m, 3H), 7.49 (d, J=8.5 Hz, 2H), 7.21-7.15 (m, 2H), 7.12 (d, J=8.8 Hz, 1H), 5.35-5.24 (m, 1H), 5.07 (dd, J=12.8, 5.5 Hz, 1H), 4.20 (dd, J=16.4, 8.3 Hz, 1H), 4.10-3.98 (m, 1H), 3.93-3.08 (m, 10H), 3.07-2.66 (m, 10H), 2.65-2.52 (m, 4H), 2.42-2.32 (m, 4H), 2.22 (s, 1H), 2.06-1.29 (m, 25H), 1.09 (d, J=6.5 Hz, 6H).

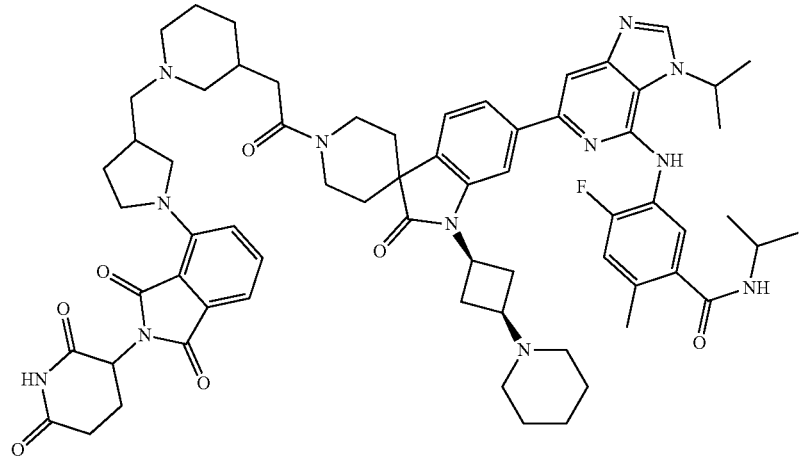 [SMILES: Cc1cc(F)c(Nc2nc(-c3ccc4c(c3)N([C@H]3C[C@@H](N5CCCCC5)C3)C(=O)C43CCN(C(=O)CC4CCCN(CC5CCN(c6cccc7c6C(=O)N(C6CCC(=O)NC6=O)C7=O)C5)C4)CC3)cc3ncn(C(C)C)c23)cc1C(=O)NC(C)C]

Example 32

5-({6-[1'-(1-{2-[(3S)-1-{2-[2,6-dioxopiperidin-3-yl]-1,3-dioxo-2,3-dihydro-1H-isoindol-4-yl}piperidin-3-yl]acetyl}pyrrolidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide

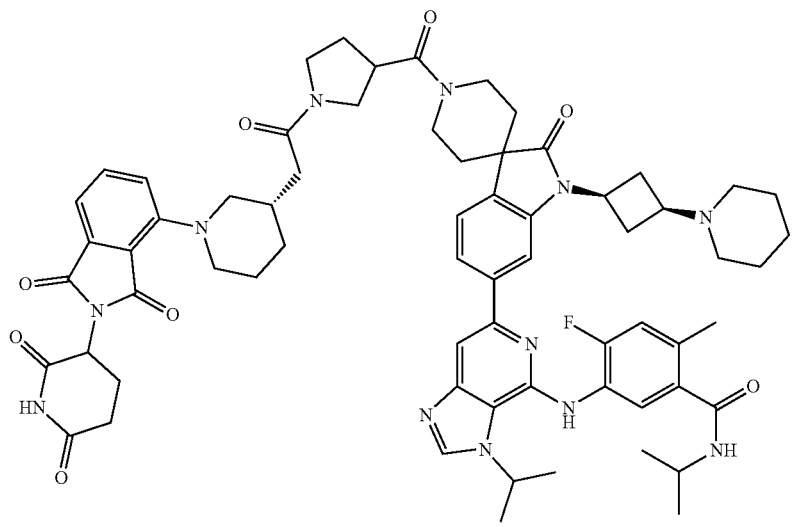 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)C[C@@H]5CCCN(c6cccc7c6C(=O)N(C6CCC(=O)NC6=O)C7=O)C5)C4)CC3)cc3ncn(C(C)C)c23)cc1C(=O)NC(C)C]

Step 1: Synthesis of [(3S)-1-[2-(2,6-dioxopiperidin-3-yl)-1,3-dioxoisoindol-4-yl]piperidin-3-yl]acetic acid. The reaction was run according to General Procedure A using (3S)-piperidin-3-ylacetic acid (143 mg, 1.00 mmol) and 2-(2,6-dioxopiperidin-3-yl)-4-fluoroisoindole-1,3-dione (276 mg, 1.00 mmol) as starting materials. Chromatography C provided the title compound (190 mg, 48%).

Step 2: Synthesis of 1-{2-[(3S)-1-[2-(2,6-dioxopiperidin-3-yl)-1,3-dioxoisoindol-4-yl]piperidin-3-yl]acetyl}pyrrolidine-3-carboxylic acid. The reaction was run according to General Procedure F using [(3S)-1-[2-(2,6-dioxopiperidin-3-yl)-1,3-dioxoisoindol-4-yl]piperidin-3-yl]acetic acid (20 mg, 0.05 mmol) and tert-butyl pyrrolidine-3-carboxylate (8.6 mg, 0.05 mmol) as staring materials. The crude material from this reaction was directly subjected to General Procedure B to afford the title compound (10 mg, 40%).

Step 3: Synthesis of 5-({6-[1'-(1-{2-[(3S)-1-{2-[2,6-dioxopiperidin-3-yl]-1,3-dioxo-2,3-dihydro-1H-isoindol-4-yl}piperidin-3-yl]acetyl}pyrrolidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide. The title compound was synthesized according to General Procedure F, using Intermediate 1 (14.5 mg), 1-(2-((3R)-1-(2-(2,6-dioxopiperidin-3-yl)-1,3-dioxoisoindolin-4-yl)piperidin-3-yl)acetyl)pyrrolidine-3-carboxylic acid (10 mg) as starting materials. Crude material was purified by reverse phase HPLC to provide the title compound (7.5 mg, 31%); LCMS: $C_{66}H_{77}FN_{12}O_8$ requires 1184.6, found 1185.9 [M+H]$^+$; $^1$H NMR (500 MHz, DMSO-d$_6$) δ 11.08 (s, 1H), 9.34 (s, 1H), 8.70 (d, J=4.9 Hz, 1H), 8.41 (s, 1H), 8.13 (d, J=7.7 Hz, 1H), 7.87 (d, J=2.8 Hz, 1H), 7.71-7.62 (m, 2H), 7.61-7.46 (m, 3H), 7.41 (t, J=8.8 Hz, 1H), 7.31 (d, J=6.9 Hz, 1H), 7.18 (d, J=12.0 Hz, 1H), 5.30 (p, J=6.6 Hz, 1H), 5.10 (dd, J=9.7, 4.5 Hz, 1H), 4.25-4.15 (m, 1H), 4.08-3.99 (m, 1H), 3.40 (d, J=11.0 Hz, 10H), 3.03-2.65 (m, 8H), 2.54 (s, 3H), 2.36 (s, 3H), 2.31-1.91 (m, 8H), 1.93-1.50 (m, 20H), 1.41 (q, J=10.5, 8.2 Hz, 1H), 1.10 (d, J=6.5 Hz, 6H).

Example 33

5-{[6-(1'-{1-[(1-{2-[2,6-dioxopiperidin-3-yl]-1,3-dioxo-2,3-dihydro-1H-isoindol-4-yl}piperidin-4-yl)methyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

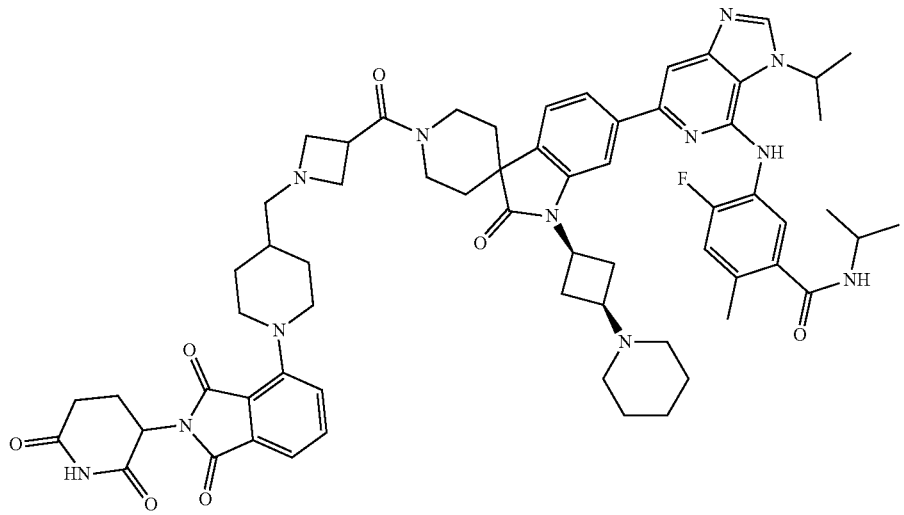 [SMILES: Cc1cc(F)c(Nc2nc(-c3ccc4c(c3)N([C@H]3C[C@@H](N5CCCCC5)C3)C(=O)C43CCN(C(=O)C4CN(CC5CCN(c6cccc7c6C(=O)N(C6CCC(=O)NC6=O)C7=O)CC5)C4)CC3)cc3ncn(C(C)C)c23)cc1C(=O)NC(C)C]

Step 1: Synthesis of 2-(2,6-dioxopiperidin-3-yl)-4-[4-(hydroxymethyl)piperidin-1-yl]isoindole-1,3-dione. The reaction was carried out according to General Procedure A using piperidin-4-ylmethanol (208 mg, 1.80 mmol) and 2-(2,6-dioxopiperidin-3-yl)-4-fluoroisoindole-1,3-dione (500 mg, 1.81 mmol) as starting materials. Chromatography B provided the title compound (500 mg, 74%).

Step 2: Synthesis of 1-[2-(2,6-dioxopiperidin-3-yl)-1,3-dioxoisoindol-4-yl]piperidine-4-carbaldehyde. To a solution of 2-(2,6-dioxopiperidin-3-yl)-4-[4-(hydroxymethyl)piperidin-1-yl]isoindole-1,3-dione (100 mg, 0.27 mmol) in DCM (1.35 mL) was added DMP (228 mg, 0.54 mmol). After stirring for 90 min, silica gel was added to the reaction and the solvents were removed under reduced pressure. The material was then purified by Chromatography A to provide the title compound (32 mg, 32%).

Step 3: Synthesis of 1-({1-[2-(2,6-dioxopiperidin-3-yl)-1,3-dioxoisoindol-4-yl]piperidin-4-yl}methyl)azetidine-3-carboxylic acid. The reductive amination was carried out according to General Procedure D using tert-butyl azetidine-3-carboxylate (6.4 mg, 0.04 mmol) and 1-[2-(2,6-dioxopiperidin-3-yl)-1,3-dioxoisoindol-4-yl]piperidine-4-carbaldehyde (15 mg, 0.04 mmol) as starting materials. The crude material from this reaction was treated directly to General Procedure B. Following Chromatography C the title compound (8 mg, 43%) was obtained.

Step 4: Synthesis of 5-{[6-(1'-{1-[(1-{2-[2,6-dioxopiperidin-3-yl]-1,3-dioxo-2,3-dihydro-1H-isoindol-4-yl}piperidin-4-yl)methyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (12.44 mg), 1-((1-(2-(2,6-dioxopiperidin-3-yl)-1,3-dioxoisoindolin-4-yl)piperidin-4-yl)methyl)azetidine-3-carboxylic acid (8 mg) as starting materials. Crude material was purified by reverse phase HPLC to provide the title compound (8.2 mg, 36%); LCMS: $C_{64}H_{75}FN_{12}O_7$ requires 1142.6, found 1144.0 [M+H]$^+$; $^1$H NMR (500 MHz, DMSO-d$_6$) δ 11.09 (s, 1H), 9.45 (s, 1H), 8.62 (s, 1H), 8.39 (s, 1H), 8.13 (d, J=7.8 Hz, 1H), 7.88 (s, 1H), 7.75-7.63 (m, 2H), 7.60 (d, J=8.1 Hz, 1H), 7.55-7.45 (m, 2H), 7.39-7.30 (m, 2H), 7.17 (d, J=12.0 Hz, 1H), 5.29 (q, J=6.4 Hz, 1H), 5.09 (dd, J=12.8, 5.5 Hz, 1H), 4.51-4.40 (m, 1H), 4.29-4.18 (m, 2H), 4.10-3.13 (m, 10H), 3.03-2.71 (m, 10H), 2.66-2.52 (m, 3H), 2.36 (s, 3H), 2.03 (s, 1H), 1.91-1.51 (m, 20H), 1.51-1.36 (m, 3H), 1.09 (d, J=6.5 Hz, 6H).

Example 34

5-{[6-(1'-{1-[2-(1-{2-[2,6-dioxopiperidin-3-yl]-1,3-dioxo-2,3-dihydro-1H-isoindol-4-yl}piperidin-4-yl)acetyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

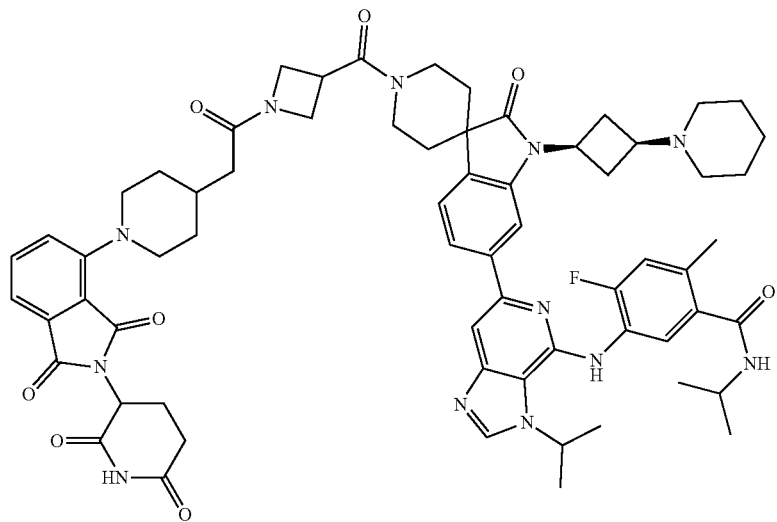 [SMILES: Cc1cc(F)c(Nc2nc(-c3ccc4c(c3)N([C@H]3C[C@@H](N5CCCCC5)C3)C(=O)C43CCN(C(=O)C4CN(C(=O)CC5CCN(c6cccc7c6C(=O)N(C6CCC(=O)NC6=O)C7=O)CC5)C4)CC3)cc3ncn(C(C)C)c23)cc1C(=O)NC(C)C]

Step 1: Synthesis of (1-{2-[2,6-dioxopiperidin-3-yl]-1,3-dioxoisoindol-4-yl}piperidin-4-yl)acetic acid. The reaction was carried out according to General Procedure A using piperidin-4-ylacetic acid (273 mg, 1.91 mmol) and 2-(2,6-dioxopiperidin-3-yl)-4-fluoroisoindole-1,3-dione (527 mg, 1.91 mmol) as starting materials. Chromatography C afforded the title compound (546 mg, 71%).

Step 2: Synthesis of 1-{2-[(3S)-1-[2-(2,6-dioxopiperidin-3-yl)-1,3-dioxoisoindol-4-yl]piperidin-3-yl]acetyl}azetidine-3-carboxylic acid. The reaction was carried out according to General Procedure F using (1-{2-[2,6-dioxopiperidin-3-yl]-1,3-dioxoisoindol-4-yl}piperidin-4-yl)acetic acid (25 mg, 0.06 mmol) and tert-butyl azetidine-3-carboxylate (10 mg, 0.06 mmol). The crude material of this reaction was then directly subjected to General Procedure B to afford the title compound (22 mg, 73%).

Step 3: Synthesis of 5-{[6-(1'-{1-[2-(1-{2-[2,6-dioxopiperidin-3-yl]-1,3-dioxo-2,3-dihydro-1H-isoindol-4-yl}piperidin-4-yl)acetyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (10 mg), 1-(2-(1-(2-(2,6-dioxopiperidin-3-yl)-1,3-dioxoisoindolin-4-yl)piperidin-4-yl)acetyl)azetidine-3-carboxylic acid (6.3 mg) as starting materials. Crude material was purified by reverse phase HPLC to provide the title compound (5.5 mg, 23%); LCMS: $C_{65}H_{75}FN_{12}O_8$ requires 1170.6, found 1172.1 [M+H]$^+$; $^1$H NMR (500 MHz, DMSO-d$_6$) δ 11.08 (s, 1H), 9.31 (s, 1H), 8.64 (s, 1H), 8.38 (s, 1H), 8.13 (dd, J=8.1, 2.3 Hz, 1H), 7.87 (s, 1H), 7.72-7.63 (m, 2H), 7.63-7.48 (m, 3H), 7.33 (t, J=7.7 Hz, 2H), 7.18 (d, J=11.2 Hz, 1H), 5.33-5.24 (m, 1H), 5.14-5.05 (m, 1H), 4.32 (dd, J=18.5, 8.1 Hz, 1H), 4.25-4.16 (m, 1H), 4.10-3.99 (m, 1H), 4.00-3.93 (m, 1H), 3.73-3.35 (m, 10H), 3.03-2.75 (m, 10H), 2.67-2.55 (m, 2H), 2.36 (d, J=4.3 Hz, 4H), 2.13-1.97 (m, 3H), 1.93-1.52 (m, 18H), 1.41 (q, J=13.3, 11.2 Hz, 2H), 1.09 (d, J=4.0 Hz, 6H).

Example 35

5-({6-[1'-(1-{[1-{2-[2,6-dioxopiperidin-3-yl]-1,3-dioxo-2,3-dihydro-1H-isoindol-4-yl}pyrrolidin-3-yl]methyl}azetidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide

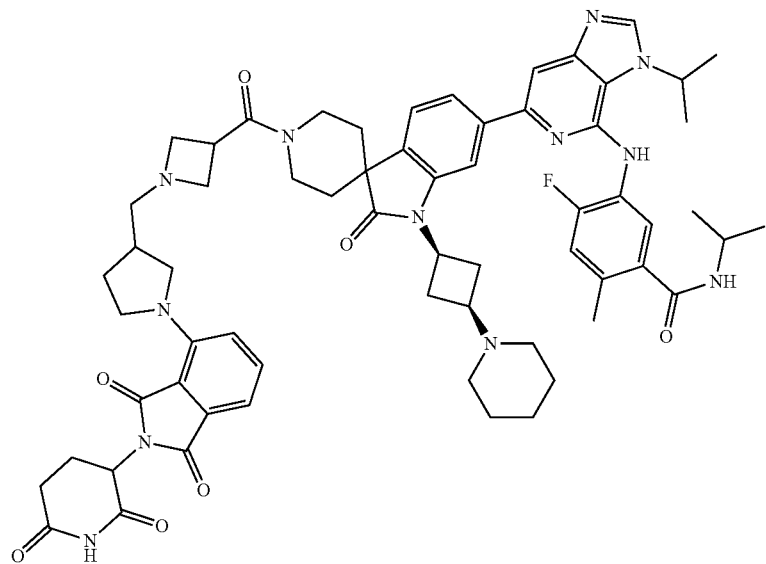 [SMILES: Cc1cc(F)c(Nc2nc(-c3ccc4c(c3)N([C@H]3C[C@@H](N5CCCCC5)C3)C(=O)C43CCN(C(=O)C4CN(CC5CCN(c6cccc7c6C(=O)N(C6CCC(=O)NC6=O)C7=O)C5)C4)CC3)cc3ncn(C(C)C)c23)cc1C(=O)NC(C)C]

Step 1: Synthesis of 2-(2,6-dioxopiperidin-3-yl)-4-[3-(hydroxymethyl)pyrrolidin-1-yl]isoindole-1,3-dione. The reaction was carried out according to General Procedure A using pyrrolidin-3-ylmethanol (220 mg, 2.17 mmol) and 2-(2,6-dioxopiperidin-3-yl)-4-fluoroisoindole-1,3-dione (500 mg, 1.81 mmol) as starting materials and heating at 80° C. Chromatography B afforded the title compound (462 mg, 71%).

Step 2: Synthesis of 1-[2-(2,6-dioxopiperidin-3-yl)-1,3-dioxoisoindol-4-yl]pyrrolidine-3-carbaldehyde. To a solution of 2-(2,6-dioxopiperidin-3-yl)-4-[3-(hydroxymethyl)pyrrolidin-1-yl]isoindole-1,3-dione (100 mg, 0.28 mmol) in DCM (1.40 mL) was added DMP (237 mg, 0.56 mmol). After stirring for 90 min, silica gel was added to the reaction and the solvents were removed under reduced pressure. The material was then purified by Chromatography A to provide the title compound (58 mg, 58%).

Step 3: Synthesis of 1-({1-[2-(2,6-dioxopiperidin-3-yl)-1,3-dioxoisoindol-4-yl]pyrrolidin-3-yl}methyl)azetidine-3-carboxylic acid. The reaction was run according to General Procedure D using 1-[2-(2,6-dioxopiperidin-3-yl)-1,3-dioxoisoindol-4-yl]pyrrolidine-3-carbaldehyde (20 mg, 0.06 mmol), tert-butyl azetidine-3-carboxylate (13.3 mg, 0.08 mmol), and the addition of TEA (0.020 mL, 0.12 mmol). The crude material was then treated according to General Procedure B. Chromatography C afforded the title compound (18.3 mg, 74%).

Step 4: Synthesis of 5-({6-[1'-(1-{[1-{2-[2,6-dioxopiperidin-3-yl]-1,3-dioxo-2,3-dihydro-1H-isoindol-4-yl}pyrrolidin-3-yl]methyl}azetidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide. The title compound was synthesized according to General Procedure F, using Intermediate 1 (28 mg), 1-({1-[2-(2,6-dioxopiperidin-3-yl)-1,3-dioxoisoindol-4-yl]pyrrolidin-3-yl}methyl)azetidine-3-carboxylic acid (18 mg) as starting materials. Crude material was purified by reverse phase HPLC to provide the title compound (4.4 mg, 9.4%); LCMS: $C_{63}H_{73}FN_{12}O_7$ requires 1128.6, found 1130.0 [M+H]$^+$; $^1$H NMR (500 MHz, DMSO-$d_6$) δ 11.07 (s, 1H), 9.49 (s, 1H), 8.60 (d, J=8.2 Hz, 1H), 8.38 (s, 1H), 8.13 (d, J=7.9 Hz, 1H), 7.88 (d, J=2.2 Hz, 1H), 7.70-7.64 (m, 1H), 7.61 (dd, J=8.6, 7.1 Hz, 2H), 7.55-7.43 (m, 2H), 7.17 (dt, J=11.9, 3.7 Hz, 2H), 7.11 (d, J=8.4 Hz, 1H), 5.27 (q, J=6.5 Hz, 1H), 5.07 (d, J=7.3 Hz, 1H), 4.50-4.37 (m, 1H), 4.31-4.15 (m, 2H), 4.08-3.91 (m, 4H), 3.84-3.29 (m, 10H), 3.02-2.74 (m, 8H), 2.66-2.55 (m, 2H), 2.36 (s, 3H), 2.19-1.95 (m, 2H), 1.89-1.48 (m, 18H), 1.41 (q, J=11.2, 10.0 Hz, 1H), 1.09 (d, J=6.5 Hz, 6H).

Example 36

5-{[6-(1'-{1-[2-(1-{2-[2,6-dioxopiperidin-3-yl]-1,3-dioxo-2,3-dihydro-1H-isoindol-4-yl}piperidin-4-yl)acetyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

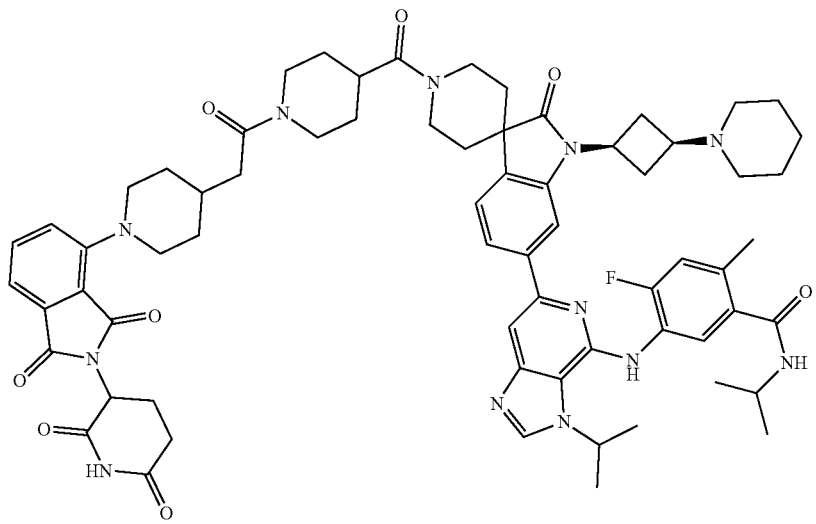 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)CC5CCN(c6cccc7c6C(=O)N(C6CCC(=O)NC6=O)C7=O)CC5)CC4)CC3)cc3ncn(C(C)C)c23)cc1C(=O)NC(C)C]

Step 1: Synthesis of 1-(2-(1-(2-(2,6-dioxopiperidin-3-yl)-1,3-dioxoisoindolin-4-yl)piperidin-4-yl)acetyl)piperidine-4-carboxylic acid. The reaction was performed according to General Procedure F using (1-{2-[2,6-dioxopiperidin-3-yl]-1,3-dioxoisoindol-4-yl}piperidin-4-yl)acetic acid (25 mg, 0.06 mmol) and tert-butyl piperidine-4-carboxylate (12 mg, 0.06 mmol). The crude material of this reaction was then subjected to General Procedure B. Chromatography C afforded the title compound (22 mg, 69%).

Step 2: Synthesis of 5-{[6-(1'-{1-[2-(1-{2-[2,6-dioxopiperidin-3-yl]-1,3-dioxo-2,3-dihydro-1H-isoindol-4-yl}piperidin-4-yl)acetyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (15 mg), 1-(2-(1-(2-(2,6-dioxopiperidin-3-yl)-1,3-dioxoisoindolin-4-yl)piperidin-4-yl)acetyl)piperidine-4-carboxylic acid (10 mg) as starting materials. Crude material was purified by reverse phase HPLC to provide the title compound (16.4 mg, 68%); LCMS: $C_{67}H_{79}FN_{12}O_8$ requires 1198.6, found 1199.9 [M+H]$^+$; $^1$H NMR (500 MHz, DMSO-$d_6$) δ 11.08 (s, 1H), 9.37 (s, 1H), 8.67 (s, 1H), 8.40 (s, 1H), 8.13 (d, J=7.8 Hz, 1H), 7.87 (s, 1H), 7.71-7.64 (m, 2H), 7.59 (d, J=8.1 Hz, 1H), 7.52 (d, J=8.4 Hz, 2H), 7.33 (dd, J=10.8, 7.8 Hz, 2H), 7.18 (d, J=12.1 Hz, 1H), 5.29 (q, J=6.8 Hz, 1H), 5.09 (dd, J=12.8, 5.5 Hz, 1H), 4.44 (s, 1H), 4.24-4.17 (m, 1H), 4.03 (h, J=6.8 Hz, 1H), 3.96-3.37 (m, 10H), 3.11 (t, J=12.5 Hz, 1H), 3.00-2.71 (m, 9H), 2.70-2.55 (m, 2H), 2.36-2.29 (m, 4H), 2.06-2.00 (m, 1H), 1.88-1.33 (m, 27H), 1.10 (d, J=6.5 Hz, 6H).

Example 37

5-{[6-(1'-{1-[(1-{2-[2,6-dioxopiperidin-3-yl]-1,3-dioxo-2,3-dihydro-1H-isoindol-4-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

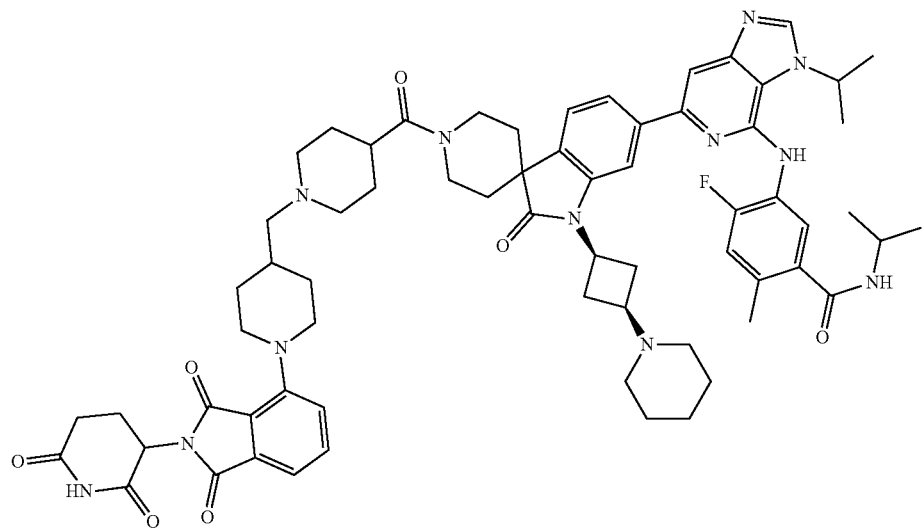 [SMILES: Cc1cc(F)c(Nc2nc(-c3ccc4c(c3)N([C@H]3C[C@@H](N5CCCCC5)C3)C(=O)C43CCN(C(=O)C4CCN(CC5CCN(c6cccc7c6C(=O)N(C6CCC(=O)NC6=O)C7=O)CC5)CC4)CC3)cc3ncn(C(C)C)c23)cc1C(=O)NC(C)C]

Step 1: Synthesis of 1-((1-(2-(2,6-dioxopiperidin-3-yl)-1,3-dioxoisoindolin-4-yl)piperidin-4-yl)methyl)piperidine-4-carboxylic acid. The reaction was performed according to General Procedure D using 1-[2-(2,6-dioxopiperidin-3-yl)-1,3-dioxoisoindol-4-yl]piperidine-4-carbaldehyde (15 mg, 0.04 mmol) and tert-butyl piperidine-4-carboxylate (7.5 mg, 0.04 mmol). The crude material of this reaction was then subjected to General Procedure B followed by Chromatography C to afford the title compound (17.8 mg, 91%).

Step 2: Synthesis of 5-{[6-(1'-{1-[(1-{2-[2,6-dioxopiperidin-3-yl]-1,3-dioxo-2,3-dihydro-1H-isoindol-4-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (7.3 mg), 1-((1-(2-(2,6-dioxopiperidin-3-yl)-1,3-dioxoisoindolin-4-yl)piperidin-4-yl)methyl)piperidine-4-carboxylic acid (5 mg) as starting materials. Crude material was purified by reverse phase HPLC to provide the title compound (8.2 mg, 64%); LCMS: $C_{66}H_{79}FN_{12}O_7$ requires 1170.6, found 1172.0 [M+H]$^+$; $^1$H NMR (500 MHz, DMSO-d$_6$) δ 11.09 (s, 1H), 9.48 (s, 1H), 8.98 (s, 1H), 8.63 (s, 1H), 8.39 (s, 1H), 8.14 (d, J=7.8 Hz, 1H), 7.88 (s, 1H), 7.74-7.63 (m, 2H), 7.60 (d, J=8.2 Hz, 1H), 7.52 (d, J=5.5 Hz, 2H), 7.36 (d, J=7.6 Hz, 2H), 7.18 (d, J=12.1 Hz, 1H), 5.32-5.18 (m, 1H), 5.09 (dd, J=12.8, 5.4 Hz, 1H), 4.24-3.11 (m, 10H), 3.09-2.71 (m, 14H), 2.66-2.56 (m 1H), 2.36 (s, 3H), 2.10-1.36 (m, 28H), 1.10 (d, J=6.6 Hz, 6H).

Example 38

5-[(6-{1'-[1-[(1-{2-[2,6-dioxopiperidin-3-yl]-1,3-dioxo-2,3-dihydro-1H-isoindol-4-yl}piperidin-4-yl)methyl]pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

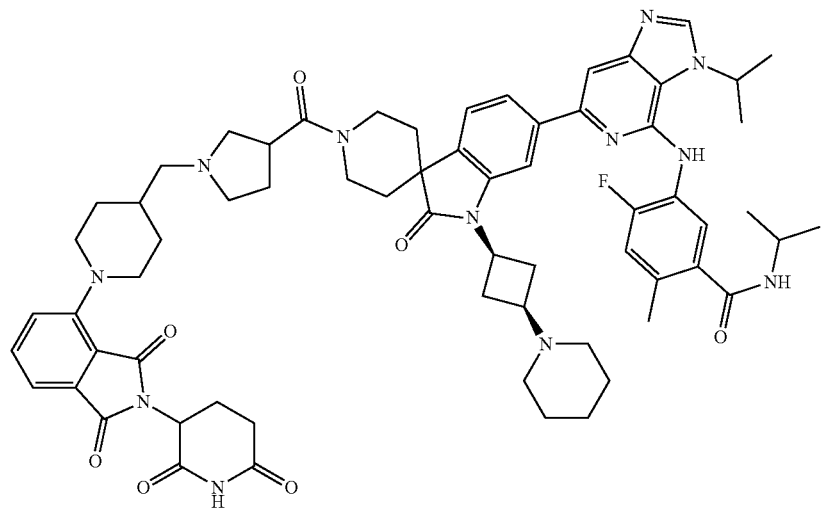 [SMILES: Cc1cc(F)c(Nc2nc(-c3ccc4c(c3)N([C@H]3C[C@@H](N5CCCCC5)C3)C(=O)C43CCN(C(=O)C4CCN(CC5CCN(c6cccc7c6C(=O)N(C6CCC(=O)NC6=O)C7=O)CC5)C4)CC3)cc3ncn(C(C)C)c23)cc1C(=O)NC(C)C]

Step 1: Synthesis of 1-((1-(2-(2,6-dioxopiperidin-3-yl)-1,3-dioxoisoindolin-4-yl)piperidin-4-yl)methyl)pyrrolidine-3-carboxylic acid. The reaction was performed according to General Procedure D using 1-[2-(2,6-dioxopiperidin-3-yl)-1,3-dioxoisoindol-4-yl]piperidine-4-carbaldehyde (15 mg, 0.04 mmol) and tert-butyl pyrrolidine-3-carboxylate (6.8 mg, 0.04 mmol). The crude material of this reaction was then subjected to General Procedure B followed by Chromatography C to afford the title compound (16.8 mg, 91%).

Step 2: Synthesis of 5-[(6-{1'-[1-[(1-{2-[2,6-dioxopiperidin-3-yl]-1,3-dioxo-2,3-dihydro-1H-isoindol-4-yl}piperidin-4-yl)methyl]pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (9.5 mg), 1-((1-(2-(2,6-dioxopiperidin-3-yl)-1,3-dioxoisoindolin-4-yl)piperidin-4-yl)methyl)pyrrolidine-3-carboxylic acid (6 mg) as starting materials. Crude material was purified by reverse phase HPLC to provide the title compound (10.5 mg, 61%); LCMS: $C_{65}H_{77}FN_{12}O_7$ requires 1156.6, found 1157.9 [M+H]$^+$; $^1$H NMR (500 MHz, DMSO-$d_6$) δ 11.09 (s, 1H), 9.69-9.44 (m, 2H), 8.64 (s, 1H), 8.40 (s, 1H), 8.14 (dd, J=7.9, 2.5 Hz, 1H), 7.89 (d, J=3.6 Hz, 1H), 7.78-7.63 (m, 2H), 7.63-7.42 (m, 3H), 7.42-7.27 (m, 2H), 7.18 (d, J=12.2 Hz, 1H), 5.28 (q, J=6.6 Hz, 1H), 5.09 (dd, J=12.7, 5.5 Hz, 1H), 4.21-3.06 (m, 11H), 3.02-2.67 (m, 10H), 2.67-2.55 (m, 1H), 2.38-2.33 (m, 4H), 2.09-1.29 (m, 28H), 1.10 (dd, J=6.6, 2.4 Hz, 6H).

Example 39

5-[(6-{1'-[1-(1-{2-[2,6-dioxopiperidin-3-yl]-1,3-dioxo-2,3-dihydro-1H-isoindol-5-yl}piperidine-4-carbonyl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

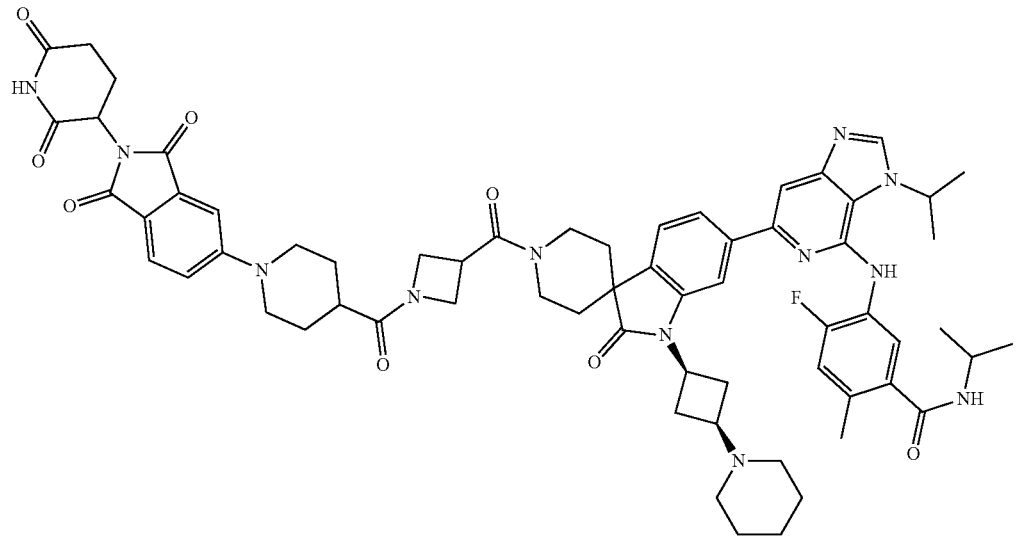 [SMILES: Cc1cc(F)c(Nc2nc(-c3ccc4c(c3)N([C@H]3C[C@@H](N5CCCCC5)C3)C(=O)C43CCN(C(=O)C4CN(C(=O)C5CCN(c6ccc7c(c6)C(=O)N(C6CCC(=O)NC6=O)C7=O)CC5)C4)CC3)cc3ncn(C(C)C)c23)cc1C(=O)NC(C)C]

Step 1: Synthesis of 1-[2-(2,6-dioxopiperidin-3-yl)-1,3-dioxoisoindol-5-yl]piperidine-4-carboxylic acid. The reaction was performed according to General Procedure A using tert-butyl piperidine-4-carboxylate (402 mg, 2.17 mmol) and 2-(2,6-dioxopiperidin-3-yl)-5-fluoroisoindole-1,3-dione (500 mg, 1.81 mmol). Chromatography B was then performed, and the resulting material was subjected to General Procedure B. Chromatography C afforded the title compound (440 mg, 63%).

Step 2: Synthesis of 1-(1-(2-(2,6-dioxopiperidin-3-yl)-1,3-dioxoisoindolin-5-yl)piperidine-4-carbonyl)azetidine-3-carboxylic acid. The reaction was performed according to General Procedure F using 1-[2-(2,6-dioxopiperidin-3-yl)-1,3-dioxoisoindol-5-yl]piperidine-4-carboxylic acid (10 mg, 0.03 mmol) and tert-butyl azetidine-3-carboxylate (4 mg, 0.03 mmol). The crude material from this reaction was subjected to General Procedure B, followed by Chromatography C to afford the title compound (10 mg, 82%).

Step 3: Synthesis of 5-[(6-{1'-[1-(1-{2-[2,6-dioxopiperidin-3-yl]-1,3-dioxo-2,3-dihydro-1H-isoindol-5-yl}piperidine-4-carbonyl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (10 mg), 1-(1-(2-(2,6-dioxopiperidin-3-yl)-1,3-dioxoisoindolin-5-yl)piperidine-4-carbonyl)azetidine-3-carboxylic acid (6.8 mg) as starting materials. Crude material was purified by reverse phase HPLC to provide the title compound (7.2 mg, 44%); LCMS: $C_{64}H_{73}FN_{12}O_8$ requires 1156.6, found 1157.8 [M+H]$^+$; $^1$H NMR (500 MHz, DMSO-d$_6$) δ 11.07 (s, 1H), 9.39 (s, 1H), 8.73 (d, J=6.2 Hz, 1H), 8.43 (s, 1H), 8.13 (d, J=7.8 Hz, 1H), 7.87 (d, J=2.6 Hz, 1H), 7.74-7.61 (m, 2H), 7.62-7.45 (m, 3H), 7.33 (s, 1H), 7.30-7.13 (m, 2H), 5.30 (q, J=6.5 Hz, 1H), 5.07 (dd, J=12.7, 5.5 Hz, 1H), 4.45-4.34 (m, 1H), 4.24-3.35 (m, 11H), 3.15-2.68 (m, 10H), 2.65-2.55 (m, 2H), 2.36 (s, 3H), 2.05-1.93 (m, 1H), 1.88-1.32 (m, 23H), 1.09 (d, J=6.5 Hz, 6H).

Example 40

5-[(6-{1'-[1-(1-{2-[2,6-dioxopiperidin-3-yl]-1,3-dioxo-2,3-dihydro-1H-isoindol-5-yl}piperidine-4-carbonyl)pyrrolidine-3-carbonyl]-2-oxo-1-[1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

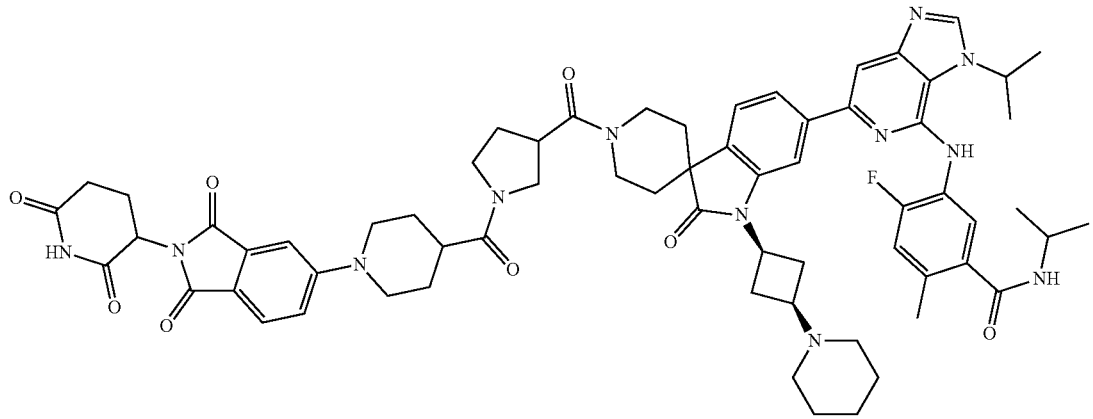 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)C5CCN(c6ccc7c(c6)C(=O)N(C6CCC(=O)NC6=O)C7=O)CC5)C4)CC3)cc3ncn(C(C)C)c23)cc1C(=O)NC(C)C]

Step 1: Synthesis of 1-(1-(2-(2,6-dioxopiperidin-3-yl)-1,3-dioxoisoindolin-5-yl)piperidine-4-carbonyl)pyrrolidine-3-carboxylic acid. The reaction was performed according to General Procedure F using 1-[2-(2,6-dioxopiperidin-3-yl)-1,3-dioxoisoindol-5-yl]piperidine-4-carboxylic acid (10 mg, 0.03 mmol) and tert-butyl pyrrolidine-3-carboxylate (4.4 mg, 0.03 mmol). The crude material from this reaction was subjected to General Procedure B, followed by Chromatography C to afford the title compound (10 g, 80%).

Step 2: Synthesis of 5-[(6-{1'-[1-(1-{2-[2,6-dioxopiperidin-3-yl]-1,3-dioxo-2,3-dihydro-1H-isoindol-5-yl}piperidine-4-carbonyl)pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (10 mg), 1-(1-(2-(2,6-dioxopiperidin-3-yl)-1,3-dioxoisoindolin-5-yl)piperidine-4-carbonyl)pyrrolidine-3-carboxylic acid (8.4 mg) as starting materials. Crude material was purified by reverse phase HPLC to provide the title compound (12.1 mg, 75%); LCMS: $C_{65}H_{75}FN_{12}O_8$ requires 1170.6, found 1172.0 [M+H]$^+$; $^1$H NMR (500 MHz, DMSO-$d_6$) δ 11.07 (s, 1H), 9.37 (s, 1H), 8.70 (s, 1H), 8.41 (s, 1H), 8.14 (d, J=7.5 Hz, 1H), 7.87 (d, J=4.8 Hz, 1H), 7.67 (dd, J=8.4, 4.5 Hz, 2H), 7.62-7.46 (m, 3H), 7.34 (t, J=2.5 Hz, 1H), 7.25 (dd, J=8.6, 2.7 Hz, 1H), 7.18 (d, J=12.1 Hz, 1H), 5.30 (p, J=6.6 Hz, 1H), 5.07 (dd, J=12.7, 5.4 Hz, 1H), 4.24-3.26 (m, 11H), 3.15-2.73 (m, 11H), 2.64-2.53 (m, 2H), 2.37-2.34 (m, 3H), 2.19-1.51 (m, 25H), 1.41 (d, J=13.0 Hz, 1H), 1.11-1.07 (m, 6H).

Example 41

5-[(6-{1'-[1-(1-{2-[2,6-dioxopiperidin-3-yl]-1,3-dioxo-2,3-dihydro-1H-isoindol-5-yl}piperidine-4-carbonyl)piperidine-4-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

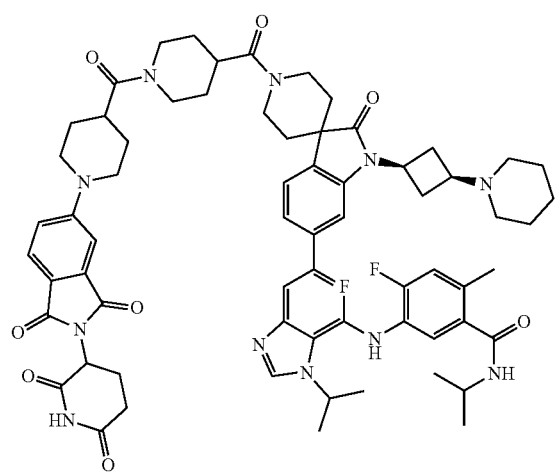

Step 1: Synthesis of 1-(1-(2-(2,6-dioxopiperidin-3-yl)-1,3-dioxoisoindolin-5-yl)piperidine-4-carbonyl)piperidine-4-carboxylic acid. The reaction was performed according to General Procedure F using 1-[2-(2,6-dioxopiperidin-3-yl)-1,3-dioxoisoindol-5-yl]piperidine-4-carboxylic acid (10 mg, 0.03 mmol) and tert-butyl piperidine-4-carboxylate (4.6 mg, 0.03 mmol). The crude material from this reaction was subjected to General Procedure B, followed by Chromatography C to afford the title compound (8.4 g, 66%).

Step 2: Synthesis of 5-[(6-{1'-[1-(1-{2-[2,6-dioxopiperidin-3-yl]-1,3-dioxo-2,3-dihydro-1H-isoindol-5-yl}piperidine-4-carbonyl)piperidine-4-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F, using Intermediate 1 (10 mg), 1-(1-(2-(2,6-dioxopiperidin-3-yl)-1,3-dioxoisoindolin-5-yl)piperidine-4-carbonyl)piperidine-4-carboxylic acid (8.4 mg) as starting materials. Crude material was purified by reverse phase HPLC to provide the title compound (8.8 mg, 54%); LCMS: $C_{66}H_{77}FN_{12}O_8$ requires 1184.6, found 1185.9 $[M+H]^+$; $^1$H NMR (500 MHz, DMSO-$d_6$) δ 11.08 (s, 1H), 9.37 (s, 1H), 8.72 (s, 1H), 8.42 (s, 1H), 8.14 (d, J=7.8 Hz, 1H), 7.88 (s, 1H), 7.67 (d, J=8.5 Hz, 2H), 7.59 (d, J=8.1 Hz, 1H), 7.52 (d, J=11.0 Hz, 2H), 7.34 (d, J=2.2 Hz, 1H), 7.25 (dd, J=8.8, 2.3 Hz, 1H), 7.18 (d, J=12.1 Hz, 1H), 5.34-5.25 (m, 1H), 5.07 (dd, J=12.8, 5.4 Hz, 1H), 4.45-4.38 (m, 1H), 4.25-4.15 (m, 1H), 4.12-3.29 (m, 10H), 3.20-2.72 (m, 13H), 2.69-2.55 (m, 2H), 2.37 (s, 3H), 2.07-1.97 (m, 1H), 1.89-1.46 (m, 24H), 1.47-1.35 (m, 2H), 1.10 (d, J=6.6 Hz, 6H).

Example 42

5-{[6-(1'-{1-[2-(7-{2-[2,6-dioxopiperidin-3-yl]-1,3-dioxo-2,3-dihydro-1H-isoindol-5-yl}-2,7-diazaspiro[3.5]nonan-2-yl)acetyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide Step 1: Synthesis of 2,7-diazaspiro[3.5]nonan-2-ylacetic acid hydrochloride. The reaction was performed according to General Procedure E using tert-butyl 2,7-diazaspiro[3.5]nonane-7-carboxylate (400 mg, 1.77 mmol) and tert-butyl 2-bromoacetate (379 mg, 1.94 mmol) as starting materials. The crude residue was then treated according to General Procedure B to afford the title compound (300 mg, 77%).

Step 2: Synthesis of (7-{2-[(2,6-dioxopiperidin-3-yl]-1,3-dioxoisoindol-5-yl}-2,7-diazaspiro[3.5]nonan-2-yl)acetic acid. The reaction was carried out according to General Procedure A using 2-(2,6-dioxopiperidin-3-yl)-5-fluoroisoindole-1,3-dione (414 mg, 1.50 mmol) and 2,7-diazaspiro[3.5]nonan-2-ylacetic acid hydrochloride (330 mg, 1.50 mmol) as starting materials. Chromatography C afforded the title compound (50 mg, 8%).

Step 3: Synthesis of 1-(2-(7-(2-(2,6-dioxopiperidin-3-yl)-1,3-dioxoisoindolin-5-yl)-2,7-diazaspiro[3.5]nonan-2-yl)acetyl)piperidine-4-carboxylic acid. The reaction was performed according to General Procedure F using (7-{2-[(2,6-dioxopiperidin-3-yl]-1,3-dioxoisoindol-5-yl}-2,7-diazaspiro[3.5]nonan-2-yl)acetic acid (20 mg, 0.05 mmol) and tert-butyl piperidine-4-carboxylate (9.2 mg, 0.05 mmol) as starting materials. The crude material of this reaction was then subjected to General Procedure B, followed by Chromatography C to afford the title compound (10 mg, 40%).

Step 4: Synthesis of 5-{[6-(1'-{1-[2-(7-{2-[2,6-dioxopiperidin-3-yl]-1,3-dioxo-2,3-dihydro-1H-isoindol-5-yl}-2,7-diazaspiro[3.5]nonan-2-yl)acetyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (10 mg), 1-(2-(7-(2-(2,6-dioxopiperidin-3-yl)-1,3-dioxoisoindolin-5-yl)-2,7-diazaspiro[3.5]nonan-2-yl)acetyl)piperidine-4-carboxylic acid (7.2 mg) as starting materials. Crude material was purified by reverse phase HPLC to provide the title compound (6.7 mg, 39%); LCMS: $C_{69}H_{82}FN_{13}O_8$ requires 1239.6, found 1240.9 $[M+H]^+$; $^1$H NMR (500 MHz, DMSO-$d_6$) δ 11.07 (s, 1H), 10.28-10.07 (m, 1H), 9.44 (s, 1H), 8.62 (s, 1H), 8.38 (s, 1H), 8.14 (d, J=7.8 Hz, 1H), 7.88 (s, 1H), 7.73-7.63 (m, 2H), 7.60 (d, J=8.5 Hz, 1H), 7.50 (d, J=11.5 Hz, 2H), 7.39-7.26 (m, 1H), 7.17 (d, J=12.1 Hz, 1H), 6.97-6.78 (m, 1H), 5.28 (q, J=6.7 Hz, 1H), 5.07 (dd, J=13.0, 5.0 Hz, 1H), 4.61-4.28 (m, 2H), 4.25-4.15 (m, 1H), 4.08-3.99 (m, 2H), 3.97-2.69 (m, 20H), 2.65-2.55 (m, 1H), 2.36 (s, 3H), 2.20-1.33 (m, 30H), 1.12-0.99 (m, 6H).

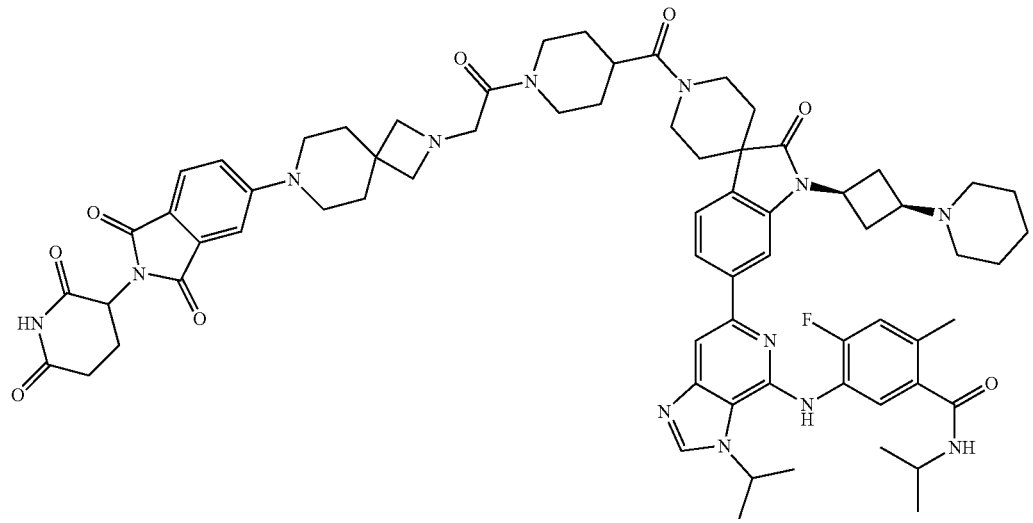 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)CN5CC6(CCN(c7ccc8c(c7)C(=O)N(C7CCC(=O)NC7=O)C8=O)CC6)C5)CC4)CC3)cc3ncn(C(C)C)c23)cc1C(=O)NC(C)C]

Example 43

5-[(6-{1'-[23-({2-[2,6-dioxopiperidin-3-yl]-1,3-di-oxo-2,3-dihydro-1H-isoindol-4-yl}amino)-3,6,9,12,15,18,21-heptaoxatricosan-1-yl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

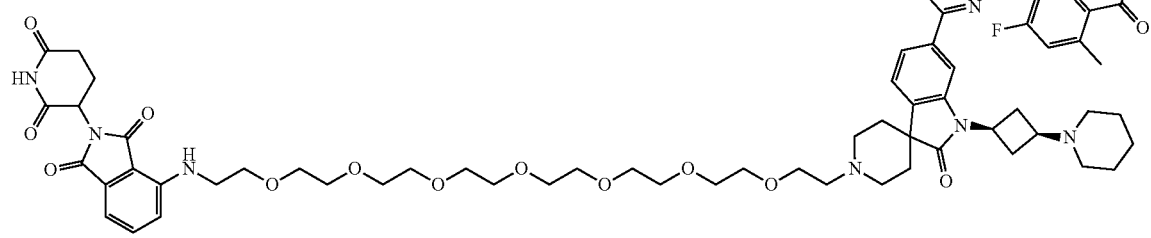

Step 1: Synthesis of 2-(2,6-dioxopiperidin-3-yl)-4-((23-hydroxy-3,6,9,12,15,18,21-heptaoxatricosyl)amino)isoindoline-1,3-dione. The reaction was carried out according to General Procedure A using 23-amino-3,6,9,12,15,18,21-heptaoxatricosan-1-ol (1.34 g, 3.62 mmol) and 2-(2,6-dioxopiperidin-3-yl)-4-fluoroisoindole-1,3-dione (1.0 g, 3.62 mmol) as starting materials. Chromatography B afforded the title compound (700 mg, 31%).

Step 2: Synthesis of 23-((2-(2,6-dioxopiperidin-3-yl)-1,3-dioxoisoindolin-4-yl)amino)-3,6,9,12,15,18,21-heptaoxatricosyl 4-methylbenzenesulfonate. To a solution of 2-(2,6-dioxopiperidin-3-yl)-4-((23-hydroxy-3,6,9,12,15,18,21-heptaoxatricosyl)amino)isoindoline-1,3-dione (2.5 g, 4.0 mmol) with pyridine (316 mg, 4.0 mmol) in DCM (15 mL) was added p-toluenesulfonyl chloride (838 mg, 4.4 mmol). The reaction was then stirred overnight before the addition of water. The organic phase was removed, and the aqueous phase extracted with DCM (2×) before drying the combined organic layers over sodium sulfate, filtering, and concentrating under reduced pressure. Chromatography B afforded the title compound (220 mg, 7%).

Step 3: Synthesis of 5-[(6-{1'-[23-({2-[2,6-dioxopiperidin-3-yl]-1,3-dioxo-2,3-dihydro-1H-isoindol-4-yl}amino)-3,6,9,12,15,18,21-heptaoxatricosan-1-yl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized by combining Intermediate 1 (19.7 mg, 1 eq), 23-((2-(2,6-dioxopiperidin-3-yl)-1,3-dioxoisoindolin-4-yl)amino)-3,6,9,12,15,18,21-heptaoxatricosyl 4-methylbenzenesulfonate (23 mg, 1 eq), sodium iodide (3.97 mg, 1 eq), and dipotassium carbonate (18.3 mg, 5 eq) in ACN (0.05 M) and the reaction mixture was heated at 80° C. for 16 hours. The reaction mixture was filtered and purified by reverse phase HPLC to provide the title compound (15.1 mg, 33%); LCMS: $C_{70}H_{92}FN_{11}O_{13}$ requires 1313.7, found 1315.0 [M+H]$^+$; $^1$H NMR (500 MHz, DMSO-$d_6$) δ 11.09 (s, 1H), 9.65-9.39 (m, 2H), 8.61 (d, J=3.6 Hz, 1H), 8.39 (d, J=21.9 Hz, 1H), 8.14 (d, J=7.9 Hz, 1H), 7.90 (d, J=25.4 Hz, 1H), 7.77-7.48 (m, 4H), 7.26-7.06 (m, 3H), 7.04 (d, J=7.0 Hz, 1H), 6.59 (s, 1H), 5.28 (s, 1H), 5.05 (dd, J=12.9, 5.4 Hz, 1H), 4.27-3.29 (m, 36H), 2.99-2.75 (m, 8H), 2.58 (d, J=19.6 Hz, 2H), 2.38-2.25 (m, 5H), 2.17 (s, 1H), 2.05-1.48 (m, 16H), 1.41 (q, J=11.9, 10.7 Hz, 1H), 1.10 (d, J=6.5 Hz, 6H).

Example 44

5-({6-[1'-(2-{4-[4-({[2-({2-[2,6-dioxopiperidin-3-yl]-1,3-dioxo-2,3-dihydro-1H-isoindol-4-yl}amino)ethyl]carbamoyl}methyl)phenyl]piperazin-1-yl}acetyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide

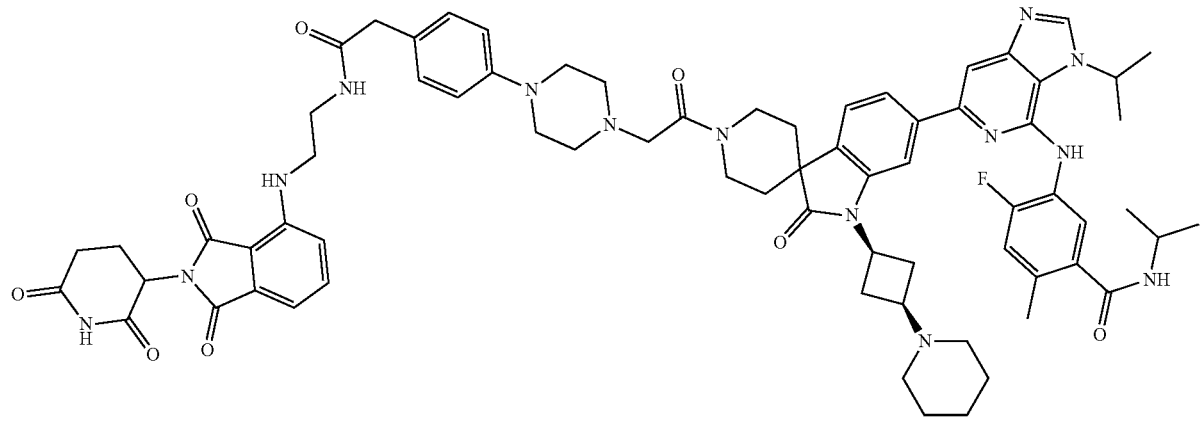 [SMILES: Cc1cc(F)c(Nc2nc(-c3ccc4c(c3)N([C@H]3C[C@@H](N5CCCCC5)C3)C(=O)C43CCN(C(=O)CN4CCN(c5ccc(CC(=O)NCCNc6cccc7c6C(=O)N(C6CCC(=O)NC6=O)C7=O)cc5)CC4)CC3)cc3ncn(C(C)C)c23)cc1C(=O)NC(C)C]

Step 1: Synthesis of ethyl 2-(4-{4-[2-(tert-butoxy)-2-oxoethyl]piperazin-1-yl}phenyl)acetate. tert-Butyl (piperazin-1-yl)acetate (0.89 g, 4.4 mmol, 1.2 eq) palladium(II) acetate (0.083 g, 0.37 mmol, 0.1 eq), and Xphos (0.176 g, 0.37 mmol, 0.1 eq) were added under argon to a stirred solution of ethyl 4-bromophenylacetate (0.90 g, 3.7 mmol, 1.0 eq), in toluene (22 mL, 0.2 M). The reaction mixture was then purged with argon for 3 min, moved to a pre-heated bath to 100° C. and stirred for 16 h. The UPLC showed the formation of the title compound. The mixture was diluted with water (20 mL) and then extracted using ethyl acetate (3×). The combined organic fractions were dried over sodium sulfate, filtered, and concentrated under reduced pressure. The crude was purified by Chromatography A to give 0.9 g (67% yield) of the title compound.

Step 2: Synthesis of potassium 2-{4-[4-(2-ethoxy-2-oxoethyl)phenyl]piperazin-1-yl}acetate. Ethyl 2-(4-{4-[2-(tert-butoxy)-2-oxoethyl]piperazin-1-yl}phenyl)acetate (0.61 g, 1.7 mmol, 1.0 eq) was dissolved in THF (12 mL, 0.14 M) and potassium trimethylsilanolate (0.216 g, 1.68 mmol, 1.0 eq) was added. The reaction mixture was left stirring overnight (progress was monitored by UPLC). The precipitated white solid was filtered off and dried to acquire 415 mg (72% yield) of the title compound.

Step 3: Synthesis of {4-[4-({[2-({2-[2,6-dioxopiperidin-3-yl]-1,3-dioxoisoindol-4-yl}amino)ethyl]carbamoyl}methyl)phenyl]piperazin-1-yl}acetic acid. The reaction was carried out according to General Procedure F, using potassium 2-{4-[4-(2-ethoxy-2-oxoethyl)phenyl]piperazin-1-yl}acetate (57 mg, 0.17 mmol) and 4-[(2-aminoethyl)amino]-2-[2,6-dioxopiperidin-3-yl]isoindole-1,3-dione hydrochloride (60 mg, 0.17 mmol) as starting materials. The crude material from this reaction was subjected to General Procedure B and this was purified according to Chromatography C to afford the title compound (40 mg, 41%).

Step 4: Synthesis of 5-({6-[1'-(2-{4-[4-({[2-({2-[2,6-dioxopiperidin-3-yl]-1,3-dioxo-2,3-dihydro-1H-isoindol-4-yl}amino)ethyl]carbamoyl}methyl)phenyl]piperazin-1-yl}acetyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide. The title compound was synthesized according to General Procedure F, using Intermediate 1 (10 mg), {4-[4-({[2-({2-[2,6-dioxopiperidin-3-yl]-1,3-dioxoisoindol-4-yl}amino)ethyl]carbamoyl}methyl)phenyl]piperazin-1-yl}acetic acid (10 mg) as starting materials. Crude material was purified by reverse phase HPLC to provide the title compound (14.1 mg, 80%); LCMS: $C_{70}H_{81}FN_{14}O_8$ requires 1264.6, found 1266.9 $[M+2H]^+$; $^1H$ NMR (500 MHz, DMSO-$d_6$) δ 11.11 (s, 1H), 9.99 (s, 1H), 9.50 (s, 1H), 8.66 (s, 1H), 8.41 (s, 1H), 8.23 (t, J=5.7 Hz, 1H), 8.14 (d, J=7.9 Hz, 1H), 7.89 (s, 1H), 7.69 (d, J=7.8 Hz, 1H), 7.64-7.42 (m, 4H), 7.25-7.08 (m, 5H), 7.04 (d, J=7.0 Hz, 1H), 6.92 (d, J=8.4 Hz, 2H), 6.74 (s, 1H), 5.36-5.21 (m, 1H), 5.07 (dd, J=12.8, 5.4 Hz, 1H), 4.54-3.04 (m, 17H), 3.04-2.72 (m, 8H), 2.68-2.55 (m, 1H), 2.36 (s, 3H), 2.04 (dd, J=10.2, 4.9 Hz, 1H), 1.92-1.38 (m, 21H), 1.10 (d, J=6.6 Hz, 6H).

Example 45

5-{[6-(1'-{1-[(1-{2-[2,6-dioxopiperidin-3-yl]-1,3-dioxo-2,3-dihydro-1H-isoindol-5-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

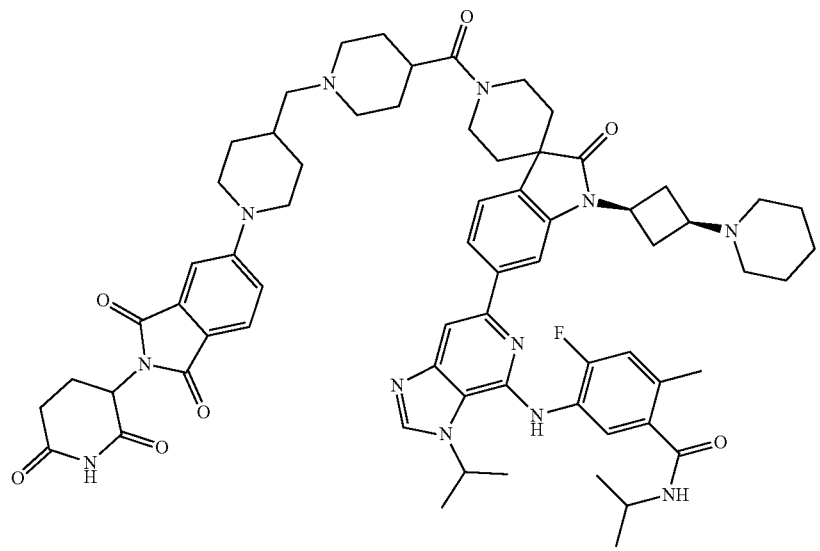 [SMILES: Cc1cc(F)c(Nc2nc(-c3ccc4c(c3)N([C@H]3C[C@@H](N5CCCCC5)C3)C(=O)C43CCN(C(=O)C4CCN(CC5CCN(c6ccc7c(c6)C(=O)N(C6CCC(=O)NC6=O)C7=O)CC5)CC4)CC3)cc3ncn(C(C)C)c23)cc1C(=O)NC(C)C]

Step 1: Synthesis of 1-((1-(2-(2,6-dioxopiperidin-3-yl)-1,3-dioxoisoindolin-4-yl)piperidin-4-yl)methyl)piperidine-4-carboxylic acid. The reaction was performed according to General Procedure D using 1-[2-(2,6-dioxopiperidin-3-yl)-1,3-dioxoisoindol-5-yl]piperidine-4-carbaldehyde (15 mg, 0.04 mmol) and tert-butyl piperidine-4-carboxylate (7.4 mg, 0.04 mmol). The crude material of this reaction was then subjected to General Procedure B followed by Chromatography C to afford the title compound (15.4 mg, 80%).

Step 2: Synthesis of 5-{[6-(1'-{1-[(1-{2-[2,6-dioxopiperidin-3-yl]-1,3-dioxo-2,3-dihydro-1H-isoindol-5-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F, using Intermediate 1 (10 mg), 1-((1-(2-(2,6-dioxopiperidin-3-yl)-1,3-dioxoisoindolin-5-yl)piperidin-4-yl)methyl)piperidine-4-carboxylic acid (6.5 mg) as starting materials. Crude material was purified by reverse phase HPLC to provide the title compound (14.3 mg, 74.1%); LCMS: $C_{66}H_{79}FN_{12}O_7$ requires 1170.6, found 1171.4 [M+H]$^+$; $^1$H NMR (500 MHz, DMSO-d$_6$) δ 11.08 (s, 1H), 9.49 (s, 1H), 8.99 (s, 1H), 8.64 (s, 1H), 8.40 (s, 1H), 8.14 (d, J=7.8 Hz, 1H), 7.88 (s, 1H), 7.68 (dd, J=10.1, 8.0 Hz, 2H), 7.59 (d, J=8.2 Hz, 1H), 7.51 (d, J=6.1 Hz, 2H), 7.37 (d, J=2.2 Hz, 1H), 7.28 (dd, J=8.8, 2.1 Hz, 1H), 7.17 (d, J=12.2 Hz, 1H), 5.37-5.20 (m, 1H), 5.07 (dd, J=12.8, 5.4 Hz, 1H), 4.25-3.36 (m, 12H), 3.19-2.74 (m, 8H), 2.66-2.53 (m, 2H), 2.36 (s, 3H), 2.20-1.49 (m, 27H), 1.47-1.21 (m, 4H), 1.10 (d, J=6.6 Hz, 6H).

Example 46

N-(2-((2-(2,6-dioxopiperidin-3-yl)-1,3-dioxoisoindolin-4-yl)amino)ethyl)-7-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)-7-azaspiro[3.5]nonane-2-carboxamide

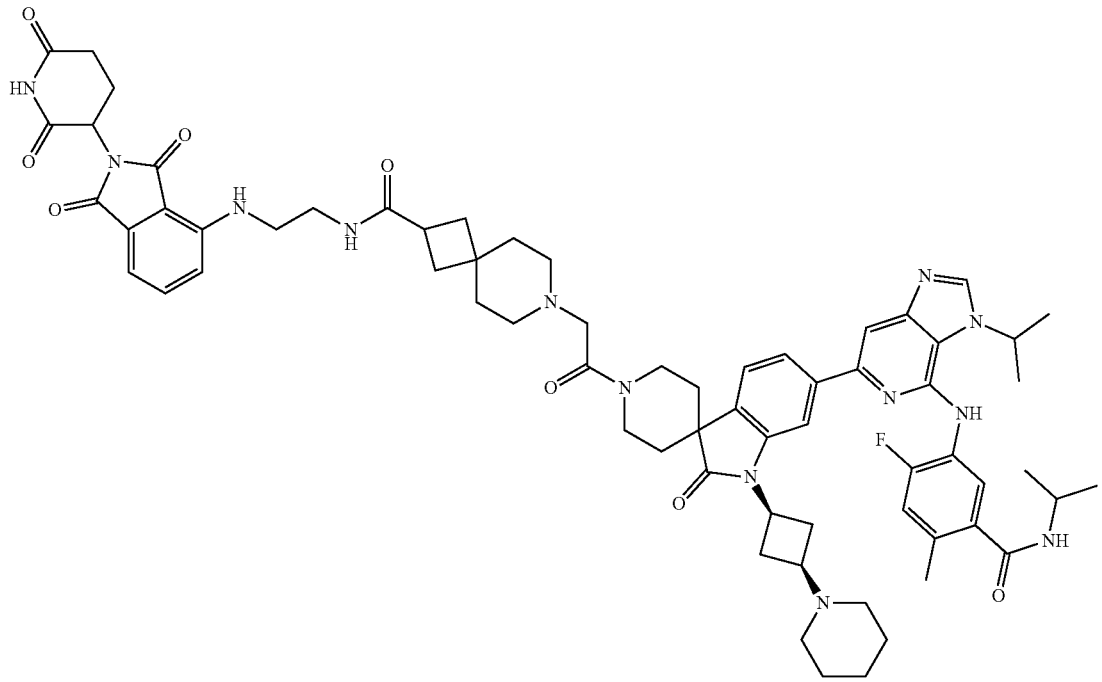 [SMILES: Cc1cc(F)c(Nc2nc(-c3ccc4c(c3)N([C@H]3C[C@@H](N5CCCCC5)C3)C(=O)C43CCN(C(=O)CN4CCC5(CC4)CC(C(=O)NCCNc4cccc6c4C(=O)N(C4CCC(=O)NC4=O)C6=O)C5)CC3)cc3ncn(C(C)C)c23)cc1C(=O)NC(C)C]

Step 1: Synthesis of N-[2-({2-[2,6-dioxopiperidin-3-yl]-1,3-dioxoisoindol-4-yl}amino)ethyl]-7-azaspiro[3.5]nonane-2-carboxamide. The reaction was performed according to General Procedure F using 4-[(2-aminoethyl)amino]-2-[2,6-dioxopiperidin-3-yl]isoindole-1,3-dione hydrochloride (55 mg, 0.16 mmol) and 7-(tert-butoxycarbonyl)-7-azaspiro[3.5]nonane-2-carboxylic acid (46 mg, 0.17 mmol). The crude material of this reaction was then subjected to General Procedure B followed by Chromatography C to afford the title compound (56 mg, 77%).

Step 2: Synthesis of (2-{[2-({2-[2,6-dioxopiperidin-3-yl]-1,3-dioxoisoindol-4-yl}amino)ethyl]carbamoyl}-7-azaspiro[3.5]nonan-7-yl)acetic acid. The title compound was synthesized according to General Procedure E, using N-[2-({2-[2,6-dioxopiperidin-3-yl]-1,3-dioxoisoindol-4-yl}amino)ethyl]-7-azaspiro[3.5]nonane-2-carboxamide (28 mg, 0.06 mmol) and tert-butyl 2-bromoacetate (12 mg, 0.06 mmol). The crude material of this reaction was then subjected to General Procedure B followed by Chromatography C to afford the title compound (28 mg, 89%).

Step 3: Synthesis of N-(2-((2-(2,6-dioxopiperidin-3-yl)-1,3-dioxoisoindolin-4-yl)amino)ethyl)-7-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)-7-azaspiro[3.5]nonane-2-carboxamide. The title compound was synthesized according to General Procedure F, using Intermediate 1 (12.7 mg, 0.02 mmol) and (2-{[2-({2-[2,6-dioxopiperidin-3-yl]-1,3-dioxoisoindol-4-yl}amino)ethyl]carbamoyl}-7-azaspiro[3.5]nonan-7-yl)acetic acid (9.0 mg, 0.02 mmol), followed by reverse phase HPLC to provide the title compound (4.9 mg, 20%); LCMS: $C_{67}H_{80}FN_{13}O_8$ requires 1213.6, found 1214.7 [M+H]$^+$; $^1$H NMR (500 MHz, Methanol-$d_4$) δ 8.73 (s, 1H), 8.08-7.97 (m, 1H), 7.82-7.67 (m, 2H), 7.63 (s, 1H), 7.57 (t, J=7.8 Hz, 1H), 7.48 (d, J=7.8 Hz, 1H), 7.19-7.11 (m, 2H), 7.08 (d, J=7.0 Hz, 1H), 5.29 (p, J=6.5 Hz, 1H), 5.10-5.02 (m, 1H), 4.40-4.03 (m, 4H), 4.03-3.87 (m, 2H), 3.72-3.57 (m, 2H), 3.57-3.38 (m, 9H), 3.15-2.62 (m, 11H), 2.43 (s, 3H), 2.22-1.48 (m, 26H), 1.14 (d, J=6.6 Hz, 6H).

Example 47

(2S,4R)-1-[(2S)-2-(2-{4-[4-(2-{6-[4-({2-fluoro-4-methyl-5-[(propan-2-yl)carbamoyl]phenyl}amino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-2-oxoethyl)phenyl]piperazin-1-yl}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide

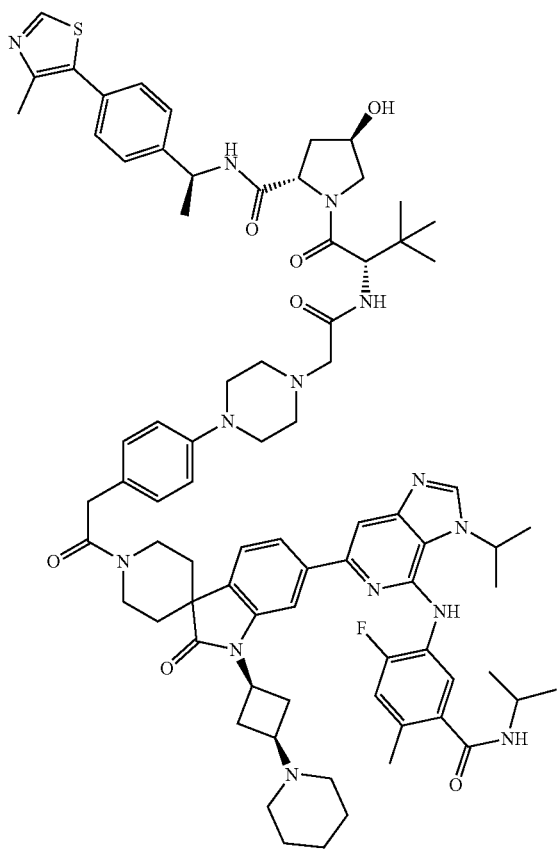 [SMILES: Cc1cc(F)c(Nc2nc(-c3ccc4c(c3)N([C@H]3C[C@@H](N5CCCCC5)C3)C(=O)C43CCN(C(=O)Cc4ccc(N5CCN(CC(=O)N[C@H](C(=O)N6C[C@H](O)C[C@H]6C(=O)N[C@@H](C)c6ccc(-c7scnc7C)cc6)C(C)(C)C)CC5)cc4)CC3)cc3ncn(C(C)C)c23)cc1C(=O)NC(C)C]

Step 1: Synthesis of tert-butyl 2-(4-(4-(2-ethoxy-2-oxoethyl)phenyl)piperazin-1-yl)acetate. tert-Butyl (piperazin-1-yl)acetate (0.89 g, 4.4 mmol, 1.2 eq) palladium(II) acetate (0.083 g, 0.37 mmol, 0.1 eq), and Xphos (0.176 g, 0.37 mmol, 0.1 eq) were added under argon to a stirred solution of ethyl 4-bromophenylacetate (0.90 g, 3.7 mmol, 1.0 eq), in anh toluene (22 mL, 0.2 M). The reaction mixture was then purged with argon for 3 min, moved to pre-heated bath to 100° C., and stirred for 16 h. The UPLC showed the formation of the title compound. The mixture was diluted with water (20 mL) and then extracted using ethyl acetate (3×). The combined organic fractions were dried over sodium sulfate, filtered, and concentrated under reduced pressure. The crude was purified by Chromatography A to give 0.9 g (67% yield) of title compound.

Step 2: Synthesis of 2-{4-[4-(2-ethoxy-2-oxoethyl)phenyl]piperazin-1-yl}acetic acid. tert-butyl 2-(4-(4-(2-ethoxy-2-oxoethyl)phenyl)piperazin-1-yl)acetate (0.13 g, 0.36 mmol, 1.0 eq) was dissolved in anh DCM (1.3 mL) followed by addition of TFA (0.275 mL, 10.0 eq) and stirred at RT for 4 h. The UPLC showed the remaining SM. Another 10 eq of TFA was added and the reaction mixture was stirred for an additional 2 h. The reaction mixture was evaporated to dryness to acquire 0.13 g (86% yield) of the title compound as a TFA salt.

Step 3: Synthesis of ethyl 2-{4-[4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]phenyl}acetate. The title compound was synthesized according to General Procedure F using (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (50 mg, 0.10 mmol) and {4-[4-(2-ethoxy-2-oxoethyl)phenyl]piperazin-1-yl}acetic acid (53 mg, 0.12 mmol). The crude material was purified using Chromatography B to yield the title compound (75 mg, 98%).

Step 4: Synthesis of {4-[4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]phenyl}acetic acid. The title compound was synthesized according to General Procedure C using ethyl 2-{4-[4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]phenyl}acetate (75 mg, 0.10 mmol). This material was used without purification.

Step 5: Synthesis of (2S,4R)-1-[(2S)-2-{2-[4-(4-{2-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]-2-oxoethyl}phenyl)piperazin-1-yl]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide. The title compound was synthesized according to General Procedure F using Intermediate 1 (15.8 mg, 0.02 mmol) and {4-[4-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperazin-1-yl]phenyl}acetic acid (15 mg, 0.02 mmol) followed by reverse phase HPLC to provide the title compound (13 mg, 44%); LCMS: $C_{78}H_{97}FN_{14}O_7S$ requires 1392.7, found 1393.8 [M+H]$^+$; $^1$H NMR (500 MHz, Methanol-$d_4$) δ 8.92-8.80 (m, 2H), 8.08-8.01 (m, 1H), 7.80-7.67 (m, 2H), 7.64-7.53 (m, 1H), 7.49-7.25 (m, 7H), 7.19-7.02 (m, 2H), 5.30 (p, J=6.6 Hz, 1H), 5.02 (t, J=6.9 Hz, 1H), 4.61-4.24 (m, 2H), 4.21-3.39 (m, 23H), 3.19-2.81 (m, 7H), 2.50-2.37 (m, 6H), 2.26-2.18 (m, 1H), 2.07-1.45 (m, 22H), 1.15-1.06 (m, 15H).

Example 48

(2S,4R)-1-((2S)-2-(2-(3-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide

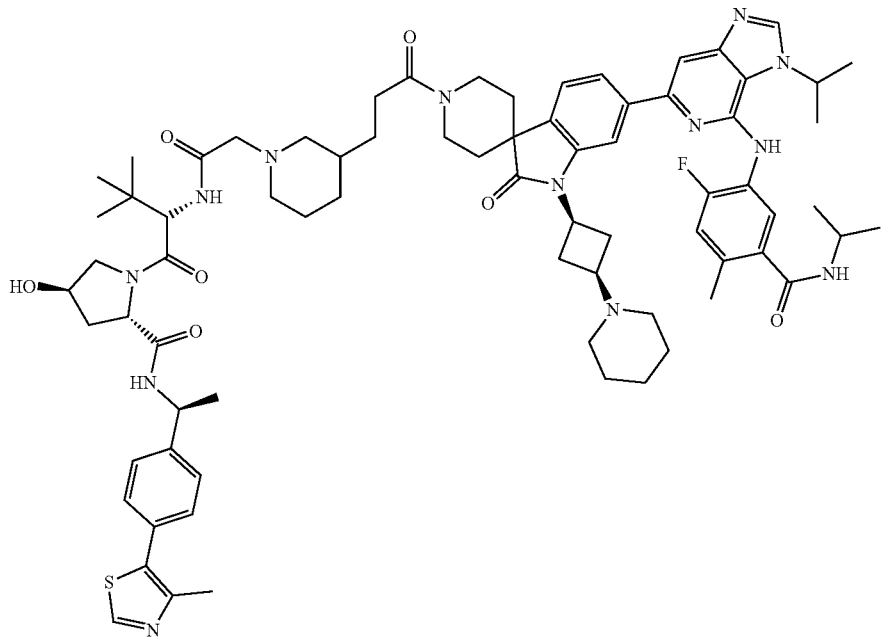

Step 1: Synthesis of ethyl 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-3-yl]propanoate. The reaction was carried out according to General Procedure F using (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (110 mg, 0.23 mmol) and [3-(3-ethoxy-3-oxopropyl)piperidin-1-yl]acetic acid (56 mg, 0.23 mmol) as starting materials. Purification using Chromatography B gave the title compound (128 mg, 83%).

Step 2: Synthesis of 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-3-yl]propanoic acid. The reaction was carried out according to General Procedure C using ethyl 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-3-yl]propanoate (128 mg, 0.19 mmol) as starting material. Residue was used without purification in the next step.

Step 3: Synthesis of (2S,4R)-1-[(2S)-2-{2-[(3RS)-3-(3-{6-[4-({2-fluoro-4-methyl-5-[(propan-2-yl)carbamoyl]phenyl}amino)-3-(propan-2-yl)-3H-imidazo[4,5-c]pyridin-6-yl]-2-oxo-1-[(1s,3s)-3-(piperidin-1-yl)cyclobutyl]-1,2-dihydrospiro[indole-3,4'-piperidin]-1'-yl}-3-oxopropyl)piperidin-1-yl]acetamido}-3,3-dimethylbutanoyl]-4-hydroxy-N-[(1S)-1-[4-(4-methyl-1,3-thiazol-5-yl)phenyl]ethyl]pyrrolidine-2-carboxamide. The title compound was synthesized according to General Procedure F using Intermediate 1 (12 mg, 0.02 mmol) and 3-[1-({[(2S)-1-[(2S,4R)-4-hydroxy-2-{[(1S)-1-[4-(4-methyl-1,3-thiazol-5-yl)phenyl]ethyl]carbamoyl}pyrrolidin-1-yl]-3,3-dimethyl-1-oxobutan-2-yl]carbamoyl}methyl)piperidin-3-yl]propanoic acid (10 mg, 0.02 mmol) followed by reverse phase HPLC to provide the title compound (10.9 mg, 43%); LCMS: $C_{74}H_{96}FN_{13}O_7S$ requires 1329.5, found 1331.2 $[M+2H]^+$; $^1$H NMR (500 MHz, Acetonitrile-$d_3$) δ 8.84-8.73 (m, 1H), 8.67 (s, 1H), 8.06-7.96 (m, 1H), 7.96-7.86 (m, 1H), 7.75-7.67 (m, 1H), 7.53-7.13 (m, 10H), 6.68 (d, J=7.8 Hz, 1H), 5.23-5.10 (m, 1H), 4.96 (s, 1H), 4.71-4.57 (m, 1H), 4.57-4.45 (m, 1H), 4.44-4.32 (m, 1H), 4.32-4.00 (m, 3H), 3.98-3.58 (m, 8H), 3.58-3.39 (m, 6H), 3.09-2.39 (m, 10H), 2.12 (d, J=5.1 Hz, 2H), 1.92-1.38 (m, 28H), 1.16 (d, J=6.6 Hz, 8H), 1.02 (d, J=8.4 Hz, 10H).

Example 49

5-[(6-{1'-[1-{1-[2-({2-[2,6-dioxopiperidin-3-yl]-1,3-dioxo-2,3-dihydro-1H-isoindol-4-yl}amino)acetyl]piperidine-4-carbonyl}pyrrolidine-3-carbonyl]-2-oxo-1-[1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

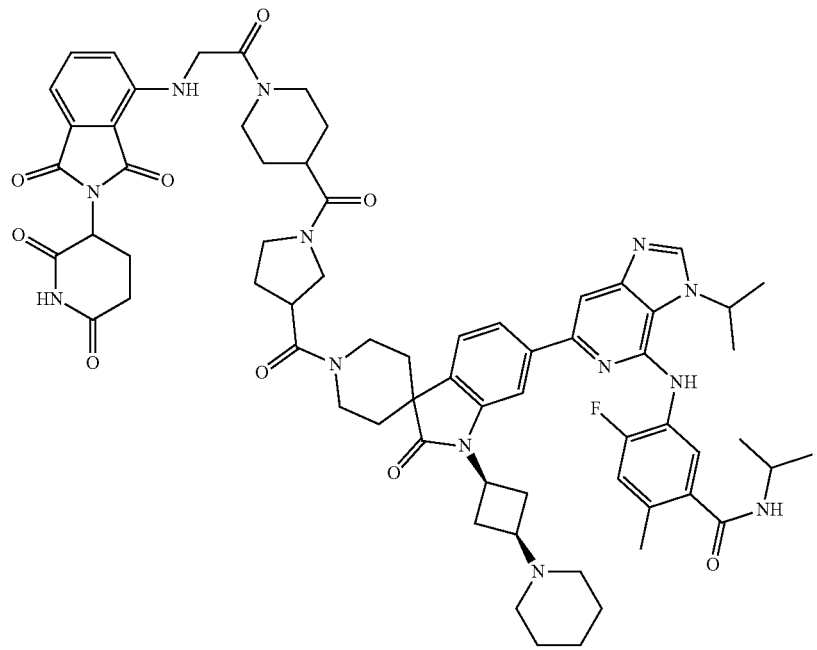 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)C5CCN(C(=O)CNc6cccc7c6C(=O)N(C6CCC(=O)NC6=O)C7=O)CC5)C4)CC3)cc3ncn(C(C)C)c23)cc1C(=O)NC(C)C]

Step 1: Synthesis of -benzyl 1-[2-({2-[2,6-dioxopiperidin-3-yl]-1,3-dioxoisoindol-4-yl}amino)acetyl]piperidine-4-carboxylate. The title compound was synthesized according to General Procedure F using ({2-[-2,6-dioxopiperidin-3-yl]-1,3-dioxoisoindol-4-yl}amino)acetic acid (175 mg, 0.39 mmol) and benzyl piperidine-4-carboxylate (86 mg, 0.39 mmol). The crude material was purified using Chromatography B to yield the title compound (200 mg, 96%).

Step 2: Synthesis of 1-[2-({2-[2,6-dioxopiperidin-3-yl]-1,3-dioxoisoindol-4-yl}amino)acetyl]piperidine-4-carboxylic acid. The title compound was synthesized by adding palladium on carbon (15 mg, 10% by weight) to benzyl 1-[2-({2-[2,6-dioxopiperidin-3-yl]-1,3-dioxoisoindol-4-yl}amino)acetyl]piperidine-4-carboxylate (200 mg, 0.38 mmol). Ethyl acetate (2 mL) and ethanol (2 mL) were then added followed by bubbling $H_2$ gas through the stirred mixture for 5 minutes. The reaction was then stirred under a balloon of $H_2$ for 5 hrs before being purged with nitrogen and filtered through celite, washing with ethyl acetate. The filtrate was concentrated and purified according to Chromatography C to provide the title compound (120 mg, 72%).

Step 3: Synthesis of 1-{1-[2-({2-[2,6-dioxopiperidin-3-yl]-1,3-dioxoisoindol-4-yl}amino)acetyl]piperidine-4-carbonyl}pyrrolidine-3-carboxylic acid. The title compound was synthesized according to General Procedure F using 1-[2-({2-[2,6-dioxopiperidin-3-yl]-1,3-dioxoisoindol-4-yl}amino)acetyl]piperidine-4-carboxylic acid (44 mg, 0.10 mmol) and tert-butyl pyrrolidine-3-carboxylate (19 mg, 0.11 mmol). The crude material was purified using Chromatography C followed by General Procedure B to afford the title compound (22 mg, 41%).

Step 4: Synthesis of 5-[(6-{1'-[1-{1-[2-({2-[2,6-dioxopiperidin-3-yl]-1,3-dioxo-2,3-dihydro-1H-isoindol-4-yl}amino)acetyl]piperidine-4-carbonyl}pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (13 mg, 0.02 mmol) and 1-{1-[2-({2-[2,6-dioxopiperidin-3-yl]-1,3-dioxoisoindol-4-yl}amino)acetyl]piperidine-4-carbonyl}pyrrolidine-3-carboxylic acid (10 mg, 0.02 mmol) followed by reverse phase HPLC to provide the title compound (13.6 mg, 60%); LCMS: $C_{67}H_{78}FN_{13}O_9$ requires 1227.6, found 1230.0 [M+2H]$^+$; $^1$H NMR (500 MHz, DMSO-d$_6$) δ 11.11 (s, 1H), 9.31 (s, 1H), 8.64 (s, 1H), 8.39 (s, 1H), 8.14 (d, J=7.9 Hz, 1H), 7.89 (d, J=4.6 Hz, 1H), 7.68 (d, J=6.8 Hz, 1H), 7.62 (t, J=8.2 Hz, 2H), 7.60-7.50 (m, 2H), 7.19 (d, J=12.0 Hz, 1H), 7.15-7.01 (m, 3H), 5.30 (p, J=7.6, 7.1 Hz, 1H), 5.08 (dd, J=12.8, 5.4 Hz, 1H), 4.42 (d, J=12.0 Hz, 1H), 4.22 (q, J=19.3, 17.2 Hz, 5H), 4.08-4.01 (m, 2H), 3.49-3.22 (m, 8H), 3.20-2.69 (m, 13H), 2.62 (d, J=3.7 Hz, 1H), 2.37 (s, 3H), 2.20-2.03 (m, 3H), 1.93-1.54 (m, 17H), 1.50-1.33 (m, 2H), 1.11 (d, J=6.6 Hz, 6H).

Example 50

4-fluoro-2-methyl-5-[(6-{2-oxo-1-[(1s,3s)-3-(piperidin-1-yl)cyclobutyl]-1'-[(1S,4s)-4-[4-({2-[2,6-dioxopiperidin-3-yl]-1,3-dioxo-2,3-dihydro-1H-isoindol-4-yl}amino)piperidine-1-carbonyl]cyclohexanecarbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

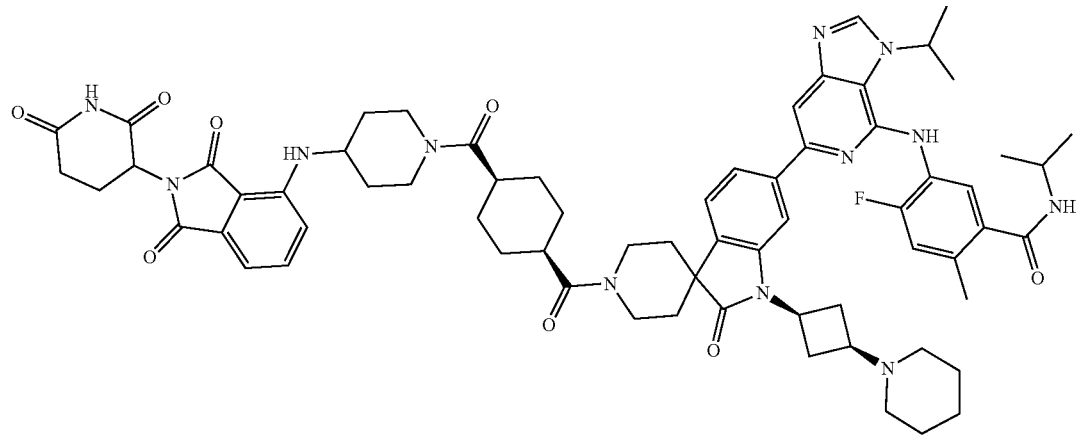 [SMILES: Cc1cc(F)c(Nc2nc(-c3ccc4c(c3)N([C@H]3C[C@@H](N5CCCCC5)C3)C(=O)C43CCN(C(=O)[C@H]4CC[C@@H](C(=O)N5CCC(Nc6cccc7c6C(=O)N(C6CCC(=O)NC6=O)C7=O)CC5)CC4)CC3)cc3ncn(C(C)C)c23)cc1C(=O)NC(C)C]

Step 1: Synthesis of tert-butyl 4-[[2-(2,6-dioxopiperidin-3-yl)-1,3-dioxoisoindol-4-yl]amino]piperidine-1-carboxylate: To a mixture of 2-(2,6-dioxopiperidin-3-yl)-4-fluoroisoindole-1,3-dione (4.0 g, 14 mmol, 1 eq.) and tert-butyl 4-aminopiperidine-1-carboxylate (3.48 g, 17.3 mmol, 1.2 eq.) in DMSO (20 mL) was added DIPEA (5.61 g, 43.4 mmol, 3 eq.). The resulting mixture was stirred at 80° C. overnight and subsequently cooled to rt. The precipitated solids were collected by filtration and washed with water (3×50 mL). This provided the title compound as a solid (4.0 g, 61%).

Step 2: Synthesis of 2-(2,6-dioxopiperidin-3-yl)-4-(piperidin-4-ylamino)isoindole-1,3-dione: The title compound was obtained following General Procedure B using tert-butyl 4-[[2-(2,6-dioxopiperidin-3-yl)-1,3-dioxoisoindol-4-yl]amino]piperidine-1-carboxylate (4.0 g, 8.8 mmol) as starting material. Following Chromatography C, the title compound was isolated (2.4 g, 77%).

Step 3: Synthesis of (1s,4s)-4-[4-([2-[2,6-dioxopiperidin-3-yl]-1,3-dioxoisoindol-4-yl]amino)piperidine-1-carbonyl]cyclohexane-1-carboxylic acid: To a mixture of 2-(2,6-dioxopiperidin-3-yl)-4-(piperidin-4-ylamino)isoindole-1,3-dione (1.3 g, 3.65 mmol, 1 eq.) and TEA (2.21 g, 21.9 mmol, 6 eq.) in DMF (8 mL) were added (1s,4s)-cyclohexane-1,4-dicarboxylic acid (0.63 g, 3.7 mmol, 1 eq.). The resulting mixture was stirred at room temperature for 30 min under nitrogen atmosphere. To the above mixture was added T3P (3.48 g, 5.47 mmol, 1.5 eq., 50% w/w in EtOAc at 0° C. The resulting mixture was stirred at room temperature overnight. Water was then added and the reaction mixture was extracted with EtOAc (3×10 mL). The combined organic layers were dried over anhydrous $Na_2SO_4$. After filtration, the filtrate was concentrated under reduced pressure. The residue was purified by Chromatography C. This provided in the title compound (230.2 mg, 7.65% yield).

Step 4: Synthesis of 4-fluoro-2-methyl-5-[(6-{2-oxo-1'-[(1r,4r)-4-[4-({2-[2,6-dioxopiperidin-3-yl]-1,3-dioxo-2,3-dihydro-1H-isoindol-4-yl}amino)piperidine-1-carbonyl]cyclohexanecarbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (10 mg) and (1s,4s)-4-[4-([2-[2,6-dioxopiperidin-3-yl]-1,3-dioxoisoindol-4-yl]amino)piperidine-1-carbonyl]cyclohexane-1-carboxylic acid (7.2 mg) followed by reverse phase HPLC to provide the title compound (11.5 mg, 64%); LCMS: $C_{67}H_{79}FN_{12}O_8$ requires 1198.6, found 1200.0 [M+H]$^+$; $^1$H NMR (500 MHz, DMSO-d$_6$) δ 11.09 (s, 1H), 9.34 (s, 1H), 8.70 (s, 1H), 8.41 (s, 1H), 8.14 (d, J=7.8 Hz, 1H), 7.87 (d, J=2.3 Hz, 1H), 7.74-7.47 (m, 5H), 7.31-7.14 (m, 2H), 7.05 (dd, J=14.7, 7.0 Hz, 1H), 6.23 (dd, J=55.9, 8.2 Hz, 1H), 5.30 (p, J=6.7 Hz, 1H), 5.08-5.01 (m, 1H), 4.32 (d, J=13.1 Hz, 3H), 4.26-4.14 (m, 4H), 4.09-3.15 (m, 9H), 3.07-2.72 (m, 8H), 2.72-2.57 (m, 2H), 2.36 (s, 3H), 2.20-1.89 (m, 4H), 1.89-1.27 (m, 23H), 1.10 (d, J=6.6 Hz, 6H).

Example 51

4-fluoro-2-methyl-5-[(6-{2-oxo-1'-[(R,4R)-4-[4-({2-[2,6-dioxopiperidin-3-yl]-1,3-dioxo-2,3-dihydro-1H-isoindol-4-yl}amino)piperidine-1-carbonyl]cyclohexanecarbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

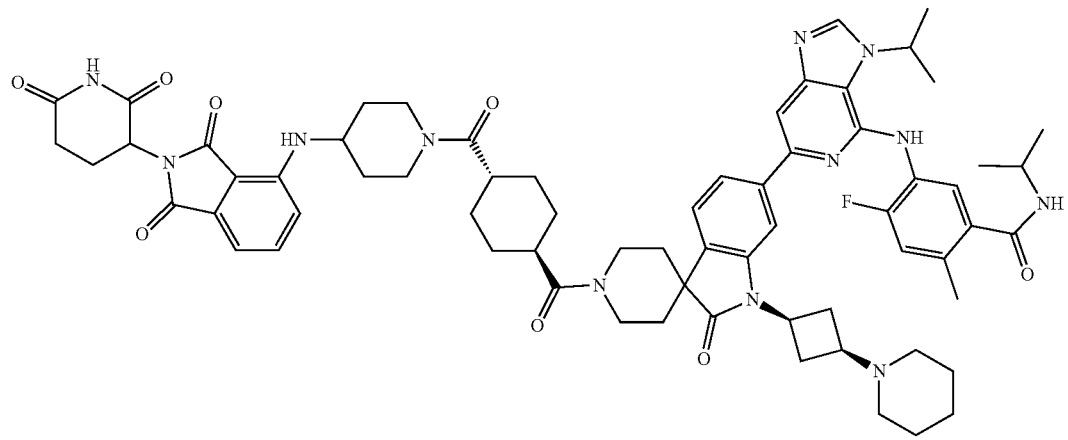 [SMILES: Cc1cc(F)c(Nc2nc(-c3ccc4c(c3)N([C@H]3C[C@@H](N5CCCCC5)C3)C(=O)C43CCN(C(=O)[C@H]4CC[C@H](C(=O)N5CCC(Nc6cccc7c6C(=O)N(C6CCC(=O)NC6=O)C7=O)CC5)CC4)CC3)cc3ncn(C(C)C)c23)cc1C(=O)NC(C)C]

Step-1: Synthesis of (1r,4r)-4-[4-([2-[2,6-dioxopiperidin-3-yl]-1,3-dioxoisoindol-4-yl]amino)piperidine-1-carbonyl]cyclohexane-1-carboxylic acid: To a mixture of 2-(2,6-dioxopiperidin-3-yl)-4-(piperidin-4-ylamino)isoindole-1,3-dione (1.7 g, 4.8 mmol, 1 eq.) and TEA (2.9 g, 29 mmol, 6 eq.) in DMF (8 mL) were added trans-cyclohexane-1,4-dicarboxylic acid (0.82 g, 4.8 mmol, 1 equiv.). The resulting mixture was stirred at room temperature for 30 min under nitrogen atmosphere. To the above mixture was added T3P (4.56 g, 7.16 mmol, 1.50 equiv., 50% w/w in EtOAc at 0° C. The resulting mixture was stirred at room temperature overnight. Water was then added, and the reaction mixture was extracted with EtOAc (3×10 mL). The combined organic layers were dried over anhydrous $Na_2SO_4$. After filtration, the filtrate was concentrated under reduced pressure. The residue was purified by C18 reverse phase column with $ACN/H_2O$ (2/1). This resulted in (1r,4r)-4-[4-([2-[2,6-dioxopiperidin-3-yl]-1,3-dioxoisoindol-4-yl]amino)piperidine-1-carbonyl]cyclohexane-1-carboxylic acid as a yellow solid (252 mg, 10% yield)

Step 2: Synthesis of 4-fluoro-2-methyl-5-[(6-{2-oxo-1'-[(1r,4r)-4-[4-({2-[2,6-dioxopiperidin-3-yl]-1,3-dioxo-2,3-dihydro-1H-isoindol-4-yl}amino)piperidine-1-carbonyl]cyclohexanecarbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (10 mg, 0.01 mmol) and (1r,4r)-4-[4-({2-[2,6-dioxopiperidin-3-yl]-1,3-dioxoisoindol-4-yl}amino)piperidine-1-carbonyl]cyclohexane-1-carboxylic acid (7.2 mg, 0.01 mmol) followed by reverse phase HPLC to provide the title compound (10.2 mg, 60%); LCMS: $C_{67}H_{79}FN_{12}O_8$ requires 1198.6, found 1200.0 [M+H]$^+$; $^1$H NMR (500 MHz, DMSO-$d_6$) δ 11.11 (s, 1H), 9.30 (d, J=9.4 Hz, 1H), 8.65 (s, 1H), 8.39 (s, 1H), 8.15 (d, J=7.8 Hz, 1H), 7.89 (s, 1H), 7.68 (d, J=7.8 Hz, 1H), 7.63 (t, J=7.4 Hz, 2H), 7.57-7.51 (m, 2H), 7.26 (d, J=8.7 Hz, 1H), 7.19 (d, J=12.0 Hz, 1H), 7.08 (d, J=7.0 Hz, 1H), 6.30 (d, J=8.3 Hz, 1H), 5.33-5.27 (m, 1H), 5.07 (dd, J=12.6, 5.4 Hz, 1H), 4.35 (s, 1H), 4.26-4.19 (m, 1H), 4.05 (q, J=6.8 Hz, 2H), 3.53 (q, J=8.2 Hz, 2H), 3.41 (d, J=11.5 Hz, 3H), 3.29-3.15 (m, 2H), 3.05-2.72 (m, 11H), 2.67-2.55 (m, 1H), 2.38 (s, 3H), 2.07-1.93 (m, 3H), 1.89-1.29 (m, 27H), 1.11 (d, J=6.5 Hz, 6H).

Example 52

4-fluoro-2-methyl-5-[(6-{2-oxo-1'-[(3R)-1-[(1R,4R)-4-({2-[2,6-dioxopiperidin-3-yl]-1,3-dioxo-2,3-di-hydro-1H-isoindol-4-yl}amino)cyclohexanecarbo-nyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

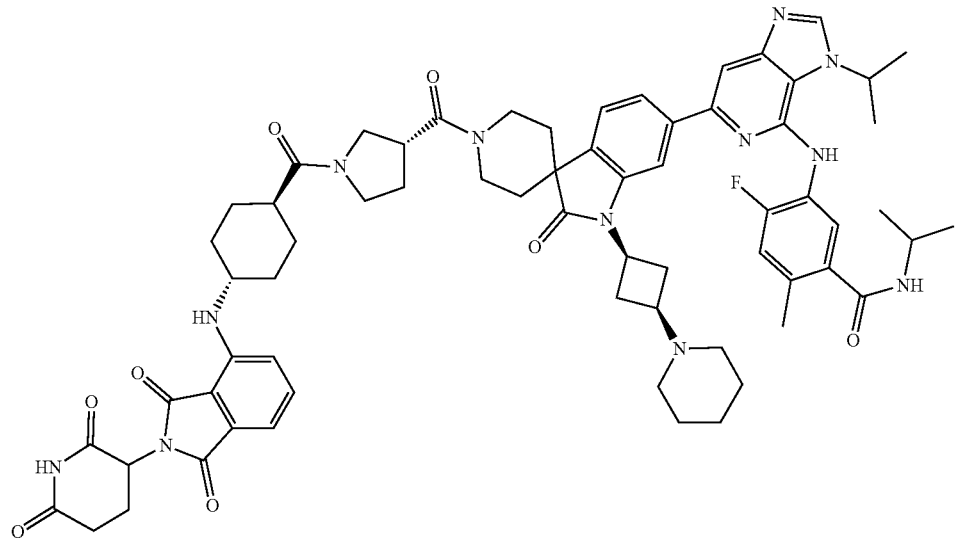 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of 1-benzyl 3-tert-butyl (3R)-pyrrolidine-1,3-dicarboxylate. To a mixture of (3R)-1-[(benzyloxy)carbonyl]pyrrolidine-3-carboxylic acid (5.0 g, 20 mmol, 1 eq.) in DCM (10 mL) was added (Z)—N,N-diisopropyl tert-butoxymethanimidamide (12 g, 64 mmol) at 0° C. The resulting mixture was stirred at room temperature overnight. The reaction was concentrated. The residue was purified by Chromatography B to afford the title compound (2.6 g, 42% yield) as a colorless oil.

Step 2: Synthesis of tert-butyl (3R)-pyrrolidine-3-carboxylate. To a stirred mixture of 1-benzyl 3-tert-butyl (3R)-pyrrolidine-1,3-dicarboxylate (2.5 g, 8.2 mmol, 1 eq.) in THF (15 mL) was added Pd/C (1 g). The resulting mixture was stirred at room temperature for 1 h under hydrogen atmosphere. The resulting mixture was purged with $N_2$ gas for 15 min and subsequently filtered. The filtrate was concentrated under reduced pressure. This gave the title compound (1.4 g, crude) as an oil.

Step 3: Synthesis of tert-butyl (3R)-1-[(1r,4r)-4-[[2-(2,6-dioxopiperidin-3-yl)-1,3-dioxoisoindol-4-yl]amino]cyclohexanecarbonyl]pyrrolidine-3-carboxylate. To a stirred mixture of (1r,4r)-4-[[2-(2,6-dioxopiperidin-3-yl)-1,3-dioxoisoindol-4-yl]amino]cyclohexane-1-carboxylic acid (500 mg, 1.25 mmol, 1 eq.) in DMF (5 mL) were added HATU (713 mg, 1.88 mmol, 1.5 eq.) and DIPEA (485 mg, 3.75 mmol, 3 eq.) at room temperature. After 30 min, the resulting mixture was added tert-butyl (3R)-pyrrolidine-3-carboxylate (214 mg, 1.25 mmol, 1 eq.) at room temperature and stirred for 3 h. The resulting mixture was extracted with EtOAc (3×30 mL). The combined organic layers were washed with water (3×20 mL), dried over anhydrous $MgSO_4$, filtered, and concentrated under reduced pressure. The residue was purified by Chromatography C to afford tert-butyl (3R)-1-[(1r,4r)-4-[[2-(2,6-dioxopiperidin-3-yl)-1,3-dioxoisoindol-4-yl]amino]cyclohexanecarbonyl]pyrrolidine-3-carboxylate (220 mg, 32% yield).

Step 4: Synthesis of (3R)-1-[(1r,4r)-4-({2-[2,6-dioxopiperidin-3-yl]-1,3-dioxoisoindol-4-yl]amino)cyclohexanecarbonyl]pyrrolidine-3-carboxylic acid. The reaction was carried out according to General Procedure B using tert-butyl (3R)-1-[(1r,4r)-4-[[2-(2,6-dioxopiperidin-3-yl)-1,3-dioxoisoindol-4-yl]amino]cyclohexanecarbonyl]pyrrolidine-3-carboxylate (200 mg, 0.362 mmol) as the starting material. The resulting residue was purified using Chromatography C to afford the title compound (105 mg, 57% yield) as a yellow solid Step 5: Synthesis of 4-fluoro-2-methyl-5-[(6-{2-oxo-1'-[(3R)-1-[(1r,4r)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (11 mg, 0.02 mmol) (3R)-1-[(1r,4r)-4-({2-[2,6-dioxopiperidin-3-yl]-1,3-dioxoisoindol-4-yl]amino)cyclohexanecarbonyl]pyrrolidine-3-carboxylic acid (7.7 mg, 0.02 mmol) followed by reverse phase HPLC to provide the title compound (1.8 mg, 10%); LCMS: $C_{66}H_{77}FN_{12}O_8$ requires 1184.6, found 1187.0 [M+2H]$^+$; $^1$H NMR (500 MHz, DMSO-$d_6$) δ 11.09 (s, 1H), 9.48-9.35 (m, 1H), 8.78 (d, J=5.3 Hz, 1H), 8.45 (s, 1H), 8.14 (d, J=7.7 Hz, 1H), 7.87 (s, 1H), 7.67 (d, J=7.7 Hz, 1H), 7.63-7.46 (m, 4H), 7.28-7.14 (m, 2H), 7.04 (d, J=7.0 Hz, 1H), 6.17 (d, J=8.1 Hz, 1H), 5.32 (p, J=6.7 Hz, 1H), 5.05 (dd, J=12.8, 5.4 Hz, 1H), 4.24-4.14 (m, 2H), 4.08-3.99 (m, 2H), 3.60-3.26 (m, 9H), 3.04-2.66 (m, 8H), 2.59 (d, J=17.3 Hz, 2H), 2.37 (s, 3H), 2.18-1.92 (m, 5H), 1.93-1.50 (m, 20H), 1.48-1.27 (m, 3H), 1.10 (d, J=6.0 Hz, 6H).

Example 53

5-[(6-{1'-[3-(1-{2-[2,6-dioxopiperidin-3-yl]-1,3-dioxo-2,3-dihydro-1H-isoindol-4-yl}piperidin-4-yl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

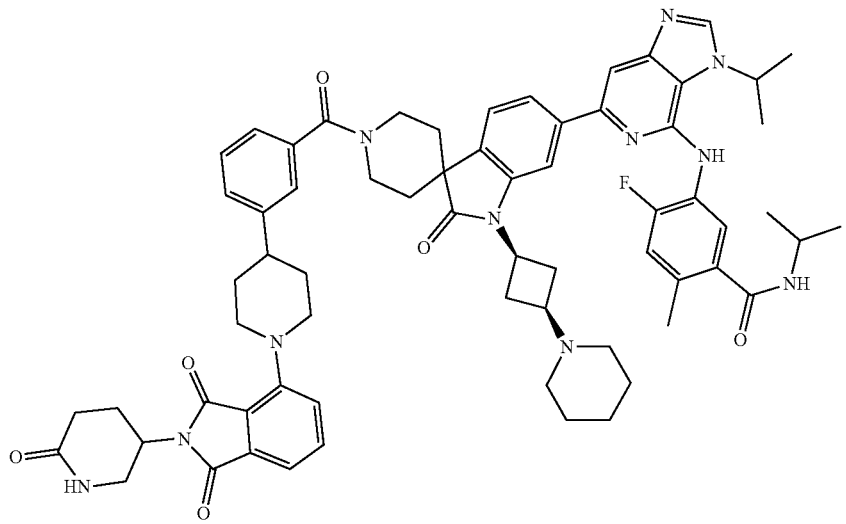 [SMILES: Cc1cc(F)c(Nc2nc(-c3ccc4c(c3)N([C@H]3C[C@@H](N5CCCCC5)C3)C(=O)C43CCN(C(=O)c4cccc(C5CCN(c6cccc7c6C(=O)N(C6CCC(=O)NC6)C7=O)CC5)c4)CC3)cc3ncn(C(C)C)c23)cc1C(=O)NC(C)C]

Step 1: Synthesis of 3-{1-[2-(2,6-dioxopiperidin-3-yl)-1,3-dioxoisoindol-4-yl]piperidin-4-yl}benzoic acid. The reaction was carried out according to General Procedure A using 2-(2,6-dioxopiperidin-3-yl)-4-fluoroisoindole-1,3-dione (300 mg, 1.09 mmol), and 3-(piperidin-4-yl)benzoic acid (245 mg, 1.19 mmol). Purification using Chromatography C gave the title compound (310 mg, 62%).

Step 2: Synthesis of 5-[(6-{1'-[3-(1-{2-[2,6-dioxopiperidin-3-yl]-1,3-dioxo-2,3-dihydro-1H-isoindol-4-yl}piperidin-4-yl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (21 mg, 0.026 mmol) and 3-(1-(2-(2,6-dioxopiperidin-3-yl)-1,3-dioxoisoindolin-4-yl)piperidin-4-yl)benzoic acid (13 mg, 0.026 mmol) followed by reverse phase HPLC to provide the title compound (31 mg, 99%); LCMS: $C_{66}H_{72}FN_{11}O_7$ requires 1149.6, found 1151.0 [M+H]$^+$; $^1$H NMR (500 MHz, Methanol-$d_4$) δ 8.97 (s, 1H), 7.99 (d, J=8.2 Hz, 1H), 7.82-7.72 (m, 2H), 7.68 (t, J=7.8 Hz, 1H), 7.62-7.52 (m, 2H), 7.48-7.32 (m, 7H), 7.16 (d, J=11.7 Hz, 1H), 5.33 (p, J=6.6 Hz, 1H), 5.10 (td, J=12.3, 11.9, 5.5 Hz, 1H), 4.40-3.48 (m, 10H), 3.15-2.62 (m, 12H), 2.44 (s, 3H), 2.17-1.67 (m, 20H), 1.57 (t, J=13.1 Hz, 1H), 1.15 (d, J=6.6 Hz, 6H).

Example 54

4-fluoro-2-methyl-5-[(6-{2-oxo-1'-[(3R)-1-[(1R,4R)-4-{[2-(2,6-dioxopiperidin-3-yl)-1,3-dioxo-2,3-dihydro-1H-isoindol-4-yl]oxy}cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

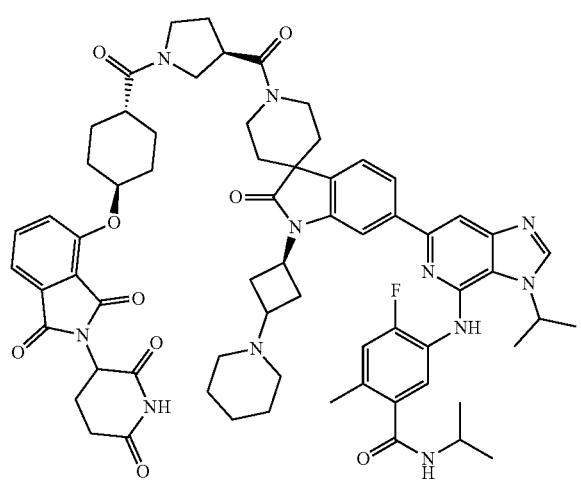

Step 1: Synthesis of 1,2-dimethyl 3-hydroxyphthalate. A solution of 4-hydroxy-2-benzofuran-1,3-dione (1.0 g, 6.09 mmol) in methanol (12 mL) was heated at reflux for 3 h before cooling to RT. The solvent was removed under vacuum and solid sodium bicarbonate (1.43 g, 17.1 mmol) and DMF (8 mL) were added in this order. Next, iodomethane (0.91 mL, 14.6 mmol) was added and the reaction stirred at 50° C. for 2 hr. The solvent was removed, and the residue was partitioned between ethyl acetate (20 mL) and water (15 mL). The organics were washed twice more with water, dried over sodium sulfate, and filtered before purification using Chromatography A to afford the title compound (950 mg, 74%).

Step 2: Synthesis of 1,2-dimethyl 3-{[(1r,4r)-4-(tert-butoxycarbonyl)cyclohexyl]oxy}phthalate. The title compound was synthesized by combining 1,2-dimethyl 3-hydroxyphthalate (1.05 g, 4.99 mmol), triphenylphosphine (1.31 g, 4.99 mmol), and tert-butyl (1s,4s)-4-hydroxycyclohexane-1-carboxylate (500 mg, 2.50 mmol), in THF (12.6 mL). The mixture was cooled to 0° C. before dropwise addition of diisopropyl azodicarboxylate (0.98 mL, 5.0 mmol). The mixture was stirred at 0° C. for 1 hr and then at rt for 16 hrs. After this time, 2N NaOH (20 mL) was added and the mixture extracted with ethyl acetate (2×20 mL). The combined organics were washed sequentially with water then brine, dried over sodium sulfate, and filtered and concentrated. The resulting residue was purified by Chromatography A to give the title compound (600 mg, 52%).

Step 3: Synthesis of 3-{[(1r,4r)-4-(tert-butoxycarbonyl)cyclohexyl]oxy}benzene-1,2-dicarboxylic acid. The title compound was synthesized by refluxing 1,2-dimethyl 3-{[(1r,4r)-4-(tert-butoxycarbonyl)cyclohexyl]oxy}phthalate (489 mg, 1.25 mmol) in ethanol (16.3 mL) containing 3N sodium hydroxide (aq., 4.1 mL) for 2 hrs. Solvents were then removed and 20 mL water was added, followed by washing with DCM (2×10 mL). The aqueous layer was then acidified to pH ~ 4 with HCl (1N, aq.). This was then extracted with ethyl acetate (3×20 mL) and the combined organics were washed sequentially with water (2×) then brine, dried over sodium sulfate, and filtered and concentrated to give the title compound (225 mg, 50%).

Step 4; Synthesis of (1r,4r)-4-{[2-(2,6-dioxopiperidin-3-yl)-1,3-dioxoisoindol-4-yl]oxy}cyclohexane-1-carboxylic acid. The title compound was synthesized by combining 3-{[(1r,4r)-4-(tert-butoxycarbonyl)cyclohexyl]oxy}benzene-1,2-dicarboxylic acid (224 mg, 0.61 mmol) and 3-aminopiperidine-2,6-dione hydrochloride (101 mg, 0.61 mmol) in pyridine (6 mL) and heating at 125° C. for 16 hrs. The reaction was then concentrated and dissolved in ethyl acetate before being washed with 1N HCl (2×20 mL), water (1×10 mL) followed by drying over sodium sulfate, filtration, and concentration under reduced pressure to give the title compound.

Step 5: Synthesis of (3R)-1-((1r,4R)-4-((2-(2,6-dioxopiperidin-3-yl)-1,3-dioxoisoindolin-4-yl)oxy)cyclohexane-1-carbonyl)pyrrolidine-3-carboxylic acid. The title compound was synthesized according to General Procedure F using (1r,4r)-4-{[2-(2,6-dioxopiperidin-3-yl)-1,3-dioxoisoindolin-4-yl]oxy}cyclohexane-1-carboxylic acid (30 mg, 0.07 mmol) and tert-butyl (3R)-pyrrolidine-3-carboxylate (19 mg, 0.11 mmol). The product of this reaction was purified using Chromatography C followed by treatment according to General Procedure B to give the title compound (20 mg, 54%).

Step 6: Synthesis of 4-fluoro-2-methyl-5-[(6-{2-oxo-1'-[(3R)-1-[(1r,4r)-4-{[2-(2,6-dioxopiperidin-3-yl)-1,3-dioxo-2,3-dihydro-1H-isoindol-4-yl]oxy}cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (30 mg, 0.04 mmol) and (3R)-1-((1r,4R)-4-((2-(2,6-dioxopiperidin-3-yl)-1,3-dioxoisoindolin-4-yl)oxy)cyclohexane-1-carbonyl)pyrrolidine-3-carboxylic acid (24 mg, 0.05 mmol) followed by reverse phase HPLC to provide the title compound (17.5 mg, 31%); LCMS: $C_{66}H_{76}FN_{11}O_9$ requires 1185.6, found 1186.9 [M+H]$^+$; $^1$H NMR (500 MHz, DMSO-$d_6$) δ 11.10 (s, 1H), 9.35 (s, 1H), 8.71 (d, J=4.0 Hz, 1H), 8.42 (s, 1H), 8.14 (d, J=7.6 Hz, 1H), 7.87 (d, J=2.8 Hz, 1H), 7.78 (t, J=7.9 Hz, 1H), 7.73-7.47 (m, 5H), 7.43 (d, J=7.2 Hz, 1H), 7.18 (d, J=11.9 Hz, 1H), 5.30 (p, J=6.7 Hz, 1H), 5.07 (dd, J=12.8, 5.5 Hz, 1H), 4.71-4.58 (m, 1H), 4.28-4.17 (m, 1H), 4.04 (q, J=6.8 Hz, 1H), 3.97-3.78 (m, 2H), 3.44-3.20 (m, 8H), 3.06-2.74 (m, 8H), 2.64-2.55 (m, 1H), 2.37 (s, 3H), 2.19-1.93 (m, 5H), 1.92-1.34 (m, 24H), 1.10 (d, J=6.3 Hz, 6H).

Example 55

1-(1-{2-[2,6-dioxopiperidin-3-yl]-1,3-dioxoisoindol-5-yl}piperidine-4-carbonyl)piperidin-4-yl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate

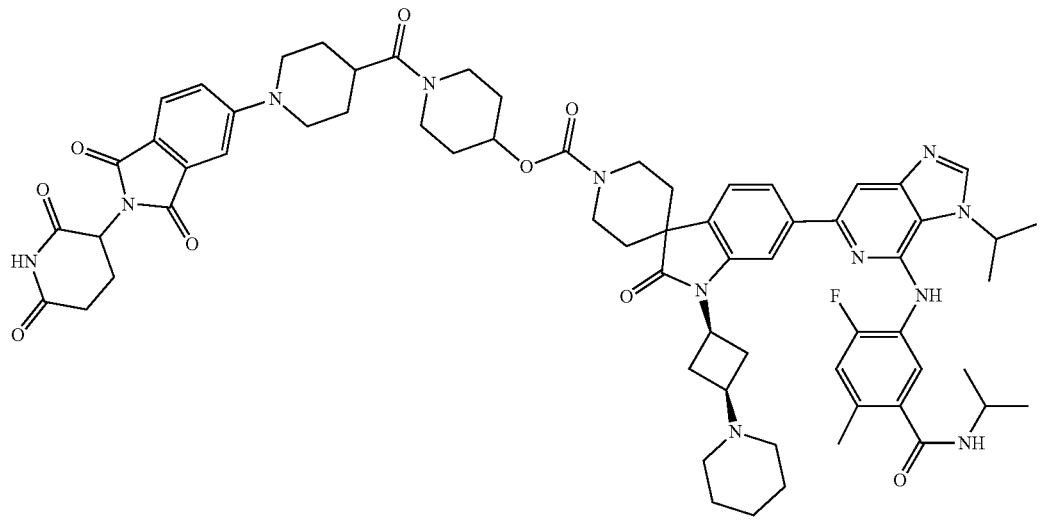 [SMILES: Cc1cc(F)c(Nc2nc(-c3ccc4c(c3)N([C@H]3C[C@@H](N5CCCCC5)C3)C(=O)C43CCN(C(=O)OC4CCN(C(=O)C5CCN(c6ccc7c(c6)C(=O)N(C6CCC(=O)NC6=O)C7=O)CC5)CC4)CC3)cc3ncn(C(C)C)c23)cc1C(=O)NC(C)C]

Step 1: Synthesis of piperidin-4-yl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate: Intermediate 1 (35 mg, 0.05 mmol) was dissolved in ACN (1 mL) and DIPEA (0.03 mL). tert-butyl 4-[(4-nitrophenoxycarbonyl) oxy]piperidine-1-carboxylate (18 mg, 0.05 mmol) was added, and the reaction was stirred at 50° C. for 4 hours. The solvents were removed by nitrogen blowdown, and the reaction was submitted to General Procedure B. Chromatography C provided title compound (27 mg, 55%).

Step 2: Synthesis of 1-(1-{2-[2,6-dioxopiperidin-3-yl]-1,3-dioxoisoindol-5-yl}piperidine-4-carbonyl)piperidin-4-yl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate: The title compound was synthesized according to General Procedure F, using piperidin-4-yl 6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidine]-1'-carboxylate (20 mg, 0.02 mmol) and 1-{2-[2,6-dioxopiperidin-3-yl]-1,3-dioxoisoindol-5-yl}piperidine-4-carboxylic acid (9.2 mg, 0.02 mmol) as starting materials. Chromatography C provided the title compound. (14.2 mg, 48%); LCMS: $C_{66}H_{77}FN_{12}O_9$ requires 1200.6, found 1202.1 [M+H]$^+$; $^1$H NMR (500 MHz, DMSO-d$_6$) δ 11.08 (s, 1H), 9.38 (d, J=9.6 Hz, 1H), 8.67 (s, 1H), 8.41 (s, 1H), 8.15 (d, J=7.9 Hz, 1H), 7.89 (s, 1H), 7.68 (d, J=8.3 Hz, 2H), 7.61 (d, J=8.2 Hz, 1H), 7.58-7.49 (m, 2H), 7.34 (d, J=2.1 Hz, 1H), 7.30-7.23 (m, 1H), 7.19 (d, J=12.1 Hz, 1H), 5.30 (t, J=6.6 Hz, 1H), 5.08 (dd, J=12.8, 5.4 Hz, 1H), 4.89 (s, 1H), 4.22 (t, J=8.3 Hz, 3H), 4.06 (p, J=7.1, 6.7 Hz, 5H), 3.59-3.46 (m, 3H), 3.41 (d, J=12.0 Hz, 4H), 3.10 (t, J=12.3 Hz, 2H), 3.05-2.74 (m, 9H), 2.68-2.54 (m, 2H), 2.38 (s, 4H), 2.07-1.99 (m, 1H), 1.94 (s, 1H), 1.85 (d, J=14.0 Hz, 3H), 1.74 (s, 6H), 1.69-1.33 (m, 16H), 1.11 (d, J=6.6 Hz, 6H).

Example 56

4-fluoro-2-methyl-5-{[6-(2-oxo-1'-{2-[(3S)-1-[(1R,4R)-4-({2-[2,6-dioxopiperidin-3-yl]-1,3-dioxo-2,3-dihydro-1H-isoindol-4-yl}amino)cyclohexanecarbonyl]pyrrolidin-3-yl]acetyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide

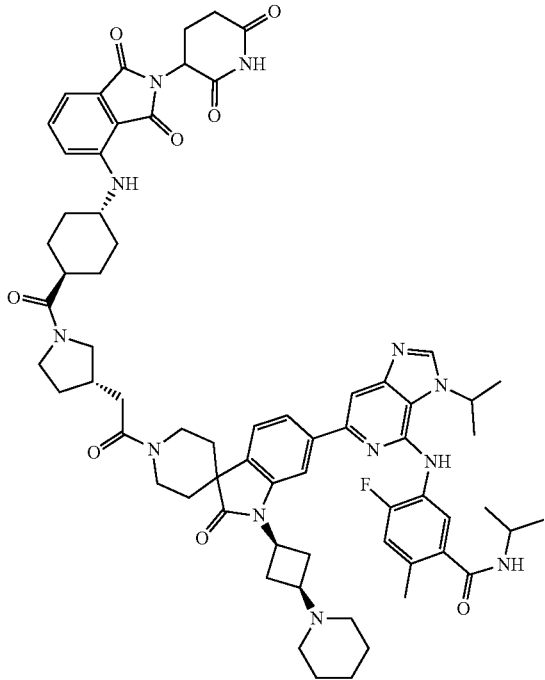 [SMILES: Cc1cc(F)c(Nc2nc(-c3ccc4c(c3)N([C@H]3C[C@@H](N5CCCCC5)C3)C(=O)C43CCN(C(=O)C[C@@H]4CCN(C(=O)[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of tert-butyl (3S)-3-[2-(benzyloxy)-2-oxoethyl]pyrrolidine-1-carboxylate. To solution of 2-[(3S)-1-[(tert-butoxy)carbonyl]pyrrolidin-3-yl]acetic acid (1.0 g, 4.4 mmol, 1.0 eq.) in DMF (10.0 mL, 0.43M), Cs$_2$CO$_3$ (1.71 g, 4.79 mmol, 1.1 eq.) was added. reaction mixture was placed in ice bath and mixed vigorously under Argon for 1 hour. Then benzyl bromide (0.570 mL 4.8 mmol, 1.2 eq.) was added dropwise, and the reaction mixture was maintained at 0° C. to RT overnight. On completion the mixture was poured into 150 mL water, extracted with ethyl acetate (5×50 mL). Combined organic layers were washed with 50 mL of brine, dried with MgSO$_4$, and solvent was evaporated in vacuo. Crude title compound (containing residual DMF as impurity) was used in next step without additional purification. (1.31 g, 94% yield).

Step 2: Synthesis of benzyl 2-[(3S)-pyrrolidin-3-yl]acetate hydrochloride. In 10 mL round bottom flask tert-butyl (3S)-3-[2-(benzyloxy)-2-oxoethyl]pyrrolidine-1-carboxylate (100 mg, 0.313 mmol, 1.0 eq.) was dissolved in DCM (5.0 mL, 0.062M) under Ar. Then 2M HCl in Et$_2$O was added (1.25 mL, 2.51 mmol, 8.0 eq.) and reaction was proceeded at RT for 5 h. After completion the reaction mixture was evaporated to dryness in vacuo. Obtained crude product (contained ~25% DMF w/w) was used in next step without further purification. (104 mg; calc. 80 mg; 99% yield).

Step 3: Synthesis of benzyl 2-[(3S)-1-[(1r,4r)-4-{[2-(2,6-dioxopiperidin-3-yl)-1,3-dioxo-2,3-dihydro-1H-isoindol-4-yl]amino}cyclohexanecarbonyl]pyrrolidin-3-yl]acetate. Benzyl 2-[(3S)-pyrrolidin-3-yl]acetate hydrochloride (80 mg, 0.31 mmol, 1.0 eq(trans)-4-{[2-(2,6-dioxopiperidin-3-yl)-1,3-dioxoisoindol-4-yl]amino}cyclohexane-1-carboxylic acid (125 mg, 0.31 mmol, 1.0 eq.), HATU (178 mg, 0.47 mmol, 1.5 eq.) and DIPEA (0.163 mL, 0.94 mmol, 3.0 eq.) were dissolved in DMF (10 mL, 0.031 M) and agitated under argon 24 h at RT. The reaction mixture was poured into 100 mL of brine, extracted with DCM (3×25 mL). Organic extract was dried with Na$_2$SO$_4$ and evaporated in vacuo. Crude product was purified by Chromatography A to give the title compound (185 mg, 98% yield).

Step 4: Synthesis of 2-[(3S)-1-[(1r,4r)-4-{[2-(2,6-dioxopiperidin-3-yl)-1,3-dioxo-2,3-dihydro-1H-isoindol-4-yl]amino}cyclohexanecarbonyl]pyrrolidin-3-yl]acetic acid. Benzyl 2-[(3S)-1-[(1r,4r)-4-{[2-(2,6-dioxopiperidin-3-yl)-1,3-dioxo-2,3-dihydro-1H-isoindol-4-yl]amino}cyclohexanecarbonyl]pyrrolidin-3-yl]acetate (188 mg 0.313 mmol, 1.0 eq) and 20% Pd(OH)$_2$/C (31 mg, 10% by wt.) were mixed in THF (5 mL, 0.06 M). Flask was equipped with hydrogen balloon, degassed and filled with hydrogen from the balloon. Reaction was stirred overnight at RT. After this time UPLC showed ~50% conversion, so another portion of catalyst (13 mg, 10% by wt) was added, the reaction mixture was degassed, filled with H$_2$ and continued ON/RT. UPLC showed 100% conversion, then the reaction mixture was filtrated through Celite and evaporated to dryness. Crude product was purified by dissolving in THF (1 mL) and precipitation with 20 mL Et$_2$O. After drying in vacuo, the title compound was obtained (91 mg, 57% yield).

Step 5: Synthesis of 4-fluoro-2-methyl-5-{[6-(2-oxo-1'-{2-[(3S)-1-[(1r,4r)-4-({2-[2,6-dioxopiperidin-3-yl]-1,3-dioxo-2,3-dihydro-1H-isoindol-4-yl}amino)cyclohexanecarbonyl]pyrrolidin-3-yl]acetyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide. The title compound was synthesized according to General Procedure F using Intermediate 1 (15 mg, 0.02 mmol) and [(3S)-1-[(1r,4r)-4-({2-[2,6-dioxopiperidin-3-yl]-1,3-dioxoisoindol-4-yl}amino)cyclohexanecarbonyl]pyrrolidin-3-yl]acetic acid (12.3 mg, 0.02 mmol) followed by reverse phase HPLC to provide the title compound (13.2 mg, 54%); LCMS: $C_{67}H_{79}FN_{12}O_8$ requires 1198.6, found 1200.0 $[M+H]^+$; $^1H$ NMR (500 MHz, DMSO-$d_6$) δ 11.09 (s, 1H), 9.33-9.19 (m, 1H), 8.62 (s, 1H), 8.37 (s, 1H), 8.13 (d, J=7.6 Hz, 1H), 7.87 (s, 1H), 7.67 (d, J=7.7 Hz, 1H), 7.63-7.54 (m, 2H), 7.51 (s, 2H), 7.24-7.14 (m, 2H), 7.03 (dd, J=7.0, 2.9 Hz, 1H), 6.16 (s, 1H), 5.04 (dd, J=12.9, 5.4 Hz, 1H), 4.21 (s, 1H), 4.03 (d, J=7.0 Hz, 1H), 3.93-3.40 (m, 8H), 3.01-2.70 (m, 10H), 2.66-2.55 (m, 2H), 2.36 (s, 3H), 2.16-1.50 (m, 31H), 1.09 (d, J=6.5 Hz, 6H).

Example 57

4-fluoro-2-methyl-5-{[6-(2-oxo-1'-{2-[(3R)-1-[(1R,4R)-4-({2-[2,6-dioxopiperidin-3-yl]-1,3-dioxo-2,3-dihydro-1H-isoindol-4-yl}amino)cyclohexanecarbonyl]pyrrolidin-3-yl]acetyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide

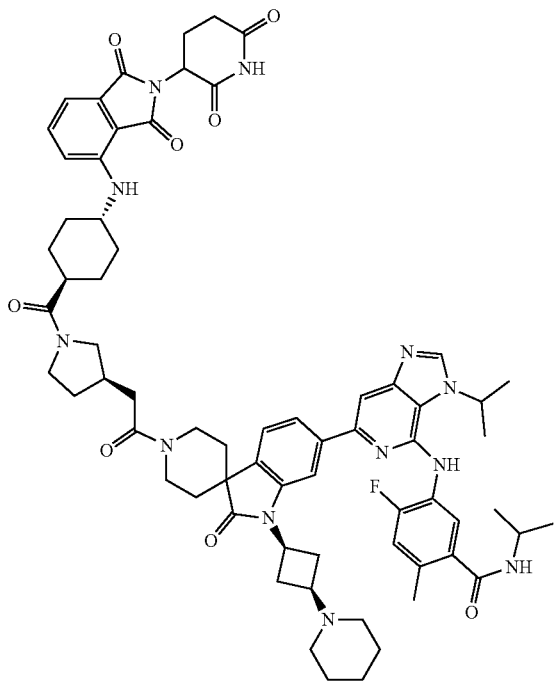 [SMILES: Cc1cc(F)c(Nc2nc(-c3ccc4c(c3)N([C@H]3C[C@@H](N5CCCCC5)C3)C(=O)C43CCN(C(=O)C[C@H]4CCN(C(=O)[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of [(3R)-1-[(1r,4r)-4-({2-[2,6-dioxopiperidin-3-yl]-1,3-dioxoisoindol-4-yl}amino)cyclohexanecarbonyl]pyrrolidin-3-yl]acetic acid. The title compound was synthesized analogously to 2-[(3S)-1-[(1r,4r)-4-{[2-(2,6-dioxopiperidin-3-yl)-1,3-dioxo-2,3-dihydro-1H-isoindol-4-yl]amino}cyclohexanecarbonyl]pyrrolidin-3-yl]acetic acid using 2-[(3R)-1-[(tert-butoxy)carbonyl]pyrrolidin-3-yl]acetic acid as the initial starting material in Step 1 of Example 56.

Step 2: Synthesis of 4-fluoro-2-methyl-5-{[6-(2-oxo-1'-{2-[(3R)-1-[(1r,4r)-4-({2-[2,6-dioxopiperidin-3-yl]-1,3-dioxo-2,3-dihydro-1H-isoindol-4-yl}amino)cyclohexanecarbonyl]pyrrolidin-3-yl]acetyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide. The title compound was synthesized according to General Procedure F using Intermediate 1 (15 mg, 0.02 mmol) and [(3R)-1-[(1r,4r)-4-({2-[2,6-dioxopiperidin-3-yl]-1,3-dioxoisoindol-4-yl}amino)cyclohexanecarbonyl]pyrrolidin-3-yl]acetic acid (12.3 mg, 0.02 mmol) followed by reverse phase HPLC to provide the title compound (7.6 mg, 28%); LCMS: $C_{67}H_{79}FN_{12}O_8$ requires 1198.6, found 1200.0 $[M+H]^+$; $^1H$ NMR (500 MHz, Methanol-$d_4$) δ 8.88-8.79 (m, 1H), 8.26-8.14 (m, 1H), 8.12-8.00 (m, 1H), 7.85-7.72 (m, 2H), 7.64 (s, 1H), 7.59-7.46 (m, 2H), 7.21-7.10 (m, 2H), 7.10-7.02 (m, 1H), 5.33 (t, J=6.9 Hz, 1H), 5.08 (dd, J=12.2, 5.6 Hz, 1H), 4.42-4.30 (m, 1H), 4.25-3.48 (m, 14H), 3.21-2.52 (m, 15H), 2.46 (s, 3H), 2.35-1.49 (m, 26H), 1.17 (d, J=6.6 Hz, 6H).

Example 58

5-[(6-{1'-[4-({4-[2-(2,6-dioxopiperidin-3-yl)-1,3-dioxo-2,3-dihydro-1H-isoindol-5-yl]piperazin-1-yl}sulfonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

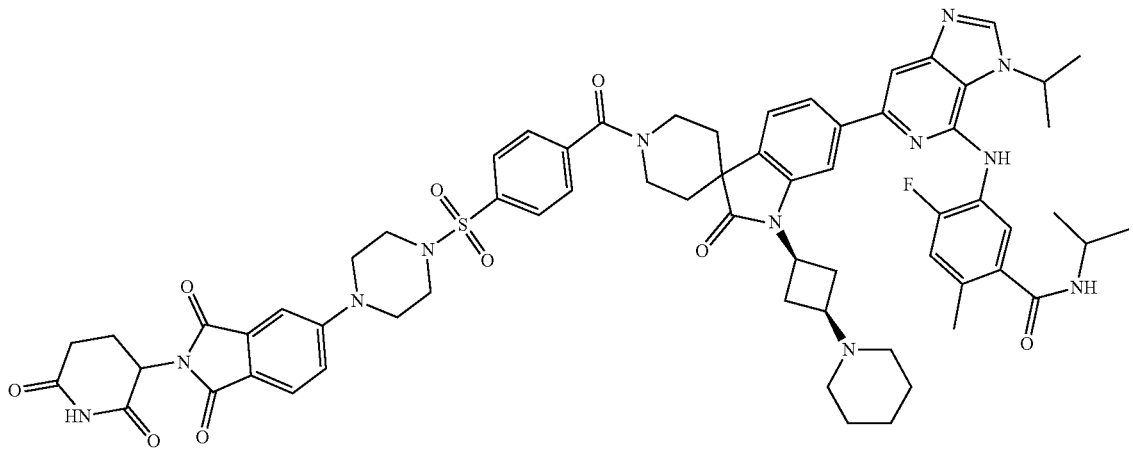 [SMILES: Cc1cc(F)c(Nc2nc(-c3ccc4c(c3)N([C@H]3C[C@@H](N5CCCCC5)C3)C(=O)C43CCN(C(=O)c4ccc(S(=O)(=O)N5CCN(c6ccc7c(c6)C(=O)N(C6CCC(=O)NC6=O)C7=O)CC5)cc4)CC3)cc3ncn(C(C)C)c23)cc1C(=O)NC(C)C]

187

Step 1: Synthesis of 4-(4-{2-[2,6-dioxopiperidin-3-yl]-1,3-dioxoisoindol-5-yl}piperazin-1-ylsulfonyl)benzoic acid. The title compound was synthesized according to General Procedure A using 2-(2,6-dioxopiperidin-3-yl)-5-fluoroisoindole-1,3-dione (450 mg, 1.63 mmol) and 4-(piperazine-1-sulfonyl)benzoic acid hydrochloride (500 mg, 1.63 mmol) to provide the title compound (75 mg, 8.7%).

Step 2: Synthesis of 5-[(6-{1'-[4-({4-[2-(2,6-dioxopiperidin-3-yl)-1,3-dioxo-2,3-dihydro-1H-isoindol-5-yl]piperazin-1-yl}sulfonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (12 mg, 0.02 mmol) and 4-{4-[2-(2,6-dioxopiperidin-3-yl)-1,3-dioxoisoindol-5-yl]piperazin-1-ylsulfonyl}benzoic acid (9.8 mg, 0.02 mmol) followed by reverse phase HPLC to provide the title compound (4.4 mg, 22%); LCMS: $C_{65}H_{71}FN_{12}O_9S$ requires 1214.5, found 1215.7 [M+H]$^+$; $^1$H NMR (500 MHz, DMSO-d$_6$) δ 11.06 (s, 1H), 9.27 (s, 1H), 8.57 (s, 1H), 8.36 (s, 1H), 8.12 (d, J=7.8 Hz, 1H), 7.90-7.83 (m, 3H), 7.76 (d, J=8.0 Hz, 2H), 7.68 (dd, J=8.5, 3.0 Hz, 2H), 7.59 (d, J=8.1 Hz, 2H), 7.51 (s, 1H), 7.34 (d, J=2.3 Hz, 1H), 7.28-7.21 (m, 1H), 7.17 (d, J=12.1 Hz, 1H), 5.28 (q, J=6.6 Hz, 1H), 5.05 (dd, J=12.7, 5.4 Hz, 1H), 4.25-3.98 (m, 4H), 3.95-3.68 (m, 4H), 3.55-3.49 (m, 3H), 3.12-2.69 (m, 12H), 2.65-2.53 (m, 1), 2.36 (s, 3H), 2.02-1.34 (m, 18H), 1.09 (d, J=6.5 Hz, 6H).

Example 59

5-[(6-{1'-[4-({1-[2-(2,6-dioxopiperidin-3-yl)-1,3-dioxo-2,3-dihydro-1H-isoindol-4-yl]piperidin-4-yl}Methyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

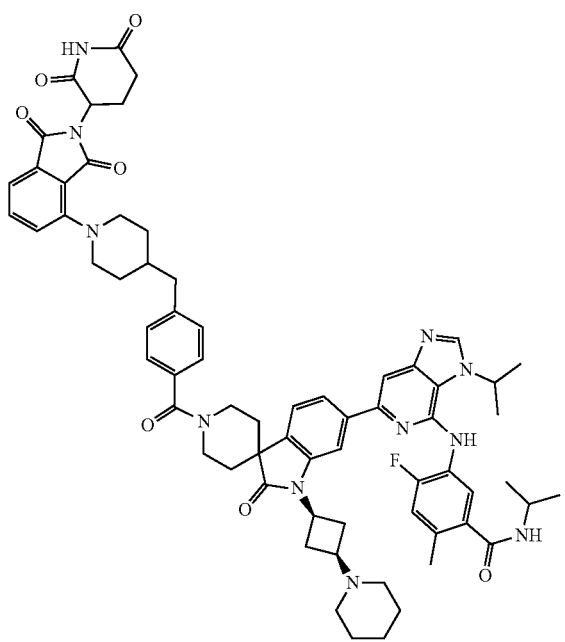 [SMILES: Cc1cc(F)c(Nc2nc(-c3ccc4c(c3)N([C@H]3C[C@@H](N5CCCCC5)C3)C(=O)C43CCN(C(=O)c4ccc(CC5CCN(c6cccc7c6C(=O)N(C6CCC(=O)NC6=O)C7=O)CC5)cc4)CC3)cc3ncn(C(C)C)c23)cc1C(=O)NC(C)C]

Step 1: Synthesis of 4-({1-[2-(2,6-dioxopiperidin-3-yl)-1,3-dioxoisoindol-4-yl]piperidin-4-yl}methyl)benzoic acid. The title compound was synthesized according to General Procedure A using 4-(piperidin-4-ylmethyl)benzoic acid hydrochloride (762 mg, 2.53 mmol) and 2-(2,6-dioxopiperidin-3-yl)-4-fluoroisoindole-1,3-dione (700 mg, 2.53 mmol) to yield the product (250 mg, 21%).

Step 2: Synthesis of 5-[(6-{1'-[4-({1-[2-(2,6-dioxopiperidin-3-yl)-1,3-dioxo-2,3-dihydro-1H-isoindol-4-yl]piperidin-4-yl}methyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (12 mg, 0.02 mmol) and 4-((1-(2-(2,6-dioxopiperidin-3-yl)-1,3-dioxoisoindolin-4-yl)piperidin-4-yl)methyl)benzoic acid (9.8 mg, 0.02 mmol) followed by reverse phase HPLC to provide the title compound (5.8 mg, 31%); LCMS: $C_{67}H_{74}FN_{11}O_7$ requires 1163.6, found 1165.9 [M+2H]$^+$; $^1$H NMR (500 MHz, DMSO-d$_6$) δ 11.08 (s, 1H), 9.29 (d, J=9.5 Hz, 1H), 8.37 (s, 1H), 8.13 (d, J=7.8 Hz, 1H), 7.88 (s, 1H), 7.67 (dt, J=11.3, 5.9 Hz, 2H), 7.60 (d, J=8.2 Hz, 2H), 7.52 (s, 1H), 7.42 (d, J=7.7 Hz, 2H), 7.31 (dd, J=7.8, 3.2 Hz, 5H), 7.18 (d, J=12.0 Hz, 1H), 5.33-5.23 (m, 1H), 5.08 (dd, J=12.9, 5.5 Hz, 1H), 4.27-4.15 (m, 1H), 4.04 (dt, J=14.0, 7.1 Hz, 2H), 3.96-3.65 (m, 4H), 3.00-2.72 (m, 10H), 2.67-2.55 (m, 4H), 2.36 (s, 3H), 2.05-1.97 (m, 1H), 1.90-1.34 (m, 23H), 1.10 (d, J=6.5 Hz, 6H).

Example 60

4-fluoro-2-methyl-5-{[6-(2-oxo-1'-{1-[(1R,4R)-4-({2-[2,6-dioxopiperidin-3-yl]-1,3-dioxo-2,3-dihydro-1H-isoindol-4-yl}amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide

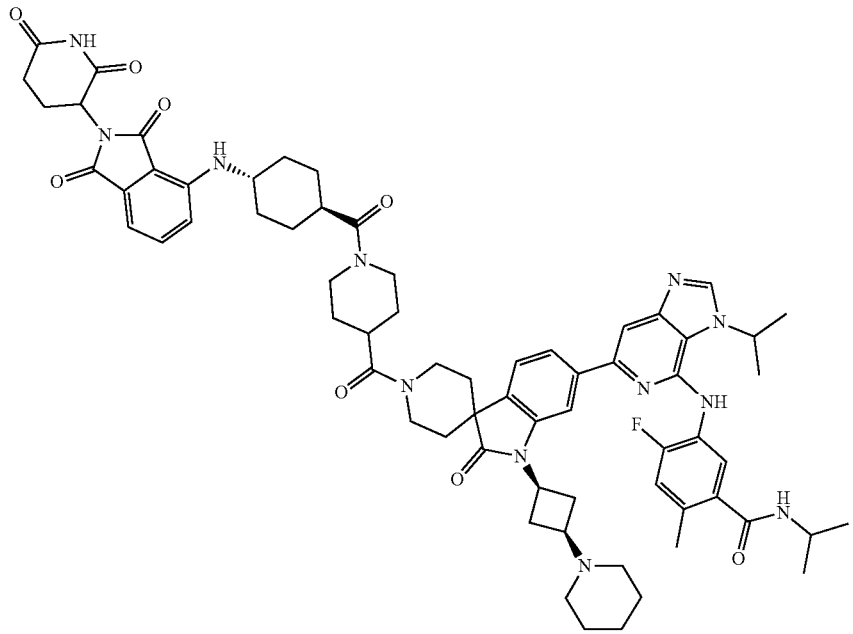 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)[C@H]5CC[C@H](Nc6cccc7c6C(=O)N(C6CCC(=O)NC6=O)C7=O)CC5)CC4)CC3)cc3ncn(C(C)C)c23)cc1C(=O)NC(C)C]

Step 1: Synthesis of 1-[(1r,4r)-4-({2-[2,6-dioxopiperidin-3-yl]-1,3-dioxo-2,3-dihydro-1H-isoindol-4-yl}amino)cyclohexanecarbonyl]piperidine-4-carboxylic acid. The title compound was synthesized according to General Procedure F using (trans)-4-{[2-(2,6-dioxopiperidin-3-yl)-1,3-dioxoisoindol-4-yl]amino}cyclohexane-1-carboxylic acid (Example 26; 40 mg, 0.1 mmol) and tert-butyl piperidine-4-carboxylate (18.5 mg, 0.1 mmol). The product was isolated using Chromatography B followed by subjecting the intermediate to General Procedure B to give the tile compound (40 mg, 78%).

Step 2: Synthesis of 4-fluoro-2-methyl-5-{[6-(2-oxo-1'-{1-[(1r,4r)-4-({2-[2,6-dioxopiperidin-3-yl]-1,3-dioxo-2,3-dihydro-1H-isoindol-4-yl}amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide. The title compound was synthesized according to General Procedure F using Intermediate 1 (15 mg, 0.02 mmol) and 1-[(1r,4r)-4-({2-[2,6-dioxopiperidin-3-yl]-1,3-dioxoisoindol-4-yl}amino)cyclohexanecarbonyl]piperidine-4-carboxylic acid (10 mg, 0.02 mmol) followed by reverse phase HPLC to provide the title compound (14.5 mg, 54%); LCMS: $C_{67}H_{79}FN_{12}O_8$ requires 1198.6, found 1199.9 [M+H]$^+$; $^1$H NMR (500 MHz, Methanol-d$_4$) δ 8.89 (d, J=8.3 Hz, 1H), 8.02 (d, J=8.1 Hz, 1H), 7.82-7.70 (m, 2H), 7.65-7.48 (m, 3H), 7.14 (dd, J=18.2, 10.2 Hz, 2H), 7.05 (d, J=7.0 Hz, 1H), 5.32 (p, J=6.6 Hz, 1H), 5.05 (dd, J=12.5, 5.4 Hz, 1H), 4.59 (s, 1H), 4.34 (p, J=8.2 Hz, 1H), 4.25-3.84 (m, 7H), 3.66 (p, J=8.2 Hz, 1H), 3.61-3.48 (m, 4H), 3.17-3.01 (m, 3H), 2.97-2.63 (m, 10H), 2.44 (s, 3H), 2.27-2.16 (m, 2H), 2.16-1.49 (m, 24H), 1.42 (p, J=12.3 Hz, 2H), 1.18-1.11 (m, 7H).

Example 61

4-fluoro-2-methyl-5-({6-[1'-(4-{methyl[(1R,4R)-4-{[2-(2,6-dioxopiperidin-3-yl)-1,3-dioxo-2,3-dihydro-1H-isoindol-4-yl]amino}cyclohexyl]carbamoyl}benzoyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide

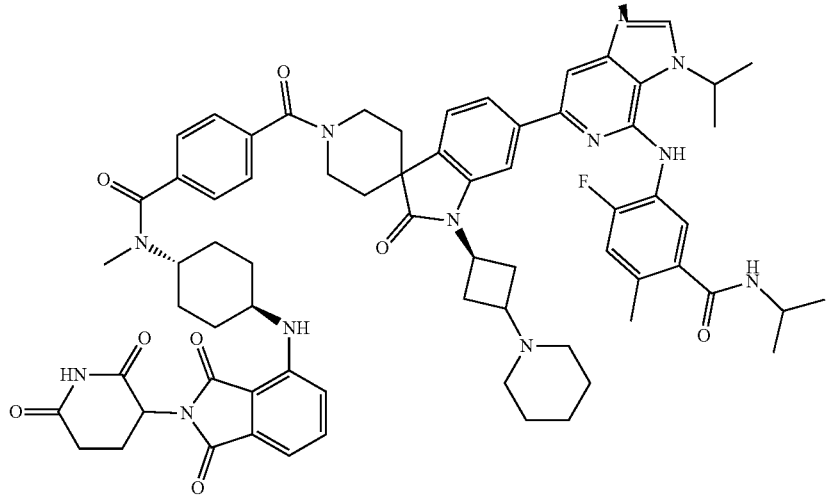

Step 1: Synthesis of methyl 4-{methyl[(1r,4r)-4-[(tert-butoxycarbonyl)amino]cyclohexyl]carbamoyl}benzoate. Following General Procedure F using methyl terephthalate (180 mg, 1.0 mmol) and tert-butyl N-[(1r,4r)-4-(methylamino)cyclohexyl]carbamate (190 mg, 0.83 mmol) the title compound was obtained (257 mg, 79%).

Step 2: Synthesis of 4-[N-methyl(1r,4r)-4-aminocyclohexaneamido]benzoic acid hydrochloride. The title compound was synthesized according to General Procedure C using methyl 4-[N-methyl(1r,4r)-4-[(tert-butoxycarbonyl)amino]cyclohexaneamido]benzoate (257 mg, 0.66 mmol) and heating the reaction at 50° C. The crude material of this reaction was then subjected to General Procedure B, followed by Chromatography C to provide the title compound (200 mg, 97%).

Step 3: Synthesis of 4-{methyl[(1r,4r)-4-{[2-(2,6-dioxopiperidin-3-yl)-1,3-dioxoisoindol-4-yl]amino}cyclohexyl]amino}benzoic acid. The title compound was synthesized according to General Procedure A using 4-[N-methyl(1r,4r)-4-aminocyclohexaneamido]benzoic acid hydrochloride (103 mg, 0.36 mmol) and 2-(2,6-dioxopiperidin-3-yl)-4-fluoroisoindole-1,3-dione (100 mg, 0.36 mmol), running the reaction for 16 hr. The crude material was purified by Chromatography C to yield the title compound (6 mg, 3.3%).

Step 4: Synthesis of 4-fluoro-2-methyl-5-({6-[1'-(4-{methyl[(1r,4r)-4-{[2-(2,6-dioxopiperidin-3-yl)-1,3-dioxo-2,3-dihydro-1H-isoindol-4-yl]amino}cyclohexyl]carbamoyl}benzoyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide. The title compound was synthesized according to General Procedure F using Intermediate 1 (28 mg, 0.04 mmol) and 1-[(1r,4r)-4-({2-[2,6-dioxopiperidin-3-yl]-1,3-dioxoisoindol-4-yl}amino)cyclohexanecarbonyl]piperidine-4-carboxylic acid (20 mg, 0.04 mmol) followed by reverse phase HPLC to provide the title compound (6.4 mg, 13%); LCMS: $C_{69}H_{77}FN_{12}O_8$ requires 1220.6, found 611.9 [(M+2H)/2]$^+$; $^1$H NMR (500 MHz, Methanol-$d_4$) δ 8.88 (s, 1H), 8.02 (d, J=8.0 Hz, 1H), 7.80-7.71 (m, 2H), 7.68-7.46 (m, 8H), 7.18-7.00 (m, 3H), 5.31 (p, J=6.5 Hz, 1H), 4.37-3.47 (m, 12H), 3.14-2.57 (m, 14H), 2.44 (s, 3H), 2.32-1.64 (m, 26H), 1.61-1.48 (m, 2H), 1.15 (d, J=6.6 Hz, 6H).

Example 62

4-fluoro-2-methyl-5-[(6-{2-oxo-1-[(1s,3s)-3-(piperidin-1-yl)cyclobutyl]-1'-[(1S,4s)-4-(4-{[2-(2,6-dioxopiperidin-3-yl)-1,3-dioxo-2,3-dihydro-1H-isoindol-4-yl](methyl)amino}piperidine-1-carbonyl)cyclohexanecarbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

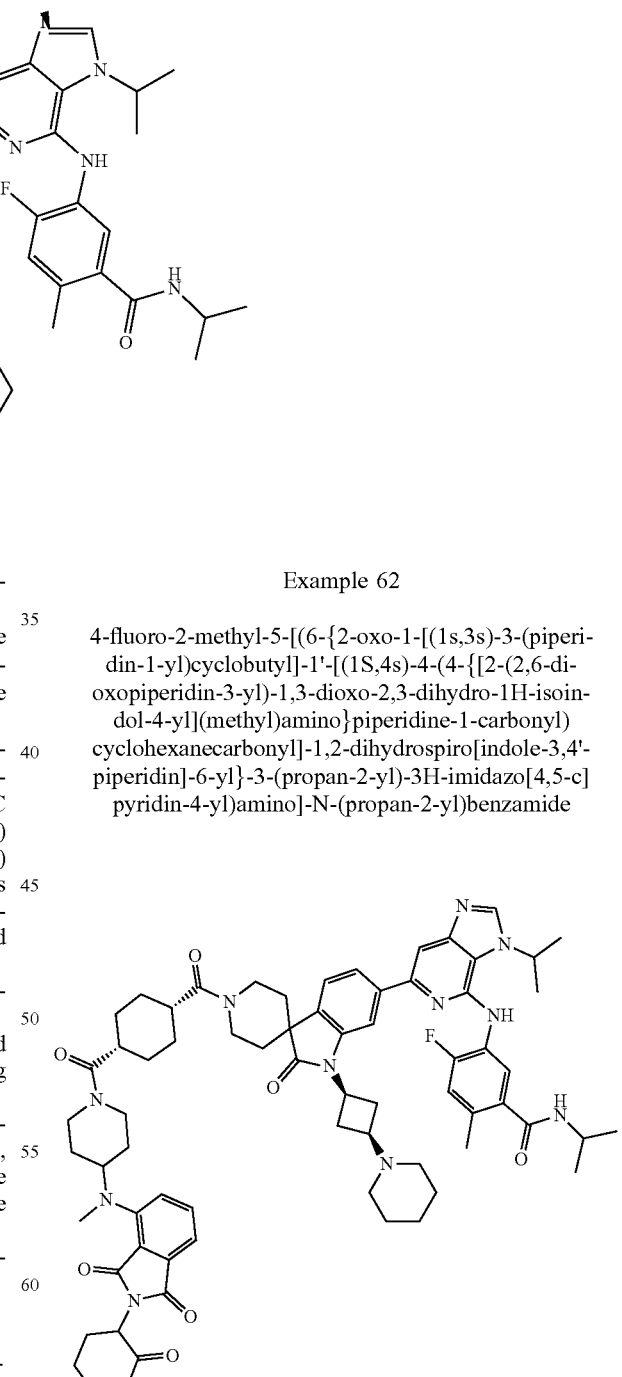

Step 1: Synthesis of methyl (1s,4s)-4-{4-[(tert-butoxycarbonyl)(methyl)amino]piperidine-1-carbonyl}cyclohexane-1-carboxylate. The title compound was synthesized according to General Procedure F using tert-butyl N-methyl-N-(piperidin-4-yl)carbamate (270 mg, 1.26 mmol) and (1s,4s)-4-(methoxycarbonyl)cyclohexane-1-carboxylic acid (234 ng, 1.26 mmol). The crude material was purified using Chromatography A to provide the title compound (400 mg, 830%).

Step 2: Synthesis of (1s,4s)-4-[4-(methylamino)piperidine-1-carbonyl]cyclohexane-1-carboxylic acid hydrochloride. The title compound was synthesized according to General Procedure C using methyl (1s,4s)-4-{4-[(tert-butoxycarbonyl)(methyl)amino]piperidine-1-carbonyl}cyclohexane-1-carboxylate (400 mg, 1.05 mmol) and heating the reaction at 50° C. The crude material of this reaction was then subjected to General Procedure B, followed by Chromatography C to provide the title compound (250 mg, 78%).

Step 3: Synthesis of (1s,4s)-4-(4-{[2-(2,6-dioxopiperidin-3-yl)-1,3-dioxoisoindol-4-yl](methyl)amino}piperidine-1-carbonyl)cyclohexane-1-carboxylic acid. The title compound was synthesized according to General Procedure A using (1s,4s)-4-[4-(methylamino)piperidine-1-carbonyl]cyclohexane-1-carboxylic acid hydrochloride (275 mg, 0.91 mmol) and 2-(2,6-dioxopiperidin-3-yl)-4-fluoroisoindole-1,3-dione (250 mg, 0.91 mmol), running the reaction for 16 hr. The crude material was purified by Chromatography C to yield the title compound (13 mg, 2.70%).

Step 4: Synthesis of 4-fluoro-2-methyl-5-[(6-{2-oxo-1-[(1s,3s)-3-(piperidin-1-yl)cyclobutyl]-1'-[(1s,4s)-4-(4-{[2-(2,6-dioxopiperidin-3-yl)-1,3-dioxo-2,3-dihydro-1H-isoindol-4-yl](methyl)amino}piperidine-1-carbonyl)cyclohexanecarbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (21 mg, 0.03 mmol) and (1s,4s)-4-(4-{[2-(2,6-dioxopiperidin-3-yl)-1,3-dioxoisoindol-4-yl](methyl)amino}piperidine-1-carbonyl)cyclohexane-1-carboxylic acid (13 mg, 0.02 mmol) followed by reverse phase HPLC to provide the title compound (14.5 mg, 46%); LCMS: $C_{68}H_{81}FN_{12}O_8$ requires 1212.6, found 1215.1 [(M+2H)]$^+$; $^1$H NMR (500 MHz, Methanol-$d_4$) δ 9.03 (s, 1H), 7.99 (d, J=8.0 Hz, 1H), 7.78 (s, 1H), 7.76-7.70 (m, 1H), 7.66-7.56 (m, 2H), 7.52 (d, J=7.8 Hz, 1H), 7.35-7.26 (m, 2H), 7.17 (d, J=11.8 Hz, 1H), 5.34 (p, J=6.6 Hz, 1H), 5.11 (dd, J=12.5, 5.5 Hz, 1H), 4.66 (d, J=13.3 Hz, 1H), 4.33 (p, J=8.3 Hz, 1H), 4.19-3.96 (m, 6H), 3.96-3.84 (m, 2H), 3.66 (p, J=8.1 Hz, 1H), 3.54 (d, J=12.2 Hz, 2H), 3.19-2.97 (m, 3H), 2.97-2.54 (m, 12H), 2.45 (s, 3H), 2.19-1.50 (m, 32H), 1.16 (d, J=6.5 Hz, 6H).

Example 63

5-{[6-(1'-{4-[(1-{2-[2,6-dioxopiperidin-3-yl]-1,3-dioxo-2,3-dihydro-1H-isoindol-4-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

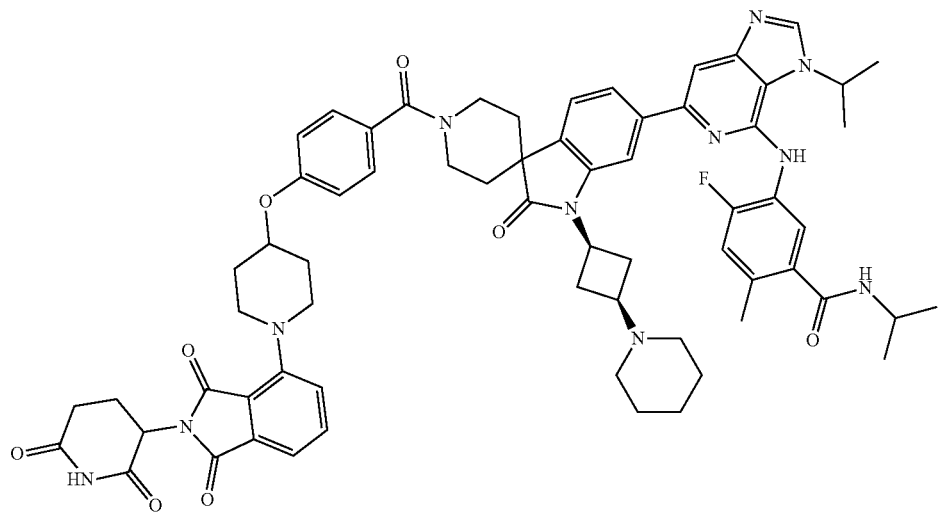 [SMILES: Cc1cc(F)c(Nc2nc(-c3ccc4c(c3)N([C@H]3C[C@@H](N5CCCCC5)C3)C(=O)C43CCN(C(=O)c4ccc(OC5CCN(c6cccc7c6C(=O)N(C6CCC(=O)NC6=O)C7=O)CC5)cc4)CC3)cc3ncn(C(C)C)c23)cc1C(=O)NC(C)C]

Step 1: Synthesis of 4-({1-[2-(2,6-dioxopiperidin-3-yl)-1,3-dioxoisoindol-4-yl]piperidin-4-yl}oxy)benzoic acid. The title compound was synthesized according to General Procedure A using 2-(2,6-dioxopiperidin-3-yl)-4-fluoroisoindole-1,3-dione (350 mg, 1.27 mmol) and 4-(piperidin-4-yloxy)benzoic acid hydrochloride (326 mg, 1.27 mmol) using DMSO as solvent. After purification, the title compound was obtained (550 mg, 91%).

Step 2: Synthesis of 5-{[6-(1'-{4-[(1-{2-[2,6-dioxopiperidin-3-yl]-1,3-dioxo-2,3-dihydro-1H-isoindol-4-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F using Intermediate 1 (13.7 mg, 0.02 mmol) and 4-({1-[2-(2,6-dioxopiperidin-3-yl)-1,3-dioxoisoindol-4-yl]piperidin-4-yl}oxy)benzoic acid (8 mg, 0.02 mmol) followed by reverse phase HPLC to provide the title compound (9.8 mg, 50%); LCMS: $C_{66}H_{72}FN_{11}O_8$ requires 1165.6, found 1166.6 [(M+H)]$^+$; $^1$H NMR (500 MHz, Methanol-$d_4$) δ 8.99 (s, 1H), 7.99 (d, J=8.1 Hz, 1H), 7.82-7.71 (m, 2H), 7.67 (dd, J=8.4, 7.2 Hz, 1H), 7.62-7.53 (m, 2H), 7.52-7.46

(m, 2H), 7.37 (dd, J=7.8, 5.0 Hz, 2H), 7.17 (d, J=11.8 Hz, 1H), 7.13-7.07 (m, 2H), 5.34 (p, J=6.5 Hz, 1H), 5.10 (dd, J=12.7, 5.5 Hz, 1H), 4.74-4.68 (m, 1H), 4.38-3.74 (m, 6H), 3.70-3.47 (m, 6H), 3.14-3.02 (m, 2H), 2.98-2.67 (m, 7H), 2.45 (s, 3H), 2.26-1.69 (m, 22H), 1.56 (q, J=14.4 Hz, 1H), 1.16 (d, J=6.5 Hz, 6H).

Example 64

5-{[6-(1'-{4-[(1-{2-[2,6-dioxopiperidin-3-yl]-1,3-dioxo-2,3-dihydro-1H-isoindol-5-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

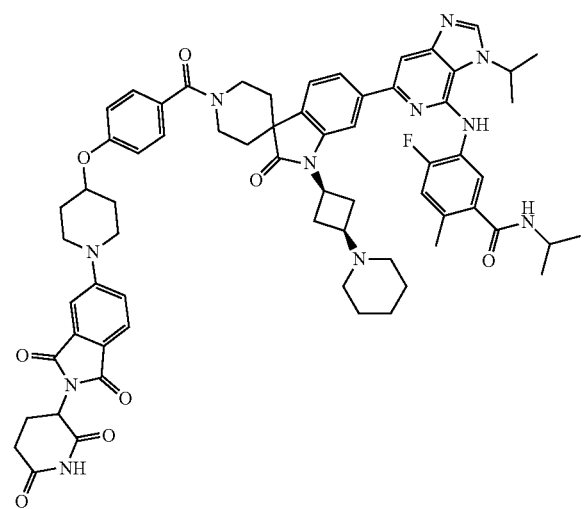 [SMILES: Cc1cc(F)c(Nc2nc(-c3ccc4c(c3)N([C@H]3C[C@@H](N5CCCCC5)C3)C(=O)C43CCN(C(=O)c4ccc(OC5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of 4-({1-[2-(2,6-dioxopiperidin-3-yl)-1,3-dioxoisoindol-5-yl]piperidin-4-yl}oxy)benzoic acid. The title compound was synthesized according to General Procedure A using 2-(2,6-dioxopiperidin-3-yl)-5-fluoroisoindole-1,3-dione (350 mg, 1.27 mmol) and 4-(piperidin-4-yloxy)benzoic acid hydrochloride (326 mg, 1.27 mmol) using DMSO as solvent and heating in microwave at 125° C. for 3 hr. After purification, the title compound was obtained (540 mg, 89%).

Step 2: Synthesis of 5-{[6-(1'-{4-[(1-{2-[2,6-dioxopiperidin-3-yl]-1,3-dioxo-2,3-dihydro-1H-isoindol-5-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F using Intermediate 1 (13.7 mg, 0.02 mmol) and 4-({1-[2-(2,6-dioxopiperidin-3-yl)-1,3-dioxoisoindol-5-yl]piperidin-4-yl}oxy)benzoic acid (8 mg, 0.02 mmol) followed by reverse phase HPLC to provide the title compound (7.5 mg, 36%); LCMS: $C_{66}H_{72}FN_{11}O_{8}$ requires 1165.6, found 1166.6 [(M+H)]$^{+}$; $^{1}$H NMR (500 MHz, Methanol-d$_{4}$) δ 8.98 (s, 1H), 8.20 (d, J=7.9 Hz, 1H), 7.99 (d, J=8.0 Hz, 1H), 7.78 (s, 1H), 7.75 (dd, J=7.9, 1.6 Hz, 1H), 7.69 (d, J=8.5 Hz, 1H), 7.62-7.54 (m, 2H), 7.54-7.47 (m, 2H), 7.39 (d, J=2.3 Hz, 1H), 7.27 (dd, J=8.6, 2.3 Hz, 1H), 7.17 (d, J=11.8 Hz, 1H), 7.13-7.07 (m, 2H), 5.33 (p, J=6.6 Hz, 1H), 5.07 (dd, J=12.4, 5.5 Hz, 1H), 4.76 (d, J=3.8 Hz, 1H), 4.33 (p, J=8.2 Hz, 1H), 4.23-4.00 (m, 4H), 3.85-3.78 (m, 3H), 3.66 (p, J=8.2 Hz, 1H), 3.59-3.42 (m, 5H), 3.16-3.04 (m, 2H), 2.98-2.79 (m, 5H), 2.79-2.63 (m, 3H), 2.45 (s, 3H), 2.21-2.05 (m, 3H), 2.05-1.65 (m, 18H), 1.63-1.52 (m, 1H), 1.16 (d, J=6.6 Hz, 6H).

Example 65

5-{[6-(1'-{1-[1-({2-[2,6-dioxopiperidin-3-yl]-1,3-dioxo-2,3-dihydro-1H-isoindol-4-yl}methyl)piperidin-4-yl]-1H-pyrazole-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

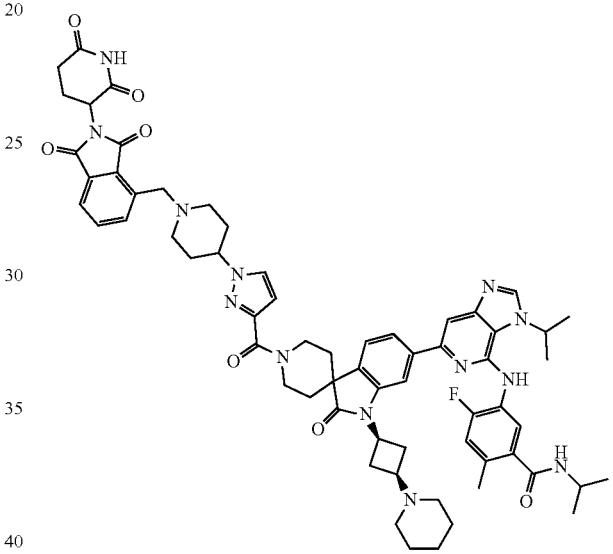

Step 1: Synthesis of tert-butyl 4-[3-(methoxycarbonyl)pyrazol-1-yl]piperidine-1-carboxylate. To a mixture of methyl 1H-pyrazole-3-carboxylate (5.99 g, 47.5 mmol, 1 eq.) in DMF (30 mL) was added NaH (2.28 g, 95 mmol) at 0° C. under nitrogen atmosphere. To the above mixture was added tert-butyl 4-bromopiperidine-1-carboxylate (25.1 g, 95 mmol) over 10 min at 0° C. The resulting mixture was stirred overnight at room temperature under nitrogen atmosphere. The reaction was quenched with sodium bicarbonate (aq. 100 mL) and the reaction mixture was extracted with ethyl acetate (3×30 mL). The combined organic layers were washed with water (3×10 mL), dried over anhydrous sodium sulfate, filtered, and concentrated. The residue was purified by Chromatography A, eluted with pet ether/EtOAc (1/1) to afford tert-butyl 4-[3-(methoxycarbonyl)pyrazol-1-yl]piperidine-1-carboxylate (750 mg, 5% yield) as an oil.

Step 2: Synthesis of 1-[1-(tert-butoxycarbonyl)piperidin-4-yl]pyrazole-3-carboxylic acid. To a mixture of tert-butyl 4-[3-(methoxycarbonyl)pyrazol-1-yl]piperidine-1-carboxylate (700 mg, 2.26 mmol, 1 equiv.) in THF (2 mL), MeOH (2 mL) and H$_{2}$O (2 mL) was added LiOH (108 mg, 4.52 mmol, 2 equiv.) at 0° C. The resulting mixture was stirred for 1 h at room temperature before being concentrated under vacuum. The mixture was acidified to pH 3 with HCl aqueous (2N) and the aqueous layer was extracted with ethyl acetate (3×10 mL). The title compound was obtained (400 mg, crude) after removal of solvent under reduced pressure.

Step-3: Synthesis of tert-butyl 4-[3-(tert-butoxycarbonyl) pyrazol-1-yl]piperidine-1-carboxylate. To a mixture of 1-[1-(tert-butoxycarbonyl)piperidin-4-yl]pyrazole-3-carboxylic acid (400 mg, 1.35 mmol, 1 equiv.) in DCM (5 mL) was added (Z)—N,N'-diisopropyltert-butoxymethanimidamide (814 mg, 4.1 mmol, 3 equiv.) at 0° C. under nitrogen atmosphere. The resulting mixture was stirred overnight at room temperature under nitrogen atmosphere. The residue was purified by Chromatography A, eluted with pet ether/ EtOAc (1/1) to afford the title compound (305 mg, 59%) as a colorless oil.

Step 4: Synthesis of tert-butyl 1-(piperidin-4-yl)pyrazole-3-carboxylate. The reaction was carried out according to General Procedure B using tert-butyl 4-[3-(tert-butoxycarbonyl)pyrazol-1-yl]piperidine-1-carboxylate (305 mg, 0.868 mmol, 1 equiv.) as the starting material. The resulting mixture was concentrated under vacuum to afford the title compound (200 mg, crude) as a crude oil.

Step 5: Synthesis of tert-butyl 1-(1-[[2-(2,6-dioxopiperidin-3-yl)-1,3-dioxoisoindol-4-yl]methyl]piperidin-4-yl) pyrazole-3-carboxylate. To a mixture of tert-butyl 1-(piperidin-4-yl)pyrazole-3-carboxylate (320 mg, 1.27 mmol, 1 eq.) in DCM (4 mL) and DMSO (1 mL) was added 2-(2,6-dioxopiperidin-3-yl)-1,3-dioxoisoindole-4-carbaldehyde (364 mg, 1.27 mmol, 1 eq.). To the above mixture was added NaBH(OAc)$_3$ (2.7 g, 13 mmol, 10 eq.) over 30 min at 0° C. The resulting mixture was stirred overnight at room temperature before being concentrated under vacuum. The residue was purified by Chromatography A, eluted with pet ether/EtOAc (1/1). This resulted in tert-butyl 1-(1-[[2-(2,6-dioxopiperidin-3-yl)-1,3-dioxoisoindol-4-yl]methyl]piperidin-4-yl)pyrazole-3-carboxylate (120 mg, 16% yield) as a white solid.

Step 6: Synthesis of 1-(1-[[2-(2,6-dioxopiperidin-3-yl)-1,3-dioxoisoindol-4-yl]methyl]piperidin-4-yl)pyrazole-3-carboxylic acid. The reaction was carried out according to General Procedure B using tert-butyl 1-(1-[[2-(2,6-dioxopiperidin-3-yl)-1,3-dioxoisoindol-4-yl]methyl]piperidin-4-yl) pyrazole-3-carboxylate (170 mg, 0.326 mmol) as the starting material. The residue was purified by Chromatography C to afford the title compound (42.5 mg, 27% yield) as a white solid Step 7: Synthesis of 5-{[6-(1'-{1-[1-({2-[2,6-dioxopiperidin-3-yl]-1,3-dioxo-2,3-dihydro-1H-isoindol-4-yl}methyl) piperidin-4-yl]-1H-pyrazole-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F using Intermediate 1 (14 mg, 0.02 mmol) and 1-[1-({2-[2,6-dioxopiperidin-3-yl]-1,3-dioxoisoindol-4-yl}methyl)piperidin-4-yl]pyrazole-3-carboxylic acid (8 mg, 0.02 mmol) followed by reverse phase HPLC to provide the title compound (9.2 mg, 44%); LCMS: C$_{64}$H$_{72}$FN$_{13}$O$_7$ requires 1153.6, found 1155.4 [(M+2H)]$^+$; $^1$H NMR (500 MHz, Methanol-d$_4$) δ 8.84 (s, 1H), 8.13-8.05 (m, 1H), 8.06-7.95 (m, 3H), 7.77 (d, J=16.5 Hz, 2H), 7.69-7.50 (m, 3H), 7.15 (d, J=11.8 Hz, 1H), 6.66-6.51 (m, 1H), 5.31 (p, J=6.6 Hz, 1H), 5.23 (dd, J=12.8, 5.5 Hz, 1H), 4.43-3.72 (m, 8H), 3.72-3.41 (m, 5H), 3.14-2.98 (m, 2H), 2.98-2.67 (m, 8H), 2.60-2.25 (m, 8H), 2.25-2.12 (m, 1H), 2.03-1.48 (m, 18H), 1.15 (d, J=6.6 Hz, 6H).

Example 66

4-fluoro-2-methyl-5-{[6-(2-oxo-1'-{1-[(1R,4R)-4-({2-[2,6-dioxopiperidin-3-yl]-1,3-dioxo-2,3-dihydro-1H-isoindol-4-yl}(methyl)amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide

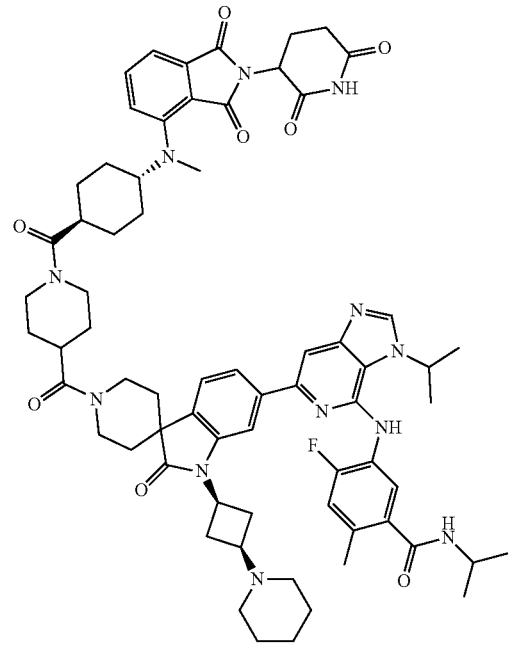 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)[C@H]5CC[C@H](N(C)c6cccc7c6C(=O)N(C6CCC(=O)NC6=O)C7=O)CC5)CC4)CC3)cc3ncn(C(C)C)c23)cc1C(=O)NC(C)C]

Step 1: Synthesis of methyl (1r,4r)-4-{[(tert-butoxy)carbonyl](methyl)amino}cyclohexane-1-carboxylate. Methyl trans-4-(tert-butoxycarbonylamino)cyclohexanecarboxylate (3.0 g, 12 mmol, 1.0 eq) was dissolved in DMF (20 mL, 0.6M) and cooled down to 0° C. on ice/salt bath. Then NaH (0.536 g, 14.0 mmol, 1.2 eq) was added and the mixture was stirred at 0° C. for 30 min. Methyl iodide (1.09 mL, 17.5 mmol, 1.5 eq) was added to the mixture, the cooling bath was removed, and the reaction was stirred at RT overnight. The mixture was then co-evaporated with toluene (3×100 mL) to remove excess of DMF azeotropically. 50 mL of saturated NH$_4$C$_1$ aq. solution was added to the remaining solid and the product was extracted with Et$_2$O (3×50 mL). The organic layers were dried with Na$_2$SO$_4$ and evaporated under vacuo to give the title compound (3.28 g, 99%).

Step 2: Synthesis of (1r,4r)-4-{[(tert-butoxy)carbonyl] (methyl)amino}cyclohexane-1-carboxylic acid. Methyl (1r, 4r)-4-{[(tert-butoxy)carbonyl](methyl)amino}cyclohexane-1-carboxylate (3.276 g, 12.07 mmol, 1.0 eq) was dissolved in THF/H$_2$O (30 mL, 5:1 v/v, 0.40M) mixture. Solid LiOH·xH$_2$O (1.04 g, 24.1 mmol, 2.0 eq) was added to the mixture and left to stir at room temperature overnight. After that period NMR showed 100% substrate consumption. THE was removed in vacuo, and residual aqueous solution was acidified with saturated aq. KHSO$_4$ solution to pH 5, extracted with ethyl acetate (4×25 mL), dried with Na$_2$SO$_4$, and evaporated under vacuum. The title compound, obtained as cream-white solid, was used in the next step without additional purification.

Step 3: Synthesis of (1r,4r)-4-(methylamino)cyclohexane-1-carboxylic acid hydrochloride. (1r,4r)-4-{[(tert-butoxy)carbonyl](methyl)amino}cyclohexane-1-carboxylic acid (2.51 g, 9.75 mmol, 1.0 eq) was placed in 250 mL round bottom flask and dissolved in dry DCM (130 mL, 0.07M). The reaction mixture was placed in an ice bath and 2M HCl solution in Et$_2$O (39 mL, 78 mmol, 8.0 eq) was added. The reaction mixture was stirred at 0° C. to RT overnight. After this time white precipitate was formed and NMR showed full conversion. The reaction mixture was evaporated in vacuo. Crude title compound was used in the next step without additional purification.

Step 4: Synthesis of (1r,4r)-4-{[2-(2,6-dioxopiperidin-3-yl)-1,3-dioxo-2,3-dihydro-1H-isoindol-4-yl](methyl)amino}cyclohexane-1-carboxylic acid: (1r,4r)-4-(methylamino)cyclohexane-1-carboxylic acid hydrochloride (1.74 g, 9.0 mmol, 1.0 eq), 2-(2,6-dioxopiperidin-3-yl)-4-fluoro-2,3-dihydro-1H-isoindole-1,3-dione (2.5 g, 9.0 mmol, 1.0 eq), KF (2.09 g, 36.0 mmol, 4.0 eq) were dissolved in DMSO (50.0 mL, 0.18M) and stirred under Argon at 120° C. overnight. Reaction mixture was poured into 1000 mL of brine, extracted with ethyl acetate (5×100 mL). The combined organic layers were dried with Na$_2$SO$_4$ and evaporated under vacuo. Crude compound was purified with Chromatography B followed by Chromatography C to give the title compound (768 mg, 21%).

Step 5: Synthesis of 1-[(1r,4r)-4-{[2-(2,6-dioxopiperidin-3-yl)-1,3-dioxoisoindol-4-yl](methyl)amino}cyclohexanecarbonyl]piperidine-4-carboxylic acid. The title compound was synthesized according to General Procedure F using (1r,4r)-4-{[2-(2,6-dioxopiperidin-3-yl)-1,3-dioxoisoindol-4-yl](methyl)amino}cyclohexane-1-carboxylic acid (100 mg, 0.24 mmol) and tert-butyl piperidine-4-carboxylate (54 mg, 0.29 mmol). Following purification, the residue was subjected to General Procedure B to yield the title compound (50 mg, 39%).

Step 6: Synthesis of 4-fluoro-2-methyl-5-{[6-(2-oxo-1'-{1-[(1r,4r)-4-({2-[2,6-dioxopiperidin-3-yl]-1,3-dioxo-2,3-dihydro-1H-isoindol-4-yl}(methyl)amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide. The title compound was synthesized according to General Procedure F using Intermediate 1 (13 mg, 0.02 mmol) and 1-[(1r,4r)-4-({2-[2,6-dioxopiperidin-3-yl]-1,3-dioxoisoindol-4-yl}(methyl)amino)cyclohexanecarbonyl]piperidine-4-carboxylic acid (9 mg, 0.02 mmol) followed by reverse phase HPLC to provide the title compound (6.2 mg, 44%); LCMS: C$_{68}$H$_{81}$FN$_{12}$O$_{8}$ requires 1212.6, found 1213.8 [(M+H)]$^+$; $^1$H NMR (500 MHz, Methanol-d$_4$) δ 8.87 (d, J=11.8 Hz, 1H), 8.03 (d, J=8.0 Hz, 1H), 7.87-7.67 (m, 2H), 7.67-7.55 (m, 2H), 7.52 (d, J=7.8 Hz, 1H), 7.28 (dd, J=11.9, 7.8 Hz, 2H), 7.16 (d, J=11.8 Hz, 1H), 5.31 (p, J=6.7 Hz, 1H), 5.10 (dd, J=12.6, 5.5 Hz, 1H), 4.62-4.50 (m, 1H), 4.34 (p, J=8.1 Hz, 1H), 4.24-3.73 (m, 8H), 3.66 (p, J=8.3 Hz, 1H), 3.54 (d, J=12.3 Hz, 2H), 3.15-2.99 (m, 3H), 2.99-2.83 (m, 8H), 2.81-2.65 (m, 4H), 2.44 (s, 3H), 2.17-2.09 (m, 1H), 2.06-1.48 (m, 30H), 1.15 (d, J=6.6 Hz, 6H).

Example 67

4-fluoro-2-methyl-5-[(6-{2-oxo-1'-[(3R)-1-[(R,4R)-4-({2-[2,6-dioxopiperidin-3-yl]-1,3-dioxo-2,3-dihydro-1H-isoindol-4-yl}(Methyl)amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide

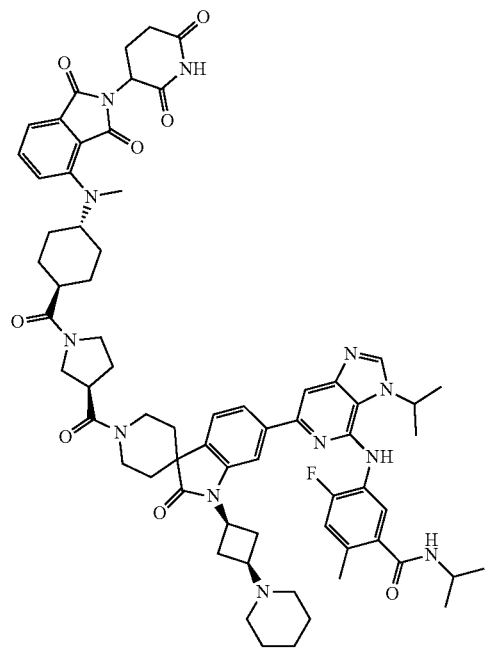 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)[C@H]5CC[C@H](N(C)c6cccc7c6C(=O)N(C6CCC(=O)NC6=O)C7=O)CC5)C4)CC3)cc3ncn(C(C)C)c23)cc1C(=O)NC(C)C]

Step 1: Synthesis of 3-benzyl 1-(tert-butyl) (R)-pyrrolidine-1,3-dicarboxylate. To solution of (3R)-1-[(tert-butoxy)carbonyl]pyrrolidine-3-carboxylic acid (5.00 g, 23.2 mmol, 1.0 eq) in anh. DMF (258 mL, 0.09 M), Cs$_2$CO$_3$ (9.08 g, 27.9 mmol, 1.2 eq) was added. The reaction mixture was placed in ice bath and stirred vigorously under argon atmosphere for 1 hour. Next benzyl bromide (3.04 mL, 25.6 mmol, 1.1 eq) was added dropwise, and the reaction mixture was maintained at 0° C. to RT overnight. After completion, reaction mixture was poured in 1800 mL of brine and extracted with ethyl acetate (5×150 mL). Combined organic layers were dried with MgSO$_4$ and solvent was evaporated in vacuo. Crude title compound (6.23 g, 88% yield) was obtained and used in next step without additional purification.

Step 2: Synthesis of benzyl (3R)-pyrrolidine-3-carboxylate hydrochloride. 3-Benzyl 1-tert-butyl (3R)-pyrrolidine-1,3-dicarboxylate (6.23 g, 20.4 mmol, 1.0 eq) was dissolved in anh DCM (255 mL, 0.08M) and cooled with ice bath under argon atmosphere. Then 2 M HCl in Et$_2$O (81.58 mL, 163 mmol, 8.0 eq) was added and the reaction proceeded from 0° C. to RT overnight. After completion, the reaction mixture was evaporated to dryness. The remaining crude solid was washed with Et$_2$O (3×50 mL) and dried in vacuum. The title compound was obtained and used in next step without additional purification (4.93 g, quant.).

Step 3: Synthesis of benzyl (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylate. (1r,4r)-4-{[2-(2,6-dioxopiperidin-3-yl)-1,3-dioxo-2,3-dihydro-1H-isoindol-4-yl](methyl)amino}cyclohexane-1-carboxylic acid (0.450 g, 1.09 mmol, 1.0 eq), HATU (0.621 g, 1.63 mmol, 1.5 eq) and DIPEA (0.758 mL, 4.35 mmol, 4.0 eq) were dissolved in anhydrous DMF (22 mL, 0.05 M) under argon atmosphere. The resulting mixture was stirred for 20 minutes and benzyl (3R)-pyrrolidine-3-carboxylate hydrochloride (0.263 g, 1.09 mmol, 1.0 eq) was added. Then reaction proceeded at room temperature overnight. Afterward, the reaction mixture was poured in 250 mL of brine, extracted with ethyl acetate (4×40 mL), dried over Na$_2$SO$_4$, concentrated in vacuo and purified by Chromatography B to give the title compound (0.379 g, 58% yield).

Step 4: Synthesis of (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylic acid. A solution of benzyl (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylate (0.379 g, 0.631 mmol, 1.0 eq) in THF (7.9 mL, 0.08 M) was degassed and 10% Pd/C (10% by weight) was added. Then the flask was filled with hydrogen from the balloon and reaction was proceeded at room temperature overnight. The reaction progress was monitored by UPLC. After 1 day in reaction mixture still was present starting material (20%), so next portion of Pd/C was added (5% by weight) and reaction was proceeded at room temperature overnight. Upon completion, reaction mixture was purged with nitrogen for 10 min and subsequently filtered through Celite, concentrated in vacuo, and purified by Chromatography B to give the title compound (0.180 g, 56% yield).

Step 5: Synthesis of 4-fluoro-2-methyl-5-[(6-{2-oxo-1'-[(3R)-1-[(1r,4r)-4-({2-[2,6-dioxopiperidin-3-yl]-1,3-dioxo-2,3-dihydro-1H-isoindol-4-yl}(methyl)amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (13 mg, 0.02 mmol) and (3R)-1-[(1r,4r)-4-{[2-(2,6-dioxopiperidin-3-yl)-1,3-dioxo-2,3-dihydro-1H-isoindol-4-yl](methyl)amino}cyclohexanecarbonyl]pyrrolidine-3-carboxylic acid (9 mg, 0.02 mmol) followed by reverse phase HPLC to provide the title compound (9.8 mg, 47%); LCMS: C$_{67}$H$_{79}$FN$_{12}$O$_8$ requires 1198.6, found 1199.6 [(M+H)]$^+$; $^1$H NMR (500 MHz, Methanol-d$_4$) δ 8.95-8.84 (m, 1H), 8.09-7.97 (m, 1H), 7.82-7.67 (m, 2H), 7.67-7.49 (m, 3H), 7.33-7.24 (m, 2H), 7.16 (d, J=11.8 Hz, 1H), 5.38-5.27 (m, 1H), 5.10 (dd, J=12.2, 5.3 Hz, 1H), 4.34 (q, J=7.9 Hz, 1H), 4.19-4.03 (m, 3H), 4.02-3.42 (m, 12H), 3.16-2.99 (m, 2H), 2.98-2.80 (m, 8H), 2.82-2.70 (m, 2H), 2.53 (q, J=12.8 Hz, 1H), 2.44 (s, 3H), 2.35-2.19 (m, 2H), 2.18-1.50 (m, 24H), 1.15 (d, J=6.6 Hz, 6H).

Example 68

5-{[6-(1'-{1-[4-({2-[2,6-dioxopiperidin-3-yl]-1,3-dioxo-2,3-dihydro-1H-isoindol-4-yl}amino)piperidine-1-carbonyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

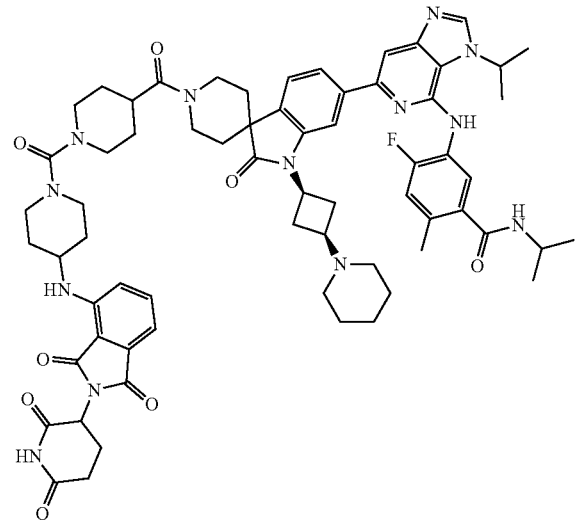 [SMILES: Cc1cc(F)c(Nc2nc(-c3ccc4c(c3)N([C@H]3C[C@@H](N5CCCCC5)C3)C(=O)C43CCN(C(=O)C4CCN(C(=O)N5CCC(Nc6cccc7c6C(=O)N(C6CCC(=O)NC6=O)C7=O)CC5)CC4)CC3)cc3ncn(C(C)C)c23)cc1C(=O)NC(C)C]

Step-1: Synthesis of tert-butyl 1-(4-[[2-(2,6-dioxopiperidin-3-yl)-1,3-dioxoisoindol-4-yl]amino]piperidine-1-carbonyl)piperidine-4-carboxylate. To a mixture of 2-(2,6-dioxopiperidin-3-yl)-4-(piperidin-4-ylamino)isoindole-1,3-dione (500 mg, 1.40 mmol, 1 eq.) and DIPEA (204 mg, 1.58 mmol, 1.13 eq.) in DCM (30 mL) were added triphosgene (156 mg, 0.526 mmol, 0.375 eq.) at 0° C. To the above mixture was added tert-butyl piperidine-4-carboxylate (260 mg, 1.403 mmol, 1 eq.) at 0° C. The resulting mixture was stirred for additional overnight at 50° C. The resulting mixture was concentrated under reduced pressure. The residue was purified by Chromatography C to afford the title compound (470 mg, 59%).

Step 2: Synthesis of 1-(4-[[2-(2,6-dioxopiperidin-3-yl)-1,3-dioxoisoindol-4-yl]amino]piperidine-1-carbonyl)piperidine-4-carboxylic acid. The reaction was carried out according to General Procedure B using tert-butyl 1-(4-[[2-(2,6-dioxopiperidin-3-yl)-1,3-dioxoisoindol-4-yl]amino]piperidine-1-carbonyl)piperidine-4-carboxylate (380 mg, 0.669 mmol) as the starting material. The resulting mixture was concentrated under reduced pressure. The residue was purified by Chromatography C to afford the title compound (131 mg, 37%).

Step 3: Synthesis of 5-{[6-(1'-{1-[4-({2-[2,6-dioxopiperidin-3-yl]-1,3-dioxo-2,3-dihydro-1H-isoindol-4-yl}amino)piperidine-1-carbonyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F using Intermediate 1 (15 mg, 0.02 mmol) and 1-[4-({2-[2,6-dioxopiperidin-3-yl]-1,3-dioxoisoindol-4-yl}amino)piperidine-1-carbonyl]piperidine-4-carboxylic acid (9 mg, 0.02 mmol) followed by reverse phase HPLC to provide the title compound (10.7 mg, 48%); LCMS: C$_{66}$H$_{78}$FN$_{13}$O$_8$ requires 1199.6, found 1200.4 [(M+H)]$^+$; $^1$H NMR (500 MHz, Methanol-d$_4$) δ 8.91 (s, 1H), 8.02 (d, J=8.1 Hz, 1H), 7.80-7.70 (m, 2H), 7.63-7.54 (m, 2H), 7.52 (d, J=7.9 Hz, 1H), 7.20-7.12 (m, 2H), 7.08 (d, J=7.1 Hz, 1H), 5.41-5.30 (m, 1H), 5.06 (dd, J=12.4, 5.5 Hz, 1H), 4.34 (p, J=8.3 Hz, 1H), 4.19-4.00 (m, 3H), 3.95 (t, J=12.5 Hz, 2H), 3.84-3.75 (m, 3H), 3.75-3.63 (m, 3H), 3.54 (d, J=12.1 Hz, 2H), 3.19-2.66 (m, 15H), 2.44 (s, 3H), 2.16-1.67 (m, 24H), 1.56 (q, J=10.4, 8.7 Hz, 2H), 1.15 (d, J=6.6 Hz, 6H).

Example 69

5-[(6-{1'-[(3R)-1-[4-({2-[2,6-dioxopiperidin-3-yl]-1,3-dioxo-2,3-dihydro-1H-isoindol-4-yl}amino)piperidine-1-carbonyl]pyrrolidine-3-carbonyl]-2-oxo-1-[(1S,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

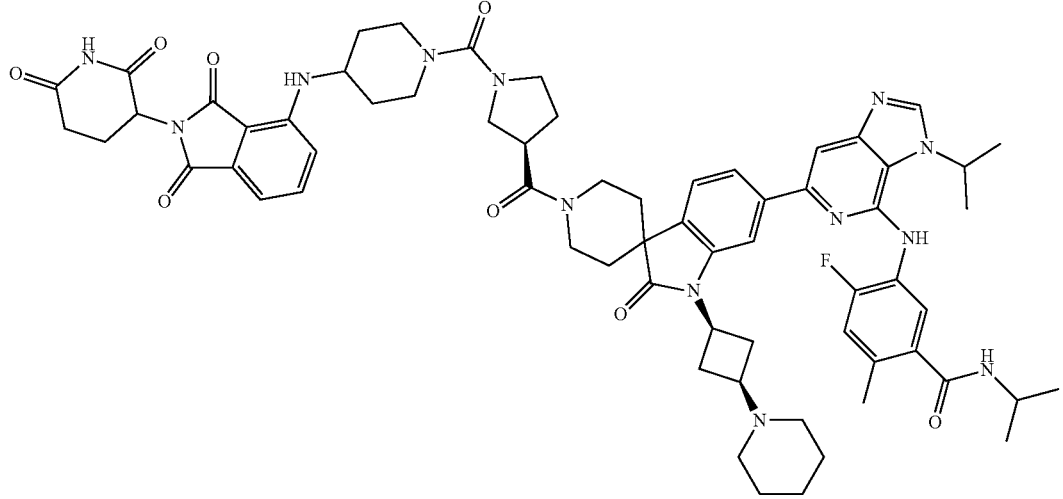 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)N5CCC(Nc6cccc7c6C(=O)N(C6CCC(=O)NC6=O)C7=O)CC5)C4)CC3)cc3ncn(C(C)C)c23)cc1C(=O)NC(C)C]

Step-1: Synthesis of methyl (3R)-1-(4-[[2-(2,6-dioxopiperidin-3-yl)-1,3-dioxoisoindol-4-yl]amino]piperidine-1-carbonyl)pyrrolidine-3-carboxylate. To a mixture of 2-(2,6-dioxopiperidin-3-yl)-4-(piperidin-4-ylamino)isoindole-1,3-dione (300 mg, 0.842 mmol, 1 eq.) in DCM (10 mL) was added triphosgene (74 mg, 0.25 mmol, 0.3 eq.) and DIPEA (652 mg, 5.05 mmol, 6 eq.) dropwise at room temperature. To the above mixture was added methyl (3R)-pyrrolidine-3-carboxylate (108 mg, 0.842 mmol, 1 eq.). The resulting mixture was stirred overnight at 50° C. The resulting mixture was concentrated under vacuum. The residue was purified by Chromatography C to afford the title compound (200 mg, 46%).

Step 2: Synthesis of (3R)-1-(4-[[2-(2,6-dioxopiperidin-3-yl)-1,3-dioxoisoindol-4-yl]amino]piperidine-1-carbonyl)pyrrolidine-3-carboxylic acid. A mixture of methyl (3R)-1-(4-[[2-(2,6-dioxopiperidin-3-yl)-1,3-dioxoisoindol-4-yl]amino]piperidine-1-carbonyl)pyrrolidine-3-carboxylate (180 mg, 0.352 mmol, 1 eq.) in conc. HCl (3 mL) was stirred for 5 h at room temperature. The residue was purified by Chromatography C to the title compound (93 mg, 53%).

Step 3: Synthesis of 5-[(6-{1'-[(3R)-1-[4-({2-[2,6-dioxopiperidin-3-yl]-1,3-dioxo-2,3-dihydro-1H-isoindol-4-yl}amino)piperidine-1-carbonyl]pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (11 mg, 0.02 mmol) and (3R)-1-(4-((2-(2,6-dioxopiperidin-3-yl)-1,3-dioxoisoindolin-4-yl)amino)piperidine-1-carbonyl)pyrrolidine-3-carboxylic acid (8 mg, 0.02 mmol) followed by reverse phase HPLC to provide the title compound (8.8 mg, 48%); LCMS: $C_{66}H_{78}FN_{13}O_8$ requires 1185.6, found 1186.8 [(M+H)]$^+$; $^1$H NMR (500 MHz, Methanol-$d_4$) δ 9.02 (d, J=4.2 Hz, 1H), 8.02-7.94 (m, 1H), 7.84-7.64 (m, 2H), 7.64-7.46 (m, 3H), 7.20-7.11 (m, 2H), 7.11-7.02 (m, 1H), 5.34 (p, J=6.6 Hz, 1H), 5.09-4.98 (m, 1H), 4.39-4.27 (m, 1H), 4.21-3.85 (m, 5H), 3.85-3.74 (m, 3H), 3.72-3.60 (m, 3H), 3.59-3.42 (m, 6H), 3.18-3.00 (m, 4H), 3.00-2.65 (m, 7H), 2.45 (s, 3H), 2.24-1.66 (m, 22H), 1.65-1.47 (m, 3H), 1.16 (d, J=6.6 Hz, 6H).

Example 70

4-fluoro-2-methyl-5-({6-[2-oxo-1'-(1-{[(1R,4R)-4-({2-[2,6-dioxopiperidin-3-yl]-1,3-dioxo-2,3-dihydro-1H-isoindol-4-yl}amino)cyclohexyl]methyl}-1H-pyrazole-4-carbonyl)-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide

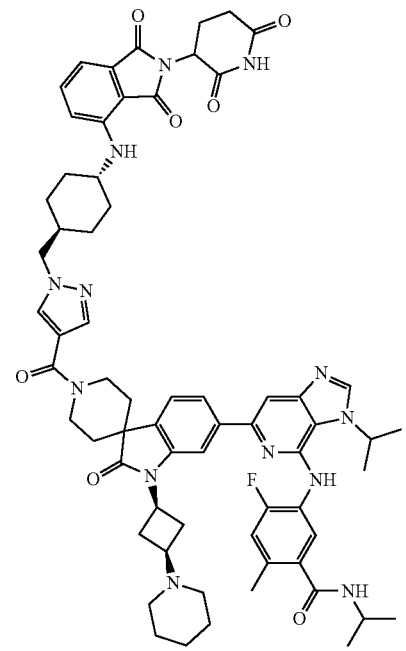 [SMILES: Cc1cc(F)c(Nc2nc(-c3ccc4c(c3)N([C@H]3C[C@@H](N5CCCCC5)C3)C(=O)C43CCN(C(=O)c4cnn(C[C@H]5CC[C@H](Nc6cccc7c6C(=O)N(C6CCC(=O)NC6=O)C7=O)CC5)c4)CC3)cc3ncn(C(C)C)c23)cc1C(=O)NC(C)C]

Step 1: Synthesis of tert-butyl N-[(1r,4r)-4-(bromomethyl)cyclohexyl]carbamate. To a solution of tert-butyl N-[(1r,4r)-4-(hydroxymethyl)cyclohexyl]carbamate (0.500 g, 2.18 mmol, 1.0 eq) in anhydrous DCM (10 mL, 0.21 M) was added carbon tetrabromide (1.08 g, 3.27 mmol, 1.5 eq) and triphenylphosphine (0.857 g, 3.27 mmol, 1.5 eq). The resulting mixture was stirred at room temperature overnight. Afterward, the reaction mixture was concentrated and the residue was triturated with methyl tert-butyl ether to remove triphenylphosphineoxide. The obtained methyl tert-butyl ether solution was concentrated in vacuo to give the title compound as a white solid (0.482 g, 75% yield).

Step 2: Synthesis of benzyl 1H-pyrazole-4-carboxylate. To solution of 1H-pyrazole-4-carboxylic acid (1.00 g, 8.92 mmol, 1.0 eq) in dry DMSO (31 mL, 0.29 M), KHCO$_3$ (1.07 g, 10.7 mmol, 1.2 eq) was added. The reaction mixture was agitated vigorously under an argon atmosphere for 30 min. Next benzyl bromide (1.00 mL, 8.47 mmol, 0.95 eq) was added dropwise and the reaction mixture was maintained at room temperature overnight. After completion, the reaction mixture was poured in 250 mL of brine, extracted with ethyl acetate (3×50 mL). Combined organic layers were dried with MgSO$_4$ and solvent was evaporated in vacuo. The crude product (1.30 g, 72% yield) was used in the next step without additional purification.

Step 3: Synthesis of benzyl 1-{[(1r,4r)-4-{[(tert-butoxy)carbonyl]amino}cyclohexyl]methyl}-1H-pyrazole-4-carboxylate. A mixture of benzyl 1H-pyrazole-4-carboxylate (0.433 g, 2.14 mmol, 1.3 eq), tert-butyl N-[(1r,4r)-4-(bromomethyl)cyclohexyl]carbamate (0.482 g, 1.65 mmol, 1.0 eq) and anhydrous K$_2$CO$_3$ (0.455 g, 3.29 mmol, 2.0 eq) in dry acetone (15 mL, 0.11 M) was heated at 60° C. overnight. After completion, the reaction mixture was concentrated, the residue was dissolved with 40 mL of DCM and washed with water (3×20 mL). Next, organic layer was dried with Na$_2$SO$_4$, evaporated to dryness, and purified by Chromatography B to give the title compound (0.360 g, 53% yield).

Step 4: Synthesis of benzyl 1-{[(1r,4r)-4-aminocyclohexyl]methyl}-1H-pyrazole-4-carboxylate hydrochloride. Benzyl 1-{[(1r,4r)-4-{[(tert-butoxy)carbonyl]amino}cyclohexyl]methyl}-1H-pyrazole-4-carboxylate (0.411 g, 0.994 mmol, 1.0 eq) was dissolved in anh DCM (14 mL, 0.07 M) and cooled with ice bath under argon atmosphere. Then 2M HCl in Et$_2$O (3.98 mL, 7.95 mmol, 8.0 eq) was added and the reaction proceeded 0° C. to RT overnight. After completion, the reaction mixture was evaporated to dryness in vacuo. The remaining crude solid was washed with Et$_2$O (3×50 mL) and dried in vacuo. Obtained product was used in the next step without additional purification (0.311 g, 89% yield).

Step 5: Synthesis of benzyl 1-{[(1r,4r)-4-{[2-(2,6-dioxopiperidin-3-yl)-1,3-dioxo-2,3-dihydro-1H-isoindol-4-yl]amino}cyclohexyl]methyl}-1H-pyrazole-4-carboxylate. A solution of benzyl 1-{[(1r,4r)-4-aminocyclohexyl]methyl}-1H-pyrazole-4-carboxylate hydrochloride (0.311 g, 0.887 mmol, 1.34 eq), 2-(2,6-dioxopiperidin-3-yl)-4-fluoroisoindoline-1,3-dione (0.183 g, 0.662 mmol, 1 eq) and DIPEA (0.46 mL, 2.65 mmol, 4 eq) in anhydrous DMSO (6.6 mL, 0.10 M) was heated in pressure vessel at 90° C. overnight. Afterward, reaction mixture was poured in 100 mL of water, extracted with ethyl acetate (5×40 mL), dried over Na$_2$SO$_4$, concentrated in vacuo, and purified by Chromatography B to give the title compound (0.189 g, 50% yield).

Step 6: Synthesis of 1-{[(1r,4r)-4-{[2-(2,6-dioxopiperidin-3-yl)-1,3-dioxo-2,3-dihydro-1H-isoindol-4-yl]amino}cyclohexyl]methyl}-1H-pyrazole-4-carboxylic acid. A solution of benzyl 1-{[(1r,4r)-4-{[2-(2,6-dioxopiperidin-3-yl)-1,3-dioxo-2,3-dihydro-1H-isoindol-4-yl]amino}cyclohexyl]methyl}-1H-pyrazole-4-carboxylate (0.379 g, 0.631 mmol, 1.0 eq) in THF (7.9 mL, 0.08 M) was degassed and 10% Pd/C (20% by weight) was added. Then the flask was filled with hydrogen from the balloon and the reaction proceeded at room temperature overnight. The reaction progress was monitored by UPLC: after 1 day in reaction mixture starting material was present (35%), so the next portion of Pd/C was added (10% by weight) and the reaction proceeded at room temperature overnight. Upon completion, the reaction mixture was filtered through Celite and concentrated in vacuo. Next, the residue was dissolved in a small portion of DCM (~2 mL) and diethyl ether (15 mL) was added dropwise until precipitation of product, then the mixture was left overnight. Afterward, the solvent was decanted and the remaining solid was dried in vacuo to give the title compound (0.157 g, 99%).

Step 7: Synthesis of 4-fluoro-2-methyl-5-({6-[2-oxo-1'-(1-{[(1r,4r)-4-({2-[2,6-dioxopiperidin-3-yl]-1,3-dioxo-2,3-dihydro-1H-isoindol-4-yl}amino)cyclohexyl]methyl}-1H-pyrazole-4-carbonyl)-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide. The title compound was synthesized according to General Procedure F using Intermediate 1 (11 mg, 0.02 mmol) and 1-{[(1r,4r)-4-({2-[2,6-dioxopiperidin-3-yl]-1,3-dioxoisoindol-4-yl}amino)cyclohexyl]methyl}pyrazole-4-carboxylic acid (8 mg, 0.02 mmol) followed by reverse phase HPLC to provide the title compound (8.1 mg, 45%); LCMS: C$_{65}$H$_{73}$FN$_{13}$O$_7$ requires 1167.6, found 1169.5 [(M+2H)]$^+$; $^1$H NMR (500 MHz, Methanol-d$_4$) δ 8.94 (s, 1H), 8.07 (s, 1H), 8.01 (d, J=8.0 Hz, 1H), 7.81 (s, 1H), 7.78 (s, 1H), 7.75 (dd, J=7.9, 1.5 Hz, 1H), 7.61 (d, J=1.5 Hz, 1H), 7.57-7.50 (m, 2H), 7.16 (d, J=11.8 Hz, 1H), 7.07 (d, J=8.6 Hz, 1H), 7.03 (d, J=7.1 Hz, 1H), 5.32 (p, J=6.6 Hz, 1H), 5.04 (dd, J=12.6, 5.4 Hz, 1H), 4.34 (p, J=8.3 Hz, 1H), 4.20-4.05 (m, 6H), 3.66 (p, J=8.1 Hz, 1H), 3.60-3.46 (m, 4H), 3.10 (d, J=10.0 Hz, 2H), 2.97-2.79 (m, 5H), 2.79-2.63 (m, 2H), 2.44 (s, 3H), 2.23-1.83 (m, 11H), 1.82-1.65 (m, 10H), 1.56 (q, J=14.4 Hz, 1H), 1.29 (q, J=10.9 Hz, 4H), 1.15 (d, J=6.6 Hz, 6H).

Example 71

5-[(6-{1'-[2-chloro-4-(4-{2-[2,6-dioxopiperidin-3-yl]-1,3-dioxo-2,3-dihydro-1H-isoindol-5-yl}piperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

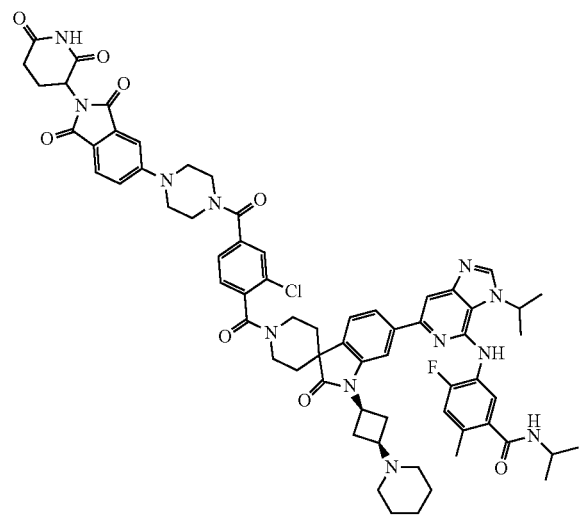 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)cc4Cl)CC3)cc3ncn(C(C)C)c23)cc1C(=O)NC(C)C]

207

Step 1: Synthesis of tert-butyl 4-[2-(2,6-dioxopiperidin-3-yl)-1,3-dioxoisoindol-5-yl]piperazine-1-carboxylate. To a mixture of 2-(2,6-dioxopiperidin-3-yl)-5-fluoroisoindole-1,3-dione (4.0 g, 15 mmol, 1 eq.) and tert-butyl piperazine-1-carboxylate (5.39 g, 28.9 mmol, 2 eq.) in DMSO (6 mL) was added DIPEA (5.61 g, 43.4 mmol, 3 eq.) at room temperature. The resulting mixture was stirred overnight at 90° C. The residue was purified Chromatography C, to afford the title compound (850 mg, 10% yield).

Step 2: Synthesis of 2-(2,6-dioxopiperidin-3-yl)-5-(piperazin-1-yl)isoindole-1,3-dione. The reaction was carried out according to General Procedure B using tert-butyl 4-[2-(2,6-dioxopiperidin-3-yl)-1,3-dioxoisoindol-5-yl]piperazine-1-carboxylate (850 mg, 1.92 mmol) as starting material. This afforded in the title compound (710 mg, crude).

Step 3: Synthesis of methyl 2-chloro-4-[4-[2-(2,6-dioxopiperidin-3-yl)-1,3-dioxoisoindol-5-yl]piperazine-1-carbonyl]benzoate. To a mixture of 3-chloro-4-(methoxycarbonyl)benzoic acid (250 mg, 1.17 mmol, 1 eq.) and TEA (354 mg, 3.50 mmol, 3 equiv) in DMF (6 mL) was added 2-(2,6-dioxopiperidin-3-yl)-5-(piperazin-1-yl)isoindole-1,3-dione (399 mg, 1.17 mmol, 1 eq.) at room temperature under nitrogen atmosphere. To the above mixture was added T3P (741 mg, 1.17 mmol, 1 equiv, 50% w/w in EtOAc over 15 min at 0° C. The resulting mixture was stirred at room temperature overnight before removal of volatiles. The residue was purified by Chromatography C to afford the title compound (240 mg, 58% yield).

Step 4: Synthesis of 2-chloro-4-[4-[2-(2,6-dioxopiperidin-3-yl)-1,3-dioxoisoindol-5-yl]piperazine-1-carbonyl]benzoic acid. The reaction was carried out according to General Procedure B using methyl 2-chloro-4-[4-[2-(2,6-dioxopiperidin-3-yl)-1,3-dioxoisoindol-5-yl]piperazine-1-carbonyl]benzoate (470 mg, 0.872 mmol, 1 equiv) as the starting material. The crude residue was purified by Chromatography C, to afford 2-chloro-4-[4-[2-(2,6-dioxopiperidin-3-yl)-1,3-dioxoisoindol-5-yl]piperazine-1-carbonyl]benzoic acid (117 mg, 24% yield).

Step 5: Synthesis of 5-[(6-{1'-[2-chloro-4-(4-{2-[2,6-dioxopiperidin-3-yl]-1,3-dioxo-2,3-dihydro-1H-isoindol-5-yl}piperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (11 mg, 0.02 mmol) and 2-chloro-4-(4-{2-[2,6-dioxopiperidin-3-yl]-1,3-dioxoisoindol-5-yl}piperazine-1-carbonyl)benzoic acid (8 mg, 0.02 mmol) followed by reverse phase HPLC to provide the title compound (11.4 mg, 60%); LCMS: $C_{66}H_{70}FClN_{12}O_8$ requires 1212.5, found 1213.4 [(M+1H)]$^+$; $^1$H NMR (500 MHz, Methanol-d$_4$) δ 8.92 (s, 1H), 8.35 (d, J=2.9 Hz, 1H), 7.97 (d, J=8.8 Hz, 1H), 7.72-7.50 (m, 4H), 7.45 (dd, J=9.0, 3.0 Hz, 1H), 5.18-5.07 (m, 1H), 4.60 (s, 1H), 4.49 (p, J=8.4 Hz, 1H), 4.28-4.09 (m, 3H), 4.09-3.85 (m, 4H), 3.68-3.51 (m, 4H), 3.27-3.10 (m, 4H), 3.10-2.95 (m, 7H), 2.95-2.70 (m, 6H), 2.40-2.27 (m, 1H), 2.19 (qd, J=13.0, 4.7 Hz, 1H), 2.07-1.71 (m, 19H), 1.68 (d, J=6.5 Hz, 6H), 1.66-1.51 (m, 2H), 1.13 (d, J=6.5 Hz, 2H), 0.94 (s, 2H).

208

Example 72

5-[(6-{1'-[4-(4-{2-[2,6-dioxopiperidin-3-yl]-1,3-dioxo-2,3-dihydro-1H-isoindol-5-yl}-2-methylpiperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

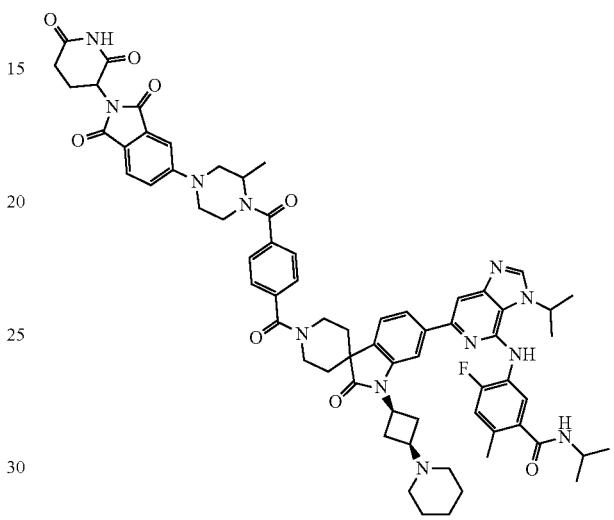

Step 1: Synthesis of 4-{4-[(tert-butoxy)carbonyl]benzoyl}-3-methylpiperazine-1-carboxylate. 4-(tert-butoxycarbonyl)benzoic acid (0.5 g, 2 mmol, 1.0 eq), HATU (1.28 g, 3.37 mmol, 1.5 eq), and N,N-diisopropylethylamine, (0.78 mL, 4.5 mmol, 2.0 eq) were mixed in DMF (4.5 mL, 0.5 M) and left to stir for 1 h, then benzyl 3-methylpiperazine-1-carboxylate (0.63 g, 2.7 mmol, 1.2 eq) was added to the reaction mixture and stirred overnight at room temperature. On completion, the reaction mixture was diluted with brine, extracted with DCM, organic layer was washed with water, dried with Na$_2$SO$_4$. The residue, obtained after solvent evaporation was purified by Chromatography B to give the title compound (0.975 g, 84%)

Step 2: Synthesis of tert-butyl 4-(2-methylpiperazine-1-carbonyl)benzoate. Benzyl 4-{4-[(tert-butoxy)carbonyl]benzoyl}-3-methylpiperazine-1-carboxylate (1.15 g, 2.22 mmol, 1.0 eq) was dissolved in tetrahydrofuran (89 mL, 0.025 M), the reaction mixture was degassed and charged with 10% Palladium on carbon 60-65% wet (1 eq) and left stirring under H$_2$ atmosphere for 16 h. The reaction mixture was filtered through a Celite pad, washed with MeOH and evaporated to give the title compound (0.75 g, 2.5 mmol, quant.

Step 3: Synthesis of tert-butyl 4-{4-[2-(2,6-dioxopiperidin-3-yl)-1,3-dioxo-2,3-dihydro-1H-isoindol-5-yl]-2-methylpiperazine-1-carbonyl}benzoate. To a solution of 2-(2,6-dioxopiperidin-3-yl)-5-fluoro-2,3-dihydro-1H-isoindole-1,3-dione (1.05 g, 3.79 mmol, 1.5 eq) in anhydrous DMSO (5.06 mL, 0.5 M), tert-butyl 4-(2-methylpiperazine-1-carbonyl)benzoate (0.856 g, 2.53 mmol, 1.0 eq) DIPEA (1.32 mL, 7.59 mmol, 3.0 eq) were added. The resulting mixture was stirred at 90° C. overnight. Then it was diluted with brine, extracted with DCM. The organic layer was washed with water, dried with Na$_2$SO$_4$ to give the crude the title compound after concentration. The crude was purified by Chromatography B to give the title compound (0.32 g, 0.571 mmol, 21%)

Step 4: Synthesis of 4-{4-[2-(2,6-dioxopiperidin-3-yl)-1,3-dioxo-2,3-dihydro-1H-isoindol-5-yl]-2-methylpiperazine-1-carbonyl}benzoic acid. tert-Butyl 4-{4-[2-(2,6-dioxopiperidin-3-yl)-1,3-dioxo-2,3-dihydro-1H-isoindol-5-yl]-2-methylpiperazine-1-carbonyl}benzoate (0.295 g, 0.527 mmol, 1.0 eq) was suspended in hexafluoro-2-propanol (3.7 mL, 35 mmol, 70 eq) and heated in microwave for 2 h at 150° C. The substrate consumption was monitored by UPLC. The volatiles were evaporated in vacuo and solid sticky residue was washed with Et$_2$O (3×15 mL) to give the title compound (0.139 g, 0.276 mmol, 53%).

Step 5: Synthesis of 5-[(6-{1'-[4-(4-{2-[2,6-dioxopiperidin-3-yl]-1,3-dioxo-2,3-dihydro-1H-isoindol-5-yl}-2-methylpiperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using Intermediate 1 (12 mg, 0.02 mmol) and (8 mg, 0.02 mmol) followed by reverse phase HPLC to provide the title compound (11 mg, 56%); LCMS: C$_{67}$H$_{73}$FN$_{12}$O$_8$ requires 1192.6, found 1194.5 [(M+2H)]$^+$; $^1$H NMR (500 MHz, Methanol-d$_4$) δ 8.94 (s, 1H), 8.00 (d, J=8.1 Hz, 1H), 7.78 (s, 1H), 7.76 (d, J=8.1 Hz, 1H), 7.71 (d, J=8.5 Hz, 1H), 7.65 (d, J=8.0 Hz, 2H), 7.63-7.55 (m, 4H), 7.37 (d, J=2.4 Hz, 1H), 7.28-7.22 (m, 1H), 7.16 (d, J=11.8 Hz, 1H), 5.33 (p, J=6.5 Hz, 1H), 5.07 (dd, J=12.4, 5.5 Hz, 1H), 4.34 (p, J=8.3 Hz, 1H), 4.14 (p, J=6.6 Hz, 2H), 4.06-3.70 (m, 4H), 3.65 (q, J=8.1 Hz, 1H), 3.54 (d, J=12.4 Hz, 2H), 3.20-3.03 (m, 4H), 3.00-2.79 (m, 6H), 2.79-2.64 (m, 2H), 2.45 (s, 3H), 2.15-2.05 (m, 1H), 2.05-1.66 (m, 17H), 1.56 (q, J=13.5, 13.0 Hz, 1H), 1.39 (s, 3H), 1.15 (d, J=6.6 Hz, 6H).

Example 73

4-fluoro-2-methyl-5-[(6-{2-oxo-1'-[(3R)-1-{[(1R,4R)-4-({2-[2,6-dioxopiperidin-3-yl]-1,3-dioxo-2,3-dihydro-1H-isoindol-4-yl}amino)cyclohexyl]methyl}pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide Step 1: Synthesis of tert-butyl N-[(1r,4r)-4-formylcyclohexyl]carbamate. To the tert-butyl trans-(4-hydroxymethyl)cyclohexylcarbamate (1.5 g, 6.541 mmol, 1.0 eq) dissolved in anhydrous DCM (21.8 mL, 0.3 M), solution of Dess-Martin periodinane (3.2 g, 7.2 mmol, 1.1 eq) in anhydrous DCM (43.6 mL, 0.15 M) was added dropwise at 0° C. The reaction mixture was stirred at room temperature for 1 h. Upon completion, reaction mixture was washed with an aqueous solution of Na$_2$S$_2$O$_3$ (3×100 mL), the organic layer was separated, washed with an aqueous solution of NaHCO$_3$ (3×100 mL), then aq layers were combined and extracted with DCM (3×50 mL). Combined organic layers were dried over Na$_2$SO$_4$ and concentrated to give the title compound. The product was used in the next step without additional purification. (0.917 g, 62% yield).

Step 2: Synthesis of benzyl (3R)-1-{[(1r,4r)-4-{[(tert-butoxy)carbonyl]amino}cyclohexyl]methyl}pyrrolidine-3-carboxylate. To a solution of benzyl (3R)-pyrrolidine-3-carboxylate hydrochloride (0.521 g, 2.16 mmol, 1.2 eq) in anhydrous DCM (30 mL, 0.06 M), DIPEA (0.625 mL, 3.59 mmol, 2.0 eq) was added and stirred for 15 min at room temperature. Next, tert-butyl N-[(1r,4r)-4-formylcyclohexyl]carbamate (0.408 g, 1.79 mmol, 1.0 eq) was added and the reaction mixture was stirred for 3 h at room temperature. STAB (1.14 g, 5.38 mmol, 3.0 eq) was added and stirring was continued at room temperature overnight. After this time reaction mixture was quenched with 10% aqueous solution of K$_2$CO$_3$ and two phases were separated. The organic layer was dried over Na$_2$SO$_4$, filtered, evaporated in vacuum to dryness, and purified by Chromatography B to give the title compound (0.482 g, 64% yield).

Step 3: Synthesis of (3R)-1-{[(1r,4r)-4-aminocyclohexyl]methyl}pyrrolidine-3-carboxylic acid. A solution of benzyl (3R)-1-{[(1r,4r)-4-{[(tert-butoxy)carbonyl]amino}cyclohexyl]methyl}pyrrolidine-3-carboxylate (0.569 g, 1.37 mmol, 1 eq) in hexafluoroisopropanol (8.20 mL, 77.9 mmol, 57.0 eq) was placed in G30 microwave vial equipped with magnetic stirring bar. The reaction mixture was heated 2 h at 140° C. and 1 h at 150° C. in a microwave. Upon completion, the reaction mixture was concentrated in vacuo and solid sticky residue was washed with Et$_2$O (3×15 mL) to give the title compound as a precipitate (0.148 g, 48% yield).

Step 4: Synthesis of (3R)-1-{[(1r,4r)-4-{[2-(2,6-dioxopiperidin-3-yl)-1,3-dioxo-2,3-dihydro-1H-isoindol-4-yl]amino}cyclohexyl]methyl}pyrrolidine-3-carboxylic acid. A

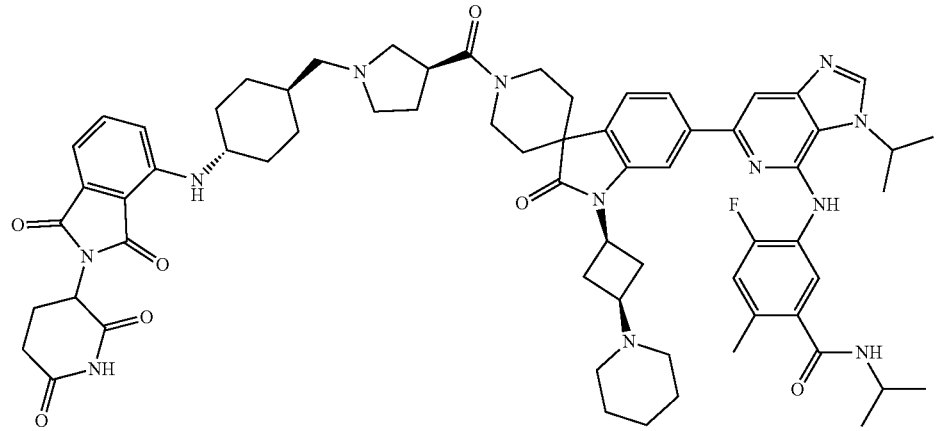 [SMILES: Cc1cc(F)c(Nc2nc(-c3ccc4c(c3)N([C@H]3C[C@@H](N5CCCCC5)C3)C(=O)C43CCN(C(=O)[C@H]4CCN(C[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

solution of (3R)-1-{[(1r,4r)-4-aminocyclohexyl]methyl}pyrrolidine-3-carboxylic acid (0.148 g, 0.654 mmol, 1.0 eq), 2-(2,6-dioxopiperidin-3-yl)-4-fluoroisoindoline-1,3-dione (0.271 g, 0.981 mmol, 1.5 eq) and potassium fluoride (0.19 g, 3.3 mmol, 5.0 eq) in anhydrous DMSO (4.36 mL, 0.15 M) was heated in pressure vessel at 120° C. for 35 h. Afterward, the reaction mixture was poured into 50 mL of water, washed with ethyl acetate (5×30 mL). The next water phase was evaporated and freeze-dried overnight to remove the remaining DMSO with water and then purified by Chromatography C to give the title compound (0.068 g, 22% yield).

Step 5: Synthesis of 4-fluoro-2-methyl-5-[(6-{2-oxo-1'-[(3R)-1-{[(1r,4r)-4-({2-[2,6-dioxopiperidin-3-yl]-1,3-dioxo-2,3-dihydro-1H-isoindol-4-yl}amino)cyclohexyl]methyl}pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide. The title compound was synthesized according to General Procedure F using Intermediate 1 (10 mg, 0.01 mmol) and (3R)-1-{[(1r,4r)-4-({2-[2,6-dioxopiperidin-3-yl]-1,3-dioxoisoindol-4-yl}amino)cyclohexyl]methyl}pyrrolidine-3-carboxylic acid (7 mg, 0.01 mmol) followed by reverse phase HPLC to provide the title compound (9.6 mg, 55%); LCMS: $C_{66}H_{79}FN_{12}O_7$ requires 1170.6, found 1172.4 [(M+2H)]$^+$; $^1$H NMR (500 MHz, Methanol-$d_4$) δ 8.75 (s, 1H), 8.05 (d, J=8.1 Hz, 1H), 7.81-7.71 (m, 2H), 7.63 (s, 1H), 7.60-7.47 (m, 2H), 7.19-7.03 (m, 3H), 5.29 (p, J=6.6 Hz, 1H), 5.06 (dd, J=12.5, 5.5 Hz, 1H), 4.41-4.27 (m, 1H), 4.19-3.47 (m, 14H), 3.20-3.00 (m, 4H), 2.98-2.57 (m, 8H), 2.43 (s, 3H), 2.30-2.05 (m, 5H), 2.06-1.80 (m, 10H), 1.80-1.63 (m, 8H), 1.55 (d, J=12.7 Hz, 1H), 1.49-1.31 (m, 4H), 1.14 (d, J=6.6 Hz, 6H).

Example 74

5-[(6-{1'-[1-(1-{2-[2,6-dioxopiperidin-3-yl]-1,3-dioxoisoindol-5-yl}piperidine-4-carbonyl)-4-methylpiperidine-4-carbonyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide Step 1: Synthesis of 4-fluoro-N-isopropyl-5-({3-isopropyl-6-[1'-(4-methylpiperidine-4-carbonyl)-2-oxo-1-[(1s,3s)-3-(piperidin-1-yl)cyclobutyl]spiro[indole-3,4'-piperidin]-6-yl]imidazo[4,5-c]pyridin-4-yl}amino)-2-methylbenzamide: The reaction was carried out according to General Procedure F, using Intermediate 1 (25 mg, 0.04 mmol) and 1-(tert-butoxycarbonyl)-4-methylpiperidine-4-carboxylic acid (8.6 mg, 0.04 mmol). Chromatography C provided tert-butyl 4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}-4-methylpiperidine-1-carboxylate which was directly submitted to General Procedure B to afford the title compound (15 mg, 51%).

Step 2: Synthesis of 5-[(6-{1'-[1-(1-{2-[2,6-dioxopiperidin-3-yl]-1,3-dioxoisoindol-5-yl}piperidine-4-carbonyl)-4-methylpiperidine-4-carbonyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide: The title compound was synthesized according to General Procedure F, using 4-fluoro-N-isopropyl-5-({3-isopropyl-6-[1'-(4-methylpiperidine-4-carbonyl)-2-oxo-1-[(1s,3s)-3-(piperidin-1-yl)cyclobutyl]spiro[indole-3,4'-piperidin]-6-yl]imidazo[4,5-c]pyridin-4-yl}amino)-2-methylbenzamide (10 mg, 0.01 mmol) and 1-{2-[2,6-dioxopiperidin-3-yl]-1,3-dioxoisoindol-5-yl}piperidine-4-carboxylic acid (5.0 mg, 0.01 mmol) as starting materials. Chromatography C provided the title compound (5.0 mg, 30%); LCMS: $C_{67}H_{79}FN_{12}O_8$ requires 1198.6, found 1200.4 [M+H]$^+$; $^1$H NMR (500 MHz, Methanol-$d_4$) δ 8.71 (s, 1H), 8.10 (d, J=8.2 Hz, 1H), 7.81-7.75 (m, 2H), 7.70 (d, J=8.4 Hz, 1H), 7.65 (s, 1H), 7.56 (d, J=7.9 Hz, 1H), 7.39 (d, J=2.2 Hz, 1H), 7.27 (d, J=8.6 Hz, 1H), 7.16 (d, J=11.9 Hz, 1H), 5.30 (t, J=6.6 Hz, 1H), 5.09 (dd, J=12.5, 5.5 Hz, 1H), 4.91 (d, J=2.7 Hz, 1H), 4.44-4.31 (m, 1H), 4.18-4.02 (m, 8H), 3.75-3.49 (m, 5H), 3.11 (d, J=12.8 Hz, 6H), 2.95-2.70 (m, 9H), 2.45 (s, 3H), 2.35 (s, 1H), 2.26 (s, 1H), 2.21-1.80 (m, 12H), 1.73 (d, J=6.6 Hz, 8H), 1.68-1.52 (m, 4H), 1.45 (s, 3H), 1.16 (d, J=6.6 Hz, 6H).

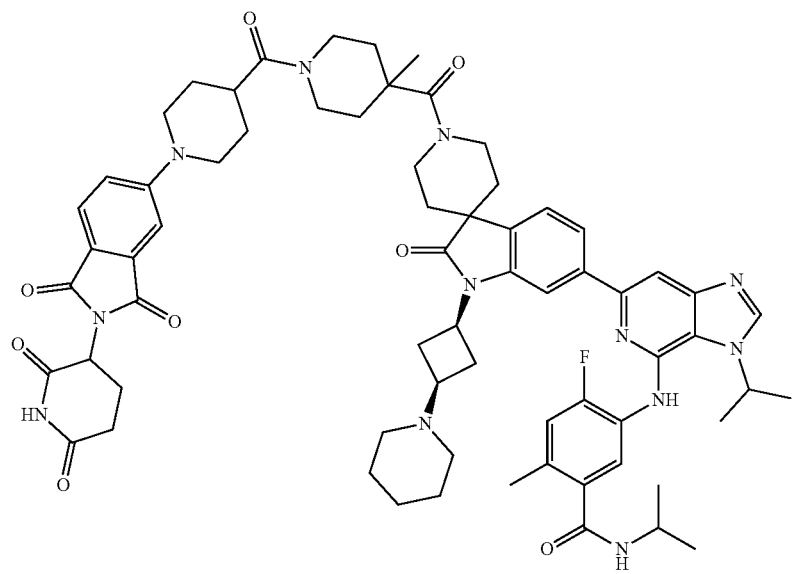 [SMILES: Cc1cc(F)c(Nc2nc(-c3ccc4c(c3)N([C@H]3C[C@@H](N5CCCCC5)C3)C(=O)C43CCN(C(=O)C4(C)CCN(C(=O)C5CCN(c6ccc7c(c6)C(=O)N(C6CCC(=O)NC6=O)C7=O)CC5)CC4)CC3)cc3ncn(C(C)C)c23)cc1C(=O)NC(C)C]

Example 75

5-[(6-{1'-[4-(4-{2-[2,6-dioxopiperidin-3-yl]-1,3-dioxo-2,3-dihydro-1H-isoindol-4-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

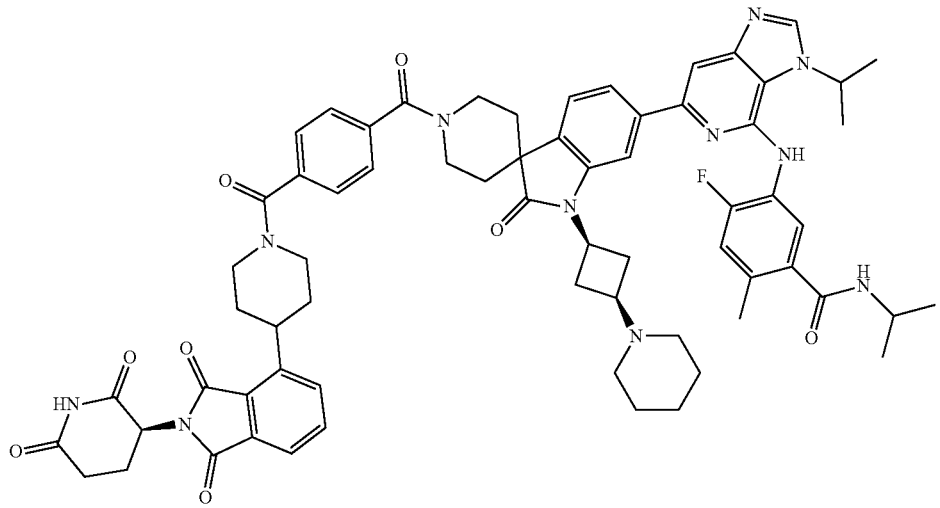 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCC(c6cccc7c6C(=O)N([C@H]6CCC(=O)NC6=O)C7=O)CC5)cc4)CC3)cc3ncn(C(C)C)c23)cc1C(=O)NC(C)C]

Step 1: Synthesis of 4-bromo-2-(2,6-dioxopiperidin-3-yl)isoindole-1,3-dione. To a mixture of 4-bromo-2-benzofuran-1,3-dione (5.0 g, 22 mmol, 1 equiv) and 3-aminopiperidine-2,6-dione hydrochloride (4.35 g, 26.4 mmol, 1.20 equiv) in AcOH (150 mL) were added NaOAc (2.17 g, 26.4 mmol, 1.2 equiv). The resulting mixture was stirred at 110° C. overnight under nitrogen atmosphere. The precipitated solids were collected by filtration and washed with water and EtOH. This resulted in the title compound (6.7 g, 90%)

Step 2: Synthesis of tert-butyl 4-[2-(2,6-dioxopiperidin-3-yl)-1,3-dioxoisoindol-4-yl]-3,6-dihydro-2H-pyridine-1-carboxylate. To a mixture of 4-bromo-2-(2,6-dioxopiperidin-3-yl)isoindole-1,3-dione (1.0 g, 3.0 mmol, 1 eq.) and tert-butyl 4-(4,4,5,5-tetramethyl-1,3,2-dioxaborolan-2-yl)-3,6-dihydro-2H-pyridine-1-carboxylate (0.92 g, 3.0 mmol, 1 eq.) in 1,4-dioxane (10 mL) were added $K_2CO_3$ (1.23 g, 8.90 mmol, 3 eq.) in $H_2O$ (1 mL) and Pd(dppf)$Cl_2$ (0.22 g, 0.30 mmol, 0.1 eq.). The resulting mixture was stirred at 100° C. overnight under nitrogen atmosphere. The resulting mixture was concentrated under vacuum. The residue was purified by Chromatography C to afford the title compound (350 mg, 27%).

Step-3: Synthesis of tert-butyl 4-[2-(2,6-dioxopiperidin-3-yl)-1,3-dioxoisoindol-4-yl]piperidine-1-carboxylate. To a mixture of tert-butyl 4-[2-(2,6-dioxopiperidin-3-yl)-1,3-dioxoisoindol-4-yl]-3,6-dihydro-2H-pyridine-1-carboxylate (460 mg, 1.05 mmol, 1 equiv) in THF (10 mL) were added Pd/C (460 mg). The resulting mixture was stirred at room temperature for 2 h under hydrogen atmosphere. The resulting mixture was filtered. The filtrate was concentrated under reduced pressure. The crude product was used in the next step directly without further purification.

Step 4: Synthesis of 2-(2,6-dioxopiperidin-3-yl)-4-(piperidin-4-yl)isoindole-1,3-dione hydrochloride. The reaction was carried out according to General Procedure B using tert-butyl 4-[2-(2,6-dioxopiperidin-3-yl)-1,3-dioxoisoindol-4-yl]piperidine-1-carboxylate (460 mg, 1.04 mmol) as the starting material. The resulting mixture was concentrated under vacuum and purified by Chromatography C to afford the title compound (271 mg, 69%).

Step 5: Synthesis of methyl 4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}benzoate. The title compound was synthesized according to General Procedure F using Intermediate 1 (41 mg, 0.06 mmol) and 4-(methoxycarbonyl)benzoic acid (10 mg, 0.06 mmol and isolated after Chromatography C (30 mg, 62%).

Step 6: Synthesis of 4-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)benzoic acid. The title compound was synthesized according to General Procedure C using methyl 4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}benzoate (30 mg, 0.03 mmol). The crude material was purified using Chromatography C to give the title compound (22 mg, 74%).

Step 7: Synthesis of 5-[(6-{1'-[4-(4-{2-[2,6-dioxopiperidin-3-yl]-1,3-dioxo-2,3-dihydro-1H-isoindol-4-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using 4-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)benzoic acid (8 mg, 0.01 mmol) and 2-[2,6-dioxopiperidin-3-yl]-4-(piperidin-4-yl)isoindole-1,3-dione (4 mg, 0.01 mmol) followed by reverse phase HPLC to provide the title compound (2.1 mg, 19%); LCMS: $C_{67}H_{72}FN_{11}O_8$ requires 1177.6, found 1178.2 [(M+H)]$^+$; $^1$H NMR (500 MHz, Methanol-$d_4$) δ 8.71 (s, 1H), 8.06 (d, J=8.1 Hz, 1H), 7.87-7.71 (m, 5H), 7.69-7.55 (m, 6H), 7.14 (d, J=11.8 Hz, 1H), 5.29 (q, J=6.6 Hz, 1H), 5.16 (s, 1H), 4.35 (p, J=8.4 Hz, 1H), 4.30-4.19 (m, 1H), 4.19-3.93 (m, 4H), 3.93-3.72 (m, 2H), 3.72-3.59 (m, 1H), 3.54 (d, J=12.5 Hz, 2H), 3.14-2.68 (m, 10H), 2.43 (s, 3H), 2.19-1.66 (m, 22H), 1.66-1.50 (m, 1H), 1.14 (d, J=6.5 Hz, 6H).

Example 76

5-[(6-{1'-[4-(4-{2-[2,6-dioxopiperidin-3-yl]-1,3-dioxo-2,3-dihydro-1H-isoindol-5-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide

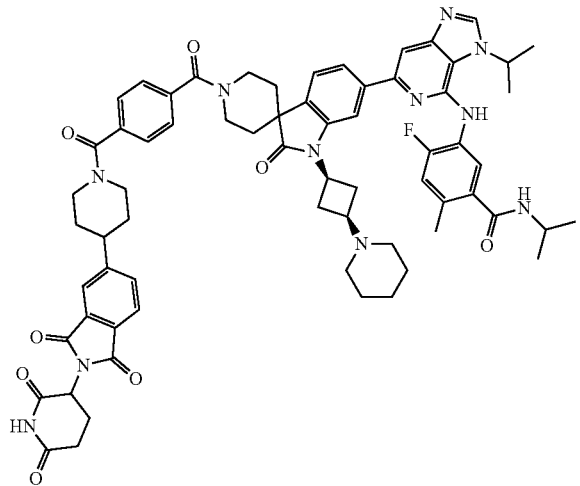 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCC(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of 5-bromo-2-(2,6-dioxopiperidin-3-yl)isoindole-1,3-dione. To a mixture of 5-bromo-2-benzofuran-1,3-dione (5.0 g, 22 mmol, 1 eq.) and 3-aminopiperidine-2,6-dione (2.82 g, 22.0 mmol, 1 equiv) in AcOH (100 mL) were added NaOAc (1.81 g, 22.0 mmol, 1 eq.). The resulting mixture was stirred at 120° C. overnight. The precipitated solids were collected by filtration and washed with water (3×100 mL). This resulted in the title compound (6 g, 73% yield).

Step 2: Synthesis of tert-butyl 4-[2-(2,6-dioxopiperidin-3-yl)-1,3-dioxoisoindol-5-yl]-3,6-dihydro-2H-pyridine-1-carboxylate. To a mixture of 5-bromo-2-(2,6-dioxopiperidin-3-yl)isoindole-1,3-dione (2.0 g, 5.93 mmol, 1 equiv) and tert-butyl 4-(4,4,5,5-tetramethyl-1,3,2-dioxaborolan-2-yl)-3,6-dihydro-2H-pyridine-1-carboxylate (2.2 g, 7.1 mmol, 1.2 eq.) in dioxane (50 mL) were added $K_3PO_4$ (2.52 g, 11.9 mmol, 2 equiv) and $Pd(PPh_3)_2C_{12}$ (0.83 g, 1.2 mmol, 0.2 equiv). The resulting mixture was stirred at 100° C. overnight under nitrogen atmosphere. The resulting mixture was concentrated under vacuum and the residue was purified by Chromatography A to yield the title compound (840 mg, 29% yield).

Step 3: Synthesis of tert-butyl 4-[2-(2,6-dioxopiperidin-3-yl)-1,3-dioxoisoindol-5-yl]piperidine-1-carboxylate. To a mixture of tert-butyl 4-[2-(2,6-dioxopiperidin-3-yl)-1,3-dioxoisoindol-5-yl]-3,6-dihydro-2H-pyridine-1-carboxylate (820 mg, 1.87 mmol, 1 eq.) in THF (20 mL) was added Pd/C (410 mg). The resulting mixture was stirred at room temperature overnight under hydrogen atmosphere. The resulting mixture was purged with nitrogen gas bubbled through the mixture and filtered over celite. The filtrate was concentrated under reduced pressure to give the title compound (600 mg, crude).

Step 4: Synthesis of 2-(2,6-dioxopiperidin-3-yl)-5-(piperidin-4-yl)isoindole-1,3-dione hydrochloride. The reaction was carried out according to General Procedure B using tert-butyl 4-[2-(2,6-dioxopiperidin-3-yl)-1,3-dioxoisoindol-5-yl]piperidine-1-carboxylate (590 mg, 1.34 mmol, 1 equiv) as the starting material. The residue was purified with Chromatography C to afford the title compound (289 mg, 56% yield).

Step 5: Synthesis of 5-[(6-{1'-[4-(4-{2-[2,6-dioxopiperidin-3-yl]-1,3-dioxo-2,3-dihydro-1H-isoindol-5-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide. The title compound was synthesized according to General Procedure F using 4-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)benzoic acid (8 mg, 0.01 mmol) and 2-(2,6-dioxopiperidin-3-yl)-5-(piperidin-4-yl)isoindoline-1,3-dione hydrochloride (4 mg, 0.01 mmol) followed by reverse phase HPLC to provide the title compound (3.3 mg, 30%); LCMS: $C_{67}H_{72}FN_{11}O_8$ requires 1177.6, found 1179.2 [(M+2H)]$^+$; $^1$H NMR (500 MHz, Methanol-$d_4$) δ 8.84 (s, 1H), 8.03 (d, J=8.1 Hz, 1H), 7.84 (d, J=5.9 Hz, 2H), 7.81-7.72 (m, 3H), 7.67-7.56 (m, 6H), 7.15 (d, J=11.8 Hz, 1H), 5.30 (p, J=6.6 Hz, 1H), 4.33 (q, J=8.4 Hz, 1H), 4.30-4.21 (m, 1H), 4.20-4.05 (m, 2H), 4.05-3.83 (m, 2H), 3.81-3.59 (m, 2H), 3.54 (d, J=12.4 Hz, 2H), 3.20-2.81 (m, 10H), 2.79-2.68 (m, 2H), 2.44 (s, 3H), 2.18-1.66 (m, 22H), 1.64-1.49 (m, 1H), 1.14 (d, J=6.5 Hz, 6H).

Example 77

5-{[6-(1'-{4-[4-({2-[2,6-dioxopiperidin-3-yl]-1,3-dioxo-2,3-dihydro-1H-isoindol-4-yl}methyl)piperidine-1-carbonyl]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide

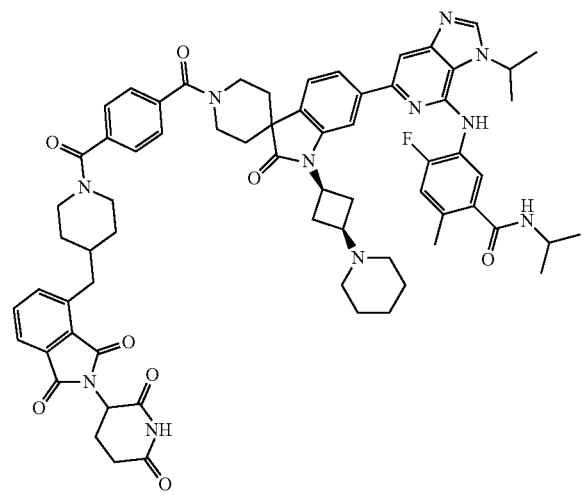 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCC(Cc6cccc7c6C(=O)N(C6CCC(=O)NC6=O)C7=O)CC5)cc4)CC3)cc3ncn(C(C)C)c23)cc1C(=O)NC(C)C]

217

Step 1: Synthesis of tert-butyl 4-[[2-(2,6-dioxopiperidin-3-yl)-1,3-dioxoisoindol-4-yl]methylidene]piperidine-1-carboxylate. To a mixture of 4-bromo-2-(2,6-dioxopiperidin-3-yl)isoindole-1,3-dione (1.0 g, 3.0 mmol, 1 eq.) and tert-butyl 4-[(4,4,5,5-tetramethyl-1,3,2-dioxaborolan-2-yl)methylidene]piperidine-1-carboxylate (0.96 g, 3.0 mmol, 1 equiv) in dioxane (5 mL) were added K$_2$CO$_3$ (1.23 g, 8.9 mmol, 3 eq.) in H$_2$O (0.5 mL) and Pd(dppf)Cl$_2$ (0.22 g, 0.1 eq.). The resulting mixture was stirred at 100° C. for 2 h under nitrogen atmosphere. The resulting mixture was concentrated under vacuum. The residue was purified Chromatography C to yield the title compound (500 mg, 33% yield).

Step 2: Synthesis of tert-butyl 4-[[2-(2,6-dioxopiperidin-3-yl)-1,3-dioxoisoindol-4-yl]methyl]piperidine-1-carboxylate. To a mixture of tert-butyl 4-[[2-(2,6-dioxopiperidin-3-yl)-1,3-dioxoisoindol-4-yl]methylidene]piperidine-1-carboxylate (490 mg, 1.08 mmol, 1 equiv) in THF (20 mL) was added Pd/C (245 mg). The resulting mixture was stirred at room temperature for 2 h under hydrogen atmosphere. Nitrogen gas was the bubbled through the mixture followed by filtration through celite. The filtrate was concentrated under reduced pressure. This resulted in the title compound (450 mg, crude).

Step 3: Synthesis of 2-(2,6-dioxopiperidin-3-yl)-4-(piperidin-4-ylmethyl)isoindole-1,3-dione hydrochloride. The reaction was carried out according to General Procedure B using tert-butyl 4-[[2-(2,6-dioxopiperidin-3-yl)-1,3-dioxoisoindol-4-yl]methyl]piperidine-1-carboxylate (490 mg, 1.08 mmol) as starting material. The crude residue was purified by Chromatography C to afford the title compound (226 mg, 53% yield).

Step 4: Synthesis of 5-{[6-(1'-{4-[4-({2-[2,6-dioxopiperidin-3-yl]-1,3-dioxo-2,3-dihydro-1H-isoindol-4-yl}methyl)piperidine-1-carbonyl]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide. The title compound was synthesized according to General Procedure F using 4-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)benzoic acid (8 mg, 0.01 mmol) and 2-(2,6-dioxopiperidin-3-yl)-4-(piperidin-4-ylmethyl)isoindole-1,3-dione hydrochloride (4 mg, 0.01 mmol) followed by reverse phase HPLC to provide the title compound (4.2 mg, 37%); LCMS: C$_{68}$H$_{74}$FN$_{11}$O$_8$ requires 1191.6, found 1192.4 [(M+H)]$^+$; $^1$H NMR (500 MHz, Methanol-d$_4$) δ 8.88 (s, 1H), 8.02 (d, J=8.1 Hz, 1H), 7.82-7.68 (m, 4H), 7.68-7.55 (m, 5H), 7.53 (d, J=7.8 Hz, 2H), 7.16 (d, J=11.9 Hz, 1H), 5.31 (p, J=6.6 Hz, 1H), 5.13 (dd, J=12.6, 5.5 Hz, 1H), 4.39-4.19 (m, 2H), 4.17-3.89 (m, 3H), 3.79-3.60 (m, 3H), 3.54 (d, J=12.1 Hz, 2H), 3.11 (d, J=7.2 Hz, 5H), 3.00-2.64 (m, 8H), 2.44 (s, 3H), 2.19-1.35 (m, 22H), 1.15 (d, J=6.6 Hz, 6H).

218

Example 78

5-((6-(1'-(4-(4-(2-(2,6-dioxopiperidin-3-yl)-1,3-dioxoisoindolin-5-yl)piperazine-1-carbonyl)benzoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

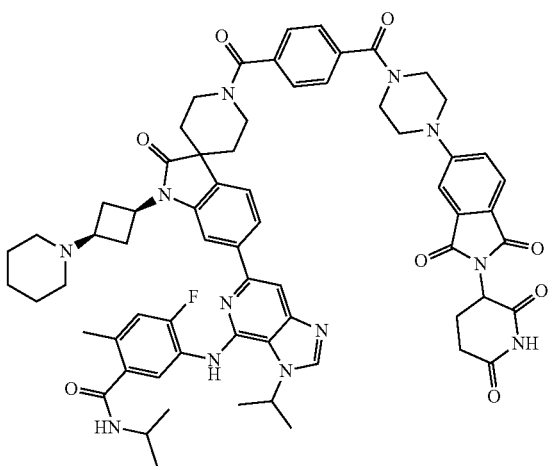 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of 2-(2,6-dioxopiperidin-3-yl)-5-(piperazin-1-yl)isoindoline-1,3-dione. The title compound was synthesized according to General Procedure A using 2-(2,6-dioxopiperidin-3-yl)-5-fluoroisoindoline-1, 3-di one (500 mg, 1.81 mmol) and 1-Boc-piperazine (337 mg, 1.81 mmol). Subsequent treatment of this material to General Procedure B afforded the title compound (278 mg, 45%).

Step 2: Synthesis of 4-(4-(2-(2,6-dioxopiperidin-3-yl)-1,3-dioxoisoindolin-5-yl)piperazine-1-carbonyl)benzoic acid. The title compound was synthesized according to General Procedure F using 2-(2,6-dioxopiperidin-3-yl)-5-(piperazin-1-yl)isoindoline-1,3-dione (100 mg, 0.29 mmol) and 4-tert-butoxycarbonylbenzoic acid (65 mg, 0.29 mmol). Subsequent treatment of this material to General Procedure B afforded the title compound (201 mg, 70%).

Step 3: Synthesis of 5-((6-(1'-(4-(4-(2-(2,6-dioxopiperidin-3-yl)-1,3-dioxoisoindolin-5-yl)piperazine-1-carbonyl)benzoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (15 mg), 4-(4-(2-(2,6-dioxopiperidin-3-yl)-1,3-dioxoisoindolin-5-yl)piperazine-1-carbonyl)benzoic acid (10.8 mg) as starting materials. Crude material was purified by reverse phase HPLC to provide the title compound (6.7 mg, 25%); LCMS: C$_{66}$H$_{71}$FN$_{12}$O$_8$ requires: 1178.6, found: m/z=1179.9 [M+H]$^+$. $^1$H NMR (500 MHz, DMSO-d$_6$) δ: 11.09 (s, 1H), 9.39 (d, J=9.9 Hz, 1H), 8.71 (s, 1H), 8.43 (s, 1H), 8.15 (d, J=7.8 Hz, 1H), 7.90 (s, 1H), 7.72 (dd, J=14.9, 8.1 Hz, 2H), 7.64-7.56 (m, 6H), 7.52 (s, 1H), 7.38 (d, J=2.3 Hz, 1H), 7.28 (dd, J=8.5, 2.3 Hz, 1H), 7.20 (d, J=12.1 Hz, 1H), 5.31 (p, J=6.7 Hz, 1H), 5.09 (dd, J=12.7, 5.5 Hz, 1H), 4.23 (q, J=8.3 Hz, 3H), 4.06 (dt, J=13.7, 6.7 Hz, 3H), 3.95-3.38 (m, 12H), 3.01-2.78 (m, 8H), 2.38 (s, 3H), 2.04 (dd, J=11.4, 5.7 Hz, 1H), 1.89-1.81 (m, 4H), 1.73 (d, J=12.3 Hz, 2H), 1.61 (d, J=6.6 Hz, 7H), 1.44 (t, J=13.2 Hz, 2H), 1.11 (d, J=6.6 Hz, 6H).

Example 79

5-((6-(1'-((1s,4S)-4-(4-(2-(2,6-dioxopiperidin-3-yl)-1,3-dioxoisoindolin-5-yl)piperazine-1-carbonyl)cyclohexane-1-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

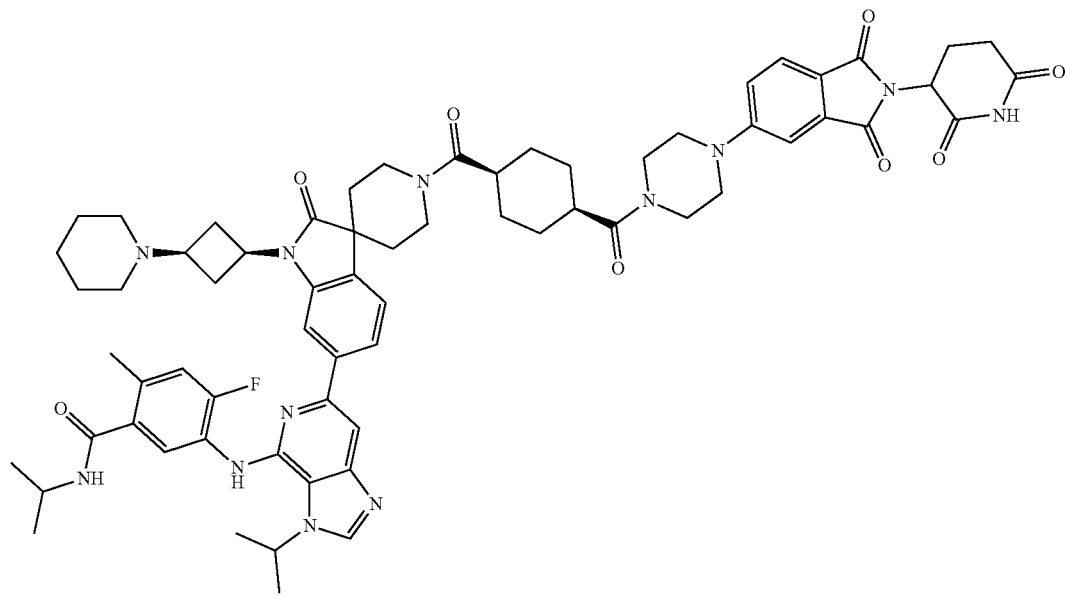 [SMILES: Cc1cc(F)c(Nc2nc(-c3ccc4c(c3)N([C@H]3C[C@@H](N5CCCCC5)C3)C(=O)C43CCN(C(=O)[C@H]4CC[C@@H](C(=O)N5CCN(c6ccc7c(c6)C(=O)N(C6CCC(=O)NC6=O)C7=O)CC5)CC4)CC3)cc3ncn(C(C)C)c23)cc1C(=O)NC(C)C]

Step 1: Synthesis of (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid. The reaction was carried out according to General Procedure F using Intermediate 1 (44 mg 0.06 mmol) and (1s,4s)-4-(methoxycarbonyl)cyclohexane-1-carboxylic acid (14.3 mg, 0.08 mmol). The title compound was isolated (32 mg, 62%) after Chromatography C.

Step 2: Synthesis of (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid. The reaction was carried out according to General Procedure C using (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid (50 mg, 0.06 mmol) as starting material. The resulting compound was used without further purification.

Step 3: Synthesis of 5-((6-(1'-((1s,4S)-4-(4-(2-(2,6-dioxopiperidin-3-yl)-1,3-dioxoisoindolin-5-yl)piperazine-1-carbonyl)cyclohexane-1-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid (17 mg), and 2-(2,6-dioxopiperidin-3-yl)-5-(piperazin-1-yl)isoindoline-1,3-dione (11.6 mg) as starting materials. Crude material was purified by reverse phase HPLC to provide the title compound (17 mg, 68%); LCMS: $C_{66}H_{77}FN_{12}O_8$ requires: 1184.6, found: m/z=1186.0 [M+H]$^+$; $^1$H NMR (500 MHz, DMSO-d$_6$) δ: 11.09 (s, 1H), 9.36 (s, 1H), 8.66 (s, 1H), 8.40 (s, 1H), 8.15 (d, J=7.9 Hz, 1H), 7.89 (s, 1H), 7.73 (d, J=8.4 Hz, 1H), 7.68 (d, J=7.9 Hz, 1H), 7.61 (d, J=8.2 Hz, 1H), 7.53 (d, J=7.5 Hz, 2H), 7.37 (d, J=2.3 Hz, 1H), 7.28 (dd, J=8.6, 2.3 Hz, 1H), 7.19 (d, J=12.1 Hz, 1H), 5.30 (p, J=6.5 Hz, 1H), 5.09 (dd, J=12.8, 5.4 Hz, 1H), 4.22 (p, J=8.3 Hz, 1H), 4.05 (h, J=6.8 Hz, 1H), 3.95-3.33 (m, 11H), 3.00-2.54 (m, 12H), 2.37 (s, 3H), 2.08-1.99 (m, 1H), 1.89-1.34 (m, 26), 1.11 (d, J=6.6 Hz, 6H).

Example 80

5-((6-(1'-(2-(((1R,4R)-4-((2-(2,6-dioxopiperidin-3-yl)-1,3-dioxoisoindolin-4-yl)amino)cyclohexyl)acetyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

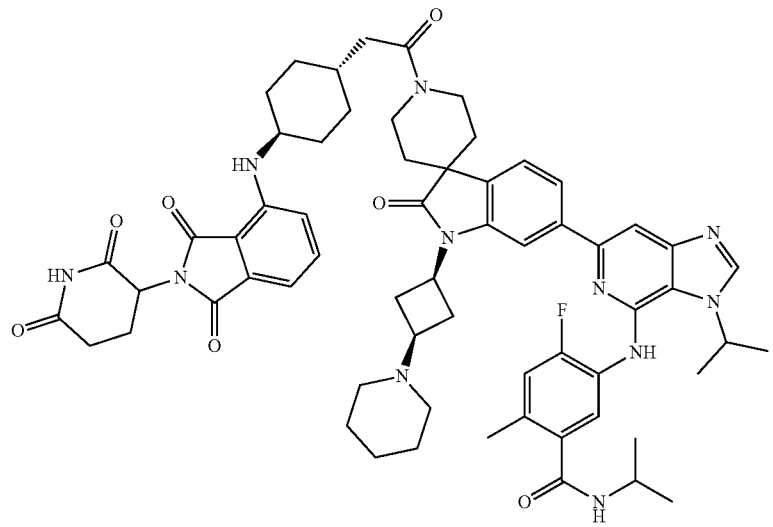 [SMILES: Cc1cc(F)c(Nc2nc(-c3ccc4c(c3)N([C@H]3C[C@@H](N5CCCCC5)C3)C(=O)C43CCN(C(=O)C[C@H]4CC[C@H](Nc5cccc6c5C(=O)N(C5CCC(=O)NC5=O)C6=O)CC4)CC3)cc3ncn(C(C)C)c23)cc1C(=O)NC(C)C]

Step 1: Synthesis of [(1r,4r)-4-{[2-(2,6-dioxopiperidin-3-yl)-1,3-dioxoisoindol-4-yl]amino}cyclohexyl]acetic acid. The reaction was carried out according to General Procedure A using [(1r,4r)-4-aminocyclohexyl]acetic acid (196 mg, 1.24 mmol) and 2-(2,6-dioxopiperidin-3-yl)-4-fluoroisoindole-1,3-dione (200 mg, 0.72 mmol) followed by Chromatography C to afford the title compound (46 mg, 15%).

Step 2: Synthesis of 5-((6-(1'-(2-(((1R,4R)-4-((2-(2,6-dioxopiperidin-3-yl)-1,3-dioxoisoindolin-4-yl)amino)cyclohexyl)acetyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (25 mg), [(1r,4r)-4-{[2-(2,6-dioxopiperidin-3-yl)-1,3-dioxoisoindol-4-yl]amino}cyclohexyl]acetic acid (15 mg) as starting materials. Crude material was purified by reverse phase HPLC to provide the title compound (13.6 mg, 34%); LCMS: $C_{62}H_{72}FN_{11}O_7$ requires: 1101.6, found: m/z=1102.9 [M+H]$^+$; $^1$H NMR (500 MHz, DMSO-d$_6$) δ: 11.11 (s, 1H), 9.31 (s, 1H), 8.62 (s, 1H), 8.38 (s, 1H), 8.14 (d, J=7.9 Hz, 1H), 7.89 (s, 1H), 7.64-7.58 (m, 2H), 7.56-7.50 (m, 2H), 7.18 (dd, J=10.4, 7.1 Hz, 2H), 7.05 (d, J=6.9 Hz, 1H), 6.21 (d, J=8.2 Hz, 1H), 5.29 (p, J=6.8 Hz, 1H), 5.06 (dd, J=12.7, 5.5 Hz, 1H), 4.23 (t, J=8.3 Hz, 1H), 4.09-4.01 (m, 1H), 3.93-3.73 (m, 4H), 3.04-2.77 (m, 8H), 2.66-2.56 (m, 2H), 2.39-2.38 (m, 5H), 2.08-2.00 (m, 4H), 1.90-1.52 (m, 18H), 1.48-1.15 (m, 7H), 1.11 (d, J=6.6 Hz, 6H).

Example 81

5-((6-(1'-((3R)-1-((1R,4R)-4-((2-(2,6-dioxopiperidin-3-yl)-1,3-dioxoisoindolin-5-yl)amino)cyclohexane-1-carbonyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

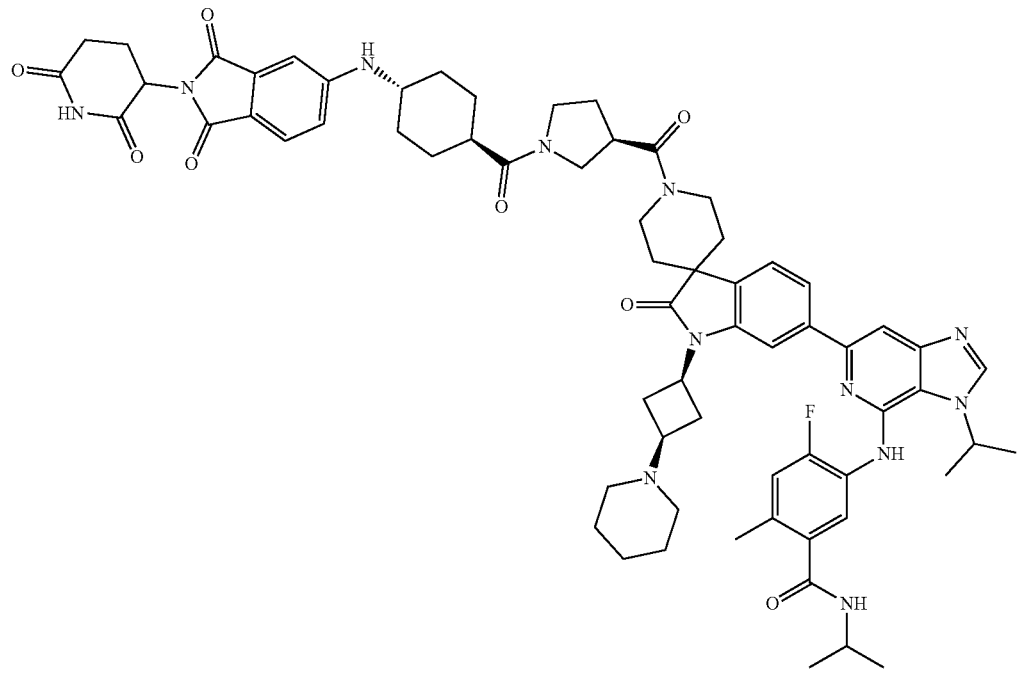 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)[C@H]5CC[C@H](Nc6ccc7c(c6)C(=O)N(C6CCC(=O)NC6=O)C7=O)CC5)C4)CC3)cc3ncn(C(C)C)c23)cc1C(=O)NC(C)C]

Step 1: Synthesis of (1s,4s)-4-({2-[2,6-dioxopiperidin-3-yl]-1,3-dioxoisoindol-5-yl}amino)cyclohexane-1-carboxylic acid. The reaction was carried out according to General Procedure A using (1r,4r)-4-aminocyclohexane-1-carboxylic acid (131 mg, 0.91 mmol) and 2-(2,6-dioxopiperidin-3-yl)-5-fluoroisoindole-1,3-dione (200 mg, 0.72 mmol) followed by Chromatography C to afford the title compound (36 mg, 120%).

Step 2: Synthesis of 4-fluoro-N-isopropyl-5-[(3-isopropyl-6-{2-oxo-1'-[(3R)-pyrrolidine-3-carbonyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide. The reaction was run according to General Procedure F using Intermediate 1 (174 mg, 0.25 mmol) and (3R)-1-(tert-butoxycarbonyl)pyrrolidine-3-carboxylic acid (63.58 g, 0.3 mmol). The product of this reaction is purified by Chromatography C, then subjected to General Procedure B to provide the title compound (48.7 mg, 25% over two steps).

Step 3: Synthesis of 5-((6-(1'-((3R)-1-((1r,4R)-4-((2-(2,6-dioxopiperidin-3-yl)-1,3-dioxoisoindolin-5-yl)amino)cyclohexane-1-carbonyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using 4-fluoro-N-isopropyl-5-[(3-isopropyl-6-{2-oxo-1'-[(3R)-pyrrolidine-3-carbonyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide (30.2 mg), (1s,4s)-4-({2-[2,6-dioxopiperidin-3-yl]-1,3-dioxoisoindol-5-yl}amino)cyclohexane-1-carboxylic acid (15 mg) as starting materials. Crude material was purified by reverse phase HPLC to provide the title compound (32.7 mg, 73%); LCMS: $C_{66}H_{77}FN_{12}O_8$ requires: 1184.6, found: m/z=1186.0 [M+H]$^+$; $^1$H NMR (500 MHz, DMSO-d$_6$) δ: 11.06 (s, 1H), 9.32 (s, 1H), 8.68 (d, J=5.9 Hz, 1H), 8.41 (s, 1H), 8.14 (dd, J=7.8, 3.3 Hz, 1H), 7.89 (s, 1H), 7.68 (d, J=7.8 Hz, 1H), 7.61 (dd, J=8.3, 4.3 Hz, 1H), 7.57 (t, J=7.2 Hz, 2H), 7.52 (s, 1H), 7.19 (d, J=11.8 Hz, 1H), 7.00 (t, J=2.7 Hz, 1H), 6.91-6.88 (m, 1H), 5.30 (p, J=6.8 Hz, 1H), 5.03 (dd, J=12.6, 5.5 Hz, 1H), 4.26-4.18 (m, 2H), 4.08-4.01 (m, 2H), 3.89 (d, J=46.9 Hz, 7H), 3.05-2.72 (m, 8H), 2.38 (s, 3H), 2.21-1.67 (m, 17H), 1.60 (d, J=6.6 Hz, 10H), 1.52-1.37 (m, 3H), 1.34-1.22 (m, 3H), 1.11 (d, J=6.4 Hz, 6H).

Example 82

5-((6-(1'-((3R)-1-(2-((1R,4R)-4-((2-(2,6-dioxopiperidin-3-yl)-1,3-dioxoisoindolin-4-yl)amino)cyclohexyl)acetyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

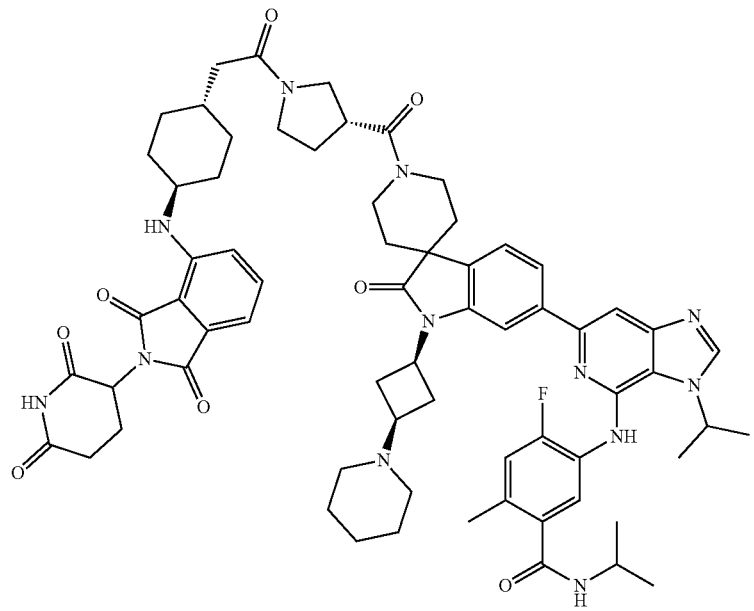 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)C[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of 4-fluoro-N-isopropyl-5-[(3-isopropyl-6-{2-oxo-1'-[(3R)-pyrrolidine-3-carbonyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide. The reaction was run according to General Procedure F using Intermediate 1 (174 mg, 0.25 mmol) and (3R)-1-(tert-butoxycarbonyl)pyrrolidine-3-carboxylic acid (63.6 mg, 0.3 mmol). The product of this reaction is purified by Chromatography C, then subjected to General Procedure B to provide the title compound (49 mg, 25% over two steps).

Step 2: Synthesis of 5-((6-(1'-((3R)-1-(2-((1r,4R)-4-((2-(2,6-dioxopiperidin-3-yl)-1,3-dioxoisoindolin-4-yl)amino)cyclohexyl)acetyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using 4-fluoro-N-isopropyl-5-[(3-isopropyl-6-{2-oxo-1'-[(3R)-pyrrolidine-3-carbonyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide (19.5 mg), of [(1r,4r)-4-{[2-(2,6-dioxopiperidin-3-yl)-1,3-dioxoisoindol-4-yl]amino}cyclohexyl]acetic acid (10 mg) as starting materials. Crude material was purified by reverse phase HPLC to provide the title compound (8 mg, 27%); LCMS: $C_{67}H_{79}FN_{12}O_8$ requires: 1198.6, found: m/z=1199.9 [M+H]$^+$; $^1$H NMR (500 MHz, DMSO-d$_6$) δ: 11.10 (s, 1H), 9.29 (s, 1H), 8.61 (s, 1H), 8.38 (s, 1H), 8.14 (d, J=7.8 Hz, 1H), 7.89 (d, J=2.9 Hz, 1H), 7.68 (d, J=7.8 Hz, 1H), 7.63-7.51 (m, 4H), 7.17 (dd, J=14.5, 10.3 Hz, 2H), 7.04 (d, J=7.1 Hz, 1H), 6.19 (d, J=8.1 Hz, 1H), 5.34-5.25 (m, 1H), 5.05 (dd, J=12.8, 5.5 Hz, 1H), 4.23 (s, 1H), 4.08-4.01 (m, 1H), 3.94-3.74 (m, 2H), 3.02-2.71 (m, 6H), 2.64-2.55 (m, 2H), 2.37 (s, 3H), 2.22-1.92 (m, 8H), 1.90-1.54 (m, 24H), 1.44-1.34 (m, 1H), 1.36-1.04 (m, 14H).

Example 83

5-((6-(1'-(6-(4-(2-(2,6-dioxopiperidin-3-yl)-1,3-di-oxoisoindolin-4-yl)piperazin-1-yl)nicotinoyl)-2-oxo-1-((1s,3s)-3-(piperidin-1-yl)cyclobutyl)spiro[indo-line-3,4'-piperidin]-6-yl)-3-isopropyl-3H-imidazo[4,5-c]pyridin-4-yl)amino)-4-fluoro-N-isopropyl-2-methylbenzamide

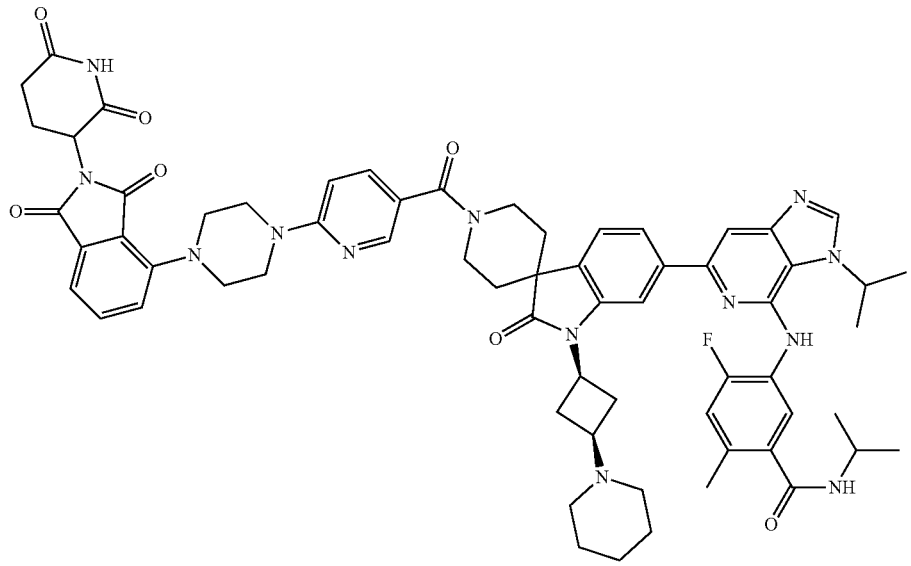 [SMILES: Cc1cc(F)c(Nc2nc(-c3ccc4c(c3)N([C@H]3C[C@@H](N5CCCCC5)C3)C(=O)C43CCN(C(=O)c4ccc(N5CCN(c6cccc7c6C(=O)N(C6CCC(=O)NC6=O)C7=O)CC5)nc4)CC3)cc3ncn(C(C)C)c23)cc1C(=O)NC(C)C]

Step 1: Synthesis of tert-butyl 4-[5-(methoxycarbonyl)pyridin-2-yl]piperazine-1-carboxylate. methyl 6-chloropyridine-3-carboxylate (532 mg, 3.08 mmol) and tert-butyl piperazine-1-carboxylate (631 mg, 3.39 mmol) were dissolved in DMF (4.85 mL). Thereafter, TEA (0.86 mL, 6.17 mmol) was added, and the reaction mixture was heated at 80° C. for 16 hours. The reaction mixture was poured into water and the precipitate was collected by filtration. The filtercake was dried under a stream of nitrogen while applying vacuum to yield the title compound (1.18 g, 126%).

Step 2: Synthesis of 6-(piperazin-1-yl)pyridine-3-carboxylic acid. A mixture of tert-butyl 4-[5-(methoxycarbonyl)pyridin-2-yl]piperazine-1-carboxylate (1.12 g, 3.49 mmol) and 2M NaOH (15 mL) in THF (15 mL) and EtOH (15 mL) was stirred at 60° C. for 4 h The mixture was cooled to room temperature and concentrated in vacuo to obtain a slurry, aq. HCl (1 M) was added to adjust to pH 7, and the mixture was filtered and dried by blowing nitrogen over the filtercake while applying vacuum to give the title compound as a white solid (797 mg, 74%). This product was then subjected to General Procedure B to afford the title compound (quant.)

Step 3: Synthesis of 6-{4-[2-(2,6-dioxopiperidin-3-yl)-1,3-dioxoisoindol-4-yl]piperazin-1-yl}pyridine-3-carboxylic acid. The reaction was carried out according to General Procedure A using 6-(piperazin-1-yl)pyridine-3-carboxylic acid (265 mg, 1.09 mmol) and 2-(2,6-dioxopiperidin-3-yl)-4-fluoroisoindole-1,3-dione (250 mg, 0.91 mmol) followed by Chromatography C to afford the title compound (313 mg, 75%).

Step 4: Synthesis of 5-((6-(1'-(6-(4-(2-(2,6-dioxopiperidin-3-yl)-1,3-dioxoisoindolin-4-yl)piperazin-1-yl)nicotinoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (20 mg), 6-{4-[2-(2,6-dioxopiperidin-3-yl)-1,3-dioxoisoindol-4-yl]piperazin-1-yl}pyridine-3-carboxylic acid (14.4 mg) as starting materials. Crude material was purified by reverse phase HPLC to provide the title compound (1.2 mg, 3.2%); LCMS: $C_{64}H_{70}FN_{13}O_7$ requires: 1151.6, found: m/z=1152.9 [M+H]$^+$; $^1$H NMR (500 MHz, DMSO-$d_6$) δ: 11.11 (s, 1H), 8.56 (s, 1H), 8.35 (d, J=12.2 Hz, 1H), 8.14 (d, J=7.7 Hz, 1H), 7.90 (s, 1H), 7.77-7.68 (m, 2H), 7.62 (d, J=7.1 Hz, 1H), 7.53 (s, 1H), 7.42 (d, J=7.8 Hz, 1H), 7.19 (d, J=12.1 Hz, 1H), 6.97 (d, J=8.7 Hz, 1H), 5.31-5.21 (m, 1), 5.16-5.08 (m, 1H), 4.26-3.84 (m, 4H), 3.80 (s, 3H), 3.02-2.71 (m, 6H), 2.66 (s, 3H), 2.07-1.44 (m, 30H), 1.25 (s, 3H), 1.11 (d, J=6.5 Hz, 6H).

Example 84

5-((6-(1'-(5-(4-(2-(2,6-dioxopiperidin-3-yl)-1,3-dioxoisoindolin-4-yl)piperazin-1-yl)pyrazine-2-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

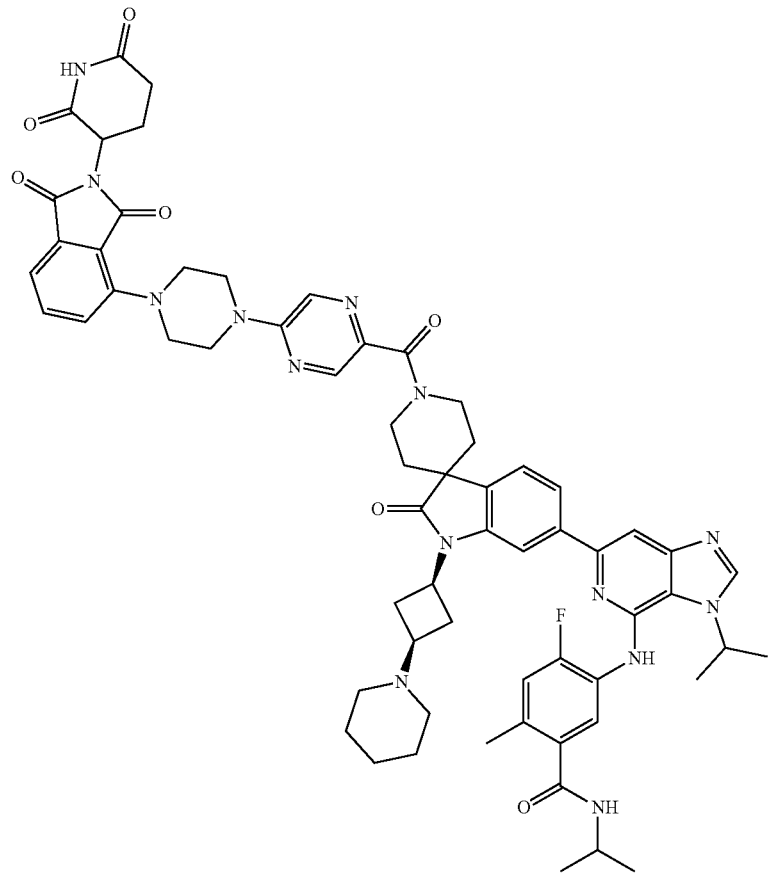 [SMILES: Cc1cc(F)c(Nc2nc(-c3ccc4c(c3)N([C@H]3C[C@@H](N5CCCCC5)C3)C(=O)C43CCN(C(=O)c4cnc(N5CCN(c6cccc7c6C(=O)N(C6CCC(=O)NC6=O)C7=O)CC5)cn4)CC3)cc3ncn(C(C)C)c23)cc1C(=O)NC(C)C]

Step 1: Synthesis of methyl 5-[4-(tert-butoxycarbonyl)piperazin-1-yl]pyrazine-2-carboxylate. methyl 5-chloropyrazine-2-carboxylate (532 mg, 3.08 mmol) and tert-butyl piperazine-1-carboxylate (631 mg, 3.39 mmol) were dissolved in DMF (4.85 mL). TEA (0.86 mL, 6.17 mmol) was added and the reaction mixture was heated at 80° C. for 3 hours. The reaction mixture was poured into water and filtered. The filtercake was dried under a stream of nitrogen while applying vacuum to yield the title compound (950 mg, 96%).

Step 2: Synthesis of 5-(piperazin-1-yl)pyrazine-2-carboxylic acid. A mixture of methyl 5-[4-(tert-butoxycarbonyl)piperazin-1-yl]pyrazine-2-carboxylate (950 mg, 2.95 mmol) and 2M NaOH (12.7 mL) in THF (12.7 mL) and EtOH (12.7 mL) was stirred at 60° C. for 4 h. The mixture was cooled to room temperature and concentrated in vacuo to obtain a slurry. Aqueous HCl (1 M) was added to adjust to pH 7. The mixture was filtered and dried by blowing nitrogen over the filtercake while applying vacuum to give the title compound as a white solid (787 mg, 87%). This product was then subjected to General Procedure B to afford the title compound (753 mg, 141%).

Step 3: Synthesis of 5-{4-[2-(2,6-dioxopiperidin-3-yl)-1,3-dioxoisoindol-5-yl]piperazin-1-yl}pyrazine-2-carboxylic acid. The reaction was carried out according to General Procedure A using 5-(piperazin-1-yl)pyrazine-2-carboxylic acid hydrochloride (243 mg, 1.00 mmol) and 2-(2,6-dioxopiperidin-3-yl)-4-fluoroisoindole-1,3-dione (250 mg, 0.91 mmol) followed by Chromatography C to afford the title compound (116 mg, 28%).

Step 4: Synthesis of 5-((6-(1'-(5-(4-(2-(2,6-dioxopiperidin-3-yl)-1,3-dioxoisoindolin-4-yl)piperazin-1-yl)pyrazine-2-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (15 mg), 5-{4-[2-(2,6-dioxopiperidin-3-yl)-1,3-dioxoisoindol-4-yl]piperazin-1-yl}pyrazine-2-carboxylic acid (10.84 mg) as starting materials. Crude material was purified by reverse phase HPLC to provide the title compound (11.7 mg, 48%); LCMS: $C_{63}H_{69}FN_{14}O_7$ requires: 1152.6, found: m/z=1153.89 [M+H]$^+$; $^1$H NMR (500 MHz, DMSO-$d_6$) δ: 11.12 (s, 1H), 9.31 (s, 1H), 8.62 (s, 1H), 8.49 (s, 1H), 8.39 (s, 2H), 8.15 (d, J=7.3 Hz, 1H), 7.89 (s, 1H), 7.76 (t, J=7.9 Hz, 1H), 7.69 (d, J=8.0 Hz, 1H), 7.63-7.52 (m, 3H), 7.45-7.40 (m, 2H), 7.19 (d, J=12.0 Hz, 1H), 5.33-5.26 (m, 1H), 5.14 (dd, J=12.9, 5.4 Hz, 1H), 4.23 (t, J=8.6 Hz, 1H), 4.10-3.87 (m, 9H), 3.03-2.77 (m, 10H), 2.38 (s, 3H), 2.10-2.01 (m, 1H), 1.93-1.53 (m, 19H), 1.49-1.37 (m, 1H), 1.25 (s, 1H), 1.11 (d, J=6.5 Hz, 6H).

Example 85

5-((6-(1'-(6-(4-(2-(2,6-dioxopiperidin-3-yl)-1,3-di-
oxoisoindolin-5-yl)piperazin-1-yl)nicotinoyl)-2-oxo-
1-((1s,3s)-3-(piperidin-1-yl)cyclobutyl)spiro[indo-
line-3,4'-piperidin]-6-yl)-3-isopropyl-3H-imidazo[4,
5-c]pyridin-4-yl)amino)-4-fluoro-N-isopropyl-2-
methylbenzamide

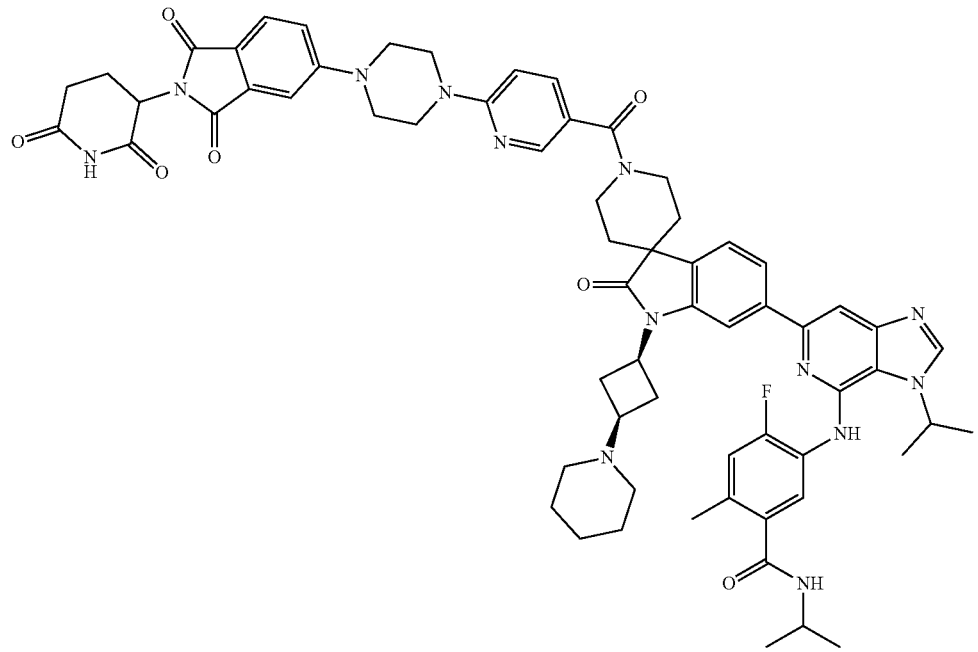 [SMILES: Cc1cc(F)c(Nc2nc(-c3ccc4c(c3)N([C@H]3C[C@@H](N5CCCCC5)C3)C(=O)C43CCN(C(=O)c4ccc(N5CCN(c6ccc7c(c6)C(=O)N(C6CCC(=O)NC6=O)C7=O)CC5)nc4)CC3)cc3ncn(C(C)C)c23)cc1C(=O)NC(C)C]

Step 1: Synthesis of tert-butyl 4-[5-(methoxycarbonyl)
pyridin-2-yl]piperazine-1-carboxylate. Methyl 6-chloro-
pyridine-3-carboxylate (532 mg, 3.08 mmol) and tert-butyl
piperazine-1-carboxylate (631 mg, 3.39 mmol) were dissolved in DMF (4.85 mL). Thereafter TEA (0.86 mL, 6.2 mmol) was added, and the reaction mixture was heated at 80° C. for 16 hours. The reaction mixture was poured into water and the precipitate was collected by filtration. The filter cake was dried under a stream of nitrogen while applying vacuum to yield the title compound (1.18 g, 126%).

Step 2: Synthesis of 6-(piperazin-1-yl)pyridine-3-carboxylic acid. A mixture of tert-butyl 4-[5-(methoxycarbonyl)pyridin-2-yl]piperazine-1-carboxylate (1.12 g, 3.49 mmol) and 2M NaOH (15 mL) in THF (15 mL) and EtOH (15 mL) was stirred at 60° C. for 4 h. The mixture was cooled to room temperature and concentrated in vacuo to obtain a slurry, aq, HCl (1 M) was added to adjust pH to 7, and the mixture was filtered and dried by blowing nitrogen over the filtercake while applying vacuum to give the title compound as a white solid (797 mg, 74%). This product was then subjected to General Procedure B to afford the title compound (690 mg, 130%).

Step 3: Synthesis of 6-{4-[2-(2,6-dioxopiperidin-3-yl)-1,3-dioxoisoindol-5-yl]piperazin-1-yl}pyridine-3-carboxylic acid. The reaction was carried out according to General Procedure A using 6-(piperazin-1-yl)pyridine-3-carboxylic acid hydrochloride (221 mg, 0.91 mmol) and 2-(2,6-dioxopiperidin-3-yl)-5-fluoroisoindole-1,3-dione (250 mg, 0.91 mmol) followed by Chromatography C to afford the title compound (284 mg, 68%).

Step 4: Synthesis of 5-((6-(1'-(6-(4-(2-(2,6-dioxopiperidin-3-yl)-1,3-dioxoisoindolin-5-yl)piperazin-1-yl)nicotinoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (15 mg), 6-{4-[2-(2,6-dioxopiperidin-3-yl)-1,3-dioxoisoindol-5-yl]piperazin-1-yl}pyridine-3-carboxylic acid (10.82 mg) as starting materials. Crude material was purified by reverse phase HPLC to provide the title compound (12.2 mg, 44%); LCMS: $C_{64}H_{70}FN_{13}O_7$ requires: 1151.55, found: m/z=1152.89 [M+H]$^+$; $^1$H NMR (500 MHz, DMSO-d$_6$) δ: 11.10 (s, 1H), 9.31 (s, 1H), 8.67 (s, 1H), 8.41 (s, 1H), 8.34 (s, 1H), 8.15 (d, J=7.7 Hz, 1H), 7.90 (s, 1H), 7.75-7.69 (m, 3H), 7.61 (d, J=8.1 Hz, 2H), 7.53 (s, 1H), 7.40 (s, 1H), 7.31 (d, J=8.8 Hz, 1H), 7.22-7.18 (m, 1H), 6.95 (d, J=8.8 Hz, 1H), 5.31 (p, J=6.4 Hz, 1H), 5.10 (dd, J=12.9, 5.4 Hz, 1H), 4.22 (q, J=8.1 Hz, 1H), 4.06 (d, J=6.8 Hz, 1H), 3.90-3.75 (m, 2H), 3.65 (s, 2H), 2.98-2.75 (m, 10H), 2.62-2.54 (m, 2H), 2.38 (s, 3H), 2.07-2.00 (m, 2H), 1.89-1.50 (m, 19H), 1.44 (t, J=13.3 Hz, 2H), 1.31-1.24 (m, 2H), 1.12 (d, J=6.5 Hz, 6H).

Example 86

5-((6-(1'-((3R)-1-(5-(4-(2-(2,6-dioxopiperidin-3-yl)-1,3-dioxoisoindolin-4-yl)piperazin-1-yl)pyrazine-2-carbonyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

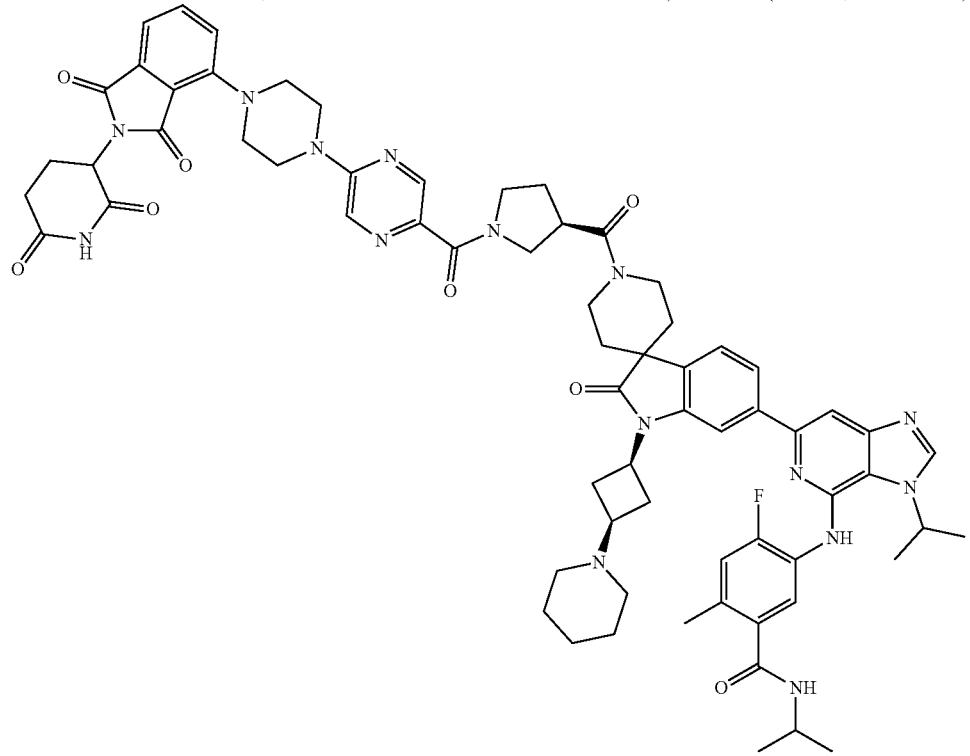 [SMILES: Cc1cc(F)c(Nc2nc(-c3ccc4c(c3)N([C@H]3C[C@@H](N5CCCCC5)C3)C(=O)C43CCN(C(=O)[C@@H]4CCN(C(=O)c5cnc(N6CCN(c7cccc8c7C(=O)N(C7CCC(=O)NC7=O)C8=O)CC6)cn5)C4)CC3)cc3ncn(C(C)C)c23)cc1C(=O)NC(C)C]

Step 1: Synthesis of methyl 5-[4-(tert-butoxycarbonyl)piperazin-1-yl]pyrazine-2-carboxylate. Methyl 5-chloropyrazine-2-carboxylate (532 mg, 3.08 mmol) and tert-butyl piperazine-1-carboxylate (631 mg, 3.39 mmol) were dissolved in DMF (4.85 mL). TEA (0.86 mL, 6.2 mmol) was added and the reaction mixture was heated at 80° C. for 3 hours. The reaction mixture was poured into water and filtered. The filtercake was dried under a stream of nitrogen while applying vacuum to yield the title compound (950 mg, 96%).

Step 2: Synthesis of 5-(piperazin-1-yl)pyrazine-2-carboxylic acid. A mixture of methyl 5-[4-(tert-butoxycarbonyl)piperazin-1-yl]pyrazine-2-carboxylate (950 mg, 2.95 mmol) and 2M NaOH (12.7 mL) in THF (12.7 mL) and EtOH (12.7 mL) was stirred at 60° C. for 4 h. The mixture was cooled to room temperature and concentrated in vacuo to obtain a slurry. Aqueous HCl (1 M) was added to adjust to pH 7. The mixture was filtered and dried by blowing nitrogen over the filtercake while applying vacuum to give the BOC-protected product (787 mg, 87%). This product was then subjected to General Procedure B to afford the title compound (753 mg, quant.).

Step 3: Synthesis of 5-{4-[2-(2,6-dioxopiperidin-3-yl)-1,3-dioxoisoindol-5-yl]piperazin-1-yl}pyrazine-2-carboxylic acid. The reaction was carried out according to General Procedure A using 5-(piperazin-1-yl)pyrazine-2-carboxylic acid hydrochloride (243 mg, 1.00 mmol) and 2-(2,6-dioxopiperidin-3-yl)-4-fluoroisoindole-1,3-dione (250 mg, 0.91 mmol) followed by Chromatography C to afford the title compound (116 mg, 28%).

Step 4: Synthesis of (3R)-1-(5-{4-[2-(2,6-dioxopiperidin-3-yl)-1,3-dioxoisoindol-4-yl]piperazin-1-yl}pyrazine-2-carbonyl)pyrrolidine-3-carboxylic acid. A mixture of methyl 5-[4-(tert-butoxycarbonyl)piperazin-1-yl]pyrazine-2-carboxylate (50 mg, 0.11 mmol), tert-butyl (3R)-pyrrolidine-3-carboxylate (18 mg, 0.11 mmol) was dissolved in DCM (1 mL). DIPEA (0.1 mL, 0.65 mmol) was added, followed by BOP (62 mg, 0.14 mmol). The reaction mixture was stirred at room temperature for 1 h, then purified according to Chromatography B. This material was then subjected to General Procedure B to afford the title compound. (8 mg, 88%)

Step 5: Synthesis of 5-((6-(1'-((3R)-1-(5-(4-(2-(2,6-dioxopiperidin-3-yl)-1,3-dioxoisoindolin-4-yl)piperazin-1-yl)pyrazine-2-carbonyl)pyrrolidine-3-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (40 mg), (3R)-1-(5-{4-[2-(2,6-dioxopiperidin-3-yl)-1,3-dioxoisoindol-4-yl]piperazin-1-yl}pyrazine-2-carbonyl)pyrrolidine-3-carboxylic acid (32 mg) as starting materials. Crude material was purified by reverse phase HPLC to provide the title compound (9.1 mg, 13%); LCMS: $C_{68}H_{76}FN_{15}O_8$ requires: 1249.60, found: m/z=1251.01 [M+H]$^+$; $^1$H NMR (500 MHz, DMSO-$d_6$) δ: 11.12 (s, 1H), 9.29 (s, 2H), 8.60 (d, J=19.4 Hz, 2H), 8.38 (s, 2H), 8.15 (d, J=8.1 Hz, 1H), 7.90 (s, 1H), 7.79-7.67 (m, 3H), 7.63-7.52 (m, 3H), 7.43 (s, 1H), 7.19 (d, J=12.2 Hz, 1H), 5.29 (s, 1H), 5.14 (d, J=11.3 Hz, 1H), 4.25-4.16 (m, 1H), 4.07-3.75 (m, 13H), 3.06-2.75 (m, 12H), 2.35 (s, 3H), 2.18-1.98 (m, 4H), 1.91-1.49 (m, 16H), 1.46-1.37 (m, 1H), 1.25 (s, 1H), 1.10 (dd, J=11.4, 6.6 Hz, 6H).

Example 87

5-((6-(1'-((3S)-1-((1R,4S)-4-((2-(2,6-dioxopiperidin-3-yl)-1,3-dioxoisoindolin-4-yl)amino)cyclohexane-1-carbonyl)pyrrolidine-3-carbonyl)-2-oxo-1-((1s,3R)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide

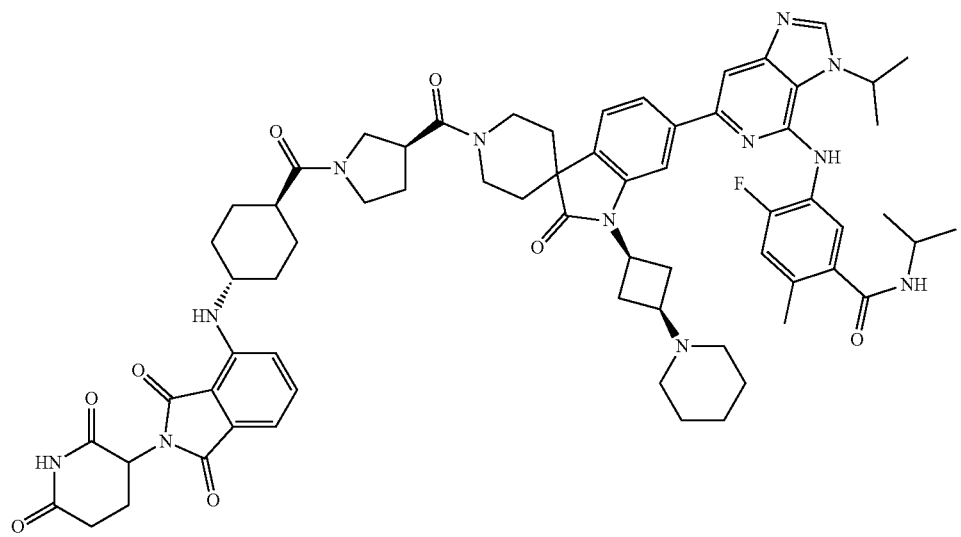 [SMILES: Cc1cc(F)c(Nc2nc(-c3ccc4c(c3)N([C@H]3C[C@@H](N5CCCCC5)C3)C(=O)C43CCN(C(=O)[C@H]4CCN(C(=O)[C@H]5CC[C@H](Nc6cccc7c6C(=O)N(C6CCC(=O)NC6=O)C7=O)CC5)C4)CC3)cc3ncn(C(C)C)c23)cc1C(=O)NC(C)C]

Step 1: Synthesis of (3S)-1-((1r,4S)-4-((2-(2,6-dioxopiperidin-3-yl)-1,3-dioxoisoindolin-4-yl)amino)cyclohexane-1-carbonyl)pyrrolidine-3-carboxylic acid. The title compound was synthesized according to General Procedure F using (trans)-4-{[2-(2,6-dioxopiperidin-3-yl)-1,3-dioxoisoindol-4-yl]amino}cyclohexane-1-carboxylic acid (Example 26; 40 mg, 0.1 mmol) and tert-butyl (S)-pyrrolidine-3-carboxylate (25 mg, 0.15 mmol). The product of this reaction was then subjected to General Procedure B to give the title compound (30 mg, 60%).

Step 2: Synthesis of 5-((6-(1'-((3S)-1-((1r,4S)-4-((2-(2,6-dioxopiperidin-3-yl)-1,3-dioxoisoindolin-4-yl)amino)cyclohexane-1-carbonyl)pyrrolidine-3-carbonyl)-2-oxo-1-((1s,3R)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide. The title compound was synthesized according to General Procedure F, using Intermediate 1 (15 mg, 0.02 mmol), (3S)-1-((1r,4S)-4-((2-(2,6-dioxopiperidin-3-yl)-1,3-dioxoisoindolin-4-yl)amino)cyclohexane-1-carbonyl)pyrrolidine-3-carboxylic acid (12 mg. 0.02 mmol) as starting materials. Crude material was purified by reverse phase HPLC to provide the title compound (11.4 mg, 48%); LCMS: $C_{66}H_{77}FN_{12}O_8$ requires: 1184.6, found: m/z=1186.0 [M+H]$^+$; $^1$H NMR (500 MHz, DMSO-d$_6$) δ: 11.11 (s, 1H), 9.34 (s, 1H), 8.68 (d, J=4.6 Hz, 1H), 8.41 (s, 1H), 8.15 (d, J=7.7 Hz, 1H), 7.89 (d, J=2.6 Hz, 1H), 7.68 (d, J=7.8 Hz, 1H), 7.64-7.50 (m, 4H), 7.26-7.15 (m, 2H), 7.05 (d, J=7.0 Hz, 1H), 6.18 (d, J=8.1 Hz, 1H), 5.31 (p, J=6.7 Hz, 1H), 5.06 (dd, J=12.8, 5.5 Hz, 1H), 4.26-3.29 (m, 17H), 3.04-2.74 (m, 7H), 2.37 (d, J=5.3 Hz, 3H), 2.13-1.98 (m, 6H), 1.89-1.67 (m, 8H), 1.60 (d, J=6.5 Hz, 9H), 1.47-1.31 (m, 3H), 1.11 (t, J=5.3 Hz, 6H).

Example 88

5-[(6-{1'-[4-(1-{[(2-{[2-(2,6-dioxopiperidin-3-yl)-1,3-dioxoisoindol-4-yl]amino}ethyl)carbamoyl]methyl}piperidin-4-yl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide

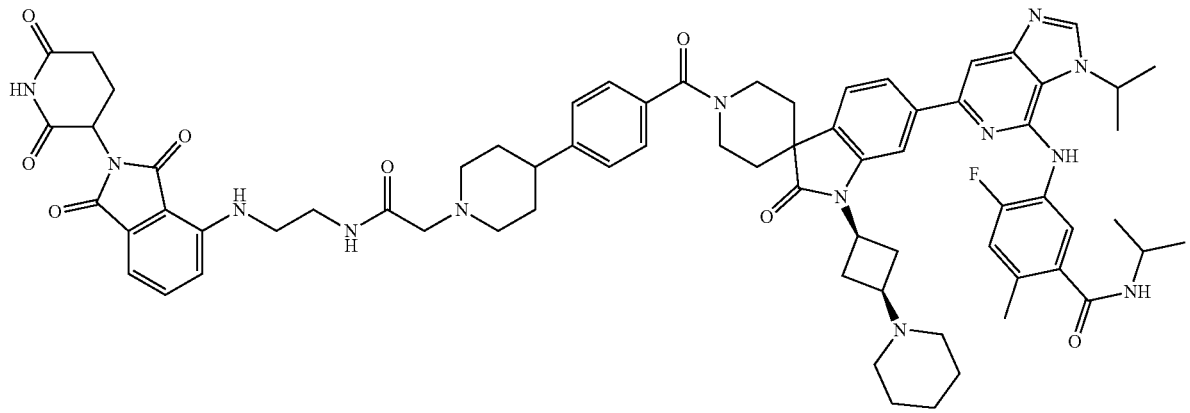 [SMILES: Cc1cc(F)c(Nc2nc(-c3ccc4c(c3)N([C@H]3C[C@@H](N5CCCCC5)C3)C(=O)C43CCN(C(=O)c4ccc(C5CCN(CC(=O)NCCNc6cccc7c6C(=O)N(C6CCC(=O)NC6=O)C7=O)CC5)cc4)CC3)cc3ncn(C(C)C)c23)cc1C(=O)NC(C)C]

Step 1: Synthesis of tert-butyl 4-(1-(2-(benzyloxy)-2-oxoethyl)piperidin-4-yl)benzoate. The reaction was carried out according to General Procedure E using tert-butyl 4-(piperidin-4-yl)benzoate (200 mg, 0.765 mmol) and benzyl 2-bromoacetate (175 mg, 0.765 mmol). Purification with Chromatography A gave the title compound (250 mg, 80%)

Step 2: Synthesis of 2-(4-(4-(tert-butoxycarbonyl)phenyl)piperidin-1-yl)acetic acid. The reaction was carried out by combining tert-butyl 4-(1-(2-(benzyloxy)-2-oxoethyl)piperidin-4-yl)benzoate (107 mg, 0.261 mmol) and 10% Pd/C (11 mg) and then methanol (15 mL) was added. The reaction was stirred under a hydrogen atmosphere for 4 h before being purged with nitrogen gas, filtered through celite, and the filtrate concentrated to give the title compound (75 mg, 90%)

Step 3: Synthesis of tert-butyl 4-(1-{[(2-{[2-(2,6-dioxopiperidin-3-yl)-1,3-dioxoisoindol-4-yl]amino}ethyl)carbamoyl]methyl}piperidin-4-yl)benzoate. The reaction was carried out according to General Procedure F, using 4-[(2-aminoethyl)amino]-2-(2,6-dioxopiperidin-3-yl)isoindole-1,3-dione (50 mg, 0.16 mmol) and 2-(4-(4-(tert-butoxycarbonyl)phenyl)piperidin-1-yl)acetic acid (50.5 mg, 0.16 mmol). Chromatography C provided the title compound (59 mg, 60%).

Step 4: Synthesis of 4-(1-{[(2-{[2-(2,6-dioxopiperidin-3-yl)-1,3-dioxoisoindol-4-yl]amino}ethyl)carbamoyl]methyl}piperidin-4-yl)benzoic acid: The reaction was carried out according to General Procedure B using tert-butyl 4-(1-{[(2-{[2-(2,6-dioxopiperidin-3-yl)-1,3-dioxoisoindol-4-yl]amino}ethyl)carbamoyl]methyl}piperidin-4-yl)benzoate (60 mg) to provide the title compound (55 mg, 95%).

Step 5: Synthesis of 5-[(6-{1'-[4-(1-{[(2-{[2-(2,6-dioxopiperidin-3-yl)-1,3-dioxoisoindol-4-yl]amino}ethyl)carbamoyl]methyl}piperidin-4-yl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide: The title compound was synthesized according to General Procedure F, using Intermediate 1 (20 mg, 0.04 mmol) and 4-(1-{[(2-{[2-(2,6-dioxopiperidin-3-yl)-1,3-dioxoisoindol-4-yl]amino}ethyl)carbamoyl]methyl}piperidin-4-yl)benzoic acid (15 mg, 0.04 mmol) as starting materials. Chromatography C provided the title compound. (5.8 mg, 13%); LCMS: $C_{70}H_{80}FN_{13}O_8$ requires 1249.6, found 1250.9 [M+H]$^+$; $^1$H NMR (500 MHz, DMSO-d$_6$) δ 11.11 (d, J=3.6 5.34-5.23 (m, 1H), 5.06 (dd, J=13.0, 5.4 Hz, 1H), 4.26-3.98 (m, 2H) 3. Hz, 1H), 9.71 (s, 1H), 9.34 (s, 1H), 8.79 (s, 1H), 8.58 (s, 1H), 8.37 (s, 1H), 8.14 (d, J=7.8 Hz, 1H), 7.97 (d, J=7.8 Hz, 1H), 7.89 (s, 1H), 7.69 (d, J=7.8 Hz, 1H), 7.66-7.56 (m, 3H), 7.56-7.45 (m, 3H), 7.41 (d, J=8.0 Hz, 1H), 7.34 (d, J=7.9 Hz, 2H), 7.24-7.15 (m, 2H), 7.07 (d, J=7.0 Hz, 1H), 6.76 (t, J=6.1 Hz, 1H), 92 (s, 4H), 3.75 (s, 2H), 3.62-3.22 (m, 12H), 3.02-2.75 (m, 8H), 2.37 (s, 3H), 2.13-1.51 (m, 16H), 1.42 (d, J=13.2 Hz, 1H), 1.24 (s, 1H), 1.11 (d, J=6.6 Hz, 6H).

Example 89

N-(2-{[2-(2,6-dioxopiperidin-3-yl)-1,3-dioxoisoindol-4-yl]amino}ethyl)-5-[(4-{[6-(4-{[2-fluoro-5-(isopropylcarbamoyl)-4-methylphenyl]amino}-3-isopropylimidazo[4,5-c]pyridin-6-yl)-2-oxo-1-[(s,3s)-3-(piperidin-1-yl)cyclobutyl]spiro[indole-3,4'-piperidin]-1'-yl]carbonyl}piperidin-1-yl)methyl]pyridine-2-carboxamide

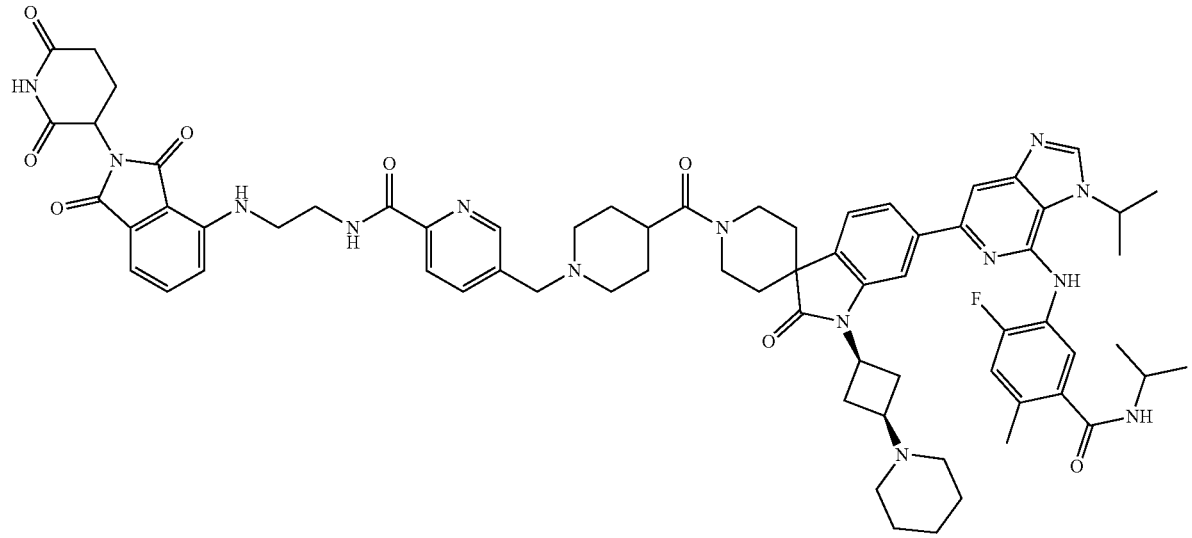 [SMILES: Cc1cc(F)c(Nc2nc(-c3ccc4c(c3)N([C@H]3C[C@@H](N5CCCCC5)C3)C(=O)C43CCN(C(=O)C4CCN(Cc5ccc(C(=O)NCCNc6cccc7c6C(=O)N(C6CCC(=O)NC6=O)C7=O)nc5)CC4)CC3)cc3ncn(C(C)C)c23)cc1C(=O)NC(C)C]

Step 1: Synthesis of tert-butyl 1-({6-[(2-{[2-(2,6-dioxopiperidin-3-yl)-1,3-dioxoisoindol-4-yl]amino}ethyl)carbamoyl]pyridin-3-yl}methyl)piperidine-4-carboxylate: The reaction was carried out according to General Procedure F, using 4-[(2-aminoethyl)amino]-2-(2,6-dioxopiperidin-3-yl)isoindole-1,3-dione (30 mg, 0.09 mmol) and 5-{[4-(tert-butoxycarbonyl)piperidin-1-yl]methyl}pyridine-2-carboxylic acid (30 mg, 0.09 mmol). Chromatography C provided the title compound (36 mg, 61%).

Step 2: Synthesis of 1-({6-[(2-{[2-(2,6-dioxopiperidin-3-yl)-1,3-dioxoisoindol-4-yl]amino}ethyl)carbamoyl]pyridin-3-yl}methyl)piperidine-4-carboxylic acid: The reaction was carried out according to General Procedure B using tert-butyl 1-({6-[(2-{[2-(2,6-dioxopiperidin-3-yl)-1,3-dioxoisoindol-4-yl]amino}ethyl)carbamoyl]pyridin-3-yl}methyl)piperidine-4-carboxylate (36 mg, 0.06 mmol) to provide the title compound (31 mg, 98%).

Step 3: Synthesis of N-(2-{[2-(2,6-dioxopiperidin-3-yl)-1,3-dioxoisoindol-4-yl]amino}ethyl)-5-[(4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}piperidin-1-yl)methyl]pyridine-2-carboxamide: The title compound was synthesized according to General Procedure F, using Intermediate 1 (37.7 mg) and 1-({6-[(2-{[2-(2,6-dioxopiperidin-3-yl)-1,3-dioxoisoindol-4-yl]amino}ethyl)carbamoyl]pyridin-3-yl}methyl)piperidine-4-carboxylic acid (30 mg) as starting materials. Chromatography C provided the title compound (29.9 mg, 45%); LCMS: $C_{69}H_{79}FN_{14}O_8$ requires 1250.6, found 1251.0 [M+H]$^+$; $^1$H NMR (500 MHz, DMSO-d$_6$) δ 11.11 (s, 1H), 9.72 (s, 1H), 9.39 (d, J=9.9 Hz, 1H), 8.80 (t, J=5.7 Hz, 1H), 8.62 (s, 1H), 8.39 (s, 1H), 8.15 (d, J=7.8 Hz, 1H), 7.89 (s, 1H), 7.69 (d, J=7.8 Hz, 1H), 7.65-7.58 (m, 3H), 7.52 (s, 1H), 7.49 (d, J=7.8 Hz, 2H), 7.34 (d, J=8.0 Hz, 2H), 7.20 (t, J=10.5 Hz, 2H), 7.07 (d, J=7.0 Hz, 1H), 6.76 (t, J=6.1 Hz, 1H), 5.29 (p, J=6.5 Hz, 1H), 5.06 (dd, J=12.8, 5.4 Hz, 1H), 4.22 (t, J=8.3 Hz, 1H), 4.15-3.99 (m, 2H), 3.93 (s, 4H), 3.91-3.25 (m, 8H), 3.05-2.77 (m, 9H), 2.38 (s, 3H), 2.09-1.94 (m, 6H), 1.94-1.69 (m, 8H), 1.60 (d, J=6.5 Hz, 8H), 1.44 (t, J=13.0 Hz, 1H), 1.11 (d, J=6.5 Hz, 6H).

Example 90

5-[(6-{1'-[2-(4-{4-[(2-{[2-(2,6-dioxopiperidin-3-yl)-1,3-dioxoisoindol-4-yl]amino}ethyl)carbamoyl]phenyl}piperidin-1-yl)acetyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide

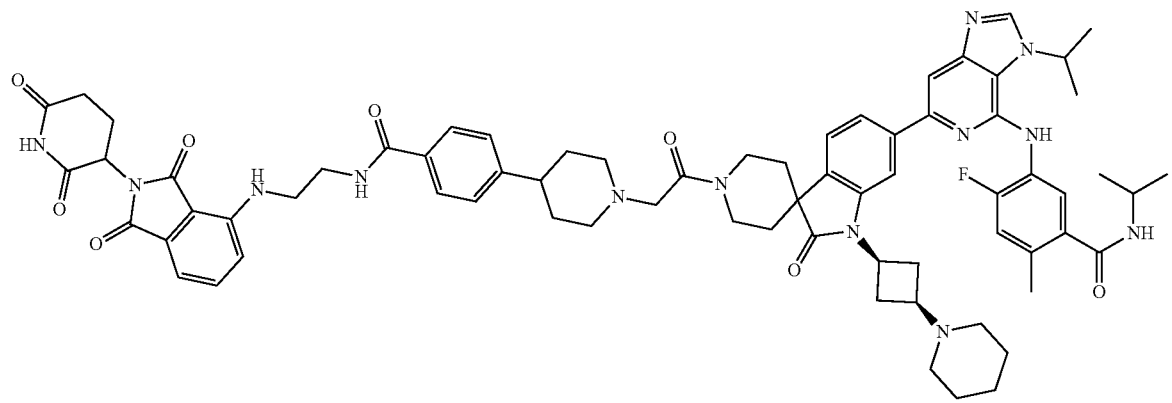 [SMILES: Cc1cc(F)c(Nc2nc(-c3ccc4c(c3)N([C@H]3C[C@@H](N5CCCCC5)C3)C(=O)C43CCN(C(=O)CN4CCC(c5ccc(C(=O)NCCNc6cccc7c6C(=O)N(C6CCC(=O)NC6=O)C7=O)cc5)CC4)CC3)cc3ncn(C(C)C)c23)cc1C(=O)NC(C)C]

Step 1: Synthesis of {4-[4-(tert-butoxycarbonyl)phenyl]piperidin-1-yl}acetic acid: The reaction was carried out according to General Procedure E followed by General Procedure C using tert-butyl 4-(piperidin-4-yl)benzoate (100 mg, 0.383 mmol) and methyl 2-bromoacetate (58.6 mg, 0.383 mmol). The title compound was obtained after Chromatography C (50 mg, 41%).

Step 2: Synthesis of tert-butyl 4-(1-{2-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]-2-oxoethyl}piperidin-4-yl)benzoate. The reaction was carried out according to General Procedure F, using Intermediate 1 (50 mg, 0.07 mmol) and {4-[4-(tert-butoxycarbonyl)phenyl]piperidin-1-yl}acetic acid (22.6 mg, 0.07 mmol). Chromatography C provided the title compound (45 mg, 63%).

Step 3: Synthesis of 4-(1-{2-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]-2-oxoethyl}piperidin-4-yl)benzoic acid. The reaction was carried out according to General Procedure B using tert-butyl 4-(1-{2-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]-2-oxoethyl}piperidin-4-yl)benzoate (45 mg) to provide the title compound (42 mg, 98%).

Step 4: Synthesis of 5-[(6-{1'-[2-(4-{4-[(2-{[2-(2,6-dioxopiperidin-3-yl)-1,3-dioxoisoindol-4-yl]amino}ethyl)carbamoyl]phenyl}piperidin-1-yl)acetyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide: The title compound was synthesized according to General Procedure F, using 4-(1-{2-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]-2-oxoethyl}piperidin-4-yl)benzoic acid (20 mg, 0.021 mmol) and 4-[(2-aminoethyl)amino]-2-(2,6-dioxopiperidin-3-yl)isoindole-1,3-dione (6.6 mg, 0.021 mmol) as starting materials. Chromatography C provided the title compound. (9.6 mg, 37%); LCMS: $C_{70}H_{80}FN_{13}O_8$ requires 1249.6, found 1252.0 [M+H]$^+$; $^1$H NMR (500 MHz, DMSO-d$_6$) δ 11.10 (d, J=4.3 Hz, 1H), 9.70-9.39 (m, 2H), 8.65 (d, J=15.5 Hz, 2H), 8.40 (s, 1H), 8.15 (d, J=7.8 Hz, 1H), 7.90 (s, 1H), 7.84 (d, J=7.9 Hz, 2H), 7.70 (d, J=7.8 Hz, 1H), 7.65-7.55 (m, 2H), 7.54 (s, 1H), 7.48 (dd, J=13.8, 8.0 Hz, 1H), 7.38 (d, J=8.0 Hz, 2H), 7.27 (d, J=8.6 Hz, 1H), 7.19 (d, J=12.1 Hz, 1H), 7.05 (d, J=6.9 Hz, 1H), 6.84 (t, J=6.0 Hz, 1H), 5.30 (p, J=6.5 Hz, 1H), 5.06 (dd, J=12.7, 5.5 Hz, 1H), 4.57-4.37 (m, 1H), 4.22 (t, J=8.3 Hz, 1H), 4.11-3.93 (m, 3H), 3.91-3.30 (m, 8H), 3.26-2.70 (m, 10H), 2.62 (s, 2H), 2.37 (s, 3H), 2.21-1.97 (m, 5H), 1.86 (d, J=13.1 Hz, 4H), 1.76 (dd, J=17.2, 10.6 Hz, 3H), 1.69-1.52 (m, 8H), 1.50-1.37 (m, 1H), 1.11 (d, J=6.5 Hz, 6H).

Example 91

5-[(6-{1'-[4-({4-[2-(2,6-dioxopiperidin-3-yl)-1,3-dioxoisoindol-5-yl]piperazin-1-yl}methyl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide

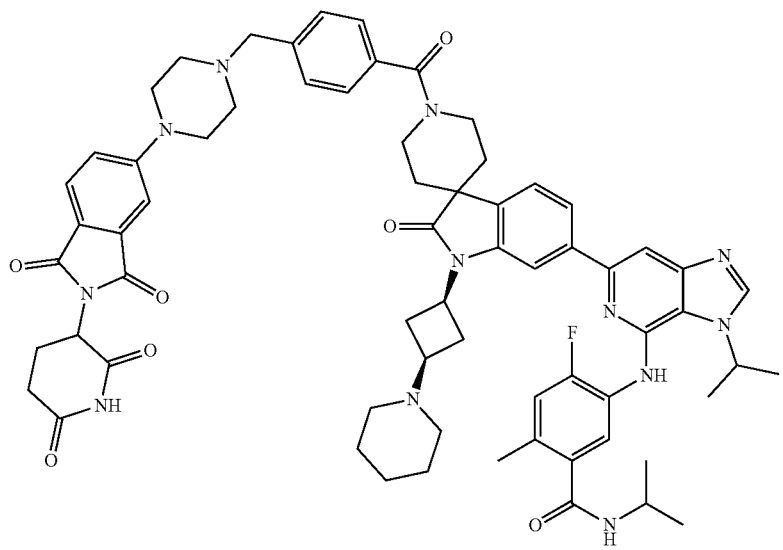 [SMILES: Cc1cc(F)c(Nc2nc(-c3ccc4c(c3)N([C@H]3C[C@@H](N5CCCCC5)C3)C(=O)C43CCN(C(=O)c4ccc(CN5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of tert-butyl 4-[(4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}phenyl)methyl]piperazine-1-carboxylate: The reaction was carried out according to General Procedure F, using Intermediate 1 (100 mg, 0.14 mmol) and 4-{[4-(tert-butoxycarbonyl)piperazin-1-yl]methyl}benzoic acid (50 mg, 0.14 mmol). Chromatography C provided the title compound (104 mg, 73%).

Step 2: Synthesis of 4-fluoro-N-isopropyl-5-[(3-isopropyl-6-{2-oxo-1'-[4-(piperazin-1-ylmethyl)benzoyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide: The reaction was carried out according to General Procedure B using tert-butyl 4-[(4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}phenyl) methyl]piperazine-1-carboxylate (100 mg, 0.1 mmol) to provide the title compound (95 mg, 98%).

Step 3: Synthesis of 5-[(6-{1'-[4-({4-[2-(2,6-dioxopiperidin-3-yl)-1,3-dioxoisoindol-5-yl]piperazin-1-yl}methyl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide: The title compound was synthesized according to General Procedure A, using 4-fluoro-N-isopropyl-5-[(3-isopropyl-6-{2-oxo-1'-[4-(piperazin-1-ylmethyl)benzoyl]-1-[(1s,3s)-3-(piperidin-1-yl)cyclobutyl]spiro[indole-3,4'-piperidin]-6-yl}imidazo[4,5-c]pyridin-4-yl)amino]-2-methylbenzamide (30 mg, 0.033 mmol) and 2-(2,6-dioxopiperidin-3-yl)-5-fluoroisoindole-1,3-dione (10 mg, 0.036 mmol) as starting materials. Chromatography C provided the title compound. (6.0 mg, 12%); LCMS: $C_{66}H_{73}FN_{12}O_7$ requires 1164.6, found 1166.0 [M+H]$^+$; $^1$H NMR (500 MHz, DMSO-d$_6$) δ 11.11 (s, 1H), 9.37 (s, 1H), 8.60 (s, 1H), 8.39 (s, 1H), 8.15 (d, J=7.3 Hz, 1H), 7.90 (s, 1H), 7.79 (d, J=8.3 Hz, 1H), 7.70 (d, J=8.1 Hz, 1H), 7.67-7.58 (m, 5H), 7.51 (d, J=26.7 Hz, 2H), 7.35 (d, J=8.6 Hz, 1H), 7.19 (d, J=11.8 Hz, 1H), 5.29 (s, 1H), 5.11 (d, J=12.9 Hz, 1H), 4.46 (s, 2H), 4.36-3.84 (m, 8H), 2.95-2.77 (m, 8H), 2.71 (s, 2H), 2.38 (s, 3H), 2.05 (s, 2H), 1.98-1.69 (m, 11H), 1.60 (d, J=6.4 Hz, 10H), 1.50-1.38 (m, 1H), 1.25 (s, 1H), 1.11 (d, J=6.5 Hz, 6H).

Example 92

5-[(6-{1'-[(4-{4-[2-(2,6-dioxopiperidin-3-yl)-1,3-dioxoisoindol-5-yl]piperazine-1-carbonyl}phenyl)methyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide

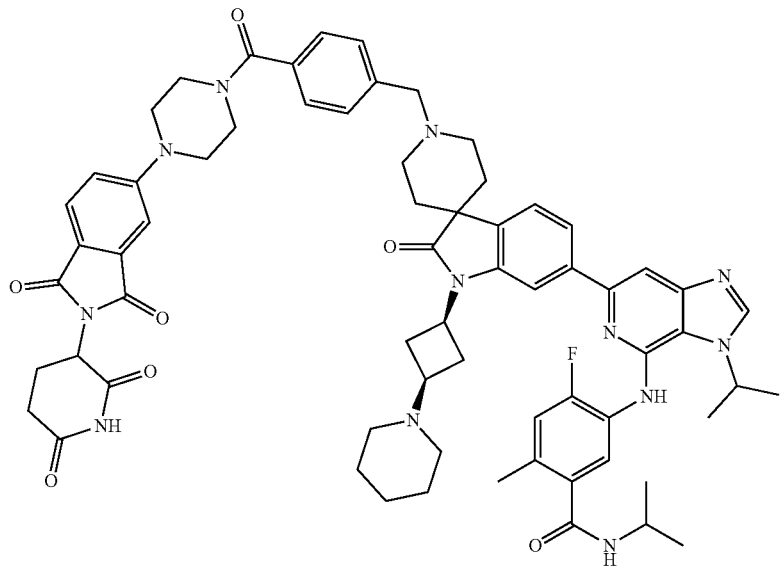 [SMILES: Cc1cc(F)c(Nc2nc(-c3ccc4c(c3)N([C@H]3C[C@@H](N5CCCCC5)C3)C(=O)C43CCN(Cc4ccc(C(=O)N5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of tert-butyl 4-(4-((6-(4-(((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)methyl)benzoyl)piperazine-1-carboxylate: The reaction was carried out according to General Procedure D, using Intermediate 1 (100 mg, 0.14 mmol) and tert-butyl 4-(4-formylbenzoyl)piperazine-1-carboxylate (50 mg, 0.14 mmol). Chromatography C provided the title compound (25 mg, 18%).

Step 2: Synthesis of 4-fluoro-N-isopropyl-5-{[3-isopropyl-6-(2-oxo-1'-{[4-(piperazine-1-carbonyl)phenyl]methyl}-1-[(1s,3s)-3-(piperidin-1-yl)cyclobutyl]spiro[indole-3,4'-piperidin]-6-yl)imidazo[4,5-c]pyridin-4-yl]amino}-2-methylbenzamide: The reaction was carried out according to General Procedure B using tert-butyl 4-(4-((6-(4-(((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indole-3,4'-piperidin]-1'-yl)methyl)benzoyl)piperazine-1-carboxylate (25 mg, 0.025 mmol) to provide the title compound (22 mg, 97%).

Step 3: Synthesis of 5-[(6-{1'-[(4-{4-[2-(2,6-dioxopiperidin-3-yl)-1,3-dioxoisoindol-5-yl]piperazine-1-carbonyl}phenyl)methyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide: The title compound was synthesized according to General Procedure F, using 4-fluoro-N-isopropyl-5-{[3-isopropyl-6-(2-oxo-1'-{[4-(piperazine-1-carbonyl)phenyl]methyl}-1-[(1s,3s)-3-(piperidin-1-yl)cyclobutyl]spiro[indole-3,4'-piperidin]-6-yl)imidazo[4,5-c]pyridin-4-yl]amino}-2-methylbenzamide (20 mg, 0.02 mmol) and 2-(2,6-dioxopiperidin-3-yl)-5-fluoroisoindole-1,3-dione (10 mg, 0.02 mmol) as starting materials. Chromatography C provided the title compound. (4.0 mg, 8%); LCMS: $C_{66}H_{73}FN_{12}O_7$ requires 1164.6, found 1167.0 [M+2H]$^+$; $^1$H NMR (500 MHz, DMSO-d$_6$) δ 11.10 (s, 1H), 9.92 (d, J=35.3 Hz, 1H), 9.45 (d, J=35.3 Hz, 1H), 8.60 (s, 1H), 8.40 (d, J=27.8 Hz, 1H), 8.17 (d, J=8.8 Hz, 1H), 7.93 (d, J=39.0 Hz, 2H), 7.78-7.66 (m, 4H), 7.65-7.56 (m, 2H), 7.54 (d, J=7.8 Hz, 1H), 7.39 (s, 1H), 7.29 (d, J=8.5 Hz, 1H), 7.19 (d, J=12.0 Hz, 1H), 5.30 (s, 1H), 5.10 (dd, J=12.8, 5.5 Hz, 1H), 4.66 (s, 1H), 4.53 (s, 1H), 4.22 (s, 1H), 3.91-3.73

(m, 2H), 3.73-3.58 (m, 7H), 3.05-2.75 (m, 10H), 2.43-1.52 (m, 24H), 1.47-1.38 (m, 1H), 1.11 (d, J=5.8 Hz, 6H).

Example 93

5-({6-[1'-(4-{3-[2-(2,6-dioxopiperidin-3-yl)-1,3-dioxoisoindol-5-yl]-3,8-diazabicyclo[3.2.1]octane-8-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide clobutyl]spiro[indole-3,4'-piperidin]-1'-yl]carbonyl}benzoic acid: The reaction was carried out according to General Procedure F using Intermediate 1 (200 mg, 0.28 mmol) and terephthalic acid (50 mg, 0.28 mmol). Chromatography C provided the title compound (132 mg, 70%).

Step 4: Synthesis of 5-({6-[1'-(4-{3-[2-(2,6-dioxopiperidin-3-yl)-1,3-dioxoisoindol-5-yl]-3,8-diazabicyclo[3.2.1]octane-8-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide: The title compound was

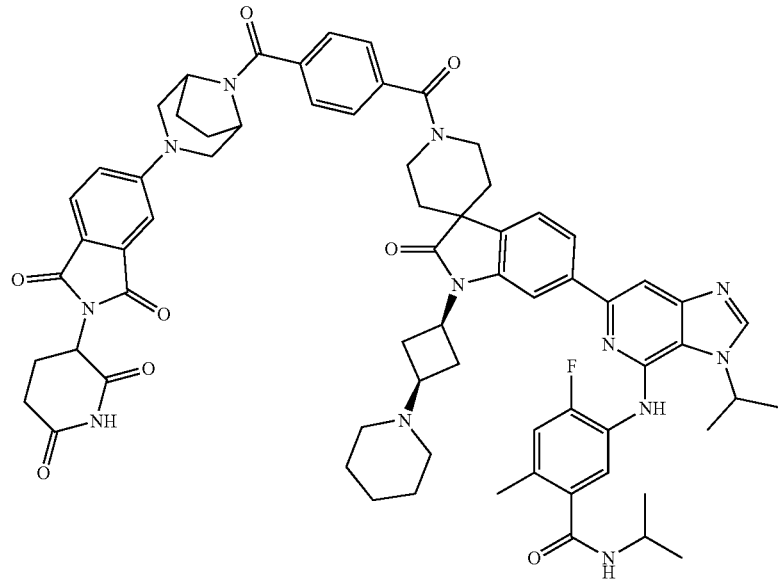 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5C6CCC5CN(c5ccc7c(c5)C(=O)N(C5CCC(=O)NC5=O)C7=O)C6)cc4)CC3)cc3ncn(C(C)C)c23)cc1C(=O)NC(C)C]

Step 1: Synthesis of tert-butyl 3-[2-(2,6-dioxopiperidin-3-yl)-1,3-dioxoisoindol-5-yl]-3,8-diazabicyclo[3.2.1]octane-8-carboxylate: The reaction was carried out according to General Procedure A, using 2-(2,6-dioxopiperidin-3-yl)-5-fluoroisoindole-1,3-dione (250 mg, 0.91 mmol) and tert-butyl 3,8-diazabicyclo[3.2.1]octane-8-carboxylate (192 mg, 0.91 mmol). Chromatography C provided the title compound (272 mg, 64%).

Step 2: Synthesis of 5-{3,8-diazabicyclo[3.2.1]octan-3-yl}-2-(2,6-dioxopiperidin-3-yl)isoindole-1,3-dione: The reaction was carried out according to General Procedure B using tert-butyl 3-[2-(2,6-dioxopiperidin-3-yl)-1,3-dioxoisoindol-5-yl]-3,8-diazabicyclo[3.2.1]octane-8-carboxylate (232 mg, 0.50 mmol). Chromatography C provided the title compound (137 mg, 75%).

Step 3: Synthesis of 4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cysynthesized according to General Procedure F, using 4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}benzoic acid (20 mg, 0.04 mmol) and 5-{3,8-diazabicyclo[3.2.1]octan-3-yl}-2-(2,6-dioxopiperidin-3-yl)isoindole-1,3-dione (10 mg, 0.04 mmol) as starting materials. Chromatography C provided the title compound. (2.0 mg, 6%); LCMS: $C_{68}H_{73}FN_{12}O_8$ requires 1204.6, found 1206.0 [M+H]$^+$; $^1$H NMR (500 MHz, DMSO-$d_6$) δ 11.09 (s, 2H), 8.18 (d, J=33.0 Hz, 1H), 8.02 (dd, J=19.3, 8.0 Hz, 4H), 7.89 (d, J=13.6 Hz, 1H), 7.72 (d, J=8.7 Hz, 2H), 7.66 (t, J=8.2 Hz, 4H), 7.60 (d, J=7.9 Hz, 2H), 7.44 (t, J=9.4 Hz, 1H), 7.33 (s, 2H), 7.21 (d, J=8.2 Hz, 3H), 5.30 (s, 1H), 5.09 (dd, J=12.5, 5.3 Hz, 1H), 4.85 (s, 1H), 3.23-3.11 (m, 7H), 3.05-2.75 (m, 8H), 2.70-2.61 (m, 2H), 2.37 (s, 3H), 2.08-1.54 (m, 15H), 1.15-1.07 (m, 6H).

Example 94

5-{[6-(1'-{[4-({4-[2-(2,6-dioxopiperidin-3-yl)-1,3-dioxoisoindol-5-yl]piperazin-1-yl}methyl)phenyl]methyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide

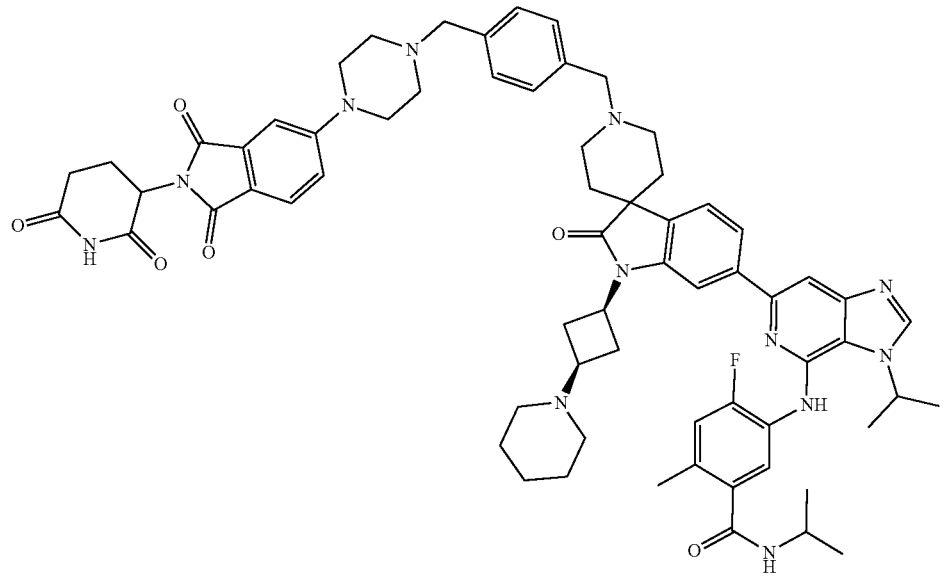 [SMILES: Cc1cc(F)c(Nc2nc(-c3ccc4c(c3)N([C@H]3C[C@@H](N5CCCCC5)C3)C(=O)C43CCN(Cc4ccc(CN5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of 4-fluoro-N-isopropyl-5-{[3-isopropyl-6-(2-oxo-1'-{[4-(piperazin-1-ylmethyl)phenyl]methyl}-1-[(1s,3s)-3-(piperidin-1-yl)cyclobutyl]spiro[indole-3,4'-piperidin]-6-yl)imidazo[4,5-c]pyridin-4-yl]amino}-2-methylbenzamide: The reaction was carried out according to General Procedure D, using Intermediate 1 (100 mg, 0.14 mmol) and tert-butyl 4-[(4-formylphenyl)methyl]piperazine-1-carboxylate (40 mg, 0.14 mmol). Chromatography C provided tert-butyl 4-({4-[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-ylmethyl]phenyl}methyl)piperazine-1-carboxylate (105 mg, 71%) which was directly submitted to General Procedure B to afford the title compound (92 mg, 98%).

Step 2: Synthesis of 5-{[6-(1'-{[4-({4-[2-(2,6-dioxopiperidin-3-yl)-1,3-dioxoisoindol-5-yl]piperazin-1-yl}methyl)phenyl]methyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide: The title compound was synthesized according to General Procedure A, using 4-fluoro-N-isopropyl-5-{[3-isopropyl-6-(2-oxo-1'-{[4-(piperazin-1-ylmethyl)phenyl]methyl}-1-[(1s,3s)-3-(piperidin-1-yl)cyclobutyl]spiro[indole-3,4'-piperidin]-6-yl)imidazo[4,5-c]pyridin-4-yl]amino}-2-methylbenzamide (30 mg, 0.03 mmol) and 2-(2,6-dioxopiperidin-3-yl)-5-fluoroisoindole-1,3-dione (10 mg, 0.03 mmol) as starting materials. Chromatography C provided the title compound. (8.0 mg, 17%); LCMS: $C_{66}H_{75}FN_{12}O_6$ requires 1150.6, found 1152.3 [M+2H]$^+$; $^1$H NMR (500 MHz, DMSO-d$_6$) δ 11.08 (s, 1H), 8.59 (s, 1H), 8.39 (d, J=26.9 Hz, 1H), 8.15 (d, J=8.2 Hz, 1H), 7.96 (s, 1H), 7.88 (s, 1H), 7.81-7.43 (m, 9H), 7.35 (d, J=8.5 Hz, 1H), 7.18 (d, J=12.1 Hz, 1H), 5.29 (d, J=6.7 Hz, 1H), 5.10 (dd, J=12.9, 5.4 Hz, 1H), 4.64 (s, 2H), 4.50 (s, 4H), 4.22 (s, 5H), 4.05 (s, 4H), 3.64-3.34 (m, 7H), 2.98-2.76 (m, 9H), 2.63 (s, 2H), 2.38 (d, J=8.5 Hz, 3H), 2.31 (s, 1H), 2.17 (s, 1H), 2.11-1.90 (m, 3H), 1.85 (d, J=13.9 Hz, 3H), 1.73 (d, J=12.2 Hz, 1H), 1.69-1.53 (m, 9H), 1.43 (d, J=14.9 Hz, 1H), 1.30-1.17 (m, 1H), 1.11 (t, J=6.3 Hz, 6H).

Example 95

5-({6-[1'-(4-{4-[2-(2,6-dioxopiperidin-3-yl)-1,3-dioxoisoindol-4-yl]piperazine-1-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide

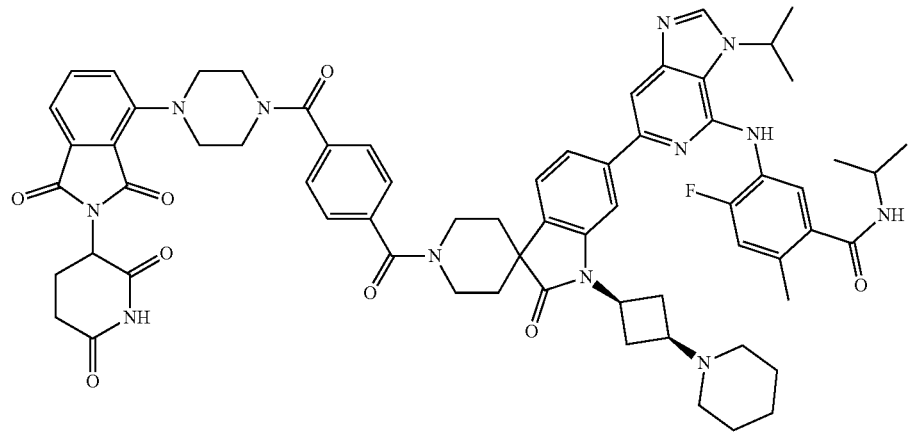 [SMILES: Cc1cc(F)c(Nc2nc(-c3ccc4c(c3)N([C@H]3C[C@@H](N5CCCCC5)C3)C(=O)C43CCN(C(=O)c4ccc(C(=O)N5CCN(c6cccc7c6C(=O)N(C6CCC(=O)NC6=O)C7=O)CC5)cc4)CC3)cc3ncn(C(C)C)c23)cc1C(=O)NC(C)C]

Step 1: Synthesis of 4-{4-[2-(2,6-dioxopiperidin-3-yl)-1,3-dioxoisoindol-4-yl]piperazine-1-carbonyl}benzoic acid: The reaction was carried out according to General Procedure A, using 2-(2,6-dioxopiperidin-3-yl)-4-fluoroisoindole-1,3-dione (250 mg, 0.91 mmol) and 4-(piperazine-1-carbonyl)benzoic acid (210 mg, 0.91 mmol). Chromatography C provided the title compound (320 mg, 68%).

Step 2: Synthesis of 5-({6-[1'-(4-{4-[2-(2,6-dioxopiperidin-3-yl)-1,3-dioxoisoindol-4-yl]piperazine-1-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide: The reaction was carried out according to General Procedure F using Intermediate 1 (30 mg, 0.04 mmol) and 4-{4-[2-(2,6-dioxopiperidin-3-yl)-1,3-dioxoisoindol-4-yl]piperazine-1-carbonyl}benzoic acid (20 mg, 0.04 mmol). Chromatography C provided the title compound (40 mg, 81%). LCMS: $C_{66}H_{71}FN_{12}O_8$ requires 1178.6, found 1180.4 [M+H]$^+$; $^1$H NMR (500 MHz, DMSO-$d_6$) δ 11.09 (s, 1H), 9.37 (d, J=9.9 Hz, 1H), 8.69 (s, 1H), 8.42 (s, 1H), 8.15 (d, J=7.8 Hz, 1H), 7.90 (s, 1H), 7.78-7.72 (m, 1H), 7.70 (d, J=7.8 Hz, 1H), 7.65-7.54 (m, 6H), 7.52 (s, 1H), 7.42 (d, J=7.1 Hz, 1H), 7.37 (d, J=8.4 Hz, 1H), 7.20 (d, J=12.2 Hz, 1H), 5.31 (p, J=6.6 Hz, 1H), 5.11 (dd, J=12.7, 5.5 Hz, 1H), 4.22 (p, J=8.5 Hz, 2H), 4.13 (s, 1H), 4.05 (dq, J=13.7, 6.7 Hz, 2H), 3.89 (s, 5H), 3.70-3.47 (m, 4H), 3.41 (d, J=11.5 Hz, 4H), 3.02-2.74 (m, 7H), 2.67-2.54 (m, 1H), 2.38 (s, 4H), 2.08-1.96 (m, 1H), 1.85 (d, J=14.4 Hz, 5H), 1.72 (s, 2H), 1.60 (d, J=6.6 Hz, 9H), 1.50-1.36 (m, 2H), 1.11 (d, J=6.5 Hz, 6H).

Example 96

4-fluoro-N-isopropyl-5-[(3-isopropyl-6-{2-oxo-1-[(1s,3s)-3-(piperidin-1-yl)cyclobutyl]-1'-[(1s,4s)-4-[4-({2-[(3S)-2,6-dioxopiperidin-3-yl]-1,3-dioxoisoindol-4-yl}oxy)piperidine-1-carbonyl]cyclohexanecarbonyl]spiro[indole-3,4'-piperidin]-6-yl}imidazo[4,5-c]pyridin-4-yl)amino]-2-methylbenzamide

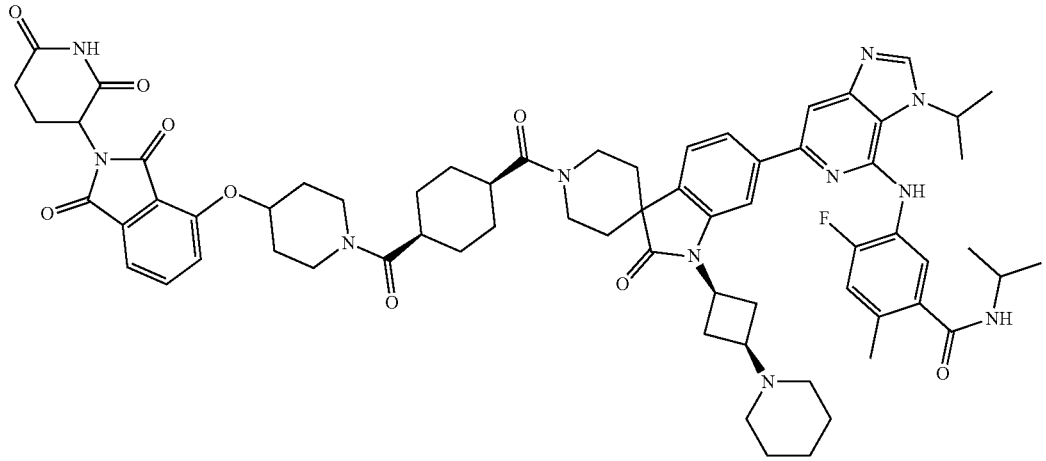 [SMILES: Cc1cc(F)c(Nc2nc(-c3ccc4c(c3)N([C@H]3C[C@@H](N5CCCCC5)C3)C(=O)C43CCN(C(=O)[C@H]4CC[C@@H](C(=O)N5CCC(Oc6cccc7c6C(=O)N(C6CCC(=O)NC6=O)C7=O)CC5)CC4)CC3)cc3ncn(C(C)C)c23)cc1C(=O)NC(C)C]

253

Step 1: Synthesis of 2-[2,6-dioxopiperidin-3-yl]-4-(piperidin-4-yloxy)isoindole-1,3-dione: 2-[2,6-dioxopiperidin-3-yl]-4-fluoroisoindole-1,3-dione (250 mg. 0.91 mmol) and tert-butyl 4-hydroxypiperidine-1-carboxylate (180 mg, 0.91 mmol) were dissolved in NMP (5 mL). Sodium Hydride (72 mg, 1.8 mmol) was added, and the reaction was stirred at 25° C. for 12 hours. The reaction mixture was poured over water (100 mL) and extracted with ethyl acetate (2×100 mL). The extract was concentrated under reduced pressure. This crude material was immediately submitted to General Procedure B. Chromatography C provided the title compound (195 mg, 60%).

Step 2: Synthesis of (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid: The reaction was carried out according to General Procedure F using Intermediate 1 (50 mg, 0.07 mmol) and (cis)-4-(methoxycarbonyl)cyclohexane-1-carboxylic acid (15 mg, 0.07 mmol). The solvents were removed by nitrogen blowdown and the crude material was immediately submitted to General Procedure C. Chromatography C provided the title compound (47 mg, 76%).

Step 3: Synthesis of 4-fluoro-N-isopropyl-5-[(3-isopropyl-6-{2-oxo-1-[(1s,3s)-3-(piperidin-1-yl)cyclobutyl]-1'-[(1s,4s)-4-[4-({2-[2,6-dioxopiperidin-3-yl]-1,3-dioxoisoindol-4-yl}oxy)piperidine-1-carbonyl]cyclohexanecarbonyl]spiro[indole-3,4'-piperidin]-6-yl}imidazo[4,5-c]pyridin-4-yl)amino]-2-methylbenzamide: The title compound was synthesized according to General Procedure F, using (1s,4s)-4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}cyclohexane-1-carboxylic acid (20 mg, 0.02 mmol) and 2-[2,6-dioxopiperidin-3-yl]-4-(piperidin-4-yloxy)isoindole-1,3-dione (8.3 mg, 0.02 mmol) as starting materials. Chromatography C provided the title compound (25.5 mg, 84%); LCMS: $C_{67}H_{78}FN_{11}O_9$ requires 1199.6, found 1202.1 [M+2H]$^+$; $^1$H NMR (500 MHz, DMSO-$d_6$) δ 11.12 (s, 1H), 9.34 (d, J=9.2 Hz, 1H), 8.67 (s, 1H), 8.40 (s, 1H), 8.15 (d, J=7.8 Hz, 1H), 7.89 (s, 1H), 7.86-7.79 (m, 1H), 7.71-7.57 (m, 3H), 7.57-7.46 (m, 3H), 7.19 (d, J=12.1 Hz, 1H), 5.36-5.25 (m, 1H), 5.10 (dd, J=12.8, 5.4 Hz, 1H), 5.00 (s, 1H), 4.22 (t, J=8.3 Hz, 2H), 4.05 (h, J=6.6 Hz, 2H), 3.92-3.60 (m, 8H), 3.53 (d, J=8.1 Hz, 4H), 3.04-2.76 (m, 8H), 2.67-2.54 (m, 2H), 2.38 (s, 3H), 2.10-1.49 (m, 24H), 1.42 (d, J=12.7 Hz, 1H), 1.31-1.14 (m, 1H), 1.11 (d, J=6.5 Hz, 6H).

Example 97

5-{[6-(1'-{4-[(1-{2-[2,6-dioxopiperidin-3-yl]-1,3-dioxoisoindol-5-yl}piperidin-4-yl)(methyl)amino]benzoyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide

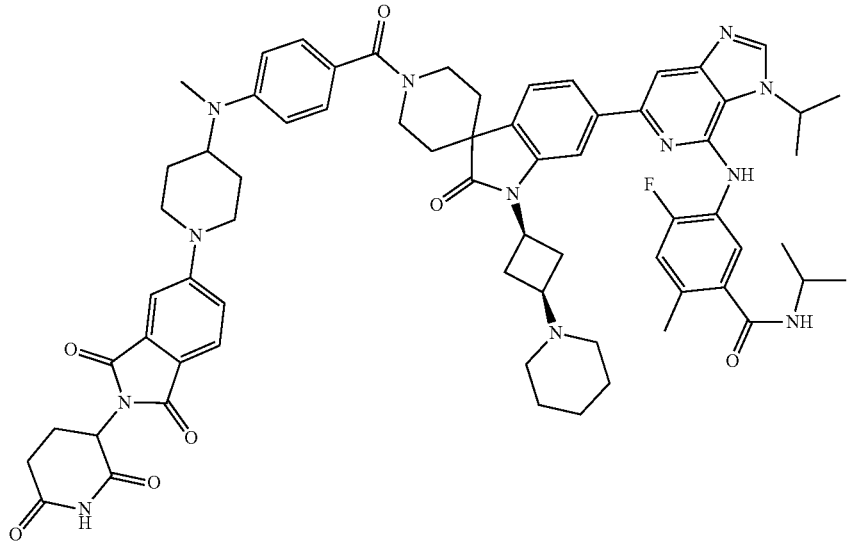 [SMILES: Cc1cc(F)c(Nc2nc(-c3ccc4c(c3)N([C@H]3C[C@@H](N5CCCCC5)C3)C(=O)C43CCN(C(=O)c4ccc(N(C)C5CCN(c6ccc7c(c6)C(=O)N(C6CCC(=O)NC6=O)C7=O)CC5)cc4)CC3)cc3ncn(C(C)C)c23)cc1C(=O)NC(C)C]

Step 1: Synthesis of 4-fluoro-N-isopropyl-5-{[3-isopropyl-6-(1'-{4-[methyl(piperidin-4-yl)amino]benzoyl}-2-oxo-1-[(1s,3s)-3-(piperidin-1-yl)cyclobutyl]spiro[indole-3,4'-piperidin]-6-yl)imidazo[4,5-c]pyridin-4-yl]amino}-2-methylbenzamide. The reaction was carried out according to General Procedure F, using Intermediate 1 (50 mg, 0.07 mmol) and 4-{[1-(tert-butoxycarbonyl)piperidin-4-yl](methyl)amino}benzoic acid (24 mg, 0.07 mmol). Chromatography C provided tert-butyl 4-((4-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidine]-1'-carbonyl)phenyl)(methyl)amino)piperidine-1-carboxylate which was directly submitted to General Procedure B to afford the title compound (43 mg, 66%).

Step 2: Synthesis of 5-{[6-(1'-{4-[(1-{2-[2,6-dioxopiperidin-3-yl]-1,3-dioxoisoindol-5-yl}piperidin-4-yl)(methyl)amino]benzoyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide: The title compound was synthesized according to General Procedure A, using 4-fluoro-N-isopropyl-5-{[3-isopropyl-6-(1'-{4-[methyl(piperidin-4-yl)amino]benzoyl}-2-oxo-1-[(1s,3s)-3-(piperidin-1-yl)cyclobutyl]spiro[indole-3,4'-piperidin]-6-yl)imidazo[4, 5-c]pyridin-4-yl]amino}-2-methylbenzamide (20 mg, 0.02 mmol) and rac-2-[(3R)-2,6-dioxopiperidin-3-yl]-5-fluoroisoindole-1,3-dione (6.0 mg, 0.02 mmol) as starting materials. Chromatography C provided the title compound. (5.5 mg, 19%); LCMS: $C_{67}H_{75}FN_{12}O_7$ requires 1178.6, found 1180.0 [M+H]$^+$; $^1$H NMR (500 MHz, DMSO-d$_6$) δ 11.10 (d, J=6.4 Hz, 1H), 9.33 (s, 1H), 8.63 (s, 1H), 8.39 (s, 1H), 8.15 (d, J=7.9 Hz, 1H), 7.89 (s, 1H), 7.76-7.56 (m, 4H), 7.53 (s, 1H), 7.43-7.24 (m, 3H), 7.19 (d, J=12.1 Hz, 1H), 6.90 (d, J=8.5 Hz, 1H), 5.36-5.22 (m, 1H), 5.17-5.00 (m, 1H), 4.21 (d, J=11.0 Hz, 2H), 4.04 (dt, J=13.5, 6.7 Hz, 2H), 3.53 (d, J=8.4 Hz, 2H), 3.41 (d, J=11.3 Hz, 2H), 3.22-3.03 (m, 2H), 3.03-2.55 (m, 13H), 2.38 (s, 3H), 2.08-1.69 (m, 16H), 1.60 (d, J=6.5 Hz, 8H), 1.42 (d, J=12.8 Hz, 2H), 1.27 (t, J=7.0 Hz, 1H), 1.11 (d, J=6.6 Hz, 6H).

Biological Example

HPK1 Cellular HiBiT Degradation Assay

Materials and Methods

A HiBiT tag was introduced by CRISPR on the N terminus of HPK1 in Jurkat cells (ATCC® TIB-152) to allow quantitation of HPK1 protein levels in a monoclonal human cell line. Cells were plated at 1×10$^6$ cells/mL, 30 uL/well (3×10$^4$ cells/well) in complete RPMI 1640 (10% heat inactivated FBS, 1% L-glutamine) in 384-well assay plates (Corning, cat. no. 3570). HPK1 chimeric targeting molecules (CTMs) were added in an 11-point dilution series (3.16-fold) with a final assay concentration range of 10 uM to 0.1 nM. The parental Jurkat cell line, with no HiBiT insertion, was included in the assay as a background control. Cells treated with a DMSO vehicle control were used to determine the maximum signal defining 100% HPK1 in the cell. Cells were incubated for 24 hours at 37° C./5% CO$_2$. Following incubation, 30 uL of complete Nano-Glo HiBiT Lytic Detection Reagent (Promega cat. no. N3040) was added. Cells were incubated for 10 minutes at room temperature and luminescence was read on an EnVision plate reader (Perkin Elmer, 0.1 sec per well). Parallel plates were assessed for viability using Cell Titer Glo (Promega) and read on an EnVision plate reader to ensure results were not the effect of cytotoxicity. Percent HPK1 remaining per sample was calculated as follows:

$$\% \, HPK1 \, remaining = \left[\frac{sample \, RLU - parental \, RLU}{average \, DMSO \, RLU - average \, parental \, RLU}\right] \times 100$$

% HPK1 remaining values were plotted as a function of compound concentration and curves were fit using the Prism (GraphPad) equation "log(inhibitor) vs response–Variable slope (four parameters)". $D_{max}$ values were calculated by identifying the lowest % remaining and subtracting from 100. $D_{max}$ values are provided in Table 1, wherein A>65%, 45%≤B≤65% and C<45%.

TABLE 1

Activity of Representative Compounds

| Example | Cellular HPK1 HiBiT: Dmax (%) |
|---|---|
| 1 | C |
| 2 | B |

TABLE 1-continued

Activity of Representative Compounds

| Example | Cellular HPK1 HiBiT: Dmax (%) |
|---|---|
| 3 | C |
| 4 | C |
| 5 | C |
| 6 | C |
| 7 | A |
| 8 | A |
| 9 | C |
| 10 | A |
| 11 | C |
| 12 | B |
| 13 | C |
| 14 | B |
| 15 | C |
| 16 | C |
| 17 | C |
| 18 | B |
| 19 | C |
| 20 | C |
| 21 | C |
| 22 | C |
| 23 | C |
| 24 | C |
| 25 | B |
| 26 | B |
| 27 | C |
| 28 | C |
| 29 | B |
| 30 | C |
| 31 | A |
| 32 | C |
| 33 | A |
| 34 | C |
| 35 | B |
| 36 | C |
| 37 | A |
| 38 | A |
| 39 | C |
| 40 | B |
| 41 | B |
| 42 | B |
| 43 | A |
| 44 | B |
| 45 | A |
| 46 | B |
| 47 | A |
| 48 | B |
| 49 | B |
| 50 | B |
| 51 | B |
| 52 | B |
| 53 | B |
| 54 | C |
| 55 | A |
| 56 | C |
| 57 | C |
| 58 | C |
| 59 | B |
| 60 | A |
| 61 | A |
| 62 | B |
| 63 | A |
| 64 | A |
| 65 | B |
| 66 | A |
| 67 | A |
| 68 | B |
| 69 | B |
| 70 | B |
| 71 | A |
| 72 | A |
| 73 | A |
| 74 | B |
| 75 | C |
| 76 | B |

TABLE 1-continued

Activity of Representative Compounds

| Example | Cellular HPK1 HiBiT: Dmax (%) |
|---|---|
| 77 | B |
| 78 | B |
| 79 | B |
| 80 | B |
| 81 | B |
| 82 | B |
| 83 | C |
| 84 | B |
| 85 | C |
| 86 | B |
| 87 | C |
| 88 | A |
| 89 | A |
| 90 | B |
| 91 | B |
| 92 | B |
| 93 | B |
| 94 | C |
| 95 | B |
| 96 | B |
| 97 | B |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having the following structure (I):

Formula (I)

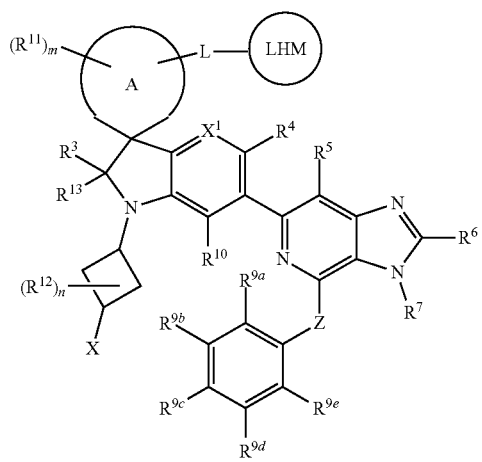

or a pharmaceutically acceptable salt thereof, wherein:
m is 0, 1, 2, 3, or 4;
n is 0, 1, 2, 3, 4, 5, or 6;
A is a $C_{3-7}$ monocyclic cycloalkyl ring or a 4-6 membered monocyclic heterocyclyl ring having 1 or 2 heteroatoms independently selected from N, O, and S;
L is a linker moiety having a length of 2-24 continuously covalently bonded atoms selected from the group consisting of C, O, N and S;
LHM is a ligase harness moiety;
$R^{11}$ is
i) selected from the group consisting of —OH, halogen, oxo, $C_{1-3}$ alkyl, and $C_{1-3}$ alkoxy; or
ii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iii) —S(O)$_2$C$_{1-6}$ alkyl,
iv) —S(O)$_2$C$_{3-7}$ monocyclic cycloalkyl,
v) $C_{1-6}$ alkyl optionally substituted with 1-3 groups independently selected from —CN, —OH, halogen, $C_{1-3}$ alkoxy, and $C_{3-7}$ monocyclic cycloalkyl, or
vi) —C(O)R$^{21}$;
each $R^{12}$ is independently selected from —OH, halogen, $C_{1-3}$ alkyl, and $C_{1-3}$ alkoxy;
$R^{21}$ is
i) H,
ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy,
v) —NH$_2$,
vi) —NH(C$_{1-6}$ alkyl), wherein the $C_{1-6}$ alkyl is optionally substituted with 1-3 groups independently selected from —CN, —OH, halogen, and $C_{1-3}$ alkoxy,
vii) —N(C$_{1-6}$ alkyl)$_2$, wherein each $C_{1-6}$ alkyl can be the same or different and wherein each $C_{1-6}$ alkyl is optionally substituted with 1-3 groups independently selected from —CN, —OH, halogen, and $C_{1-3}$ alkoxy,
viii) $C_{1-6}$ alkoxy optionally substituted with 1-3 groups independently selected from —OH, halogen, $C_{1-3}$ alkyl, and $C_{3-7}$ monocyclic cycloalkyl, or
ix) $C_{1-6}$ alkyl optionally substituted with 1-3 groups independently selected from
a) —CN,
b) —OH,
c) halogen,
d) $C_{1-3}$ alkoxy, e) $C_{3-7}$ monocyclic cycloalkyl optionally substituted with 1-3 groups independently selected from —CN, —OH, halogen, $C_{1-3}$ alkyl, and $C_{1-3}$ alkoxy,
f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy, and
g) —OC(O)$C_{1-6}$ alkyl optionally substituted with one —OH;

$R^3$ and $R^{13}$ are each H, or
$R^3$ and $R^{13}$ together form =O;
X is —NR$^{15}$R$^{16}$, wherein R$^{15}$ and R$^{16}$ are independently
i) H,
ii) $C_{3-7}$ monocyclic cycloalkyl optionally substituted with 1-3 groups independently selected from —OH, halogen, $C_{1-3}$ alkyl, and $C_{1-3}$ alkoxy,
iii) 4-7 membered monocyclic heterocyclyl having 1 or 2 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
iv) —C(O)$C_{1-6}$ alkyl, wherein the $C_{1-6}$ alkyl is optionally substituted with 1-3 groups independently selected from —CN, —OH, halogen, and $C_{1-3}$ alkoxy, or
v) $C_{1-6}$ alkyl optionally substituted with 1-6 groups independently selected from
  a) —CN,
  b) —OH,
  c) halogen,
  d) $C_{1-3}$ alkoxy,
  e) $C_{3-7}$ monocyclic cycloalkyl optionally substituted with 1-3 groups independently selected from —OH, halogen, $C_{1-3}$ alkyl, and $C_{1-3}$ alkoxy, and
  f) 5-6 membered monocyclic heterocyclyl having 1 or 2 heteroatoms independently selected from N, O, and S, wherein the 5-6 membered monocyclic heterocyclyl is optionally substituted with 1-3 groups independently selected from —OH, halogen, oxo, $C_{1-3}$ alkyl, and $C_{1-3}$ alkoxy; or
X is a 4-10 membered monocyclic, fused bicyclic, bridged bicyclic, or spirocyclic heterocyclyl having 1-3 heteroatoms independently selected from N, O, and S, wherein the 4-10 membered monocyclic, fused bicyclic, bridged bicyclic, or spirocyclic heterocyclyl is optionally substituted with 1-5 R$^{18}$;
each R$^{18}$ is independently
i) —CN,
ii) a halogen,
iii) —OH,
iv) $C_{1-6}$ alkoxy optionally substituted with 1-3 groups independently selected from —OH, halogen, $C_{1-3}$ alkoxy, and $C_{3-7}$ monocyclic cycloalkyl,
v) $C_{1-6}$ alkyl optionally substituted with 1-3 groups independently selected from —OH, halogen, $C_{1-3}$ alkoxy, and $C_{3-7}$ monocyclic cycloalkyl,
vi) —COOH, or
vii) —C(O)N(R$^{22}$)$_2$, wherein each R$^{22}$ is independently H or $C_{1-6}$ alkyl;
$X^1$ is N or CR$^{17}$;
R$^4$, R$^5$, R$^6$, R$^{10}$ and R$^{17}$ are each independently H, halogen, $C_{1-3}$ alkyl, or $C_{1-3}$ alkoxy;

R$^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;
Z is —O—, —C(R$^8$)$_2$—, or —NR$^8$—;
each R$^8$ is independently H or $C_{1-3}$ alkyl;
R$^{9a}$, R$^{9b}$, R$^{9c}$, R$^{9d}$, and R$^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —NH$_2$,
v) —NH($C_{1-6}$ alkyl), wherein the $C_{1-6}$ alkyl is optionally substituted with 1-3 groups independently selected from —OH, halogen, and $C_{1-3}$ alkoxy,
vi) —N($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —P(O)($C_{1-6}$ alkyl)$_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —S(O)$_2$$C_{1-6}$ alkyl,
ix) —S(O)$_2$N(R$^{23}$)$_2$, wherein each R$^{23}$ is independently H or $C_{1-6}$ alkyl,
x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  f) —NR$^{20}$C(O)O$C_{1-3}$ alkyl, wherein R$^{20}$ is H or $C_{1-3}$ alkyl,
xi) $C_{3-7}$ monocyclic cycloalkyl optionally substituted with 1-3 groups independently selected from —OH, halogen, $C_{1-3}$ alkyl, and $C_{1-3}$ alkoxy,
xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
xiv) —COOH,
xv) —C(O)N(R$^{19}$)$_2$, or
xvi) —$C_{1-3}$ alkylene-C(O)N(R$^{19}$)$_2$,
wherein one or more of R$^{9a}$, R$^{9b}$, R$^{9c}$, R$^{9d}$, and R$^{9e}$ is —C(O)N(R$^{19}$)$_2$ or —$C_{1-3}$ alkylene-C(O)N(R$^{19}$)$_2$; and each $R^{19}$ is independently
i) H,
ii) —S(O)$_2$C$_{1-6}$ alkyl,
iii) C$_{1-6}$ alkyl optionally substituted with 1-6 groups independently selected from —CN, —OH, halogen, C$_{1-3}$ alkoxy, and C$_{3-7}$ monocyclic cycloalkyl,
iv) C$_{3-7}$ monocyclic cycloalkyl optionally substituted with 1-6 groups independently selected from —CN, —OH, halogen, C$_{1-6}$ alkyl, and C$_{1-6}$ alkoxy, wherein the C$_{1-6}$ alkyl is optionally substituted with 1-3 groups independently selected from —CN, —OH, halogen, and C$_{1-3}$ alkoxy, or
v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, C$_{1-3}$ alkyl, and C$_{1-3}$ alkoxy.

2. The compound of claim 1 wherein, Z is NH, X$^1$ is CH, R$^6$ is H, and the compound has a structure of Formula (Ia):

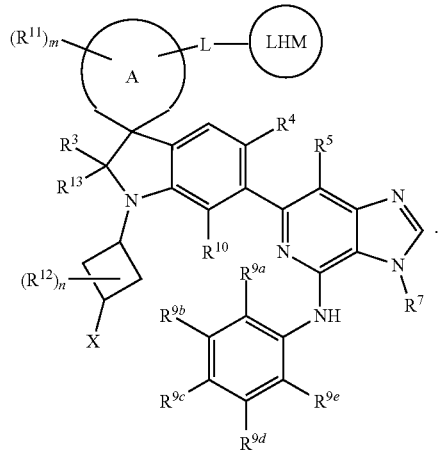

Formula (Ia)

3. The compound of claim 1 wherein the compound has a structure of Formula (Ib):

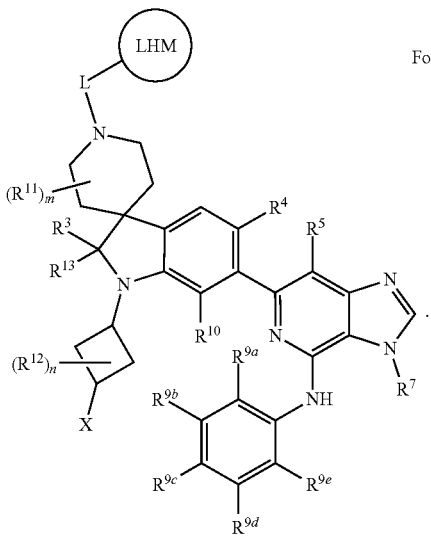

Formula (Ib)

4. The compound of claim 3 wherein R$^3$ and R$^{13}$ together form =O.

5. The compound of claim 3 wherein X is piperdinyl.

6. The compound of claim 3 wherein n is 0 and m is 0.

7. The compound of claim 3,
wherein
each R$^{9a}$, R$^{9b}$, R$^{9c}$, R$^{9d}$, and R$^{9e}$ is independently H, halogen, C$_{1-6}$ alkyl, or —C(O)N(R$^{19}$)$_2$, wherein R$^{19}$ is C$_{1-6}$ alkyl;
R$^4$, R$^5$ and R$^{10}$ are each H; and
R$^7$ is C$_{1-6}$ alkyl.

8. The compound of claim/wherein the compound has a structure of Formula (Ic):

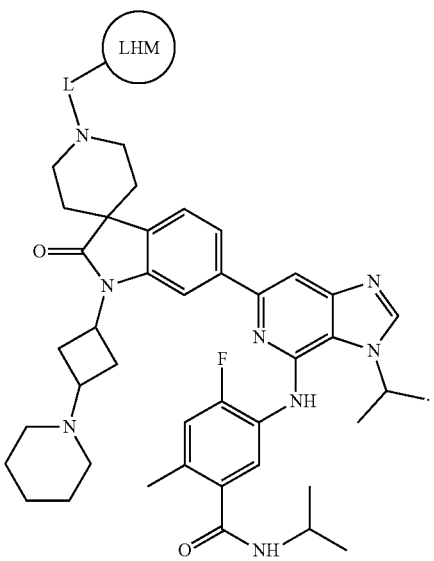

(Formula (Ic)

9. The compound of claim 1, wherein L is

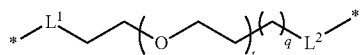

wherein,
t is 0, 1, 2, 3, 4, 5, 6, or 7;
q is 0, 1, 2, 3, 4, 5, 6, or 7;
L$^1$ is a direct bond, —C(O)NH—, or —C(O)—; and
L$^2$ is —C(O)NH—, —O—, or —NH—.

10. The compound of claim 9, wherein L has one of the following structures:

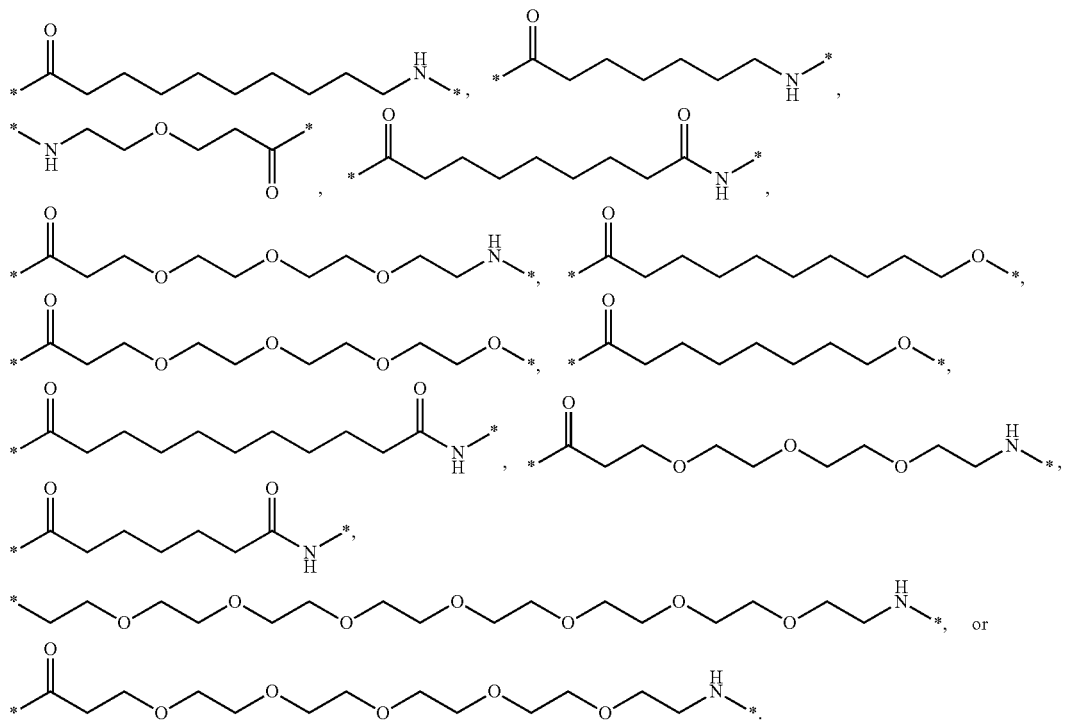
11. The compound of claim 1, wherein L is
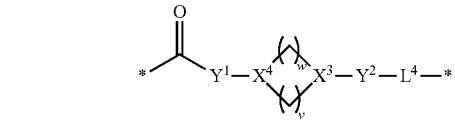
wherein,
w is 1, 2, or 3;
v is 1 or 2;
p is 1, 2, 3, 4, or 5;
$Y^1$ is a direct bond, —$(CH_2)_p$—, or —O—;
$Y^2$ is a direct bond, —$(CH_2)_p$—, —C(O)—, or —C(O)—$CH_2$—,
$X^3$ and $X^4$ are independently N or C(R), wherein R is H or $C_{1-3}$alkyl;
$L^4$ is a direct bond, —NH—, —NHC(O)—, or
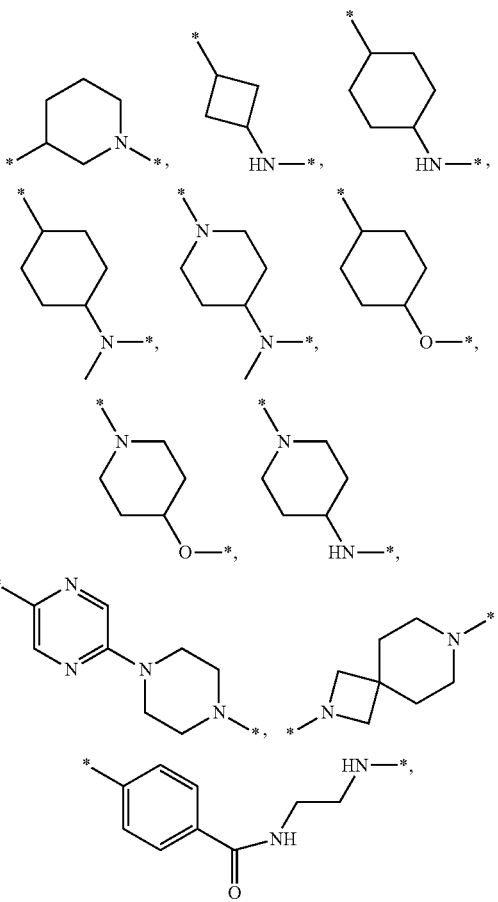

265
-continued
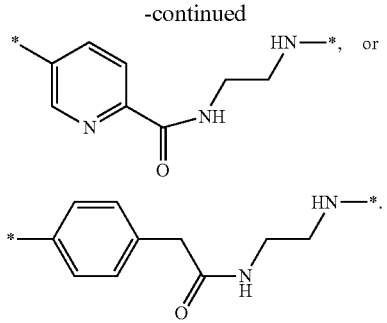
12. The compound of claim 11, wherein L has one of the following structures:
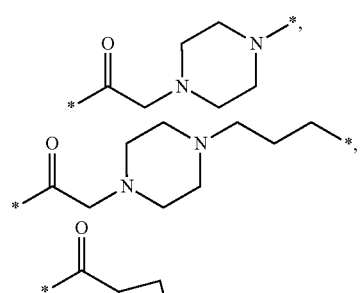
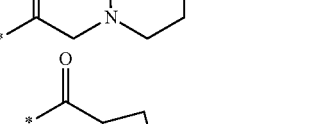
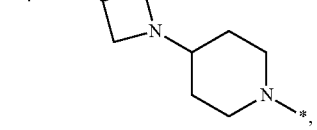
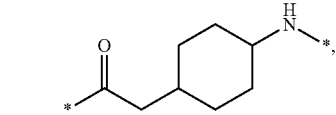
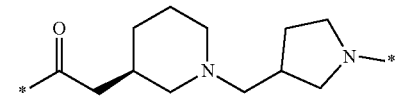
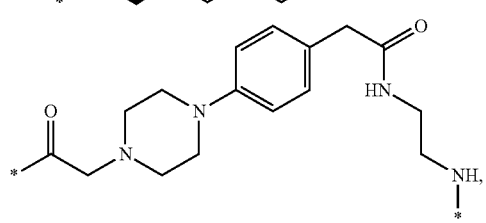
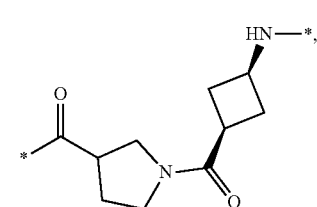
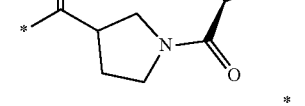
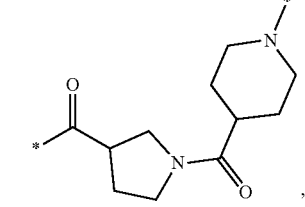
266
-continued
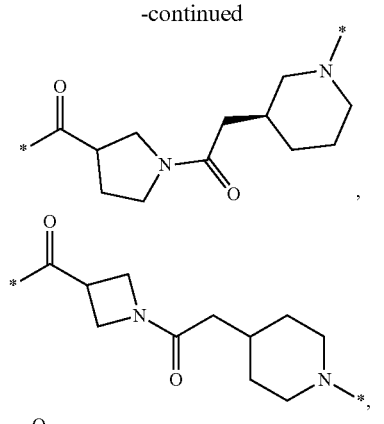
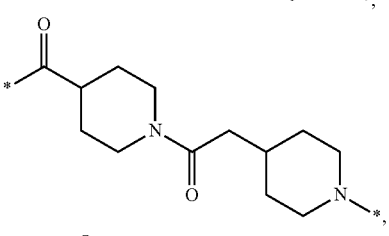
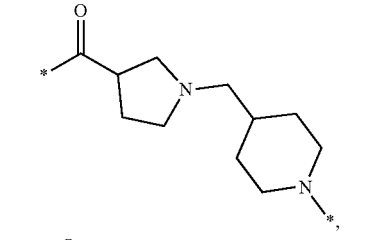
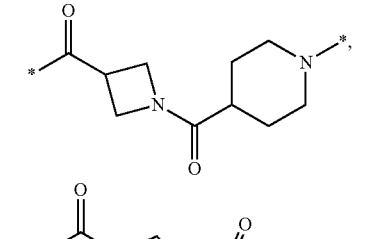
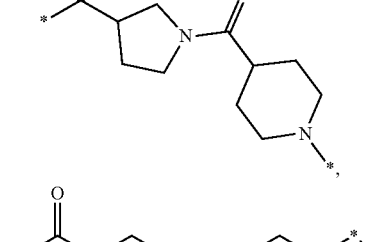
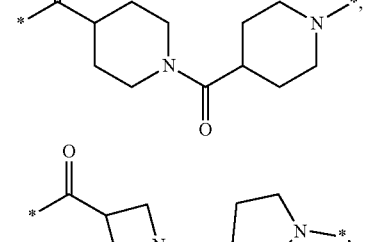
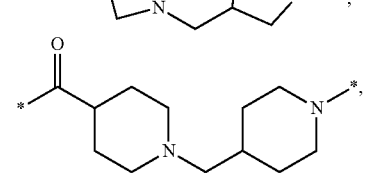

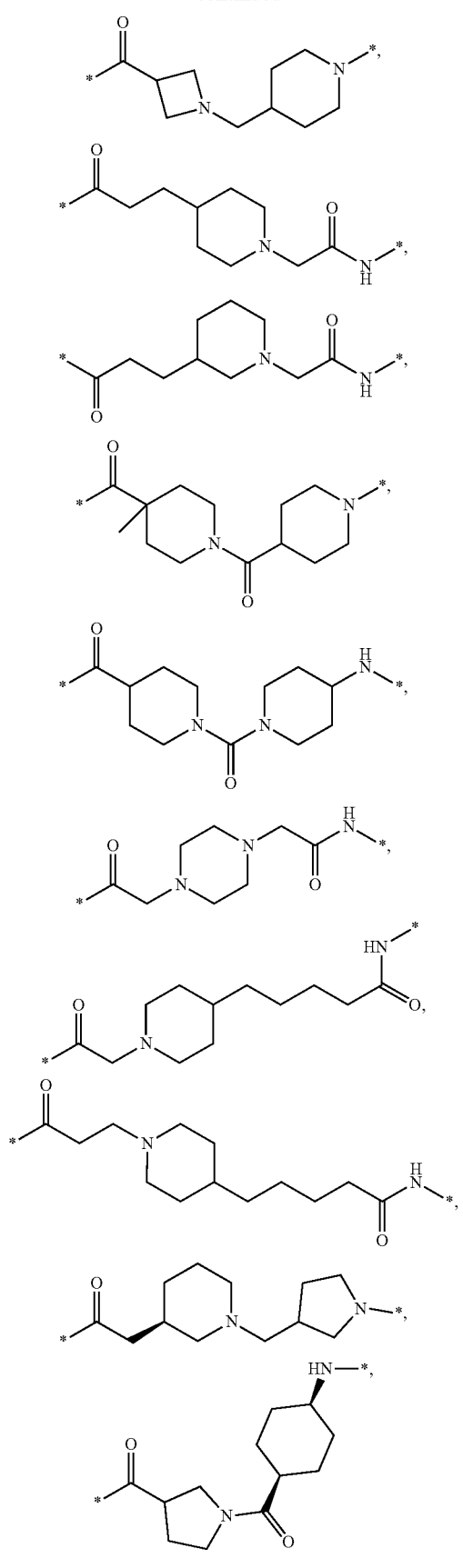
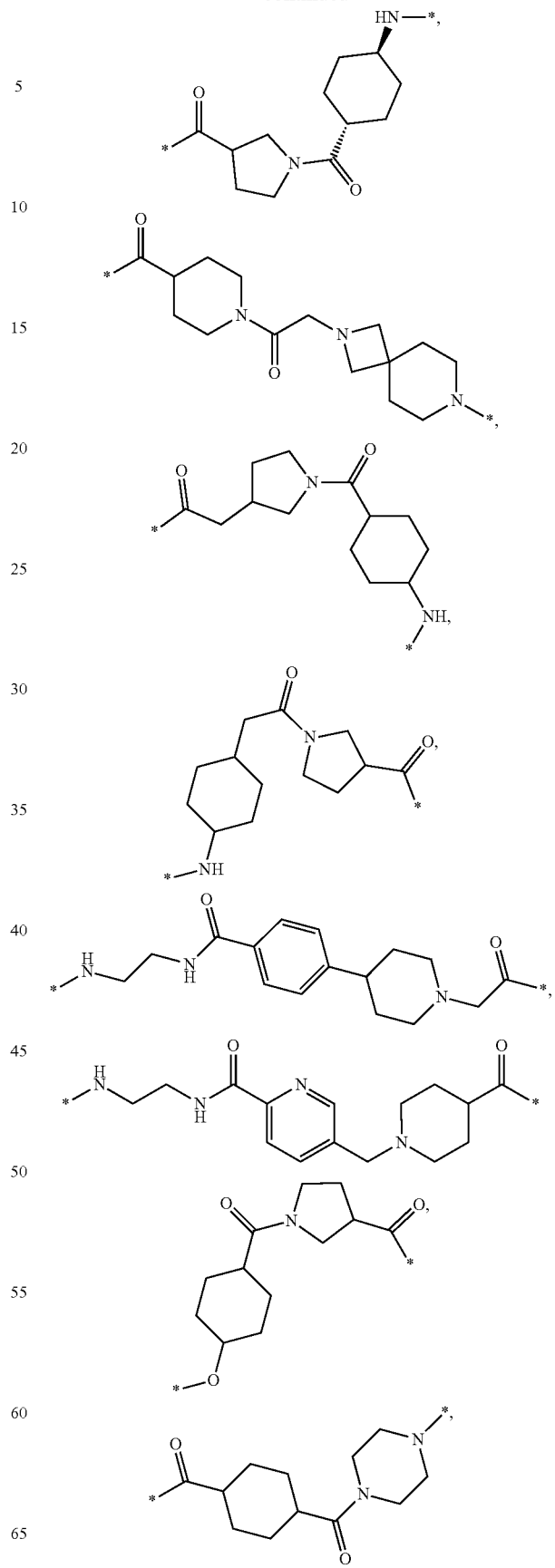

269
-continued
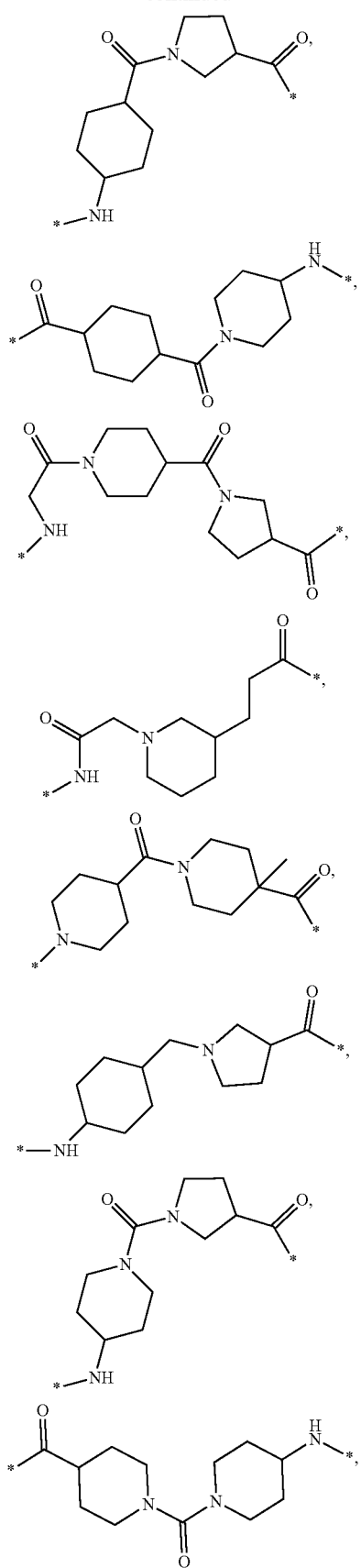
270
-continued
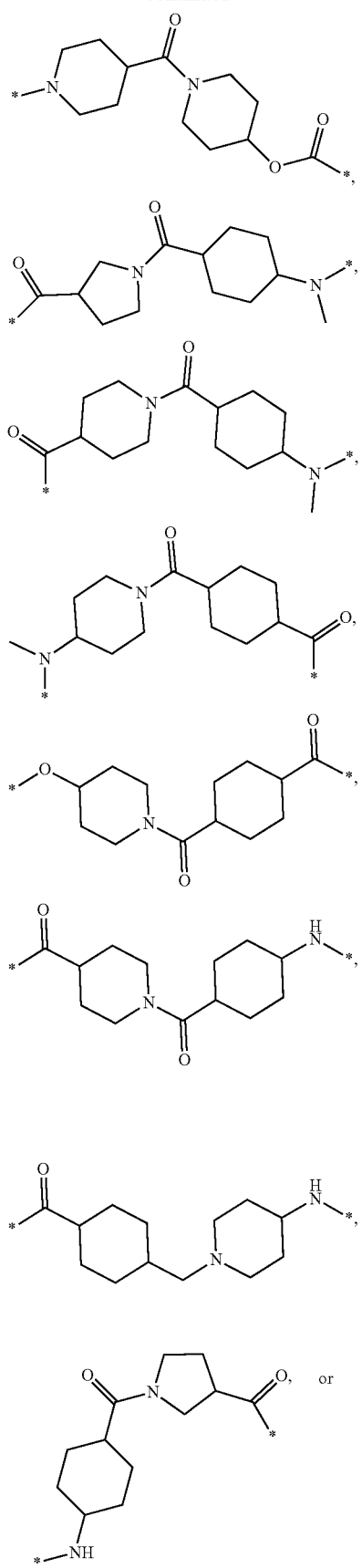

-continued
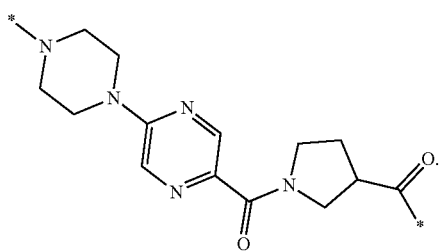
13. The compound of claim 1, wherein L is any one of the following structures:
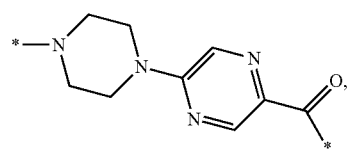
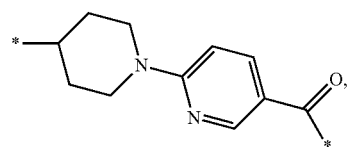
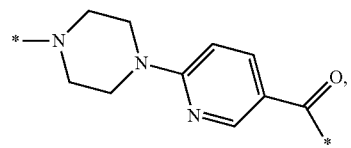
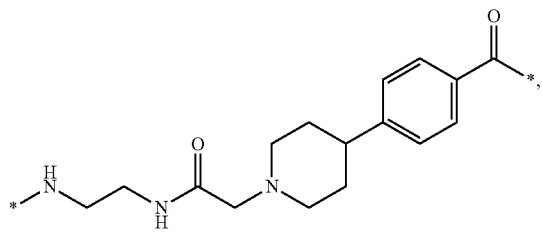
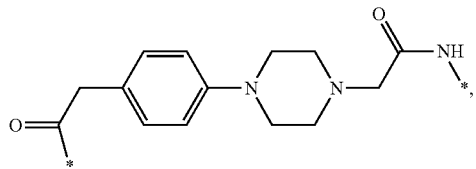
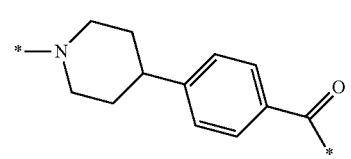
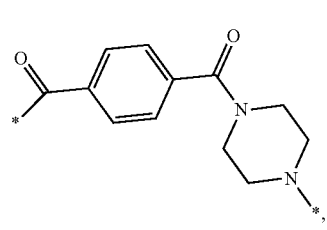
-continued
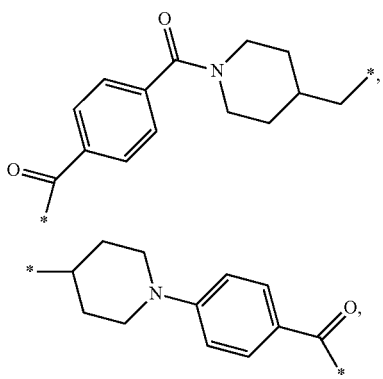
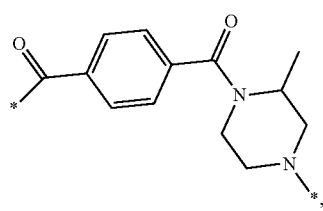
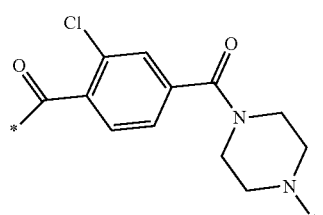
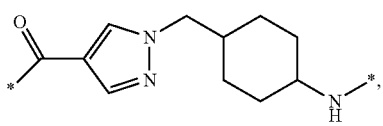
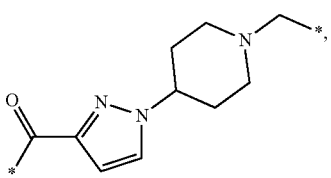
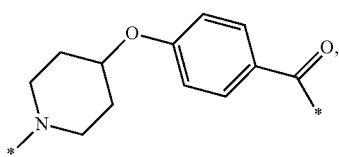
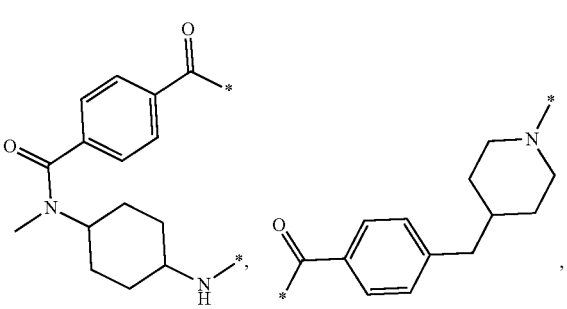

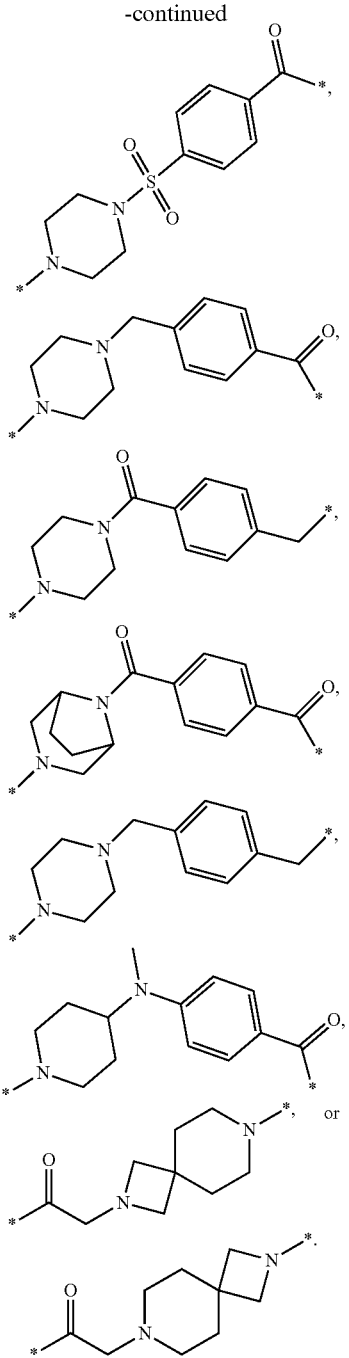

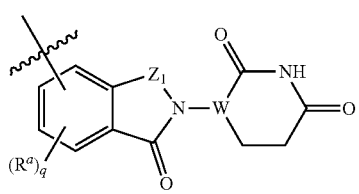

14. The compound of claim 1, wherein the LHM targets CRBN and has a structure of Formula (Id):

Formula (Id)

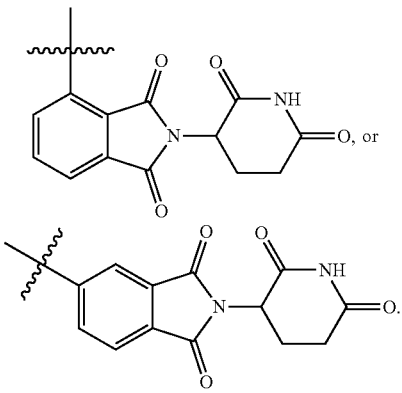

wherein,

W is —C(R$^g$)— or —N—;

Z$_1$ is —C(O)—, —C(S)—, —C(NR$^g$)—, —C(R$^g$)$_2$—, —C(R$^g$)$_2$—C(O)—, —C(O)—N(R$^g$)—, —CR$^g$=CR$^g$—, —C(R$^g$)=N—, —C(R$^g$)$_2$—C(S)—, or —C(R$^g$)$_2$—C(R$^g$)$_2$—;

q is 0, 1 or 2;

R$^g$ is hydrogen or C$_{1-6}$ alkyl; and

R$^a$ is C$_{1-6}$alkyl, halo, halo C$_{1-6}$alkyl, —N(R$^g$)$_2$, CN, nitro, —O—C$_{1-4}$alkyl, or hydroxyl.

15. The compound of claim 14 wherein the LHM has one of the following structures:

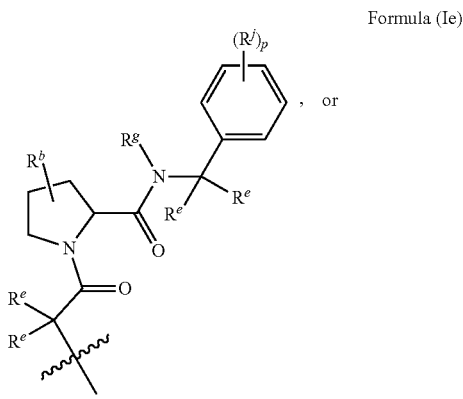

16. The compound of claim 1 wherein the LHM targets VHL and has a structure of Formula (Ie) or (If):

Formula (Ie)

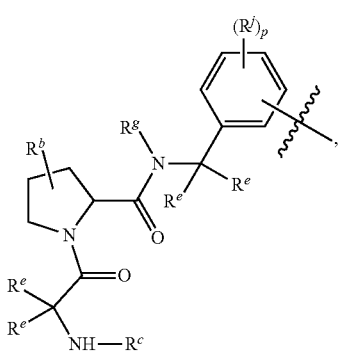

Formula (If)

wherein, p is 0 or 1;

R$^j$ is 5-6 member heteroaryl optionally substituted with 1 to 3 R$^k$, each R$^k$ is independently halo, oxo, —CN, —OH, C$_{1-6}$ alkyl, C$_{3-8}$ cycloalkyl, or —O—C$_{1-6}$ alkyl;

each R$^e$ is independently hydrogen, C$_{1-6}$ alkyl or C$_{3-8}$ cycloalkyl;

R$^g$ is hydrogen or C$_{1-6}$ alkyl;

R$^b$ is hydrogen or hydroxyl; and

R$^c$ is —C(O)R$^f$, wherein R$^f$ is C$_{1-6}$ alkyl or C$_{3-8}$ cycloalkyl, each being optionally substituted with halo or —CN.

17. The compound of claim 16 wherein the LHM has one of the following structures:

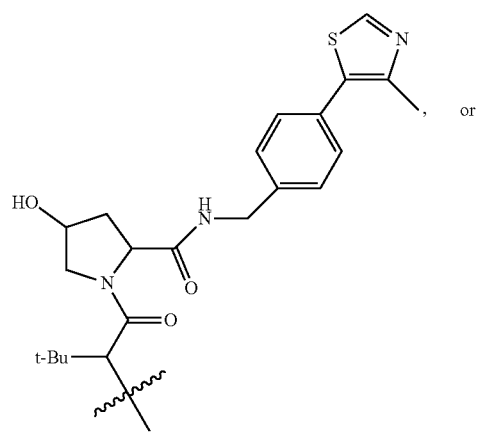, or

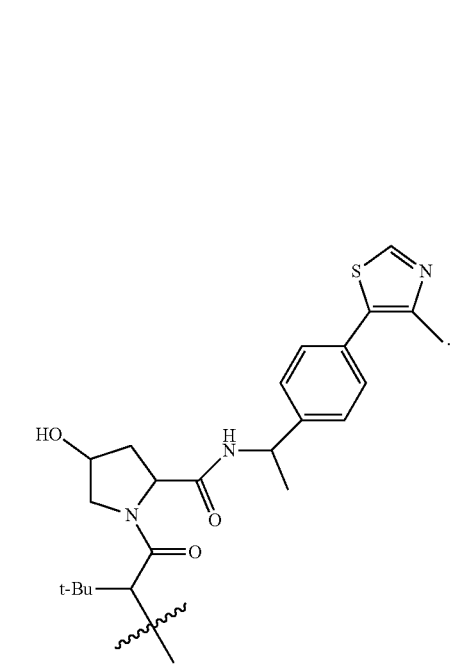

18. The compound of claim 16 wherein the LHM has one of the following structures:

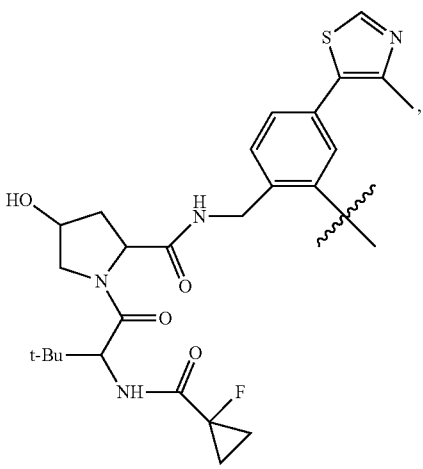,

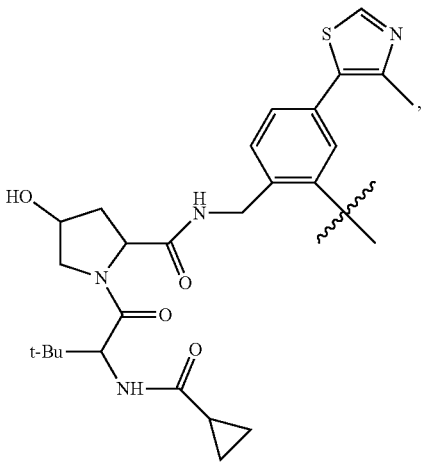,

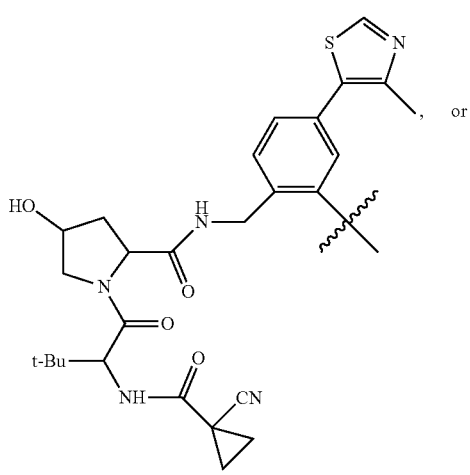, or

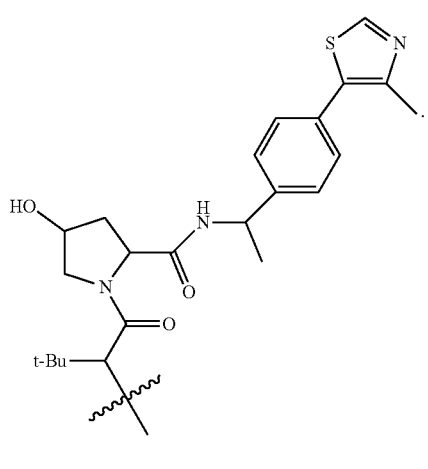

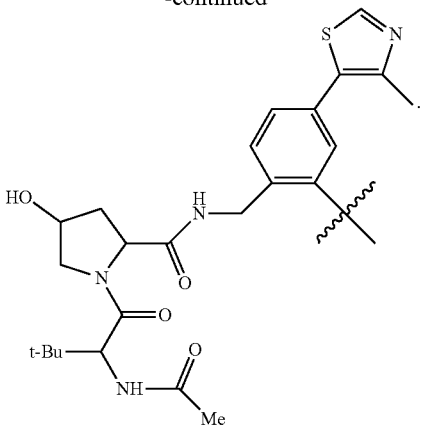

19. The compound of claim 1 selected from the group consisting of:

5-((6-(1'-(10-((2-(2,6-dioxopiperidin-3-yl)-1,3-dioxoisoindolin-4-yl)amino)decanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(1-((2-(2,6-dioxopiperidin-3-yl)-1,3-dioxoisoindolin-4-yl)amino)-3,6,9,12-tetraoxapentadecan-15-oyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(8-((2-(2,6-dioxopiperidin-3-yl)-1,3-dioxoisoindolin-5-yl)amino)octanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(10-((2-(2,6-dioxopiperidin-3-yl)-1,3-dioxoisoindolin-5-yl)amino)decanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(3-(2-(2-(2-((2-(2,6-dioxopiperidin-3-yl)-1,3-dioxoisoindolin-5-yl)amino)ethoxy)ethoxy)ethoxy)propanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

(2S,4R)—N-(2-((10-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-10-oxodecyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide;

(2S,4R)-1-((S)-2-(7-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-7-oxoheptanamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(11-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-11-oxoundecanamido)-3,3-dimethylbutanoyl)-4-hydroxy-N—((S)-1-(4-(4-methylthiazol-5-yl)phenyl)ethyl)pyrrolidine-2-carboxamide;

(2S,4R)—N-(2-(2-(2-(2-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropoxy)ethoxy)ethoxy)ethoxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide;

(2S,4R)-1-((S)-2-(9-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-9-oxononanamido)-3,3-dimethylbutanoyl)-4-hydroxy-N—((S)-1-(4-(4-methylthiazol-5-yl)phenyl)ethyl)pyrrolidine-2-carboxamide;

5-((6-(1'-(3-(2-((2-(2,6-dioxopiperidin-3-yl)-1,3-dioxoisoindolin-4-yl)amino)ethoxy)propanoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(1-((2-(2,6-dioxopiperidin-3-yl)-1,3-dioxoisoindolin-4-yl)amino)-3,6,9,12,15-pentaoxaoctadecan-18-oyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

(2S,4R)—N-(2-((8-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-8-oxooctyl)oxy)-4-(4-methylthiazol-5-yl)benzyl)-1-((S)-2-(1-fluorocyclopropane-1-carboxamido)-3,3-dimethylbutanoyl)-4-hydroxypyrrolidine-2-carboxamide;

(2S,4R)-1-((S)-2-(2-(4-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-3-oxopropyl)piperidin-1-yl)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(2-(4-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(5-(1-(2-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-1'-yl)-2-oxoethyl)piperidin-4-yl)pentanamido)-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-(5-(1-(3-(6-(4-((2-fluoro-5-(isopropylcarbamoyl)-4-methylphenyl)amino)-3-isopropyl-3H-imidazo[4,5-c]pyridin-6-yl)-2-oxo-1-((1s,3s)-3-(piperidin-1-yl)cyclobutyl)spiro[indoline-3,4'-piperidin]-

1'-yl)-3-oxopropyl)piperidin-4-yl)pentanamido)-3,3-dimethylbutanoyl)-4-hydroxy-N—((S)-1-(4-(4-methylthiazol-5-yl)phenyl)ethyl)pyrrolidine-2-carboxamide;

5-{[6-(1'-{2-[4-(3-{2-[2,6-dioxopiperidin-3-yl]-1,3-dioxo-2,3-dihydro-1H-isoindol-4-yl}propyl)piperazin-1-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-[(6-{1'-[2-(2-{2-[2,6-dioxopiperidin-3-yl]-1,3-dioxo-2,3-dihydro-1H-isoindol-5-yl}-2,7-diazaspiro[3.5]nonan-7-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridine-4-yl)amino]-4-fluoro-2-methyl-N-(propan-2-yl)benzamide;

5-[(6-{1'-[2-(4-{2-[(3RS)-2,6-dioxopiperidin-3-yl]-1,3-dioxo-2,3-dihydro-1H-isoindol-5-yl}piperazin-1-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

5-[(6-{1'-[1-(1-{2-[2,6-dioxopiperidin-3-yl]-1,3-dioxo-2,3-dihydro-1H-isoindol-5-yl}piperidin-4-yl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

5-[(6-{1'-[1-(1-{2-[(3RS)-2,6-dioxopiperidin-3-yl]-1,3-dioxo-2,3-dihydro-1H-isoindol-4-yl}piperidine-4-carbonyl)pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

4-fluoro-2-methyl-5-[(6-{2-oxo-1'-[1-[(1r,4r)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;

4-fluoro-2-methyl-5-[(6-{2-oxo-1-[(1s,3s)-3-(piperidin-1-yl)cyclobutyl]-1'-[1-[(1s,4s)-4-({2-[2,6-dioxopiperidin-3-yl]-1,3-dioxo-2,3-dihydro-1H-isoindol-4-yl}amino)cyclohexanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;

5-[(6-{1'-[2-(7-{2-[2,6-dioxopiperidin-3-yl]-1,3-dioxo-2,3-dihydro-1H-isoindol-5-yl}-2,7-diazaspiro[3.5]nonan-2-yl)acetyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

5-{[6-(1'-{2-[(3S)-1-({1-[2-(2,6-dioxopiperidin-3-yl)-1,3-dioxo-2,3-dihydro-1H-isoindol-5-yl]pyrrolidin-3-yl}methyl)piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

4-fluoro-2-methyl-5-[(6-{2-oxo-1-[(1s,3s)-3-(piperidin-1-yl)cyclobutyl]-1'-[1-[(1s,3s)-3-({2-[2,6-dioxopiperidin-3-yl]-1,3-dioxo-2,3-dihydro-1H-isoindol-4-yl}amino)cyclobutanecarbonyl]pyrrolidine-3-carbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;

5-{[6-(1'-{2-[(3S)-1-{[1-{2-[2,6-dioxopiperidin-3-yl]-1,3-dioxo-2,3-dihydro-1H-isoindol-4-yl}pyrrolidin-3-yl]methyl}piperidin-3-yl]acetyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-({6-[1'-(1-{2-[(3S)-1-{2-[2,6-dioxopiperidin-3-yl]-1,3-dioxo-2,3-dihydro-1H-isoindol-4-yl}piperidin-3-yl]acetyl}pyrrolidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide;

5-{[6-(1'-{1-[(1-{2-[2,6-dioxopiperidin-3-yl]-1,3-dioxo-2,3-dihydro-1H-isoindol-4-yl}piperidin-4-yl)methyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-{[6-(1'-{1-[2-(1-{2-[2,6-dioxopiperidin-3-yl]-1,3-dioxo-2,3-dihydro-1H-isoindol-4-yl}piperidin-4-yl)acetyl]azetidine-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-({6-[1'-(1-{[1-{2-[2,6-dioxopiperidin-3-yl]-1,3-dioxo-2,3-dihydro-1H-isoindol-4-yl}pyrrolidin-3-yl]methyl}azetidine-3-carbonyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-4-fluoro-2-methyl-N-(propan-2-yl)benzamide;

5-{[6-(1'-{1-[2-(1-{2-[2,6-dioxopiperidin-3-yl]-1,3-dioxo-2,3-dihydro-1H-isoindol-4-yl}piperidin-4-yl)acetyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-{[6-(1'-{1-[(1-{2-[2,6-dioxopiperidin-3-yl]-1,3-dioxo-2,3-dihydro-1H-isoindol-4-yl}piperidin-4-yl)methyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;

5-[(6-{1'-[1-[(1-{2-[2,6-dioxopiperidin-3-yl]-1,3-dioxo-2,3-dihydro-1H-isoindol-4-yl}piperidin-4-yl)methyl]pyrrolidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

5-[(6-{1'-[1-(1-{2-[2,6-dioxopiperidin-3-yl]-1,3-dioxo-2,3-dihydro-1H-isoindol-5-yl}piperidine-4-carbonyl)azetidine-3-carbonyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;

5-[(6-{1'-[1-(1-{2-[2,6-dioxopiperidin-3-yl]-1,3-dioxo-2,3-dihydro-1H-isoindol-5-yl}piperidine-4-carbonyl)pyrrolidine-3-carbonyl]-2-oxo-1-[(1s,3s)-3-(piperidin-1-yl)cyclobutyl]-1,2-dihydrospiro[indole-3,4'- piperidin]-6-yl}-3-(propan-2-yl)-3H-imidazo[4,5-c]
pyridin-4-yl)amino]-4-fluoro-2-methyl-N-(propan-2-
yl)benzamide;

5-[(6-{1'-[1-(1-{2-[2,6-dioxopiperidin-3-yl]-1,3-dioxo-2,
3-dihydro-1H-isoindol-5-yl}piperidine-4-carbonyl)pi-
peridine-4-carbonyl]-2-oxo-1-[(1s,3s)-3-(piperidin-1-
yl)cyclobutyl]-1,2-dihydrospiro[indole-3,4'-piperidin]-
6-yl}-3-(propan-2-yl)-3H-imidazo[4,5-c]pyridin-4-yl)
amino]-4-fluoro-2-methyl-N-(propan-2-yl)benzamide;

5-{[6-(1'-{1-[2-(7-{2-[2,6-dioxopiperidin-3-yl]-1,3-di-
oxo-2,3-dihydro-1H-isoindol-5-yl}-2,7-diazaspiro[3.5]
nonan-2-yl)acetyl]piperidine-4-carbonyl}-2-oxo-1-
[(1s,3s)-3-(piperidin-1-yl)cyclobutyl]-1,2-dihydrospiro
[indole-3,4'-piperidin]-6-yl)-3-(propan-2-yl)-3H-
imidazo[4,5-c]pyridin-4-yl]amino}-4-fluoro-2-methyl-
N-(propan-2-yl)benzamide;

5-[(6-{1'-[23-({2-[2,6-dioxopiperidin-3-yl]-1,3-dioxo-2,
3-dihydro-1H-isoindol-4-yl}amino)-3,6,9,12,15,18,21-
heptaoxatricosan-1-yl]-2-oxo-1-[(1s,3s)-3-(piperidin-
1-yl)cyclobutyl]-1,2-dihydrospiro[indole-3,4'-
piperidin]-6-yl}-3-(propan-2-yl)-3H-imidazo[4,5-c]
pyridin-4-yl)amino]-4-fluoro-2-methyl-N-(propan-2-
yl)benzamide;

5-({6-[1'-(2-{4-[4-({[2-({2-[2,6-dioxopiperidin-3-yl]-1,
3-dioxo-2,3-dihydro-1H-isoindol-4-yl}amino)ethyl]
carbamoyl}methyl)phenyl]piperazin-1-yl}acetyl)-2-
oxo-1-[(1s,3s)-3-(piperidin-1-yl)cyclobutyl]-1,2-
dihydrospiro[indole-3,4'-piperidin]-6-yl]-3-(propan-2-
yl)-3H-imidazo[4,5-c]pyridin-4-yl}amino)-4-fluoro-2-
methyl-N-(propan-2-yl)benzamide;

5-{[6-(1'-{1-[(1-{2-[2,6-dioxopiperidin-3-yl]-1,3-dioxo-
2,3-dihydro-1H-isoindol-5-yl}piperidin-4-yl)methyl]
piperidine-4-carbonyl}-2-oxo-1-[(1s,3s)-3-(piperidin-
1-yl)cyclobutyl]-1,2-dihydrospiro[indole-3,4'-
piperidin]-6-yl)-3-(propan-2-yl)-3H-imidazo[4,5-c]
pyridin-4-yl]amino}-4-fluoro-2-methyl-N-(propan-2-
yl)benzamide;

N-(2-((2-(2,6-dioxopiperidin-3-yl)-1,3-dioxoisoindolin-
4-yl)amino)ethyl)-7-(2-(6-(4-((2-fluoro-5-(isopropyl-
carbamoyl)-4-methylphenyl)amino)-3-isopropyl-3H-
imidazo[4,5-c]pyridin-6-yl)-2-oxo-1-((1s,3s)-3-
(piperidin-1-yl)cyclobutyl)spiro[indoline-3,4'-
piperidin]-1'-yl)-2-oxoethyl)-7-azaspiro[3.5]nonane-2-
carboxamide;

(2S,4R)-1-[(2S)-2-(2-{4-[4-(2-{6-[4-({2-fluoro-4-
methyl-5-[(propan-2-yl)carbamoyl]phenyl}amino)-3-
(propan-2-yl)-3H-imidazo[4,5-c]pyridin-6-yl]-2-oxo-
1-[(1s,3s)-3-(piperidin-1-yl)cyclobutyl]-1,2-
dihydrospiro[indole-3,4'-piperidin]-1'-yl}-2-oxoethyl)
phenyl]piperazin-1-yl}acetamido)-3,3-
dimethylbutanoyl]-4-hydroxy-N-[(1S)-1-[4-(4-methyl-
1,3-thiazol-5-yl)phenyl]ethyl]pyrrolidine-2-
carboxamide;

(2S,4R)-1-((2S)-2-(2-(3-(3-(6-(4-((2-fluoro-5-(isopropyl-
carbamoyl)-4-methylphenyl)amino)-3-isopropyl-3H-
imidazo[4,5-c]pyridin-6-yl)-2-oxo-1-((1s,3s)-3-(pip-
eridin-1-yl)cyclobutyl)spiro[indoline-3,4'-piperidin]-
1'-yl)-3-oxopropyl)piperidin-1-yl)acetamido)-3,3-
dimethylbutanoyl)-4-hydroxy-N—((S)-1-(4-(4-
methylthiazol-5-yl)phenyl)ethyl)pyrrolidine-2-
carboxamide;

5-[(6-{1'-[1-[2-({2-[2,6-dioxopiperidin-3-yl]-1,3-di-
oxo-2,3-dihydro-1H-isoindol-4-yl}amino)acetyl]pip-
eridine-4-carbonyl]pyrrolidine-3-carbonyl}-2-oxo-1-
[(1s,3s)-3-(piperidin-1-yl)cyclobutyl]-1,2-dihydrospiro
[indole-3,4'-piperidin]-6-yl}-3-(propan-2-yl)-3H-
imidazo[4,5-c]pyridin-4-yl)amino]-4-fluoro-2-methyl-
N-(propan-2-yl)benzamide;

4-fluoro-2-methyl-5-[(6-{2-oxo-1-[(1s,3s)-3-(piperidin-
1-yl)cyclobutyl]-1'-[(1s,4s)-4-[4-({2-[2,6-dioxopiperi-
din-3-yl]-1,3-dioxo-2,3-dihydro-1H-isoindol-4-
yl}amino)piperidine-1-carbonyl]
cyclohexanecarbonyl]-1,2-dihydrospiro[indole-3,4'-
piperidin]-6-yl}-3-(propan-2-yl)-3H-imidazo[4,5-c]
pyridin-4-yl)amino]-N-(propan-2-yl)benzamide;

4-fluoro-2-methyl-5-[(6-{2-oxo-1'-[(1r,4r)-4-[4-({2-[2,6-
dioxopiperidin-3-yl]-1,3-dioxo-2,3-dihydro-1H-isoin-
dol-4-yl}amino)piperidine-1-carbonyl]cyclohexan-
ecarbonyl]-1-[(1s,3s)-3-(piperidin-1-yl)cyclobutyl]-1,
2-dihydrospiro[indole-3,4'-piperidin]-6-yl}-3-(propan-
2-yl)-3H-imidazo[4,5-c]pyridin-4-yl)amino]-N-
(propan-2-yl)benzamide;

4-fluoro-2-methyl-5-[(6-{2-oxo-1'-[(3R)-1-[(1r,4r)-4-
({2-[2,6-dioxopiperidin-3-yl]-1,3-dioxo-2,3-dihydro-
1H-isoindol-4-yl}amino)cyclohexanecarbonyl]pyrroli-
dine-3-carbonyl]-1-[(1s,3s)-3-(piperidin-1-yl)
cyclobutyl]-1,2-dihydrospiro[indole-3,4'-piperidin]-6-
yl}-3-(propan-2-yl)-3H-imidazo[4,5-c]pyridin-4-yl)
amino]-N-(propan-2-yl)benzamide;

5-[(6-{1'-[3-(1-{2-[2,6-dioxopiperidin-3-yl]-1,3-dioxo-2,
3-dihydro-1H-isoindol-4-yl}piperidin-4-yl)benzoyl]-
2-oxo-1-[(1s,3s)-3-(piperidin-1-yl)cyclobutyl]-1,2-di-
hydrospiro[indole-3,4'-piperidin]-6-yl}-3-(propan-2-
yl)-3H-imidazo[4,5-c]pyridin-4-yl)amino]-4-fluoro-2-
methyl-N-(propan-2-yl)benzamide;

4-fluoro-2-methyl-5-[(6-{2-oxo-1'-[(3R)-1-[(1r,4r)-4-{
[2-(2,6-dioxopiperidin-3-vi)-1,3-dioxo-2,3-dihydro-
1H-isoindol-4-yl]oxy}cyclohexanecarbonyl]pyrroli-
dine-3-carbonyl]-1-[(1s,3s)-3-(piperidin-1-yl)
cyclobutyl]-1,2-dihydrospiro[indole-3,4'-piperidin]-6-
yl}-3-(propan-2-yl)-3H-imidazo[4,5-c]pyridin-4-yl)
amino]-N-(propan-2-yl)benzamide;

1-(1-{2-[2,6-dioxopiperidin-3-yl]-1,3-dioxoisoindol-5-
yl}piperidine-4-carbonyl)piperidin-4-yl 6-(4-{[2-
fluoro-5-(isopropylcarbamoyl)-4-methylphenyl]
amino}-3-isopropylimidazo[4,5-c]pyridin-6-yl)-2-oxo-
1-[(1s,3s)-3-(piperidin-1-yl)cyclobutyl]spiro[indole-3,
4'-piperidine]-1'-carboxylate;

4-fluoro-2-methyl-5-{[6-(2-oxo-1'-{2-[(3S)-1-[(1r,4r)-4-
({2-[2,6-dioxopiperidin-3-yl]-1,3-dioxo-2,3-dihydro-
1H-isoindol-4-yl}amino)cyclohexanecarbonyl]pyrroli-
din-3-yl]acetyl}-1-[(1s,3s)-3-(piperidin-1-yl)
cyclobutyl]-1,2-dihydrospiro[indole-3,4'-piperidin]-6-
yl)-3-(propan-2-yl)-3H-imidazo[4,5-c]pyridin-4-yl]
amino}-N-(propan-2-yl)benzamide;

4-fluoro-2-methyl-5-{[6-(2-oxo-1'-{2-[(3R)-1-[(1r,4r)-4-
({2-[2,6-dioxopiperidin-3-yl]-1,3-dioxo-2,3-dihydro-
1H-isoindol-4-yl}amino)cyclohexanecarbonyl]pyrroli-
din-3-yl]acetyl}-1-[(1s,3s)-3-(piperidin-1-yl)
cyclobutyl]-1,2-dihydrospiro[indole-3,4'-piperidin]-6-
yl)-3-(propan-2-yl)-3H-imidazo[4,5-c]pyridin-4-yl]
amino}-N-(propan-2-yl)benzamide;

5-[(6-{1'-[4-({4-[2-(2,6-dioxopiperidin-3-yl)-1,3-dioxo-
2,3-dihydro-1H-isoindol-5-yl]piperazin-1-yl}sulfonyl)
benzoyl]-2-oxo-1-[(1s,3s)-3-(piperidin-1-yl)cy-
clobutyl]-1,2-dihydrospiro[indole-3,4'-piperidin]-6-
yl}-3-(propan-2-yl)-3H-imidazo[4,5-c]pyridin-4-yl)
amino]-4-fluoro-2-methyl-N-(propan-2-yl)benzamide;

5-[(6-{1'-[4-({1-[2-(2,6-dioxopiperidin-3-yl)-1,3-dioxo-
2,3-dihydro-1H-isoindol-4-yl]piperidin-4-yl}methyl)
benzoyl]-2-oxo-1-[(1s,3s)-3-(piperidin-1-yl)cy-
clobutyl]-1,2-dihydrospiro[indole-3,4'-piperidin]-6- yl}-3-(propan-2-yl)-3H-imidazo[4,5-c]pyridin-4-yl)
amino]-4-fluoro-2-methyl-N-(propan-2-yl)benzamide;
4-fluoro-2-methyl-5-{[6-(2-oxo-1'-{1-[(1r,4r)-4-({2-[2,6-dioxopiperidin-3-yl]-1,3-dioxo-2,3-dihydro-1H-isoindol-4-yl}amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide;
4-fluoro-2-methyl-5-({6-[1'-(4-{methyl[(1r,4r)-4-{[2-(2,6-dioxopiperidin-3-yl)-1,3-dioxo-2,3-dihydro-1H-isoindol-4-yl]amino}cyclohexyl]carbamoyl}benzoyl)-2-oxo-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide;
4-fluoro-2-methyl-5-[(6-{2-oxo-1-[(1s,3s)-3-(piperidin-1-yl)cyclobutyl]-1'-[(1s,4s)-4-(4-{[2-(2,6-dioxopiperidin-3-yl)-1,3-dioxo-2,3-dihydro-1H-isoindol-4-yl](methyl)amino}piperidine-1-carbonyl)cyclohexanecarbonyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;
5-{[6-(1'-{4-[(1-{2-[2,6-dioxopiperidin-3-yl]-1,3-dioxo-2,3-dihydro-1H-isoindol-4-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;
5-{[6-(1'-{4-[(1-{2-[2,6-dioxopiperidin-3-yl]-1,3-dioxo-2,3-dihydro-1H-isoindol-5-yl}piperidin-4-yl)oxy]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;
5-{[6-(1'-{1-[i-({2-[2,6-dioxopiperidin-3-yl]-1,3-dioxo-2,3-dihydro-1H-isoindol-4-yl}methyl)piperidin-4-yl]-1H-pyrazole-3-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;
4-fluoro-2-methyl-5-{[6-(2-oxo-1'-{1-[(1r,4r)-4-({2-[2,6-dioxopiperidin-3-yl]-1,3-dioxo-2,3-dihydro-1H-isoindol-4-yl}(methyl)amino)cyclohexanecarbonyl]piperidine-4-carbonyl}-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-N-(propan-2-yl)benzamide;
4-fluoro-2-methyl-5-[(6-{2-oxo-1'-[(3R)-1-[(1r,4r)-4-({2-[2,6-dioxopiperidin-3-yl]-1,3-dioxo-2,3-dihydro-1H-isoindol-4-yl](methyl)amino)cyclohexanecarbonyl]pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;
5-{[6-(1'-{1-[4-({2-[2,6-dioxopiperidin-3-yl]-1,3-dioxo-2,3-dihydro-1H-isoindol-4-yl}amino)piperidine-1-carbonyl]piperidine-4-carbonyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;
5-[(6-{1'-[(3R)-1-[4-({2-[2,6-dioxopiperidin-3-yl]-1,3-dioxo-2,3-dihydro-1H-isoindol-4-yl}amino)piperidine-1-carbonyl]pyrrolidine-3-carbonyl-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;
4-fluoro-2-methyl-5-({6-[2-oxo-1'-(1-{[(1r,4r)-4-({2-[2,6-dioxopiperidin-3-yl]-1,3-dioxo-2,3-dihydro-1H-isoindol-4-yl}amino)cyclohexyl]methyl}-1H-pyrazole-4-carbonyl)-1-[(1s,3s)-3-(piperidin-1-yl)cyclobutyl]-1,2-dihydrospiro[indole-3,4'-piperidin]-6-yl]-3-(propan-2-yl)-3H-imidazo[4,5-c]pyridin-4-yl}amino)-N-(propan-2-yl)benzamide;
5-[(6-{1'-[2-chloro-4-(4-{2-[2,6-dioxopiperidin-3-yl]-1,3-dioxo-2,3-dihydro-1H-isoindol-5-yl}piperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;
5-[(6-{1'-[4-(4-{2-[2,6-dioxopiperidin-3-yl]-1,3-dioxo-2,3-dihydro-1H-isoindol-5-yl}-2-methylpiperazine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;
4-fluoro-2-methyl-5-[(6-{2-oxo-1'-[(3R)-1-{[(1r,4r)-4-({2-[2,6-dioxopiperidin-3-yl]-1,3-dioxo-2,3-dihydro-1H-isoindol-4-yl}amino)cyclohexyl]methyl}pyrrolidine-3-carbonyl]-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-N-(propan-2-yl)benzamide;
5-[(6-{1'-[1-(1-{2-[2,6-dioxopiperidin-3-yl]-1,3-dioxoisoindol-5-yl}piperidine-4-carbonyl)-4-methylpiperidine-4-carbonyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide;
5-[(6-{1'-[4-(4-{2-[2,6-dioxopiperidin-3-yl]-1,3-dioxo-2,3-dihydro-1H-isoindol-4-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;
5-[(6-{1'-[4-(4-{2-[2,6-dioxopiperidin-3-yl]-1,3-dioxo-2,3-dihydro-1H-isoindol-5-yl}piperidine-1-carbonyl)benzoyl]-2-oxo-1-[(1s,3s)-3-(piperidin-1-yl)cyclobutyl]-1,2-dihydrospiro[indole-3,4'-piperidin]-6-yl}-3-(propan-2-yl)-3H-imidazo[4,5-c]pyridin-4-yl)amino]-4-fluoro-2-methyl-N-(propan-2-yl)benzamide;
5-{[6-(1'-{4-[4-({2-[2,6-dioxopiperidin-3-yl]-1,3-dioxo-2,3-dihydro-1H-isoindol-4-yl}methyl)piperidine-1-carbonyl]benzoyl}-2-oxo-1-[(1s,3s)-3-(piperidin-1-yl)cyclobutyl]-1,2-dihydrospiro[indole-3,4'-piperidin]-6-yl)-3-(propan-2-yl)-3H-imidazo[4,5-c]pyridin-4-yl]amino}-4-fluoro-2-methyl-N-(propan-2-yl)benzamide;
5-((6-(1'-(4-(4-(2-(2,6-dioxopiperidin-3-yl)-1,3-dioxoisoindolin-5-yl)piperazine-1-carbonyl)benzoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;
5-((6-(1'-((1s,4S)-4-(4-(2-(2,6-dioxopiperidin-3-yl)-1,3-dioxoisoindolin-5-yl)piperazine-1-carbonyl)cyclohexane-1-carbonyl)-2-oxo-1-((1s,3S)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;
5-((6-(1'-(2-((1r,4R)-4-((2-(2,6-dioxopiperidin-3-yl)-1,3-dioxoisoindolin-4-yl)amino)cyclohexyl)acetyl)-2-oxo- 1-((1s,3S)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-((3R)-1-((1r,4R)-4-((2-(2,6-dioxopiperidin-3-yl)-1,3-dioxoisoindolin-5-yl)amino)cyclohexane-1-carbonyl)pyrrolidine-3-carbonyl)-2-oxo-1-((1s,3S)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-((3R)-1-(2-((1r,4R)-4-((2-(2,6-dioxopiperidin-3-yl)-1,3-dioxoisoindolin-4-yl)amino)cyclohexyl)acetyl)pyrrolidine-3-carbonyl)-2-oxo-1-((1s,3S)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(6-(4-(2-(2,6-dioxopiperidin-3-yl)-1,3-dioxoisoindolin-4-yl)piperazin-1-yl)nicotinoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(5-(4-(2-(2,6-dioxopiperidin-3-yl)-1,3-dioxoisoindolin-4-yl)piperazin-1-yl)pyrazine-2-carbonyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-(6-(4-(2-(2,6-dioxopiperidin-3-yl)-1,3-dioxoisoindolin-5-yl)piperazin-1-yl)nicotinoyl)-2-oxo-1-((1s,3s)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-((3R)-1-(5-(4-(2-(2,6-dioxopiperidin-3-yl)-1,3-dioxoisoindolin-4-yl)piperazin-1-yl)pyrazine-2-carbonyl)pyrrolidine-3-carbonyl)-2-oxo-1-((is,3S)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-((6-(1'-((3S)-1-((1r,4S)-4-((2-(2,6-dioxopiperidin-3-yl)-1,3-dioxoisoindolin-4-yl)amino)cyclohexane-1-carbonyl)pyrrolidine-3-carbonyl)-2-oxo-1-((1s,3R)-3-(piperidin-1-yl)cyclobutyl)spiro[indoline-3,4'-piperidin]-6-yl)-3-isopropyl-3H-imidazo[4,5-c]pyridin-4-yl)amino)-4-fluoro-N-isopropyl-2-methylbenzamide;

5-[(6-{1'-[4-(1-{[(2-{[2-(2,6-dioxopiperidin-3-yl)-1,3-dioxoisoindol-4-yl]amino}ethyl)carbamoyl]methyl}piperidin-4-yl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide;

N-(2-{[2-(2,6-dioxopiperidin-3-yl)-1,3-dioxoisoindol-4-yl]amino}ethyl)-5-[(4-{[6-(4-{[2-fluoro-5-(isopropylcarbamoyl)-4-methylphenyl]amino}-3-isopropylimidazo[4,5-c]pyridin-6-yl)-2-oxo-1-[(1s,3s)-3-(piperidin-1-yl)cyclobutyl]spiro[indole-3,4'-piperidin]-1'-yl]carbonyl}piperidin-1-yl)methyl]pyridine-2-carboxamide;

5-[(6-{1'-[2-(4-{4-[(2-{[2-(2,6-dioxopiperidin-3-yl)-1,3-dioxoisoindol-4-yl]amino}ethyl)carbamoyl]phenyl}piperidin-1-yl)acetyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide;

5-[(6-{1'-[4-({4-[2-(2,6-dioxopiperidin-3-yl)-1,3-dioxoisoindol-5-yl]piperazin-1-yl}methyl)benzoyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide;

5-[(6-{1'-[(4-{4-[2-(2,6-dioxopiperidin-3-yl)-1,3-dioxoisoindol-5-yl]piperazine-1-carbonyl}phenyl)methyl]-2-oxo-1-[(1s,3s)-3-(piperidin-1-yl)cyclobutyl]spiro[indole-3,4'-piperidin]-6-yl}-3-isopropylimidazo[4,5-c]pyridin-4-yl)amino]-4-fluoro-N-isopropyl-2-methylbenzamide;

5-({6-[1'-(4-{3-[2-(2,6-dioxopiperidin-3-yl)-1,3-dioxoisoindol-5-yl]-3,8-diazabicyclo[3.2.1]octane-8-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide;

5-{[6-(1'-{[4-({4-[2-(2,6-dioxopiperidin-3-yl)-1,3-dioxoisoindol-5-yl]piperazin-1-yl}methyl)phenyl]methyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide;

5-({6-[1'-(4-{4-[2-(2,6-dioxopiperidin-3-yl)-1,3-dioxoisoindol-4-yl]piperazine-1-carbonyl}benzoyl)-2-oxo-1-[(1s,3s)-3-(piperidin-1-yl)cyclobutyl]spiro[indole-3,4'-piperidin]-6-yl]-3-isopropylimidazo[4,5-c]pyridin-4-yl}amino)-4-fluoro-N-isopropyl-2-methylbenzamide;

4-fluoro-N-isopropyl-5-[(3-isopropyl-6-{2-oxo-1-[(1s,3s)-3-(piperidin-1-yl)cyclobutyl]-1'-[(1s,4s)-4-[4-({2-[(3S)-2,6-dioxopiperidin-3-yl]-1,3-dioxoisoindol-4-yl}oxy)piperidine-1-carbonyl]cyclohexanecarbonyl]spiro[indole-3,4'-piperidin]-6-yl}imidazo[4,5-c]pyridin-4-yl)amino]-2-methylbenzamide; and 5-{[6-(1'-{4-[(1-{2-[2,6-dioxopiperidin-3-yl]-1,3-dioxoisoindol-5-yl}piperidin-4-yl)(methyl)amino]benzoyl}-2-oxo-1-[(1s,3s)-3-(piperidin-1-yl)cyclobutyl]spiro[indole-3,4'-piperidin]-6-yl)-3-isopropylimidazo[4,5-c]pyridin-4-yl]amino}-4-fluoro-N-isopropyl-2-methylbenzamide.

20. A pharmaceutical composition comprising the compound of claim 1, or a pharmaceutically acceptable salt thereof, and a pharmaceutically acceptable excipient or carrier.

21. A method of treating a disease or disorder associated with increased hematopoietic progenitor kinase 1 (HPK1) activity in a subject in need thereof, the method comprising administering to the subject a therapeutically effective amount of a compound of claim 1.

22. A method of increasing T-cell activation in a subject in need thereof, the method comprising administering to the subject a therapeutically effective amount of a compound of claim 1.

23. A method of treating cancer associated with HPK1 activity in a subject in need thereof, the method comprising administering to the subject a therapeutically effective amount of a compound of claim 1.

24. A method of inhibiting the growth or proliferation of cancer cells in a subject in need thereof, wherein the cancer is associated with HPK1 activity, the method comprising administering to the subject a therapeutically effective amount of a compound of claim 1.

25. A method of treating or preventing a hepatitis B virus (HBV) infection in a subject in need thereof, the method comprising administering to the subject a therapeutically effective amount of a compound of claim 1.

26. A method of treating or preventing a human immunodeficiency virus (HIV) infection in a subject in need thereof, the method comprising administering to the subject a therapeutically effective amount of a compound of claim 1.

27. A compound having a structure of Formula (II):

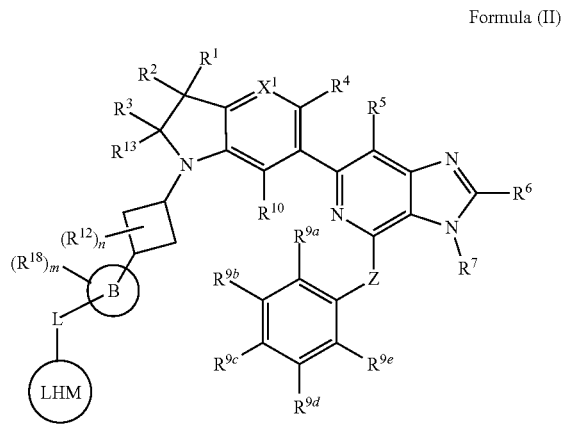

Formula (II)

or a pharmaceutically acceptable salt thereof,
wherein:
m is 0, 1, 2, 3, 4 or 5;
n is 0, 1, 2, 3, 4, 5, or 6;
B is a 4-10 membered monocyclic, fused bicyclic, bridged bicyclic, or spirocyclic heterocyclyl ring having 1-3 heteroatoms independently selected from N, O, and S;
L is a linker moiety having a length of 2-24 continuously covalently-bonded atoms selected from the group consisting of C, O, N and S;
LHM is a ligase harness moiety;
one of $R^1$ and $R^2$ is H, —CN, —OH, halogen, or $C_{1-6}$ alkyl, and the other of $R^1$ and $R^2$ is H, halogen, or $C_{1-6}$ alkyl, wherein each $C_{1-6}$ alkyl is optionally substituted with 1-3 groups independently selected from —OH and halogen, or
$R^1$ and $R^2$ together with the carbon to which they are attached form a $C_{3-7}$ monocyclic cycloalkyl or a 4-6 membered monocyclic heterocyclyl having 1 or 2 heteroatoms independently selected from N, O, and S, wherein the $C_{3-7}$ monocyclic cycloalkyl and the 4-6 membered monocyclic heterocyclyl are each optionally substituted with one $R^{11}$ and are each optionally substituted with 1-3 groups independently selected from —OH, halogen, oxo, $C_{1-3}$ alkyl, and $C_{1-3}$ alkoxy, or
$R^1$ and $R^2$ together form =O;
$R^{11}$ is
i) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
i) —S(O)$_2$C$_{1-6}$ alkyl,
ii) —S(O)$_2$C$_{3-7}$ monocyclic cycloalkyl,
iii) $C_{1-6}$ alkyl optionally substituted with 1-3 groups independently selected from —CN, —OH, halogen, $C_{1-3}$ alkoxy, and $C_{3-7}$ monocyclic cycloalkyl, or
iv) —C(O)R$^{21}$;

$R^{21}$ is
i) H,
ii) $C_{3-7}$ monocyclic or bridged bicyclic cycloalkyl optionally substituted with 1-3 groups independently selected from —CN, —OH, halogen, $C_{1-3}$ alkyl, and $C_{1-3}$ alkoxy, wherein the $C_{1-3}$ alkyl is optionally substituted with 1-3 groups independently selected from —OH, halogen, and $C_{1-3}$ alkoxy,
iii) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, $C_{1-3}$ alkyl, and $C_{1-3}$ alkoxy,
iv) 5-6 membered monocyclic heteroaryl having 1-4 heteroatoms independently selected from N, O, and S, wherein the 5-6 membered monocyclic heteroaryl is optionally substituted with 1-3 groups independently selected from —CN, —OH, halogen, $C_{1-3}$ alkyl, and $C_{1-3}$ alkoxy,
v) —NH$_2$,
vi) —NH(C$_{1-6}$ alkyl), wherein the C$_{1-6}$ alkyl is optionally substituted with 1-3 groups independently selected from —CN, —OH, halogen, and C$_{1-3}$ alkoxy,
vii) —N(C$_{1-6}$ alkyl)$_2$, wherein each C$_{1-6}$ alkyl can be the same or different and wherein each C$_{1-6}$ alkyl is optionally substituted with 1-3 groups independently selected from —CN, —OH, halogen, and C$_{1-3}$ alkoxy,
viii) C$_{1-6}$ alkoxy optionally substituted with 1-3 groups independently selected from —OH, halogen, C$_{1-3}$ alkyl, and C$_{3-7}$ monocyclic cycloalkyl, or
ix) C$_{1-6}$ alkyl optionally substituted with 1-3 groups independently selected from
a) —CN,
b) —OH,
c) halogen,
d) C$_{1-3}$ alkoxy,
e) C$_{3-7}$ monocyclic cycloalkyl optionally substituted with 1-3 groups independently selected from —CN, —OH, halogen, C$_{1-3}$ alkyl, and C$_{1-3}$ alkoxy,
f) 4-6 membered monocyclic heterocyclyl having 1 or 2 heteroatoms independently selected from N, O, and S, wherein the 4-6 membered monocyclic heterocyclyl is optionally substituted with 1-3 groups independently selected from —CN, —OH, halogen, oxo, C$_{1-3}$ alkyl, and C$_{1-3}$ alkoxy, and
g) —OC(O)C$_{1-6}$ alkyl optionally substituted with one —OH;
$R^3$ and $R^{13}$ are each H, or
$R^3$ and $R^{13}$ together form =O;
each $R^{12}$ is independently selected from —OH, halogen, C$_{1-3}$ alkyl, and C$_{1-3}$ alkoxy;
each $R^{18}$ is independently
i) —CN,
ii) a halogen,
iii) —OH,
iv) C$_{1-6}$ alkoxy optionally substituted with 1-3 groups independently selected from —OH, halogen, C$_{1-3}$ alkoxy, and C$_{3-7}$ monocyclic cycloalkyl,
v) C$_{1-6}$ alkyl optionally substituted with 1-3 groups independently selected from —OH, halogen, C$_{1-3}$ alkoxy, and C$_{3-7}$ monocyclic cycloalkyl,
vi) —COOH, or
vii) —C(O)N(R$^{22}$)$_2$, wherein each R$^{22}$ is independently H or C$_{1-6}$ alkyl;

$X^1$ is N or $CR^{17}$;

$R^4$, $R^5$, $R^6$, $R^{10}$ and $R^{17}$ are each independently H, halogen, $C_{1-3}$ alkyl, or $C_{1-3}$ alkoxy;

$R^7$ is
i) H,
ii) $C_{1-6}$ alkyl optionally substituted with 1-3 groups independently selected from —OH, halogen, $C_{1-3}$ alkoxy, and $C_{3-7}$ monocyclic cycloalkyl, or
iii) $C_{3-7}$ monocyclic cycloalkyl optionally substituted with 1-3 groups independently selected from —OH, halogen, $C_{1-3}$ alkyl, and $C_{1-3}$ alkoxy;

Z is —O—, —$C(R')_2$—, or —$NR^8$—;

each $R^8$ is independently H or $C_{1-3}$ alkyl;

$R^{9a}$, $R^{9b}$, $R^{9c}$, $R^{9d}$, and $R^{9e}$ are independently
i) H,
ii) halogen,
iii) $C_{1-6}$ alkoxy optionally substituted with 1-3 groups independently selected from —OH, halogen, $C_{1-3}$ alkyl, and $C_{3-7}$ monocyclic cycloalkyl,
iv) —$NH_2$,
v) —$NH(C_{1-6}$ alkyl), wherein the $C_{1-6}$ alkyl is optionally substituted with 1-3 groups independently selected from —OH, halogen, and $C_{1-3}$ alkoxy,
vi) —$N(C_{1-6}$ alkyl$)_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
vii) —$P(O)(C_{1-6}$ alkyl$)_2$, wherein each $C_{1-6}$ alkyl can be the same or different, and wherein each $C_{1-6}$ alkyl is optionally substituted with 1-3 groups independently selected from —OH, halogen, and $C_{1-3}$ alkoxy,
viii) —$S(O)_2C_{1-6}$ alkyl,
ix) —$S(O)_2N(R^{23})_2$, wherein each $R^{23}$ is independently H or $C_{1-6}$ alkyl,
x) $C_{1-6}$ alkyl optionally substituted with 1-3 groups independently selected from
  a) —OH,
  b) halogen,
  c) $C_{1-3}$ alkoxy,
  d) $C_{3-7}$ monocyclic cycloalkyl,
  e) 5-6 membered monocyclic heterocyclyl having 1 or 2 heteroatoms independently selected from N, O, and S, wherein the 5-6 membered monocyclic heterocyclyl is optionally substituted with 1-3 groups independently selected from oxo and $C_{1-3}$ alkyl, and
  f) —$NR^{20}C(O)OC_{1-3}$ alkyl, wherein $R^{20}$ is H or $C_{1-3}$ alkyl,
xi) $C_{3-7}$ monocyclic cycloalkyl optionally substituted with 1-3 groups independently selected from —OH, halogen, $C_{1-3}$ alkyl, and $C_{1-3}$ alkoxy,
xii) 5-6 membered monocyclic heteroaryl having 1-4 heteroatoms independently selected from N, O, and S, wherein the 5-6 membered monocyclic heteroaryl is optionally substituted with 1-3 groups independently selected from —OH, halogen, $C_{1-3}$ alkyl, and $C_{1-3}$ alkoxy,
xiii) 4-6 membered monocyclic heterocyclyl having 1-3 heteroatoms independently selected from N, O, and S, wherein the 4-6 membered monocyclic heterocyclyl is optionally substituted with 1-3 groups independently selected from —OH, halogen, oxo, $C_{1-3}$ alkyl, and $C_{1-3}$ alkoxy,
xiv) —COOH,
xv) —$C(O)N(R^{19})_2$, or
xvi) —$C_{1-3}$ alkylene-$C(O)N(R^{19})_2$, wherein one or more of $R^{9a}$, $R^{9b}$, $R^{9c}$, $R^{9d}$, and $R^{9e}$ is —$C(O)N(R^{19})_2$ or —$C_{1-3}$ alkylene-$C(O)N(R^{19})_2$; and each $R^{19}$ is independently
i) H,
ii) —$S(O)_2C_{1-6}$ alkyl,
iii) $C_{1-6}$ alkyl optionally substituted with 1-6 groups independently selected from —CN, —OH, halogen, $C_{1-3}$ alkoxy, and $C_{3-7}$ monocyclic cycloalkyl,
iv) $C_{3-7}$ monocyclic cycloalkyl optionally substituted with 1-6 groups independently selected from —CN, —OH, halogen, $C_{1-6}$ alkyl, and $C_{1-6}$ alkoxy, wherein the $C_{1-6}$ alkyl is optionally substituted with 1-3 groups independently selected from —CN, —OH, halogen, and $C_{1-3}$ alkoxy, or
v) 4-6 membered monocyclic heterocyclyl having 1-3 heteroatoms independently selected from N, O, and S, wherein the 4-6 membered monocyclic heterocyclyl is optionally substituted with 1-6 groups independently selected from —CN, —OH, halogen, oxo, $C_{1-3}$ alkyl, and $C_{1-3}$ alkoxy.

28. The compound of claim 27 wherein, Z is NH, $X^1$ is CH, $R^6$ is H, and the compound has a structure of Formula (IIa):

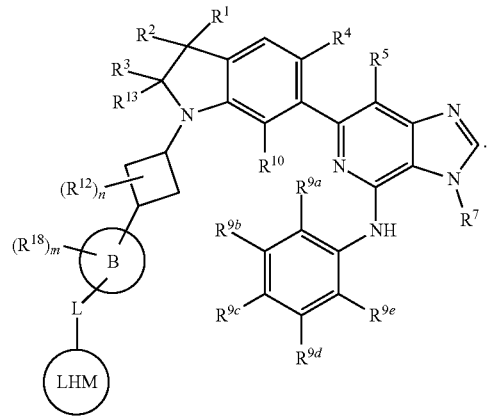

Formula (IIa)

29. The compound of claim 28 wherein the compound has a structure of Formula (IIb):

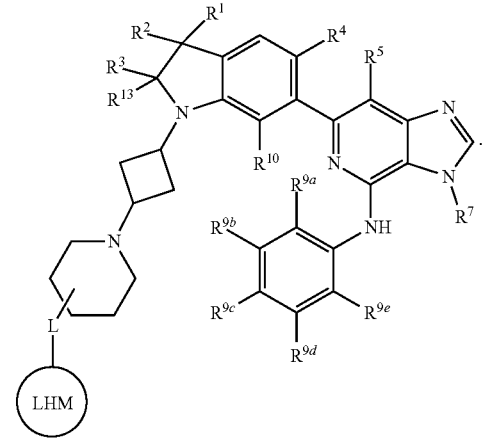

Formula (IIb)

30. The compound of claim 29, wherein
each $R^{9a}$, $R^{9b}$, $R^{9c}$, $R^{9d}$, and $R^{9e}$ is independently H, halogen, $C_{1-6}$ alkyl, or —C(O)N($R^{19}$)$_2$; wherein $R^{19}$ is $C_{1-6}$ alkyl;
$R^4$, $R^5$ and $R^{10}$ are each H; and
$R^7$ is $C_{1-6}$ alkyl.

31. The compound of claim 29, wherein $R^3$ and $R^{13}$ together form =O; and $R^1$ and $R^2$ together with the carbon to which they are attached form a 4-6 membered monocyclic heterocyclyl having 1 or 2 heteroatoms independently selected from N, O, and S, and wherein the 4-6 membered monocyclic heterocyclyl is optionally substituted with one $R^{11}$.

32. The compound of claim 29 wherein the compound has a structure of Formula (IIc):

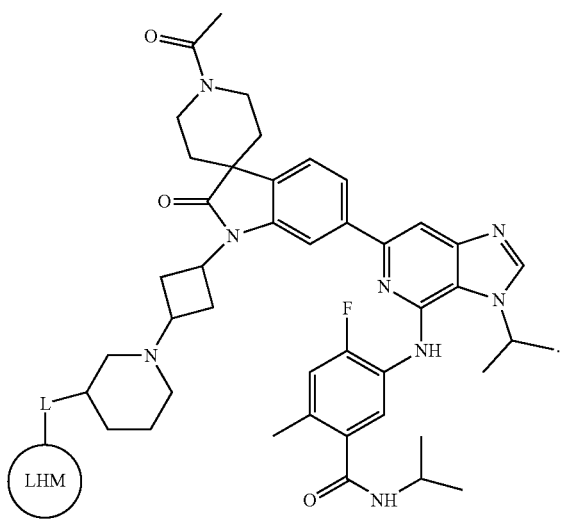

Formula (IIc)

33. The compound of claim 32, wherein L is

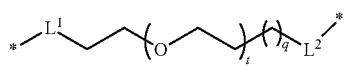

wherein,
t is 0, 1, 2, 3, 4, 5, 6, or 7;
q is 0, 1, 2, 3, 4, 5, 6, or 7;
$L^1$ is a direct bond, —C(O)NH—, or —C(O)—; and
$L^2$ is —C(O)NH—, —O—, or —NH—.

34. The compound of claim 33 wherein t is 0, q is 5 or 7, $L^1$ is —C(O)NH—, and $L^2$ is —O—, or —NH—.

35. The compound of claim 27 wherein the LHM targets VHL and has a structure of Formula (If):

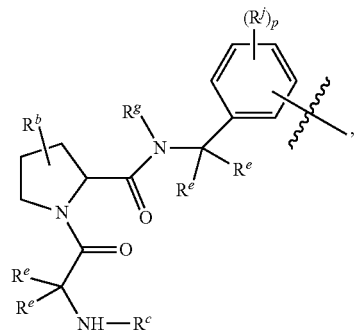

Formula (If)

wherein,
p is 0 or 1;
$R^j$ is 5-6 member heteroaryl optionally substituted with 1 to 3 $R^k$,
each $R^k$ is independently halo, oxo, —CN, —OH, $C_{1-6}$ alkyl, $C_{3-8}$ cycloalkyl, or —O—$C_{1-6}$ alkyl;
each $R^e$ is independently hydrogen, $C_{1-6}$ alkyl or $C_{3-8}$ cycloalkyl;
$R^g$ is hydrogen or $C_{1-6}$ alkyl;
$R^b$ is hydrogen or hydroxyl;
$R^c$ is —C(O)$R^f$, wherein $R^f$ is $C_{1-6}$ alkyl or $C_{3-8}$ cycloalkyl, each being optionally substituted with halo or —CN.

36. The compound of claim 35 wherein the LHM has one of the following structures:

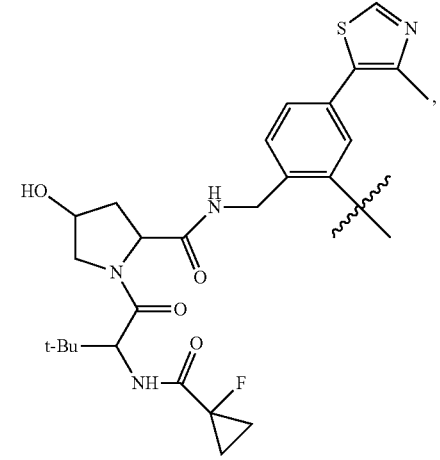

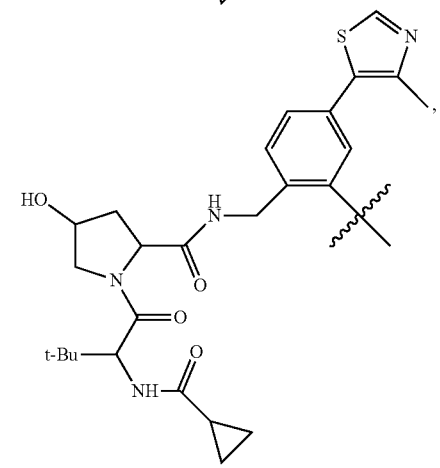

-continued

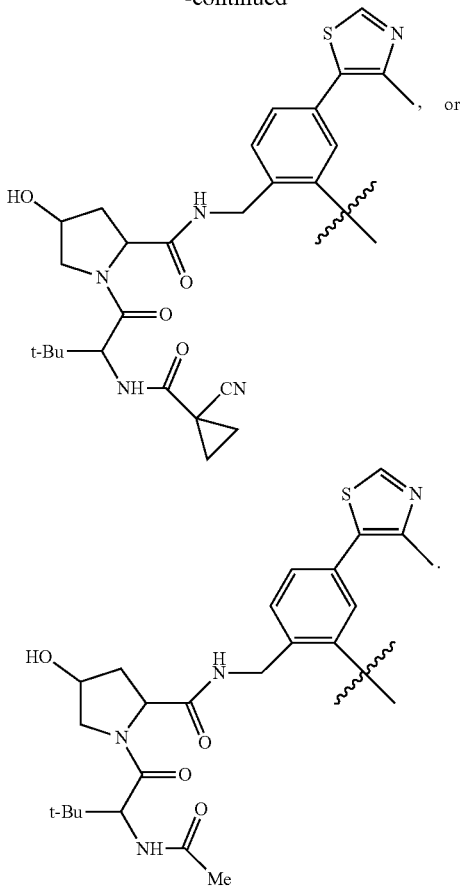

, or

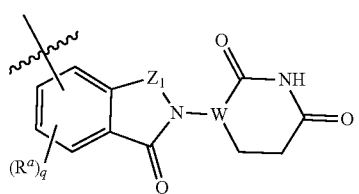

.

37. The compound of claim 28 wherein the LHM targets CRBN and has a structure of Formula (Id)

Formula (Id)

![Formula Id structure]

wherein,
W is —C($R^g$)— or —N—;
$Z_1$ is —C(O)—, —C(S)—, —C($NR^g$)—, —C($R^g$)$_2$—, —C($R^g$)$_2$—C(O)—, —C(O)—N($R^g$)—, —$CR^g$=$CR^g$—, —C($R^g$)=N—, —C($R^g$)$_2$—C(S)—, or —C($R^g$)$_2$—C($R^g$)$_2$—;

q is 0, 1 or 2;
$R^g$ is hydrogen or $C_{1-6}$ alkyl; and
$R^a$ is $C_{1-6}$alkyl, halo, halo $C_{1-6}$alkyl, —N($R^g$)$_2$, CN, nitro, hydroxyl, or —O—$C_{1-4}$alkyl.

38. The compound of claim 37 wherein W is —CH—; and $Z_1$ is —C(O)—, —CH$_2$—, —CH$_2$—C(O)—, or —CH=CH—.

39. The compound of claim 38 wherein the LHM has one of the following structures.

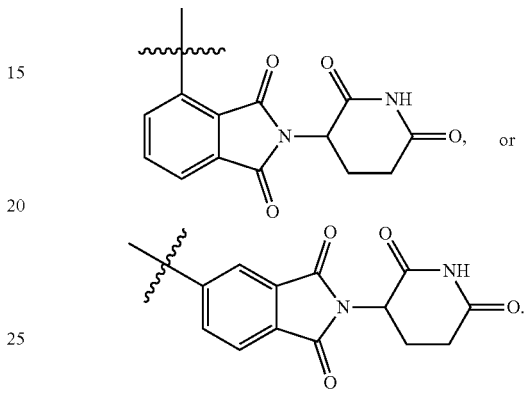

40. The compound of claim 27 selected from the group consisting of
(3R)-1-((1s,3S)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(9-((2-(2,6-dioxopiperidin-3-yl)-1,3-dioxoisoindolin-5-yl)amino)nonyl)piperidine-3-carboxamide;
(R)-1-((1s,3S)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(7-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)heptyl)piperidine-3-carboxamide; and
(R)-1-((1s,3S)-3-(1'-acetyl-6-(4-((2-fluoro-5-(isopropylcarbamoyl)-4-methylphenyl)amino)-3-isopropyl-3H-imidazo[4,5-c]pyridin-6-yl)-2-oxospiro[indoline-3,4'-piperidin]-1-yl)cyclobutyl)-N-(9-(2-(((2S,4R)-1-((S)-2-(1-fluorocyclopropane-1-carboxamido)-3,3-dimethylbutanoyl)-4-hydroxypyrrolidine-2-carboxamido)methyl)-5-(4-methylthiazol-5-yl)phenoxy)nonyl)piperidine-3-carboxamide.

* * * * *

UNITED STATES PATENT AND TRADEMARK OFFICE
CERTIFICATE OF CORRECTION

PATENT NO. : 11,739,101 B2
APPLICATION NO. : 17/308879
DATED : August 29, 2023
INVENTOR(S) : Hunter P. Shunatona et al.

It is certified that error appears in the above-identified patent and that said Letters Patent is hereby corrected as shown below:

In the Claims

Column 262, Claim 8, Line 15:
"The compound of claim/wherein" should be: --The compound of claim 7 wherein--.

Signed and Sealed this
Ninth Day of April, 2024

Katherine Kelly Vidal
*Director of the United States Patent and Trademark Office*